(12) United States Patent
Meyers et al.

(10) Patent No.: US 7,214,502 B2
(45) Date of Patent: May 8, 2007

(54) 3714, 16742, 23546, AND 13887 NOVEL PROTEIN KINASE MOLECULES AND USES THEREFOR

(75) Inventors: Rachel Meyers, Newton, MA (US); John Joseph Hunter, Somerville, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 526 days.

(21) Appl. No.: 10/393,316

(22) Filed: Mar. 20, 2003

(65) Prior Publication Data
US 2003/0175786 A1    Sep. 18, 2003

Related U.S. Application Data

(63) Continuation of application No. 09/815,915, filed on Mar. 23, 2001, now abandoned.

(60) Provisional application No. 60/191,846, filed on Mar. 24, 2000.

(51) Int. Cl.
*C12Q 1/48* (2006.01)
*C12N 9/12* (2006.01)

(52) U.S. Cl. .................................... 435/15; 435/194

(58) Field of Classification Search ................ 435/15, 435/194
See application file for complete search history.

(56) References Cited

FOREIGN PATENT DOCUMENTS

| WO | WO 96/13597 A2 | 5/1996 |
|----|----|----|
| WO | WO 00/11165 A1 | 3/2000 |
| WO | WO 00/73469 A2 | 12/2000 |
| WO | WO 01/38503 A2 | 5/2001 |
| WO | WO 01/40285 A1 | 6/2001 |
| WO | WO 01/54733 A1 | 8/2001 |
| WO | WO 02/06330 A2 | 1/2002 |
| WO | WO 02/18557 A2 | 3/2002 |

OTHER PUBLICATIONS

Krupa A et al 2004 Structural Modes of Stabilization of Permissive Phosphorylation sites in Prtoein Kinases: Distinct Startegies in Ser/Thr and Tyr kinases JMB 339: 1025-1039.*
Levitzki A Protein Kinase Inhibitors as a therapeutic Modlaity. Acc. Chem. Res. 2003, 36, 462-469.*
Horberg JJ et al Canver: A systems Biology disease. Biosystems 83 (2006) 81-90.*
GenBank Acc: Y10725, Jan. 23, 1997.
Rashidul Alam M. et al., The Journal of Biological Chemistry, Nov. 8, 1996, pp. 28636-28640, vol. 271, No. 45.
Maucuer A. et al., The Journal of Biological Chemistry, Sep. 12, 1997, pp. 23151-23156, vol. 272, No. 37.

* cited by examiner

*Primary Examiner*—Maryam Monshipouri

(57) ABSTRACT

The invention provides isolated nucleic acids molecules, designated 3714, 16742, 23546, or 13887 nucleic acid molecules, which encode novel protein kinases. The invention also provides antisense nucleic acid molecules, recombinant expression vectors containing 3714, 16742, 23546, or 13887 nucleic acid molecules, host cells into which the expression vectors have been introduced, and nonhuman transgenic animals in which a 3714, 16742, 23546, or 13887 gene has been introduced or disrupted. The invention sill further provides isolated 3714, 16742, 23546, or 13887 proteins, fusion proteins, antigenic peptides and anti-3714, -16742, -23546, or -13887 antibodies. Diagnostic, screening, and therapeutic methods utilizing compositions of the invention are also provided.

5 Claims, 51 Drawing Sheets

```
NCSSSYMCGCGKCSSGYSSSSGRRGSMRSMRSMMGCGGCGGCGGCAGCCGGAGCAGTAGGCACCCGAGCAGCGCCAGCG SEQ ID NO:1
                                                                    M   V   I   M   SEQ ID NO:2
4
GCCGAGCGGGCGGCTTCCTGGCCTGGGCGCTCCGGTGGCGGCGGAGGTGCGCGCGGAGCC ATG GTT ATC ATG
12                                                            ↑SEQ ID NO:3→

S   E   F   S   A   D   P   A   G   Q   G   Q   G   Q   Q   K   P   L   R   V
24
TCG GAG TTC AGC GCG GAC CCC GCG GGC CAG GGT CAG GGC CAG CAG AAG CCC CTC CGG GTG
72

G   F   Y   D   I   E   R   T   L   G   K   G   N   F   A   V   V   K   L   A
44
GGT TTT TAC GAC ATC GAG CGG ACC CTG GGC AAA GGC AAC TTC GCG GTG GTG AAG CTG GCG
132

R   H   R   V   T   K   T   Q   V   A   I   K   I   I   D   K   T   R   L   D
64
CGG CAT CGA GTC ACC AAA ACG CAG GTT GCA ATA AAA ATA ATT GAT AAA ACA CGA TTA GAT
192

S   S   N   L   E   K   I   Y   R   E   V   Q   L   M   K   L   L   N   H   P
84
TCA AGC AAT TTG GAG AAA ATC TAT CGT GAG GTT CAG CTG ATG AAG CTT CTG AAC CAT CCA
252

H   I   I   K   L   Y   Q   V   M   E   T   K   D   M   L   Y   I   V   T   E
104
CAC ATC ATA AAG CTT TAC CAG GTT ATG GAA ACA AAG GAC ATG CTT TAC ATC GTC ACT GAA
312

F   A   K   N   G   E   M   F   D   Y   L   T   S   N   G   H   L   S   E   N
124
TTT GCT AAA AAT GGA GAA ATG TTT GAT TAT TTG ACT TCC AAC GGG CAC CTG AGT GAG AAC
372

E   A   R   K   K   F   W   Q   I   L   S   A   V   E   Y   C   H   D   H   H
144
GAG GCG CGG AAG AAG TTC TGG CAA ATC CTG TCG GCC GTG GAG TAC TGT CAC GAC CAT CAC
432

I   V   H   R   D   L   K   T   E   N   L   L   L   D   G   N   M   D   I   K
164
ATC GTC CAC CGG GAC CTC AAG ACC GAG AAC CTC CTG CTG GAT GGC AAC ATG GAC ATC AAG
492

L   A   D   F   G   F   G   N   F   Y   K   S   G   E   P   L   S   T   W   C
184
CTG GCA GAT TTT GGA TTT GGG AAT TTC TAC AAG TCA GGA GAG CCT CTG TCC ACG TGG TGT
552

```
              G   S   P   P   Y   A   A   P   E   V   F   E   G   K   E   Y   E   G   P   Q
GGG AGC CCC CCG TAT GCC GCC CCG GAA GTC TTT GAG GGG AAG GAG TAT GAA GGC CCC CAG
612

L   D   I   W   S   L   G   V   V   L   Y   V   L   V   C   G   S   L   P   F
224
CTG GAC ATC TGG AGC CTG GGC GTG GTG CTG TAC GTC CTG GTC TGC GGT TCT CTC CCC TTC
672

D   G   P   N   L   P   T   L   R   Q   R   V   L   E   G   R   F   R   I   P
244
GAT GGG CCT AAC CTG CCG ACG CTG AGA CAG CGG GTG CTG GAG GGC CGC TTC CGC ATC CCC
732

F   F   M   S   Q   D   C   E   S   L   I   R   R   M   L   V   V   D   P   A
264
TTC TTC ATG TCT CAA GAC TGT GAG AGC CTG ATC CGC CGC ATG CTG GTG GTG GAC CCC GCC
792

R   R   I   T   I   A   Q   I   R   Q   H   R   W   M   R   A   E   P   C   L
284
AGG CGC ATC ACC ATC GCC CAG ATC CGG CAG CAC CGG TGG ATG CGG GCT GAG CCC TGC TTG
852

P   G   P   A   C   P   A   F   S   A   H   S   Y   T   S   N   L   G   D   Y
304
CCG GGA CCC GCC TGC CCC GCC TTC TCC GCA CAC AGC TAC ACC TCC AAC CTG GGC GAC TAC
912

D   E   Q   A   L   G   I   M   Q   T   L   G   V   D   R   Q   R   T   V   E
324
GAT GAG CAG GCG CTG GGT ATC ATG CAG ACC CTG GGC GTG GAC CGG CAG AGG ACG GTG GAG
972

S   L   Q   N   S   S   Y   N   H   F   A   A   I   Y   Y   L   L   L   E   R
344
TCA CTG CAA AAC AGC AGC TAT AAC CAC TTT GCT GCC ATT TAT TAC CTC CTC CTT GAG CGG
1032

L   K   E   Y   R   N   A   Q   C   A   R   P   G   P   A   R   Q   P   R   P
364
CTC AAG GAG TAT CGG AAT GCC CAG TGC GCC CGC CCC GGG CCT GCC AGG CAG CCG CGG CCT
1092

R   S   S   D   L   S   G   L   E   V   P   Q   E   G   L   S   T   D   P   F
384
CGG AGC TCG GAC CTC AGT GGT TTG GAG GTG CCT CAG GAA GGT CTT TCC ACC GAC CCT TTC
1152

R   P   A   L   L   C   P   Q   P   Q   T   L   V   Q   S   V   L   Q   A   E
404
CGA CCT GCC TTG CTG TGC CCG CAG CCG CAG ACC TTG GTG CAG TCC GTC CTC CAG GCC GAG
1212

M   D   C   E   L   Q   S   S   L   Q   W   P   L   F   F   P   V   D   A   S
424
ATG GAC TGT GAG CTC CAG AGC TCG CTG CAG TGG CCC TTG TTC TTC CCG GTG GAT GCC AGC
1272
```

*FIG. 1B*

```
    C   S   G   V   F   R   P   R   P   V   S   P   S   S   L   L   D   T   A   I
444
TGC AGC GGA GTG TTC CGG CCC CGG CCC GTG TCC CCA AGC AGC CTG CTG GAC ACA GCC ATC
1332

S   E   E   A   R   Q   G   P   G   L   E   E   E   Q   D   T   Q   E   S   L
464
AGT GAG GAG GCC AGG CAG GGG CCG GGC CTA GAG GAG GAG CAG GAC ACG CAG GAG TCC CTG
1392

P   S   S   T   G   R   R   H   T   L   A   E   V   S   T   R   L   S   P   L
484
CCC AGC AGC ACG GGC CGG AGG CAC ACC CTG GCC GAG GTC TCC ACC CGC CTC TCC CCA CTC
1452

T   A   P   C   I   V   V   S   P   S   T   T   A   S   P   A   E   G   T   S
504
ACC GCG CCA TGT ATA GTC GTC TCC CCC TCC ACC ACG GCA AGT CCT GCA GAG GGA ACC AGC
1512

S   D   S   C   L   T   F   S   A   S   K   S   P   A   G   L   S   G   T   P
524
TCT GAC AGT TGT CTG ACC TTC TCT GCG AGC AAA AGC CCC GCG GGG CTC AGT GGC ACC CCG
1572

A   T   G   G   L   L   G   A   C   S   P   V   R   L   A   S   P   F   L   G
544
GCC ACT CAG GGG CTG CTG GGC GCC TGC TCC CCG GTC AGG CTG GCC TCG CCC TTC CTG GGG
1632

S   Q   S   A   T   P   V   L   Q   A   Q   G   G   L   G   G   A   V   L   L
564
TCG CAG TCC GCC ACC CCA GTG CTG CAG GCT CAG GGG GGC TTG GGA GGA GCT GTT CTG CTC
1692

P   V   S   F   Q   E   G   R   R   A   S   D   T   S   L   T   Q   G   L   K
584
CCT GTC AGC TTC CAG GAG GGA CGG CGG GCG TCG GAC ACC TCA CTG ACT CAA GGG CTG AAG
1752

A   F   R   Q   Q   L   R   K   T   T   R   T   K   G   F   L   G   L   N   K
604
GCC TTT CGG CAG CAG CTG AGG AAG ACC ACG CGG ACC AAA GGG TTT CTG GGA CTG AAC AAA
1812

I   K   G   L   A   R   Q   V   C   Q   V   P   A   S   R   A   S   R   G   G
624
ATC AAG GGG CTG GCT CGC CAG GTG TGC CAG GTC CCT GCC AGC CGG GCC AGC AGG GGC GGC
1872

L   S   P   F   H   A   P   A   Q   S   P   G   L   H   G   G   A   A   G   S
644
CTG AGC CCC TTC CAC GCC CCT GCA CAG AGC CCA GGC CTG CAC GGC GGC GCA GCC GGC AGC
1932
```

*FIG. 1C*

```
      R   E   G   W   S   L   L   E   E   V   L   E   Q   Q   R   L   L   Q   L   Q
664
     CGG GAC GGC TGG AGC CTG CTG GAG GAG GTG CTA GAG CAG CAG AGG CTG CTC CAG TTA CAG
1992

H   H   P   A   A   A   P   G   C   S   Q   A   P   Q   P   A   P   A   P   F
684
     CAC CAC CCG GCC GCT GCA CCC GGC TGC TCC CAG GCC CCC CAG CCG GCC CCT GCC CCG TTT
2052

V   I   A   P   C   D   G   P   G   A   A   P   L   P   S   T   L   L   T   S
704
     GTG ATC GCC CCC TGT GAT GGC CCT GGG GCT GCC CCG CTC CCC AGC ACC CTC CTC ACG TCG
2112

G   L   P   L   L   P   P   P   L   L   Q   T   G   A   S   P   V   A   S   A
724
     GGG CTC CCG CTG CTG CCG CCC CCA CTC CTG CAG ACC GGC GCG TCC CCG GTG GCC TCA GCG
2172

A   Q   L   L   D   T   H   L   H   I   G   T   G   P   T   A   L   P   A   V
744
     GCG CAG CTC CTG GAC ACA CAC CTG CAC ATT GGC ACC GGC CCC ACC GCC CTC CCC GCT GTG
2232

P   P   P   R   L   A   R   L   A   P   G   C   E   P   L   G   L   L   Q   G
764
     CCC CCA CCA CGC CTG GCC AGG CTG GCC CCA GGT TGT GAG CCC CTG GGG CTG CTG CAG GGG
2292

D   C   E   M   E   D   L   M   P   C   S   L   G   T   F   V   L   V   Q   *
784
     GAC TGT GAG ATG GAG GAC CTG ATG CCC TGC TCC CTA GGC ACG TTT GTC CTG GTG CAG TGA
2352                                                                    ←SEQ ID NO:3↑

GGGCAGCCCTGCATCCTGGCACGGACACTGACTCTTACAGCAATAACTTCAGAGGAGGTGAAGACATCTGGCCTCAAAG

CCAAGAACTTTCTAGAAGCGAAATAAGCAATACGTTAGGTGTTTTGGCTTTTTAGTTTATTTTTGTTTTATTTTTTTCT

TGCACTGAGTGACCTCAACTTTGAGTAGGGACTGGAAACTTTAGGAAGAAAGATAATTGAGGGGCGTGTCTGGGGGCGG

GGGCAGGAGGGGAGCGGGGTGGAGGGAACACGTGCAGTGCCGTGGTGTGGGGATCTCGGCCCCTCTCTCTGGGTTCGTC

GTGGTTGAGATGATTACCTCGGACGTCTACGGAAACGAGCGGGCGCATTTGTTGTCCGCTTGTGTGTGTGTGTGTGTGT

GTGTGTGTGCCCCGTGCATTGATTACTATCCATTTCTTTAGTCAAGGCTCTCCACTTCCTGATTTCTGCTTTTAAGAAA

ACT
```

FIG. 1D

```
        *->yelleklGeGsfGkVykakhk.tgkivAvKilkkesls.......lr    SEQ ID NO:13
          y + ++lG+G+f++V++a+h+ t+ +vA+Ki++k +l++++ ++  r
3714   27    YDIERTLGKGNFAVVKLARHRvTKTQVAIKIIDKTRLDssnlekiYR   73

EiqilkrlsHpNIvrllgvfedtddhlylvmEymegGdLfdylrrngpls
          E+q++k l+Hp+I++l+ v+e t+d ly+v+E++ +G++fdyl++ng+ls
3714   74 EVQLMKLLNHPHIIKLYQVME-TKDMLYIVTEFAKNGEMFDYLTSNGHLS 122 ekeakkialQilrGleYLHsngivHRDLKpeNILldengtvKiaDFGLAr
          e+ea+k ++Qil+++eY+H+++ivHRDLK+eN+Lld n+++K+aDFG+
3714  123 ENEARKKFWQILSAVEYCHDHHIVHRDLKTENLLLDGNMDIKLADFGFGN 172 ll...eklttfvGTpwYmmAPEvileg.rgysskvDvWSlGviLyElltg
          +++++e+l+t +G+p+Y  APEv  eg+++ +++ D+WSlGv+Ly l++g
3714  173 FYksgEPLSTWCGSPPYA-APEV-FEGkEYEGPQLDIWSLGVVLYVLVCG 220 gplfpgadlpaftggdevdgliifvlklPfsdelpktridpleelfrikk
                                     lPf++       +l  l + ++
3714  221 -----------------------SLPFDG-------PNLPTLRQRVL   237 r.rlplpsncSeelkdLlkkcLnkDPskRpGsatakeilnhpwf<-*
          ++r+++p   S ++ +L++++L +DP++R+   t+ +i +h w+
3714  238 EgRFRIPFFMSQDCESLIRRMLVVDPARRI---TIAQIRQHRWM       278
```

*FIG. 3*

```
TCCAACTCTACGTCTKTSKTTKYKTYKTTTKYTGTTSYGCGSTKWYASAKMYMMRMKYYYTRAAAAMCMARAAAGTTAA  SEQ ID NO:4

CYKGKWARKTTWRKYYTTTTTKKYYTTTWWTYCMRGKYCCSGRWYCSGKKGKKGKKSMAAWYMAAAGAACTGCTCCTCA

GTGGATGTTGCCTTTACTTCTAGGCCTGTACGGAAGTGTTACTTCTGCTCTAAAAGCTGCGGAATTCTAATACGACTCA

CTATAGGGAGTCGACCCACGCGTCCGCAGCGGAGGCGCGAGCTGCCCGATAATGGCGGCCTGCAGAGCCCATGAGAGGG
```
                                              M   V   S   S   Q   P   K   Y   D    SEQ ID NO:5
9
`AGAAGCGGCAGCGTCTACCCTGAGAAACCTCGACCTTGAAG ATG GTG AGT AGC CAG CCA AAG TAC GAT`
27                                             ↑SEQ ID NO:6→

L   I   R   E   V   G   R   S   Y   G   V   V   Y   E   A   V   I   R   K
29
`CTA ATA CGG GAG GTA GGC CGA GGT AGT TAC GGT GTT GTG TAT GAA GCA GTC ATC AGA AAG`
87

T   S   A   R   V   A   V   K   K   I   R   C   H   A   P   E   N   V   E   L
49
`ACC TCT GCA CGG GTG GCA GTG AAG AAA ATT CGA TGT CAC GCA CCT GAA AAT GTT CAA CTA`
147

A   L   R   E   F   W   A   L   S   S   I   K   S   Q   H   P   N   V   I   H
69
`GCC CTT CGT GAG TTC TGG GCA CTA AGC AGT ATC AAG AGC CAA CAT CCA AAT GTG ATT CAC`
207

L   E   E   C   I   L   Q   K   D   G   M   V   Q   K   M   S   H   G   S   N
89
`TTG GAG GAA TGC ATC CTA CAA AAG GAT GGG ATG GTG CAA AAG ATG TCC CAC GGC TCT AAT`
267

S   S   L   Y   L   Q   L   V   E   T   S   L   K   G   E   I   A   F   D   P
109
`TCT TCC CTT TAT TTA CAG CTT GTA GAA ACT TCA TTA AAA GGA GAA ATT GCC TTT GAT CCC`
327

R   S   A   Y   Y   L   W   F   V   M   D   F   C   D   G   G   D   M   N   E
129
`AGA AGC GCC TAT TAT TTG TGG TTT GTG ATG GAT TTT TGT GAC GGA GGA GAT ATG AAT GAG`
387

Y   L   L   S   R   K   P   N   R   K   T   N   T   S   F   M   L   Q   L   S
149
`TAT CTG TTG TCC AGG AAG CCC AAT CGT AAA ACT AAC ACC AGC TTC ATG CTT CAG CTG AGC`
447

S   A   L   A   F   L   H   K   N   Q   I   I   H   R   D   L   K   P   D   N
169
`AGT GCC CTG GCT TTC TTG CAT AAA AAC CAG ATC ATC CAC CGA GAT CTT AAG CCT GAT AAC`
507

*FIG. 4A*

```
    I   L   I   S   Q   T   R   L   D   T   S   D   L   E   P   T   L   K   V   A
189
ATC CTG ATT TCT CAA ACC AGG TTG GAT ACC AGT GAC TTG GAA CCT ACC CTC AAA GTG GCT
567

D   F   G   L   S   K   V   C   S   A   S   G   Q   N   P   E   E   P   V   S
209
GAT TTT GGT CTA AGT AAA GTT TGT TCA GCC TCT GGG CAG AAC CCA GAA GAA CCT GTC AGT
627

V   N   K   C   F   L   S   T   A   C   G   T   D   F   Y   M   A   P   E   V
229
GTA AAC AAG TGT TTC CTT TCC ACA GCA TGT GGA ACA GAT TTT TAC ATG GCT CCT GAA GTT
687

W   E   G   H   Y   T   A   K   A   D   I   F   A   L   G   I   I   I   W   A
249
TGG GAA GGA CAT TAC ACA GCA AAA GCT GAC ATC TTT GCT CTG GGG ATT ATC ATC TGG GCA
747

M   L   E   R   I   T   F   I   D   T   E   T   K   K   E   L   L   G   S   Y
269
ATG CTG GAA AGG ATC ACA TTC ATA GAC ACA GAG ACA AAG AAG GAA CTC TTG GGG AGT TAC
807

V   K   Q   G   T   E   I   V   P   V   G   E   A   L   L   E   N   P   K   M
289
GTA AAA CAA GGA ACT GAG ATT GTG CCT GTT GGG GAG GCA CTT CTG GAA AAT CCC AAA ATG
867

E   L   L   I   P   V   K   K   K   S   M   N   G   R   M   K   Q   L   I   K
309
GAA CTT CTC ATT CCT GTG AAG AAA AAA TCT ATG AAT GGG CGA ATG AAA CAA CTG ATT AAG
927

E   M   L   A   A   N   P   Q   D   R   P   D   A   F   E   L   E   L   R   L
329
GAA ATG CTG GCT GCA AAC CCT CAG GAT CGT CCA GAT GCT TTT GAA CTA GAA CTC AGA TTA
987

V   Q   I   A   F   K   D   S   S   W   E   T   *
342
GTA CAA ATT GCA TTT AAA GAT AGC AGC TGG GAA ACG TGA
1026                                    ↑SEQ ID NO:6↑
CACATATTATTTGCAAATACCATGGATGATATGCTGCTTCTGTTTAACAGTGATGCAACATTATGTGGCTGAAAAAGAA
TATAAAAAGCTAGACTCTACCCTCTAAGGGTTTAGATTTTTTGTGGGATTTTTTTTTCCTCATTTTTCTTAAATCCAA
GTTGGCCGTTTTATTAGTATGTTTCAAATGTGTATTACCAATGTGGGTGTAAATTTTTAAAAAATGATTATTGATAGAA
GTTTGGCAGGAAAATTCTTTAGGAGCTAACAGGAGAAGAGAGTCCAGTTTTCTGGAAATATGTCTTTAAGTATTTTAGA
CATTCCTCGTCAGTATTAGGAATTTCCATGGGAAAAGAAGGTTGCATGCTGGTAATGCCACCTTTGAAACTTTGTAAAG
GAAACAAAAAGGATATATTAAAGGATATGAAAGTATGGGAATGGGCCCCTTTTGCTTCCATAAAAAAAAAAACGCCCCTT
```

*FIG. 4B*

TGTTAAAAATATTTGGAGGGGGGTGGGGTTTTAGAAAATTAGGGGGAAAAACAGACAAAAAAAAAAACCCCTTCTATTT
TTTACCCCCCCC

```
          *->yelleklGeGsfGkVykakhk.tgkivAvKilk...kesls..lrEi    SEQ ID NO:14
             y l++++G+Gs+G+Vy+a+ ++t  +vAvK+++ +  e+++   lrE
16742    8   YDLIREVGRGSYGVVYEAVIRkTSARVAVKKIRchaPENVElaLREF    54 qilkrls..HpNIvrllgvfed........................
             l +++++HpN++ l +   ++++  ++ +++++++    +   +++ +++
16742   55   WALSSIKsqHPNVIHLEECILQkdgmvqkmshgsnsslylqlvetslkge 104

......tddhlylvmEymegGdLfdylrrngplsekeakkialQilrGle
                   ++++  +l++vm++++gGd+++yl +++  + k     +++lQ+ ++l+
16742  105   iafdprSAYYLWFVMDFCDGGDMNEYLLSRK-PNRKTNTSFMLQLSSALA 153

YLHsngivHRDLKpeNILlden........gtvKiaDFGLArll......
             +LH n i+HRDLKp+NIL+++ +  ++++ +  t+K+aDFGL+++ + ++++
16742  154   FLHKNQIIHRDLKPDNILISQTrldtsdlePTLKVADFGLSKVCsasgqn  203

.........eklttfvGTpwYmmAPEvilegrgysskvDvWSlGviLyEl
             ++++ + ++ +l+t +GT  Ym APEv  e  +y+ k+D+ +lG+i++ +
16742  204   peepvsvnkCFLSTACGTDFYM-APEV-WE-GHYTAKADIFALGIIIWAM 250 ltggplfpgadl.paftg.gdevdqli.if.vlklPfsdelpktridple
             l + + +++  +       g +v q  +i++v++   ++         ++e
16742  251   LERITFIDTETKkE---LlGSYVKQGTeIVpVGEALLEN------PKME  290 elfrikkrrlplpsncSeelkdLlkkcLnkDPskRpGsatakei<-*
             l  kk+          +    +k+L+k++L+ +P++Rp    a e+
16742  291   LLIPVKKK------SMNGRMKQLIKEMLAANPQDRP---DAFEL       325
```

FIG. 6

CACGCGTCCGGGCAGCAGCAGTAACAGCAGCAGCAGCCGCCGCCGCCGCCGCCAGTAAACGCGGACCGTACCCCAGGGG SEQ ID NO:7

ACTACCCAGCCGGCCGGCCCTGGAAGCCGCGCTCGGGTCCCGCCGCAGTCGGCGGTGGGGGATGGGCAGGCAGTGGCGG

TCCCGCCTGCCGAGGGTTAACCCCCGCCGGTCCCGGTCCTGAGCTGGACCAGAGCCCTCCTCCAGAAACCCCTGCGTCC

GCCACGGCCCAGGTTAAATGGAAACCACCCTTGGGAACTGGATGCCTGTGTAGCTGTTCTACCATATCAGTGTATTGCA

```
    M   S   G   G   G   E   Q   L   D   I   L   S   V   G   I   L   V   K   E   R     SEQ ID NO:8
20
   ATG AGT GGG GGA GGA GAG CAG CTG GAT ATC CTG AGT GTT GGA ATC CTA GTG AAA GAA AGA
↑SEQ ID NO:9→

W   K   V   L   R   K   I   G   G   G   G   F   G   E   I   Y   D   A   L   D
40
   TGG AAA GTG TTG AGA AAG ATT GGG GGT GGG GGC TTT GGA GAA ATT TAC GAT GCC TTG GAC
120

M   L   T   R   E   N   V   A   L   K   V   E   S   A   Q   Q   P   K   Q   V
60
   ATG CTC ACC AGG GAA AAT GTT GCA CTG AAG GTG GAA TCA GCT CAA CAA CCA AAA CAA GTT
180

L   K   M   E   V   A   V   L   K   K   L   Q   G   K   D   H   V   C   R   F
80
   CTG AAA ATG GAA GTT GCT GTT TTG AAA AAG CTG CAA GGG AAA GAC CAT GTT TGT AGA TTT
240

I   G   C   G   R   N   D   R   F   N   Y   V   V   M   Q   L   Q   G   R   N
100
   ATT GGC TGT GGG AGG AAT GAT CGA TTC AAC TAT GTG GTC ATG CAG TTG CAG GGT CGG AAT
300

L   A   D   L   R   R   S   Q   S   R   G   T   F   T   I   S   T   T   L   R
120
   CTG GCA GAT CTT CGC CGT AGC CAG TCC CGA GGC ACA TTC ACC ATT AGT ACC ACT CTC CGG
360

L   G   R   Q   I   L   E   S   I   E   S   I   H   S   V   G   F   L   H   R
140
   CTG GGT AGA CAG ATT TTG GAG TCT ATT GAA AGC ATT CAT TCT GTG GGA TTC TTG CAT CGA
420

D   I   K   P   S   N   F   A   M   G   R   F   P   S   T   C   R   K   C   Y
160
   GAC ATC AAA CCG TCG AAC TTC GCT ATG GGT CGC TTT CCT AGT ACA TGT AGG AAA TGT TAC
480

M   L   D   F   G   L   A   R   Q   F   T   N   S   C   G   D   V   R   P   P
180
   ATG CTT GAT TTT GGC TTG GCT CGA CAA TTT ACC AAT TCC TGT GGT GAC GTC AGA CCA CCT
540
```

FIG. 7A

```
  R   A   V   A   G   F   R   G   T   V   R   Y   A   S   I   N   A   H   R   N
200
CGA GCT GTG GCA GGT TTT CGA GGG ACA GTT CGT TAT GCA TCA ATC AAC GCA CAT CGG AAC
600

R   E   M   G   R   H   D   D   L   W   S   L   F   Y   M   L   V   E   F   V
220
AGG GAA ATG GGA AGA CAT GAT GAC CTT TGG TCC TTA TTC TAC ATG TTG GTG GAG TTT GTG
660

V   G   Q   L   P   W   R   K   I   K   D   K   E   Q   V   G   S   I   K   E
240
GTT GGT CAG CTG CCC TGG AGA AAA ATA AAG GAC AAG GAG CAA GTA GGC TCT ATT AAG GAG
720

R   Y   D   H   R   L   M   L   K   H   L   P   P   E   F   S   I   F   L   D
260
AGA TAT GAC CAC AGG CTC ATG TTG AAA CAT CTC CCT CCA GAA TTC AGC ATC TTT CTA GAC
780

H   I   S   S   L   D   Y   F   T   K   P   D   Y   Q   L   L   T   S   V   F
280
CAT ATC TCT TCT TTG GAT TAT TTT ACA AAA CCA GAC TAC CAG CTT CTT ACA TCC GTG TTT
840

D   N   S   I   K   T   F   G   V   I   E   S   D   P   F   D   W   E   K   T
300
GAC AAT AGC ATC AAG ACT TTT GGA GTA ATT GAG AGT GAC CCT TTT GAC TGG GAG AAG ACT
900

G   N   D   G   S   L   T   T   T   T   T   S   T   T   P   Q   L   H   T   R
320
GGA AAT GAT GGC TCC CTA ACA ACC ACC ACT ACT TCT ACC ACC CCT CAG TTG CAC ACT CGC
960

L   T   P   A   A   I   G   I   A   N   A   T   P   I   P   G   D   L   L   R
340
TTG ACC CCT GCT GCA ATT GGA ATT GCC AAT GCT ACT CCC ATC CCT GGA GAC TTG CTT CGA
1020

E   N   T   D   E   V   F   P   D   E   Q   L   S   D   G   E   N   G   I   P
360
GAA AAT ACA GAT GAG GTA TTT CCA GAT GAA CAG CTT AGC GAT GGA GAA AAT GGC ATC CCT
1080

V   G   V   S   P   D   K   L   P   G   S   L   G   H   P   R   P   Q   E   K
380
GTT GGT GTG TCA CCA GAT AAA TTG CCT GGA TCT CTG GGA CAC CCC CGT CCC CAG GAG AAG
1140

D   V   W   E   E   M   D   A   N   K   N   K   I   K   L   G   I   C   K   A
400
GAT GTT TGG GAA GAG ATG GAT GCC AAC AAA AAC AAG ATA AAG CTT GGA ATT TGT AAG GCT
1200

```
    G   S   P   I   R   V   R   S   E   I   T   Q   P   D   R   D   I   P   L   V
GCT ACT GAA GAG GAG AAC AGC CAT GGC CAG GCA AAT GGT CTT CTC AAT GCT CCA AGC CTT
1260

G                                                                            
440
GGG TCA CCA ATT CGT GTC CGC TCA GAG ATT ACT CAG CCA GAC AGA GAT ATT CCA CTG GTG
130

R   K   L   R   S   I   H   S   F   E   L   E   K   R   L   T   L   E   P   K
460
CGA AAG TTA CGT TCC ATT CAC AGC TTT GAG CTG GAA AAA CGT CTG ACC CTG GAG CCA AAG
1380

P   D   T   D   K   F   L   E   T   C   L   E   K   M   Q   K   D   T   S   A
480
CCA GAC ACT GAC AAG TTC CTT GAG ACC TGC CTG GAG AAA ATG CAG AAA GAT ACC AGT GCA
1440

G   K   E   S   I   L   P   A   L   L   H   K   P   C   V   P   A   V   S   R
500
GGA AAA GAA TCT ATT CTC CCT GCT CTG CTG CAT AAG CCT TGC GTT CCT GCT GTG TCC CGT
1500

T   D   H   I   W   H   Y   D   E   E   Y   L   P   D   A   S   K   P   A   S
520
ACT GAC CAC ATC TGG CAC TAT GAT GAA GAA TAT CTT CCA GAT GCC TCC AAG CCT GCT TCT
1560

A   N   T   P   E   Q   A   D   G   G   G   S   N   G   F   I   A   V   N   L
540
GCC AAC ACC CCT GAG CAG GCA GAT GGT GGT GGC AGC AAT GGA TTT ATA GCT GTT AAC CTG
1620

S   S   C   K   Q   E   I   D   S   K   E   W   V   I   V   D   K   E   Q   D
560
AGC TCT TGC AAG CAA GAA ATT GAT TCC AAA GAA TGG GTG ATT GTG GAC AAG GAG CAG GAC
1680

L   Q   D   F   R   T   N   E   A   V   G   H   K   T   T   G   S   P   S   D
580
CTT CAG GAT TTT AGG ACA AAT GAG GCT GTA GGA CAT AAA ACA ACT GGA AGT CCT TCT GAT
1740

E   E   P   E   V   L   Q   V   L   E   A   S   P   Q   D   E   K   L   Q   L
600
GAG GAG CCT GAA GTA CTT CAA GTC CTG GAG GCA TCA CCT CAA GAT GAA AAG CTC CAG TTA
1800

G   P   W   A   E   N   D   H   L   K   K   E   T   S   G   V   V   L   A   L
620
GGT CCT TGG GCA GAA AAT GAT CAT TTA AAG AAG GAA ACC TCA GGT GTG GTC TTA GCA CTT
1860

S   A   E   G   P   P   T   A   A   S   E   Q   Y   T   D   R   L   E   L   Q
640
TCT GCA GAG GGT CCT CCT ACT GCT GCT TCA GAA CAA TAT ACA GAT AGG CTG GAA CTC CAG
1920
```

FIG. 7C

```
      P   G   A   A   S   Q   F   I   A   A   T   P   T   S   L   M   E   A   Q   A
660
CCT GGA GCT GCT AGT CAG TTT ATT GCA GCG ACG CCC ACA AGT CTA ATG GAG GCG CAG GCA
1980

E   G   P   L   T   A   I   T   I   P   R   P   S   V   A   S   T   Q   S   T
680
GAA GGA CCC CTT ACA GCG ATT ACA ATT CCT AGA CCT TCT GTG GCA TCT ACA CAG TCA ACT
2040

S   G   S   F   H   C   G   Q   Q   P   E   K   K   D   L   Q   P   M   E   P
700
TCA GGA AGC TTT CAC TGT GGT CAG CAG CCA GAG AAG AAA GAT CTT CAG CCC ATG GAG CCC
2100

T   V   E   L   Y   S   P   R   E   N   F   S   G   L   V   V   T   E   G   E
720
ACT GTG GAA CTT TAC TCT CCA AGG GAA AAC TTC TCT GGC TTG GTT GTG ACA GAG GGT GAA
2160

P   P   S   G   G   S   R   T   D   L   G   L   Q   I   D   H   I   G   H   D
740
CCT CCT AGT GGA GGA AGC AGA ACA GAT TTG GGG CTT CAG ATA GAT CAC ATT GGT CAT GAC
2220

M   L   P   N   I   R   E   S   N   K   S   Q   D   L   G   P   K   E   L   P
760
ATG TTA CCC AAC ATT AGA GAA AGT AAC AAA TCT CAA GAC CTG GGA CCA AAA GAA CTT CCT
2280

D   H   N   R   L   V   V   R   E   F   E   N   L   P   G   E   T   E   E   K
780
GAT CAT AAT AGA CTG GTT GTG AGA GAA TTT GAA AAT CTC CCT GGG GAA ACT GAA GAG AAA
2340

S   I   L   L   E   S   D   N   E   D   E   K   L   S   R   G   Q   H   C   I
800
AGC ATC CTT TTA GAG TCA GAT AAT GAA GAT GAG AAG TTA ACT AGA GGG CAG CAT TGT ATT
2400

E   I   S   S   L   P   G   D   L   V   I   V   E   K   D   H   S   A   T   T
820
GAG ATC TCC TCT CTC CCA GGA GAT TTG GTA ATT GTG GAA AAG GAT CAC TCA GCT ACT ACT
2460

E   P   L   D   V   T   K   T   Q   T   F   S   V   V   P   N   Q   D   K   N
840
GAA CCT CTT GAT GTG ACA AAA ACA CAG ACT TTT AGT GTG GTG CCA AAT CAA GAC AAA AAT
2520

N   E   I   M   K   L   L   T   V   G   T   S   E   I   S   S   R   D   I   D
860
AAT GAG ATA ATG AAG CTT CTG ACA GTT GGA ACT TCA GAA ATT TCT TCC AGA GAC ATT GAC
2580
```

FIG. 7D

```
  P   H   V   E   G   Q   I   G   Q   V   A   E   M   Q   K   N   K   I   S   K
880
CCA CAT GTT GAA GGT CAG ATA GGC CAA GTG GCA GAA ATG CAA AAA AAT AAG ATA TCT AAG
2640

D   D   D   I   M   S   E   D   L   P   G   H   Q   G   D   L   S   T   F   L
900
GAT GAT GAC ATC ATG AGT GAA GAC TTG CCA GGT CAT CAA GGA GAC CTC TCT ACT TTT TTG
2700

H   Q   E   G   K   R   E   K   I   T   P   R   N   G   E   L   F   H   C   V
920
CAC CAA GAG GGC AAG AGA GAG AAA ATC ACC CCT AGA AAT GGA GAA CTA TTT CAT TGT GTT
2760

S   E   N   E   H   G   A   P   T   R   K   D   M   V   R   S   S   F   V   T
940
TCA GAG AAT GAA CAT GGT GCC CCA ACC CGG AAG GAT ATG GTT AGG TCA TCC TTT GTA ACT
2820

R   H   S   R   I   P   V   L   A   Q   E   I   D   S   T   L   E   S   S   S
960
AGA CAC AGC CGA ATC CCT GTT TTA GCA CAA GAG ATA GAC TCA ACT TTG GAA TCA TCC TCT
2880

P   V   S   A   K   E   K   L   L   Q   K   K   A   Y   Q   P   D   L   V   K
980
CCA GTT TCT GCA AAA GAA AAG CTC CTC CAA AAG AAA GCC TAT CAG CCA GAC CTA GTC AAG
2940

L   L   V   E   K   R   Q   F   K   S   F   L   G   D   L   S   S   A   S   D
1000
CTT CTG GTG GAA AAA AGA CAA TTC AAG TCC TTC CTT GGC GAC CTC TCA AGT GCC TCT GAT
3000

K   L   L   E   E   K   L   A   T   V   P   A   P   F   C   E   E   E   V   L
1020
AAA TTG CTA GAG GAG AAA CTA GCT ACT GTT CCT GCT CCC TTT TGT GAG GAG GAA GTG CTC
3060

T   P   F   S   R   L   T   V   D   S   H   L   S   R   S   A   E   D   S   F
1040
ACT CCC TTT TCA AGA CTG ACA GTA GAT TCT CAC CTG AGT AGG TCA GCT GAA GAT AGC TTT
3120

L   S   P   I   I   S   Q   S   R   K   S   K   I   P   R   P   V   S   W   V
1060
CTG TCA CCC ATC ATC TCC CAG TCT AGA AAG AGC AAA ATT CCA AGG CCA GTT TCA TGG GTC
3180

N   T   D   Q   V   N   S   S   T   S   S   Q   F   F   P   R   P   P   P   G
1080
AAC ACA GAT CAG GTC AAT AGC TCA ACT TCG TCT CAG TTC TTT CCT CGG CCA CCA CCA GGA
3240

```
                S   N   S   D   S   D   L   F   S   R   L   A   Q   I   L   Q   N   G   S   Q
              1120
AAG CCA CCC ACG AGG CCT GGA GTA GAA GCC AGG CTA CGC AGA TAT AAA GTC CTA GGG AGT
3300
                S   N   S   D   S   D   L   F   S   R   L   A   Q   I   L   Q   N   G   S   Q
              1120
AGT AAC TCC GAC TCA GAC CTT TTC TCC CGC CTG GCC CAA ATT CTT CAA AAT GGA TCT CAG
3360

K   P   R   S   T   T   Q   C   K   S   P   G   S   P   H   N   P   K   T   P
              1140
AAA CCC CGG AGC ACT ACT CAG TGC AAG AGT CCA GGA TCT CCT CAC AAT CCA AAA ACA CCA
3420

P   K   S   P   V   V   P   R   R   S   P   S   A   S   P   R   S   S   S   L
              1160
CCC AAG AGT CCA GTT GTC CCT CGC AGG AGT CCC AGT GCC TCT CCT CGA AGC TCA TCC TTG
3480

P   R   T   S   S   S   P   S   R   A   G   R   P   H   H   D   Q   R   S
              1180
CCT CGC ACG TCT AGT TCC TCA CCA TCT AGG GCT GGA CGG CCC CAC CAT GAC CAG AGG AGT
3540

S   S   P   H   L   G   R   S   K   S   P   P   S   H   S   G   S   S   S   S
              1200
TCG TCC CCA CAT CTG GGG AGA AGC AAG TCA CCT CCC AGC CAC TCA GGA TCT TCC TCC TCC
3600

R   R   S   C   Q   Q   E   H   C   K   P   S   K   N   G   L   K   G   S   G
              1220
AGG AGG TCC TGC CAA CAG GAG CAT TGC AAA CCC AGC AAG AAT GGC CTG AAA GGA TCC GGC
3660

S   L   H   H   H   S   A   S   T   K   T   P   Q   G   K   S   K   P   A   S
              1240
AGC CTC CAC CAC CAC TCA GCC AGC ACT AAA ACC CCC CAA GGG AAG AGT AAG CCA GCC AGT
3720

K   L   S   R   *
              1245
AAA CTC AGC AGA TAG
3735   ←SEQ ID NO:9↑
```

GAGCCAGGCTGCATCTCTTTGAAAGGTGTGAGATCTTCCTCCTAAACCTGATGCATGTGTGTCCCTGTACTTTCTATGT

AAAAAAATCAGTGTTGATCTTCTCTTGCAAAAGAAAGTAACATGATCAATTATTTATAAGAAGACATAATACATGATAA

GGAATTACCTAAGGCAGGCAGCAAGTAGATTAGGAATCAATGTCTTTGTACAAGAAGGAAAAATAGAGCAAAAATCCAA

GGGGGAGAAACTCATTAAAATGAGCTCTCATTTTTTAAGCTGCCTTTGAAACAAAAGAGTTGAGGATAGGAGATAGAAT

GGAATTTTAGGGGGGTTGCCTAATTTTTTTAAGCCTCAATTCAAAGATTATATAGCAAAAGTGAAACTTCTTGTTTGAT

ATTTTCATTCAAAACTTTCCCACCCTGAAGAGTCATTGATCAGATATTAGATTATATAAGAAGTCTGTTGCCAGGGAGC

CAGTATTCATGTATATTTGGCTTGTGTGTTTATTTCCTGTATTGAGAATGAACACCTTTACTTTGCCTCATTCCTAGTA

FIG. 7F

```
CCCTCCCTGGAGTTCAGATTTTTTTTTAAAATTTTGTATGTCTCGTCTGATTCAATCTCTCTGCTTTTATTTTATGGTC
CTAGTTGTACTATCAAATCCAATTACTTTTTTTTAGGTCCCCCTGATTTTTTTTTTTTAGAGCAAGAGTTCTTAACAT
ATTACATTTTTATTATGAAAAATAAGAAAGTTAGGTAAAGGAAAGAAAAGTCTAACTAGAGCTATTTTGCAGGCTTTAG
TGTTTAGGGAGAGAAAGAAAGTGTGGGTTAATAGCCTTCAAGATAGAAGATGCCCTTTCATCTCTGTTAAGTGTCCTCC
TTTAGAAACTTGAGTAGAAGGAAAACTGACCAGAGTAGACTGCTTCCTTAAGTCTTCTGGGTTCCAACTGTTTGTAATA
TCAGCATCCAAGATGATACGAGGGAAGCACAATGCTTTGGACTGTGATTTGAGATTTAGAAATAAATTAGATATATTAT
TGAGGCTTAGAATCCTCAAACTTTGTATTTTATACATTTAGCCAATAAGGAATTAATATCTGGGGAAATAAATTTAGGC
AAATAAAAAAAAAAAAAAAAAAAAAAACCTGCTTCTCCTGTGTTTTAGTTCAACATTTGGGCTTCTTGGCCTGATTTTC
ATACAATCTCAATTTACGAAGCTGTAAAGAGGAAGATATTTGTTCTAATCTCACTCTTCTAATAGGAATCAGGCAAATG
AAAGTCTACCAGACTTTTAAAATGGGCTGTTTTTATACTCTCTAGGTGTTTTGTGTTGTAAAGACCTTATTAAGGTCAG
GTAAATTGGTCTGCTTGCTGTTGAAATTTGCCTTCTAGCAAACATATGTGCTTTCTGTTTGACCTTGTGTTTGCTGCCA
AACCTAATACAGTTGAATTGGGAAAC
```

```
        *->yelleklGeGsfGkVykakhk.tgkivAvKilkkesls...lrEiqi    SEQ ID NO:15
           +++l+k+G G+fG++y a ++ t + vA+K+ ++++ ++   +E+++
23546  21     WKVLRKIGGGGFGEIYDALDMlTRENVALKVESAQQPKqvlKMEVAV  67 lkrls.HpNIvrllgvfedtddhlylvmEymegGdLfdylrrng..plse
           lk+l++ ++++r++g  +  d+   y+vm++ +   L+d+ r++ ++ ++
23546  68  LKKLQgKDHVCRFIGCGR-NDRFNYVVMQLQGR-NLADLRRSQSrgTFTI 115 keakkialQilrGleYLHsngivHRDLKpeNILlden....gtvKiaDFG
           +++  +Qil+  +e +Hs g++HRD+Kp+N+   +  +++  ++   DFG
23546 116  STTLRLGRQILESIESIHSVGFLHRDIKPSNFAMGRFpstcRKCYMLDFG 165

LArll..........eklttfvGTpwYmmAPEvilegrgysskvDvWSlG
           LAr+++++ ++ +++     +f GT +Y +      ++r+ ++  D WSl
23546 166  LARQFtnscgdvrppRAVAGFRGTVRYA-SINA-HRNREMGRHDDLWSLF 213 viLyElltggplfpgadlpaftggdevdqliifvlklPfsdelpktridp
           ++L E +  g                             +lP++    i+
23546 214  YMLVEFVVG------------------------QLPWRK------IKD 231 leelfrikkr......rlplpsncS<-*
           e++ +ik+r +++  +  lp+++S
23546 232  KEQVGSIKERydhrlmLKHLPPEFS    256
```

FIG. 9

```
GTCTAATCTCTTCTAGGCCCCGCCCCTTCTGAGCCCCCCCTCCTTCGGCCTGTATGATAGGCTCTTCCTCCATTTCCGG   SEQ ID NO:10
CTTCTGGGACTCGGGTGCACCACGGCTTCCGGTGTCATGGCTGCTTGAAGTCCCGGGAGTCGGTGAGGCGGCTGCAGGT
CCCTCCCTGCGGAGCCGCTGGTCCGGCTGGCGGAGATGTGACCGCGGGCCCGGCCGGCCTGCCTCAGGCGTCGCGTCAG
                                   M   A   G   S   G   C   A   W   G   A   E   P   SEQ ID NO:11
 12
CTCCCGTGTCCGTGCCCTTAACCCACACCG  ATG GCG GGA TCC GGC TGC GCC TGG GGC GCG GAG CCG
 36                              ↑SEQ ID NO:12→

P   R   F   L   E   A   F   G   R   L   W   Q   V   Q   S   R   L   G   S   G
 32
CCG CGT TTT CTG GAG GCC TTC GGG CGG CTG TGG CAG GTA CAG AGC CGT CTG GGT AGC GGC
 96

S   S   A   S   V   Y   R   V   R   C   C   G   N   P   G   S   P   P   G   A
 52
TCC TCC GCC TCG GTG TAT CGG GTT CGC TGC TGC GGC AAC CCT GGC TCG CCC CCC GGC GCC
156

L   K   Q   F   L   P   P   G   T   T   G   A   A   A   S   A   A   E   Y   G
 72
CTC AAG CAG TTC TTG CCG CCA GGA ACC ACC GGG GCT GCG GCC TCT GCC GCC GAG TAT GGT
216

F   R   K   E   R   A   A   L   E   Q   L   Q   G   H   R   N   I   V   T   L
 92
TTC CGC AAA GAG AGG GCG GCG CTG GAA CAG TTG CAG GGT CAC AGA AAC ATC GTG ACT TTG
276

Y   G   V   F   T   I   H   F   S   P   N   V   P   S   R   C   L   L   L   E
112
TAT GGA GTG TTT ACA ATC CAC TTT TCT CCA AAT GTG CCA TCA CGC TGT CTG TTG CTT GAA
336

L   L   D   V   S   V   S   E   L   L   L   Y   S   S   H   Q   G   C   S   M
132
CTC CTG GAT GTC AGT GTT TCG GAA TTG CTC TTA TAT TCC AGT CAC CAG GGT TGT TCC ATG
396

W   M   I   Q   H   C   A   R   D   V   L   E   A   L   A   F   L   H   H   E
152
TGG ATG ATA CAG CAT TGT GCC CGA GAT GTT TTG GAG GCC CTT GCT TTT CTT CAT CAT GAG
456

G   Y   V   H   A   D   L   K   P   R   N   I   L   W   S   A   E   N   E   C
172
GGC TAT GTC CAT GCG GAC CTC AAA CCA CGT AAC ATA TTG TGG AGT GCA GAG AAT GAA TGT
516

```
           TTT AAA CTC ATT GAC TTT GGA CTT AGC TTC AAA GAA GGC AAT CAG GAT GTA AAG TAT ATT
           576

Q    T   D   G   Y   R   A   P   E   A   E   L   Q   N   C   L   A   Q   A   G
       212
       CAG  ACA GAC GGG TAT CGG GCT CCA GAA GCA GAA TTG CAA AAT TGC TTG GCC CAG GCT GGC
       636

L    Q   S   D   T   E   C   T   S   A   V   D   L   W   S   L   G   I   I   L
       232
       CTG  CAG AGT GAT ACA GAA TGT ACC TCA GCT GTT GAT CTG TGG AGC CTA GGA ATC ATT TTA
       696

L    E   M   F   S   G   M   K   L   K   H   T   V   R   S   Q   E   W   K   A
       252
       CTG  GAA ATG TTC TCA GGA ATG AAA CTG AAA CAT ACA GTC AGA TCT CAG GAA TGG AAG GCA
       756

N    S   S   A   I   I   D   H   I   F   A   S   K   A   V   V   N   A   A   I
       272
       AAC  AGT TCT GCT ATT ATT GAT CAC ATA TTT GCC AGT AAA GCA GTG GTG AAT GCC GCA ATT
       816

P    A   Y   H   L   R   D   L   I   K   S   M   L   H   D   D   P   S   R   R
       292
       CCA  GCC TAT CAC CTA AGA GAC CTT ATC AAA AGC ATG CTT CAT GAT GAT CCA AGC AGA AGA
       876

I    P   A   E   M   A   L   C   S   P   F   F   S   I   P   F   A   P   H   I
       312
       ATT  CCT GCT GAA ATG GCA TTG TGC AGC CCA TTC TTT AGC ATT CCT TTT GCC CCT CAT ATT
       936

E    D   L   V   M   L   P   T   P   V   L   R   L   L   N   V   L   D   D   D
       332
       GAA  GAT CTG GTC ATG CTT CCC ACT CCA GTG CTA AGA CTG CTG AAT GTG CTG GAT GAT GAT
       996

Y    L   E   N   E   E   E   Y   E   D   V   V   E   D   V   K   E   E   C   Q
       352
       TAT  CTT GAG AAT GAA GAG GAA TAT GAA GAT GTT GTA GAA GAT GTA AAA GAG GAG TGT CAA
       1056

K    Y   G   P   V   V   S   L   L   V   P   K   E   N   P   G   R   G   Q   V
       372
       AAA  TAT GGA CCA GTG GTA TCT CTA CTT GTT CCA AAG GAA AAT CCT GGC AGA GGA CAA GTC
       1116

F    V   E   Y   A   N   A   G   D   S   K   A   A   Q   K   L   L   T   G   R
       392
       TTT  GTT GAG TAT GCA AAT GCT GGT GAT TCC AAA GCT GCG CAG AAA TTA CTG ACT GGA AGG
       1176

M    F   D   G   K   F   V   V   A   T   F   Y   P   L   S   A   Y   K   R   G
       412
       ATG  TTT GAT GGG AAG TTT GTT GTG GCT ACA TTC TAC CCG CTG AGT GCC TAC AAG AGG GGA
       1236
```

FIG. 10B

```
 Y   L   Y   Q   T   L   L   *
420
TAT CTG TAT CAA ACC TTG CTT TAA
1260            ←SEQ ID NO:12→
```

TCAGTAACCTAAGGACTGTTTCCTTTTTCTCCTCTTCCATTTCTTGGGTTATTCCACATATGAATGCAGGACTACCCCC

TTACCATTTTAAGAAGGTACTTTATACATTTATTTAATCCTACTAATGTGCAGCCATTGCCCAAGCAGTGACTGCGTTG

CATACATTTGGCACTGAGTAGGACAAGACCTCTCAGCTATACATTGAGGGGTTTTAGAGCATCCATGTGGGCAACCCTT

TTTTGTGCGGGAGAGCAGGTGTTGCTCTTCAGTATGTAGCCTAAAAAAATCTTAATTATTTCATGGATCATGAAGCAAG

GATGAATAATATCATGTCTTGGTAAATACTAACAAATTTGTTAGGTTTGGTGACATCATTTACAGATTATTTCTTTATG

TTGTCCAGTGGTTCTTCCTTATTGTTGATATCCATAAGCTGGCACTGGATGCTCTCAGTAATGTTAAGTAATTGTCAAG

CAGCAGTTACCTACTGTGTTCTTAACACTGAGTTGTGAATTTTTTCTTAAAGCAGTACTGTAGTACTGAATATTCCTTT

AAAGGAACTGCAGTGAGCCTATCTAAGTTTTTTTAAATTAAGGCTTTTAAAATAGAAAGCTGATGCTTGATCTTGCACA

ATTTTTATGTCTAGTATGTATGCTTGAGTGAATGTGCGAGTATGAATGATTAGAGAAAATTTGAGTCAGTGTACTTTAT

AGTGTGAATCCTGTGAGCTAATACAGTCTATACTTATTTCTTCCCTACCTGTTTCACATCCGTAAGATTTAAGATATAC

ATTTTTTGAGAGGTAGTCTGTCTGATACAATGTAAATGACAAAACATAATTCCTGAGAGGCCCAGAACAAACTGGAGTC

TAGCCTGGAGTTAAATTGAGACTTCTAAAATGATTGGAACAAAGACTAAGTTGTGCCAGATGTAAATCAACCCCTCTTT

TAGTTTACTTTAGACTTTGTATTAGCTCATCTTTTTTGTAGTAAATCTATAGTTTTAAGGTTTCTCAAGATGTGGCTCT

ACCTACTATGATGAAAATTGAAGTGGGTCAAAAGAATTAGATGTACCTGCCCGGGCGGCCGCTCGAAAA

FIG. 10C

```
            *->yelleklGeGsfGkVykakhk...tgkivAvKilk.....kesls..        SEQ ID NO:16
            +++ +lG+Gs+++Vy+++  +++   + A+K++ +++++    s
  13887  23 WQVQSRLGSGSSASVYRVRCCgnpGSPPGALKQFLppgttGAAASaa 69

....lrEigilkrls.HpNIvrllgvfed....tddhlylvmEymegGdL
            + + + E + 1 +l++H NIv+l+gvf+ + ++  ++ +l +E+++   +
  13887  70 eygfRKERAALEQLQgHRNIVTLYGVFTIhfspNVPSRCLLLELLDV-SV 118 fdylrrng..plsekeakkialQilrGleYLHsngivHRDLKpeNILlde
            ++l + ++  s++ ++++a+++l++l++LH +g vH DLKp+NIL +
  13887 119 SELLLYSShqGCSMWMIQHCARDVLEALAFLHHEGYVHADLKPRNILWSA 168 n.gtvKiaDFGLArll....eklttfvGTpwYmmAPEvi.........le
            ++   K++DFGL+ +  +++++k+ +   T +Y+ APE   ++  + +l+
  13887 169 EnECFKLIDFGLSFKEgnqdVKYIQ---TDGYR-APEAElqnclaqagLQ 214 g.rgysskvDvWSlGviLyElltggplfpgadlpaftg.gdevdqliifv
            ++++ +s+vD WSlG+iL E+++g              + +++       v
  13887 215 SdTECTSAVDLWSLGIILLEMFSG-----------MKLkHT--------V 245 lklPfsdelpktridpleelfrikkr.rlplpsncSee.lkdLlkkcLnk
            ++++           + +++ +++ ++ ++  ++  +l+dL+k++L+
  13887 246 RSQEWK--------ANSSAIIDHIFAsKAVVNAAIPAYhLRDLIKSMLHD 287

DPskRpGsatakeilnhpwf<-*
            DPs+R+   a+ +l++p+f
  13887 288 DPSRRI---PAEMALCSPFF   304
```

*FIG. 12*

| PASS STELL | LIVER PILL | CONTROL LIVER 330 | LF/NDR 184 | LF/NDR 679 | LN | TENSIL | TH1 24 HR. MP39 | TH2 24 HR. MP39 | CD4+ REST | CD8 | CD14 | CD18 |
|---|---|---|---|---|---|---|---|---|---|---|---|---|
| 28.14 | 29.41 | 20.50 | 36.16 | 32.20 | 26.23 | 24.58 | 24.57 | 26.16 | 26.98 | 24.71 | 25.57 | 23.89 |
| 10.04 | 18.74 | 18.03 | 28.33 | 22.00 | 17.83 | 16.01 | 18.46 | 16.88 | 17.12 | 17.96 | 15.82 | 16.58 |
| 128.06 | 20.58 | 25.03 | 102.24 | 34.43 | 144.14 | 105.84 | 84.20 | 74.04 | 53.11 | 202.36 | 27.11 | 160.00 |

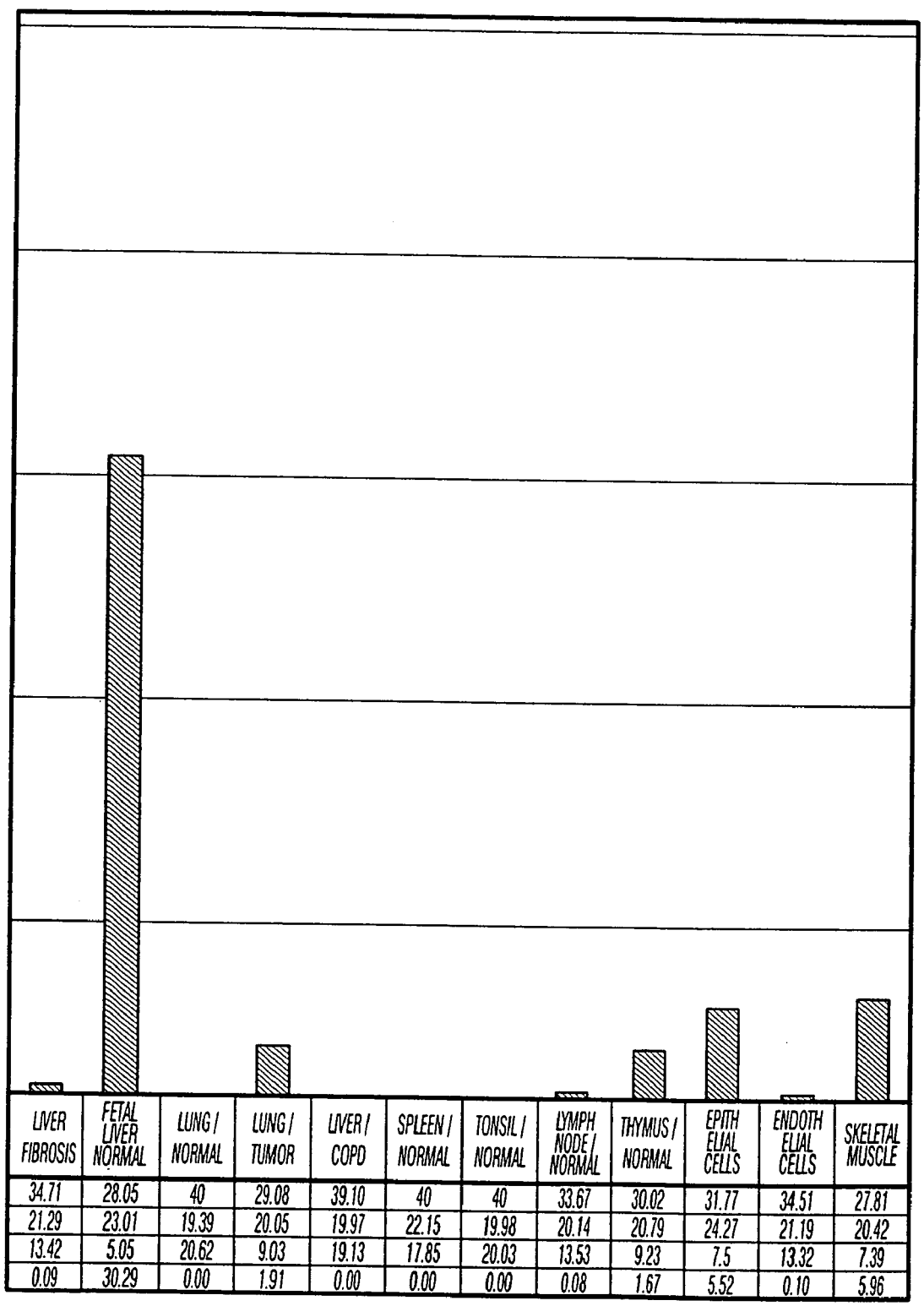
FIG. 29-C

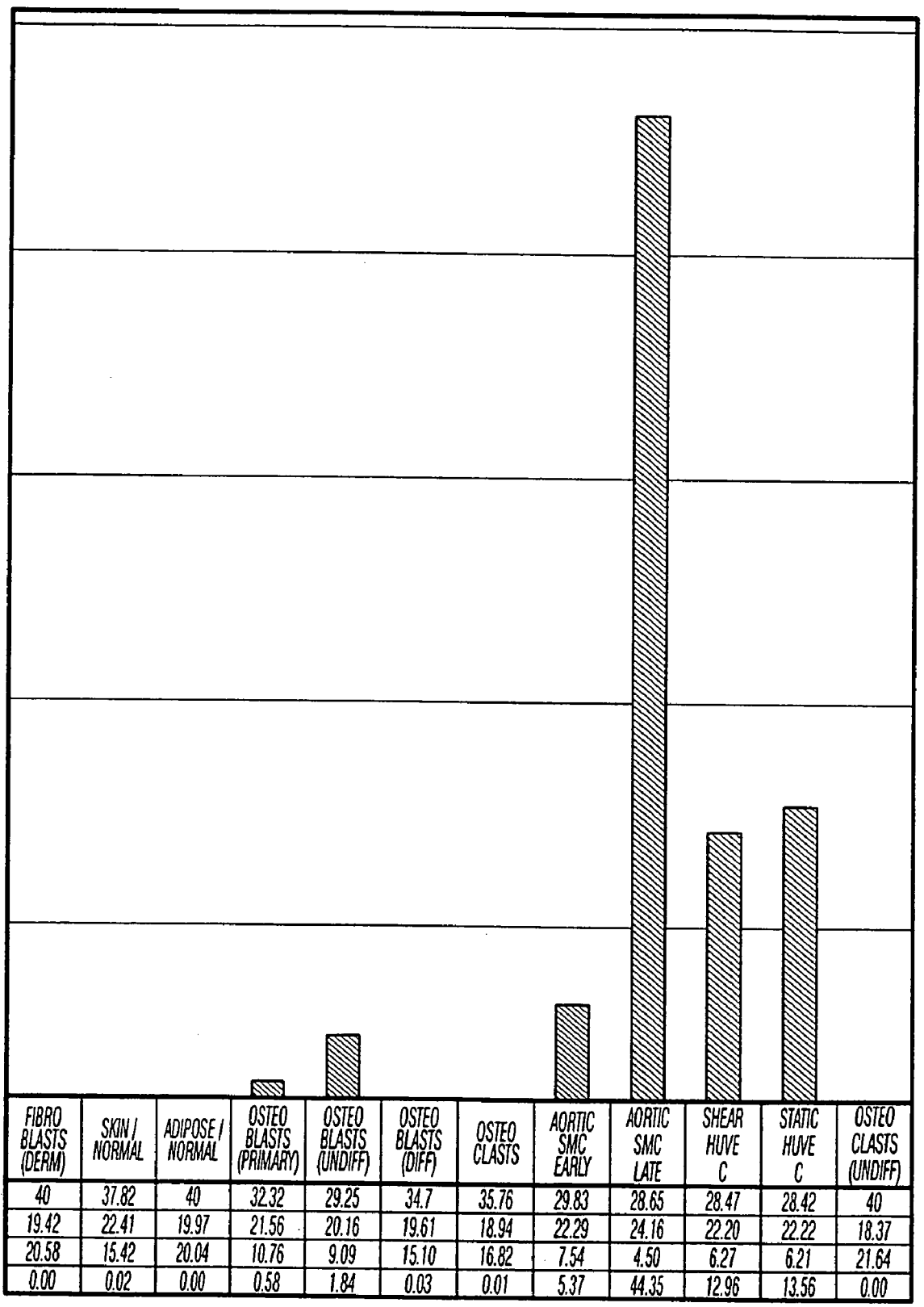
FIG. 29-D

3714, 16742, 23546, AND 13887 NOVEL PROTEIN KINASE MOLECULES AND USES THEREFOR

This application is a continuation of U.S. patent application Ser. No. 09/815,915 filed on Mar. 23, 2001 (now abandoned), which claims the benefit of U.S. Provisional Application Ser. No. 60/191,846 filed on Mar. 24, 2000. The entire contents of each of the above referenced patent applications are incorporated by this reference.

BACKGROUND OF THE INVENTION

Phosphate tightly associated with protein has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated proteins implies the existence of one or more protein kinases capable of phosphorylating amino acid residues on proteins, and also of protein phosphatases capable of hydrolyzing phosphorylated amino acid residues on proteins.

Kinases play a critical role in the mechanism of intracellular signal transduction. They act on the hydroxyamino acids of target proteins to catalyze the transfer of a high energy phosphate group from adenosine triphosphate (ATP). This process is known as protein phosphorylation. Along with phosphatases, which remove phosphates from phosphorylated proteins, kinases participate in reversible protein phosphorylation. Reversible phosphorylation acts as the main strategy for regulating protein activity in eukaryotic cells.

Protein kinases play critical roles in the regulation of biochemical and morphological changes associated with cell proliferation, differentiation, growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721).

Kinases vary widely in their selectivity and specificity of target proteins. They still may, however, comprise the largest known enzyme superfamily. Protein kinases can be divided into two main groups based on either amino acid sequence similarity or specificity for either serine/threonine or tyrosine residues. Serine/threonine specific kinases are often referred to as STKs while tyrosine specific kinases are referred to as PTKs. A small number of dual-specificity kinases are structurally like the serine/threonine-specific group. Within the broad classification, kinases can be further sub-divided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) *Science* 241: 42–52).

Almost all kinases contain a catalytic domain composed of 250–300 conserved amino acids. This catalytic domain may be viewed as composed of 11 subdomains. Some of these subdomains apparently contain distinct amino acid motifs which confer specificity as a STK or PTK or both. Kinases may also contain additional amino acid sequences, usually between 5 and 100 residues, flanking or occurring within the catalytic domain. These residues apparently act to regulate kinase activity and to determine substrate specificity. (Reviewed in Hardie, G. and Hanks, S. (1995) The Protein Kinase Facts Book, Vol.1:7–20 Academic Press, San Diego, Calif.)

Approximately one third of the known oncogenes encode PTKs. PTKs may occur as either transmembrane or soluble proteins. Transmembrane PTKs act as receptors for many growth factors. Interaction of a growth factor to its cognate receptor initiates the phosphorylation of specific tyrosine residues in the receptor itself as well as in certain second messenger proteins. Growth factors found to associate with such PTK receptors include epidermal growth factor, platelet-derived growth factor, fibroblast growth factor, hepatocyte growth factor, insulin and insulin-like growth factors, nerve growth factor, vascular endothelial growth factor, and macrophage colony stimulating factor.

Soluble PTKs often interact with the cytosolic domains of plasma membrane receptors. Receptors that signal through such PTKs include cytokine, hormone, and antigen-specific lymphocytic receptors. Many PTKs were identified as oncogene products by the observation that PTK activation was no longer subject to normal cellular controls. Also, increased tyrosine phosphorylation activity is often observed in cellular transformation, or oncogenesis, (Carbonneau, H. and Tonks, N. K. (1992) *Annu. Rev. Cell Biol.* 8:463–93.) PTK regulation may therefore be an important strategy in controlling some types of cancer.

SUMMARY OF THE INVENTION

The present invention is based, at least in part, on the discovery of novel nucleic acid molecules and proteins encoded by such nucleic acid molecules, referred to herein as "kinases" or by the individual clone names "3714, 16742, 23546, or 13887". The 3714, 16742, 23546, or 13887 nucleic acid and protein molecules of the present invention are useful as modulating agents in regulating a variety of cellular processes, e.g., including cell proliferation, differentiation, growth and division. In particular, the kinase and its related nucleic acids will be advantageous in the regulation of any cellular function uncontrolled proliferation and differentiation, such as in cases of cancer. Other situations where the kinases of the invention are of particular advantage are in cases of autoimmune disorders or undesired inflammation. Accordingly, in one aspect, this invention provides isolated nucleic acid molecules encoding 3714, 16742, 23546, or 13887 proteins or biologically active portions thereof, as well as nucleic acid fragments suitable as primers or hybridization probes for the detection of 3714-, 16742-, 23546-, or 13887-encoding nucleic acids.

In one embodiment, a 3714 nucleic acid molecule of the invention is at least 50%, 55%, 60%, 65%, 70%, 75%, 80%, 85%, 90%, 95%, 98% or more homologous to a nucleotide sequence (e.g., to the entire length of the nucleotide sequence) including SEQ ID NO:1, SEQ ID NO:3, or a complement thereof. In another embodiment, a 16742 nucleic acid molecule is 50%, 55%, 60%, 65%, 70%, 75%, 80%, 85%, 86%, 90%, 95%, 98% homologous to a nucleotide sequence including SEQ ID NO:4, SEQ ID NO: 6, or a complement thereof. In yet another embodiment, a 23546 nucleic acid molecule is 50%, 55%, 60%, 65%, 70%, 75%, 80%, 85%, 90%, 95%, 97%, 98% homologous to a nucleotide sequence including SEQ ID NO:7, SEQ ID NO:9, or a complement thereof. In yet another embodiment, a 13887 nucleic acid molecule is 50%, 55%, 60%, 65%, 70%, 75%, 80%, 85%, 86%, 90%, 95%, 98% homologous to a nucleotide sequence including SEQ ID NO:10, SEQ ID NO:12, or a complement thereof.

In another embodiment, a 3714, 16742, 23546, or 13887 nucleic acid molecule includes a nucleotide sequence encoding a protein having an amino acid sequence sufficiently homologous to the amino acid sequence of SEQ ID NO:2, SEQ ID NO:5, SEQ ID NO:8, or SEQ ID NO:11. In a preferred embodiment, a 3714 nucleic acid molecule includes a nucleotide sequence encoding a protein having an amino acid sequence at least 50%, 55%, 60%, 65%, 70%, 75%, 80%, 85%, 90%, 95%, 98% or more homologous to an amino acid sequence including SEQ ID NO:2 (e.g., the entire amino acid sequence of SEQ ID NO:2). In a further preferred embodiment, a 16742 nucleic acid molecule includes a nucleotide sequence encoding a protein having an amino acid sequence at least 50%, 55%, 60%, 65%, 70%, 75%, 80%, 85%, 90%, 95%, 98% or more homologous to an amino acid sequence including SEQ ID NO:5 (e.g., the entire amino acid sequence of SEQ ID NO:5). In another preferred embodiment, a 23546 nucleic acid molecule includes a nucleotide sequence encoding a protein having an amino acid sequence at least 50%, 55%, 60%, 65%, 70%, 75%, 80%, 85%, 90%, 95%, 98% or more homologous to an amino acid sequence including SEQ ID NO:8 (e.g., the entire amino acid sequence of SEQ ID NO:8). In another preferred embodiment, a 13887 nucleic acid molecule includes a nucleotide sequence encoding a protein having an amino acid sequence at least 50%, 55%, 60%, 65%, 70%, 75%, 80%, 85%, 90%, 95%, 98% or more homologous to an amino acid sequence including SEQ ID NO:11 (e.g., the entire amino acid sequence of SEQ ID NO:11).

In another preferred embodiment, an isolated nucleic acid molecule encodes the amino acid sequence of a human 3714, 16742, 23546, or 13887. In yet another preferred embodiment, the nucleic acid molecule includes a nucleotide sequence encoding a protein which includes the amino acid sequence of SEQ ID NO:2, SEQ ID NO:5, SEQ ID NO:8, or SEQ ID NO:11. In yet another preferred embodiment, the nucleic acid molecule includes a nucleotide sequence encoding a protein having the amino acid sequence of SEQ ID NO:2, SEQ ID NO:5, SEQ ID NO:8, or SEQ ID NO:11.

Another embodiment of the invention features nucleic acid molecules, preferably 3714, 16742, 23546, or 13887 nucleic acid molecules, which specifically detect 3714, 16742, 23546, or 13887 nucleic acid molecules relative to nucleic acid molecules encoding non-3714, -16742, -23546, or -13887 proteins. For example, in one embodiment, such a nucleic acid molecule is at least 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO:1, SEQ ID NO:4, SEQ ID NO:7, SEQ ID NO:10, or a complement thereof.

In other preferred embodiments, the nucleic acid molecule encodes a naturally occurring allelic variant of a polypeptide which includes the amino acid sequence of SEQ ID NO:2, wherein the nucleic acid molecule hybridizes to a nucleic acid molecule which includes SEQ ID NO:1 or SEQ ID NO:3 under stringent conditions. In other preferred embodiments, the nucleic acid molecule encodes a naturally occurring allelic variant of a polypeptide which includes the amino acid sequence of SEQ ID NO:5, wherein the nucleic acid molecule hybridizes to a nucleic acid molecule which includes SEQ ID NO:4 or SEQ ID NO:6 under stringent conditions. In other preferred embodiments, the nucleic acid molecule encodes a naturally occurring allelic variant of a polypeptide which includes the amino acid sequence of SEQ ID NO:8, wherein the nucleic acid molecule hybridizes to a nucleic acid molecule which includes SEQ ID NO:7 or SEQ ID NO:9 under stringent conditions. In other preferred embodiments, the nucleic acid molecule encodes a naturally occurring allelic variant of a polypeptide which includes the amino acid sequence of SEQ ID NO:11, wherein the nucleic acid molecule hybridizes to a nucleic acid molecule which includes SEQ ID NO:10 or SEQ ID NO:12 under stringent conditions.

Another embodiment of the invention provides an isolated nucleic acid molecule which is antisense to a 3714, 16742, 23546, or 13887 nucleic acid molecule, e.g., the coding strand of a 3714, 16742, 23546, or 13887 nucleic acid molecule.

Another aspect of the invention provides a vector comprising a 3714, 16742, 23546, or 13887 nucleic acid molecule. In certain embodiments, the vector is a recombinant expression vector. In another embodiment, the invention provides a host cell containing a vector of the invention. The invention also provides a method for producing a protein, preferably a 3714, 16742, 23546, or 13887 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant 3714, 16742, 23546, or 13887 proteins and polypeptides.

In one embodiment, the isolated protein, preferably a 3714 protein, includes at least one Ser/Thr kinase site. In another embodiment, the isolated protein, preferably a 3714 protein, includes at least one Ser/Thr kinase site and has an amino acid sequence which is at least 50%, 55%, 60%, 65%, 70%, 75%, 80%, 81%, 85%, 90%, 95%, 99% or more homologous to an amino acid sequence including SEQ ID NO:2. In an even further embodiment, the isolated protein, preferably a 3714 protein, includes at least one Ser/Thr kinase site and plays a role in signaling pathways associated with cellular growth, e.g., signaling pathways associated with cell cycle regulation. In another embodiment, the isolated protein, preferably a 3714 protein, includes at least one Ser/Thr kinase site and is encoded by a nucleic acid molecule having a nucleotide sequence which hybridizes under stringent hybridization conditions to a nucleic acid molecule comprising the nucleotide sequence of SEQ ID NO:1 or SEQ ID NO:3.

In another embodiment, the isolated protein, preferably a 16742 protein, includes at least one Ser/Thr kinase site and at least one ATP-binding region. In another embodiment, the isolated protein, preferably a 16742 protein, includes at least one Ser/Thr kinase site, at least one ATP-binding region and has an amino acid sequence which is at least 50%, 55%, 60%, 65%, 70%, 75%, 80%, 85%, 90%, 95%, 98% or more homologous to an amino acid sequence including SEQ ID NO:5. In an even further embodiment, the isolated protein, preferably a 16742 protein, includes at least one Ser/Thr kinase site, at least one ATP-binding region and plays a role in signaling pathways associated with cellular growth, e.g., signaling pathways associated with cell cycle regulation. In another embodiment, the isolated protein, preferably a 16742 protein, includes at least one Ser/Thr kinase site, at least one ATP-binding region and is encoded by a nucleic acid molecule having a nucleotide sequence which hybridizes under stringent hybridization conditions to a nucleic acid molecule comprising the nucleotide sequence of SEQ ID NO:4 or SEQ ID NO:6.

In yet another embodiment, the isolated protein, preferably a 23546 protein, includes at least one Ser/Thr kinase site. In another embodiment, the isolated protein, preferably a 23546 protein, includes at least one Ser/Thr kinase site and has an amino acid sequence which is at least 50%, 55%, 60%, 65%, 70%, 75%, 80%, 85%, 90%, 95%, 98% or more homologous to an amino acid sequence including SEQ ID NO:8. In an even further embodiment, the isolated protein, preferably a 23546 protein, includes at least one Ser/Thr kinase site and plays a role in signaling pathways associated with cellular growth, e.g., signaling pathways associated with cell cycle regulation. In another embodiment, the isolated protein, preferably a 23546 protein, includes at least one Ser/Thr kinase site and is encoded by a nucleic acid molecule having a nucleotide sequence which hybridizes under stringent hybridization conditions to a nucleic acid molecule comprising the nucleotide sequence of SEQ ID NO:7 or SEQ ID NO:9.

In another embodiment, the isolated protein, preferably a 13887 protein, includes at least one Ser/Thr kinase domain, and at least one ATP-binding site. In another embodiment, the isolated protein, preferably a 13887 protein, includes at least one Ser/Thr kinase domain, and at least one ATP-binding site and has an amino acid sequence which is at least 50%, 55%, 60%, 65%, 70%, 75%, 80%, 85%, 90%, 95%, 98% or more homologous to an amino acid sequence including SEQ ID NO:11. In a further embodiment, the isolated protein, preferably a 13887 protein, includes at least one Ser/Thr kinase domain, and at least one ATP-binding site and plays a role in signaling pathways associated with cellular growth, e.g., signaling pathways associated with cell cycle regulation. In another embodiment, the isolated protein, preferably a 13887 protein, includes at least one Ser/Thr kinase domain, and at least one ATP-binding site and is encoded by a nucleic acid molecule having a nucleotide sequence which hybridizes under stringent hybridization conditions to a nucleic acid molecule comprising the nucleotide sequence of SEQ ID NO:10 or SEQ ID NO:12.

In another embodiment, the isolated protein, preferably a 3714, 16742, 23546, or 13887 protein, has an amino acid sequence sufficiently homologous to the amino acid sequence of SEQ ID NO:2, SEQ ID NO:5, SEQ ID NO:8, or SEQ ID NO:11. In a preferred embodiment, the protein, preferably a 3714, 16742, 23546, or 13887 protein, has an amino acid sequence at least about 50%, 55%, 59%, 60%, 65%, 70%, 75%, 80%, 81%, 85%, 90%, 95%, 98% or more homologous to an amino acid sequence including SEQ ID NO:2, SEQ ID NO:5, SEQ ID NO:8, or SEQ ID NO:11 (e.g., the entire amino acid sequence of SEQ ID NO:2, SEQ ID NO:5, SEQ ID NO:8, or SEQ ID NO:11). In another embodiment, the invention features fragments of the proteins having the amino acid sequence of SEQ ID NO:2, SEQ ID NO:5, SEQ ID NO:8, or SEQ ID NO:11, wherein the fragment comprises at least 15 amino acids (e.g., contiguous amino acids) of the amino acid sequence of SEQ ID NO:2, SEQ ID NO:5, SEQ ID NO:8, or SEQ ID NO:11, respectively. In another embodiment, the protein, preferably a 3714, 16742, 23546, or 13887 protein, has the amino acid sequence of SEQ ID NO:2, SEQ ID NO:5, SEQ ID NO:8, or SEQ ID NO:11.

Another embodiment of the invention features an isolated protein, preferably a 3714, 16742, 23546, or 13887 protein, which is encoded by a nucleic acid molecule having a nucleotide sequence at least about 50%, 55%, 60%, 62%, 65%, 70%, 75%, 78%, 80%, 85%, 86%, 90%, 95%, 97%, 98% or more homologous to a nucleotide sequence (e.g., to the entire length of the nucleotide sequence) including SEQ ID NO:1, SEQ ID NO:3, SEQ ID NO:4, SEQ ID NO:6, SEQ ID NO:7, SEQ IDNO:9,SEQ ID NO:10, SEQ ID NO:12, or a complement thereof. This invention further features an isolated protein, preferably a 3714, 16742, 23546, or 13887 protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement thereof.

The proteins of the present invention or biologically active portions thereof, can be operatively linked to a non-3714, -16742, -23546, or -13887 polypeptide (e.g., heterologous amino acid sequences) to form fusion proteins. The invention further features antibodies, such as monoclonal or polyclonal antibodies, that specifically bind proteins of the invention, preferably 3714, 16742, 23546, or 13887 proteins. In addition, the 3714, 16742, 23546, or 13887 proteins or biologically active portions thereof can be incorporated into pharmaceutical compositions, which optionally include pharmaceutically acceptable carriers.

In another aspect, the present invention provides a method for detecting the presence of a 3714, 16742, 23546, or 13887 nucleic acid molecule, protein or polypeptide in a biological sample by contacting the biological sample with an agent capable of detecting a 3714, 16742, 23546, or 13887 nucleic acid molecule, protein or polypeptide such that the presence of a 3714, 16742, 23546, or 13887 nucleic acid molecule, protein or polypeptide is detected in the biological sample.

In another aspect, the present invention provides a method for detecting the presence of 3714, 16742, 23546, or 13887 activity in a biological sample by contacting the biological sample with an agent capable of detecting an indicator of 3714, 16742, 23546, or 13887 activity such that the presence of 3714, 16742, 23546, or 13887 activity is detected in the biological sample.

In another aspect, the invention provides a method for modulating 3714, 16742, 23546, or 13887 activity comprising contacting a cell capable of expressing 3714, 16742, 23546, or 13887 with an agent that modulates 3714, 16742, 23546, or 13887 activity such that 3714, 16742, 23546, or 13887 activity in the cell is modulated. In one embodiment, the agent inhibits 3714, 16742, 23546, or 13887 activity. In another embodiment, the agent stimulates 3714, 16742, 23546, or 13887 activity. In one embodiment, the agent is an antibody that specifically binds to a 3714, 16742, 23546, or 13887 protein. In another embodiment, the agent modulates expression of 3714, 16742, 23546, or 13887 by modulating transcription of a 3714, 16742, 23546, or 13887 gene or translation of a 3714, 16742, 23546, or 13887 mRNA. In yet another embodiment, the agent is a nucleic acid molecule having a nucleotide sequence that is antisense to the coding strand of a 3714, 16742, 23546, or 13887 mRNA or a 3714, 16742, 23546, or 13887 gene.

In one embodiment, the methods of the present invention are used to treat a subject having a disorder characterized by aberrant 3714, 16742, 23546, or 13887 protein or nucleic acid expression or activity by administering an agent which is a 3714, 16742, 23546, or 13887 modulator to the subject. In one embodiment, the 3714, 16742, 23546, or 13887 modulator is a 3714, 16742, 23546, or 13887 protein. In another embodiment the 3714, 16742, 23546, or 13887 modulator is a 3714, 16742, 23546, or 13887 nucleic acid molecule. In yet another embodiment, the 3714, 16742, 23546, or 13887 modulator is a peptide, peptidomimetic, or other small molecule. In a preferred embodiment, the disorder characterized by aberrant 3714, 16742, 23546, or 13887 protein or nucleic acid expression is a cellular growth related disorder.

The present invention also provides a diagnostic assay for identifying the presence or absence of a genetic alteration characterized by at least one of (i) aberrant modification or mutation of a gene encoding a 3714, 16742, 23546, or 13887 protein; (ii) misregulation of the gene; and (iii) aberrant post-translational modification of a 3714, 16742, 23546, or 13887 protein, wherein a wild-type form of the gene encodes a protein with a 3714, 16742, 23546, or 13887 activity.

In another aspect the invention provides a method for identifying a compound that binds to or modulates the activity of a 3714, 16742, 23546, or 13887 protein, by providing an indicator composition comprising a 3714, 16742, 23546, or 13887 protein having 3714, 16742, 23546, or 13887 activity, contacting the indicator composition with a test compound, and determining the effect of the test compound on 3714, 16742, 23546, or 13887 activity in the indicator composition to identify a compound that modulates the activity of a 3714, 16742, 23546, or 13887 protein.

Other features and advantages of the invention will be apparent from the following detailed description and claims.

BRIEF DESCRIPTION OF THE DRAWINGS

FIGS. 1A–D depict a cDNA sequence (SEQ ID NO:1) and predicted amino acid sequence (SEQ ID NO:2) of human 3714. The location of the methionine-initiated open reading frame of human 3714 (without the 5' and 3' untranslated regions) of SEQ ID NO:1 is shown also as the coding sequence, SEQ ID NO:3.

FIG. 3 depicts an alignment of the protein kinase domain of human 3714 with a consensus amino acid sequence derived from a hidden Markov model (HMM) from PFAM. The upper sequence is the consensus amino acid sequence (SEQ ID NO:13), while the lower amino acid sequence corresponds to amino acids 27 to 237 of SEQ ID NO:2.

FIGS. 4A–C depict a cDNA sequence (SEQ ID NO:4) and predicted amino acid sequence (SEQ ID NO:5) of human 16742. The location of the methionine-initiated open reading frame of human 16742 (without the 5' and 3' untranslated regions) is shown also as the coding sequence, SEQ ID NO:6.

FIG. 5 depicts a hydropathy plot of human 16742. Relatively hydrophobic residues are shown above the dashed horizontal line, and relatively hydrophilic residues are shown below the dashed horizontal line. The location of the transmembrane domains, and the extracellular and intracellular loops is also indicated. The cysteine residues (cys) and N-glycosylation sites (Ngly) are indicated by short vertical lines just below the hydropathy trace. The numbers corresponding to the amino acid sequence of human 16742 are indicated. Polypeptides of the invention include fragments which include: all or part of a hydrophobic sequence, e.g., a sequence above the dashed line, e.g., the sequence from about amino acid 115 to 125, from about 145 to 155, and from about 240 to 255 of SEQ ID NO:5; all or part of a hydrophilic sequence, e.g., a sequence below the dashed line, e.g., the sequence from about amino acid 80 to 90, from about 130 to 140, and from about 295 to 305 of SEQ ID NO:5; a sequence which includes a Cys, or a glycosylation site.

FIG. 6 depicts an alignment of the protein kinase domain of human 16742 with a consensus amino acid sequence derived from a hidden Markov model (HMM) from PFAM. The upper sequence is the consensus amino acid sequence (SEQ ID NO:14), while the lower amino acid sequence corresponds to amino acids 8 to 325 of SEQ ID NO:5.

FIGS. 7A–G depict a cDNA sequence (SEQ ID NO:7) and predicted amino acid sequence (SEQ ID NO:8) of human 23546. The location of the methionine-initiated open reading frame of human 23546 (without the 5' and 3' untranslated regions) is shown also as the coding sequence, SEQ ID NO:9.

Figure 8:
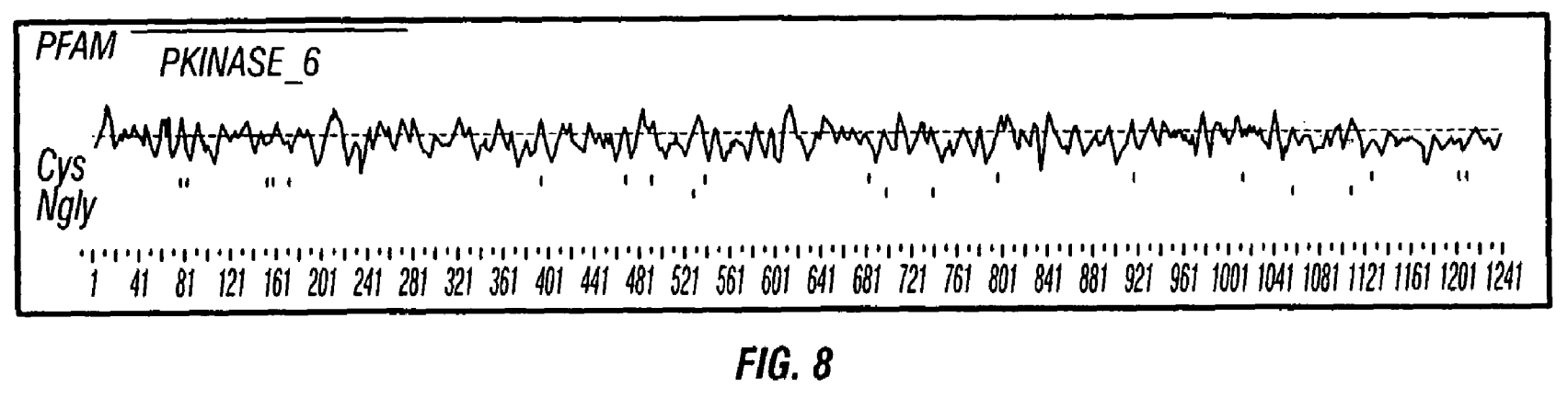

FIG. 8 depicts a hydropathy plot of human 23546. Relatively hydrophobic residues are shown above the dashed horizontal line, and relatively hydrophilic residues are shown below the dashed horizontal line. The cysteine residues (cys) and N-glycosylation sites (Ngly) are indicated by short vertical lines just below the hydropathy trace. The numbers corresponding to the amino acid sequence of human 23546 are indicated. Polypeptides of the invention include fragments which include: all or part of a hydrophobic sequence, e.g., a sequence above the dashed line, e.g., the sequence from about amino acid 210 to 220, from about 325 to 335, and from about 485 to 495 of SEQ ID NO:8; all or part of a hydrophilic sequence, e.g., a sequence below the dashed line, e.g., the sequence from about amino acid 225 to 245, from about 375 to 395, and from about 505 to 530 of SEQ ID NO:8; a sequence which includes a Cys, or a glycosylation site.

FIG. 9 depicts an alignment of the protein kinase domain of human 23546 with a consensus amino acid sequence derived from a hidden Markov model (HMM) from PFAM. The upper sequence is the consensus amino acid sequence (SEQ ID NO:15), while the lower amino acid sequence corresponds to amino acids 21 to 256 of SEQ ID NO:8.

FIGS. 10A–C depict a cDNA sequence (SEQ ID NO:10) and predicted amino acid sequence (SEQ ID NO:11) of human 13887. The location of the methionine-initiated open reading frame of human 13887 (without the 5' and 3' untranslated regions) is shown also as the coding sequence, SEQ ID NO:12.

FIG. 12 depicts an alignment of the protein kinase domain of human 13887 with a consensus amino acid sequence derived from a hidden Markov model (HMM) from PFAM. The upper sequence is the consensus amino acid sequence (SEQ ID NO:16), while the lower amino acid sequence corresponds to amino acids 23 to 304 of SEQ ID NO:11.

FIG. 29A–D is a panel bar graph depicting the relative expression of 13887 RNA relative to a no template controls in a panel of human tissues or cells, including but not limited to aorta, fetal heart, normal heart, normal vein, brain cortex, brain hypothalamus, glial cells, brain glioblastoma, normal breast, breast tumor, ovary, pancreas, colon, kidney, liver, lung, spleen, tonsil, lymph node, thymus, epithelial, endothelial, skeletal, fibroblasts, skin, adipose, bone cells (e.g., differentiated and undifferentiated osteoclasts and osteoblasts), aortic smooth muscle cells (SMC) (early), aortic SMC (late), shear and static human umbilical vein endothelial cells (HUVEC), among others, detected using real-time quantitative RT-PCR Taq Man analysis. The graph indicates significant expression in brain cortex and hypothalamus, and glial cells, as well as aortic SMC (late).

DETAILED DESCRIPTION OF THE INVENTION

Figure 2:
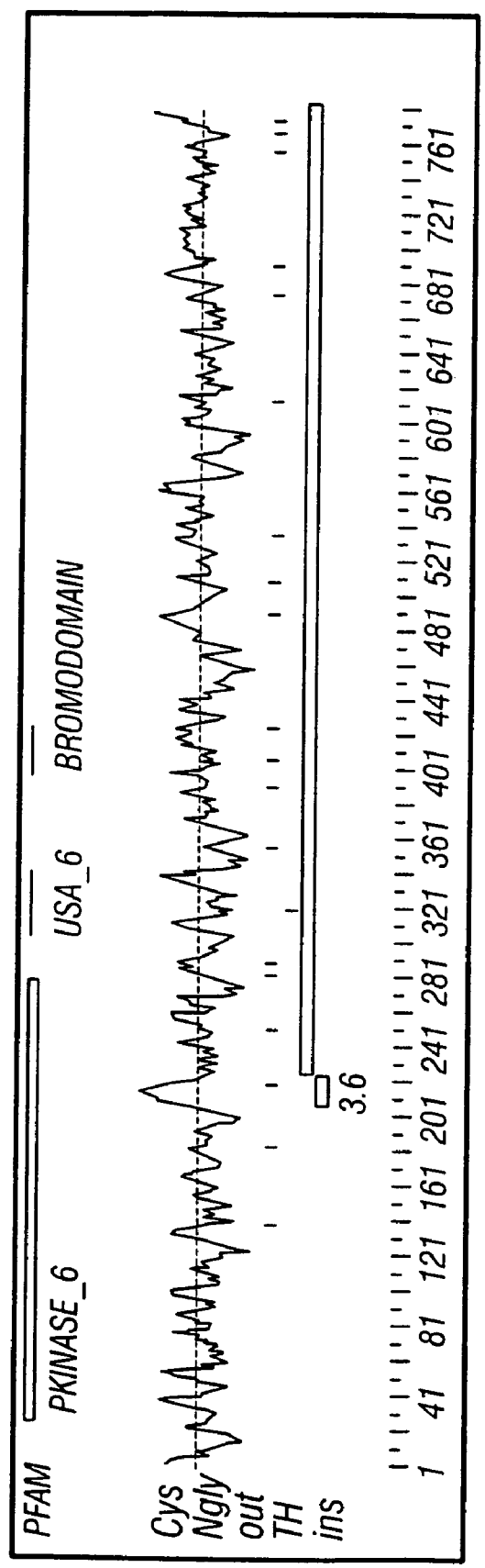
FIG. 2 depicts a hydropathy plot of human 3714. Relatively hydrophobic residues are shown above the dashed horizontal line, and relatively hydrophilic residues are shown below the dashed horizontal line. The location of the transmembrane domains, and the extracellular loops is also indicated. The cysteine residues (cys) and N-glycosylation sites (Ngly) are indicated by short vertical lines just below the hydropathy trace. The numbers corresponding to the amino acid sequence of human 3714 are indicated. Polypeptides of the invention include fragments which include: all or part of a hydrophobic sequence, e.g., a sequence above the dashed line, e.g., the sequence from about amino acid 420 to 430, from about 530 to 540, and from about 685 to 695 of SEQ ID NO:2; all or part of a hydrophilic sequence, e.g., a sequence below the dashed line, e.g., the sequence from about amino acid 275 to 285, from about 450 to 470, and from about 590 to 600 of SEQ ID NO:2; a sequence which includes a Cys, or a glycosylation site.

The present invention is based, at least in part, on the discovery of novel molecules, referred to herein as "3714, 16742, 23546, or 13887" nucleic acid and polypeptide molecules, which play a role in or function in signaling pathways associated with cellular growth. In one embodiment, the 3714, 16742, 23546, or 13887 molecules modulate the activity of one or more proteins involved in cellular growth or differentiation, e.g., cardiac cell growth or differentiation. In another embodiment, the 3714, 16742, 23546, or 13887 molecules of the present invention are capable of modulating the phosphorylation state of a 3714, 16742, 23546, or 13887 molecule or one or more proteins involved in cellular growth or differentiation.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. As referred to herein, protein kinases preferably include a catalytic domain of about 200–400 amino acid residues in length, preferably about 200–300 amino acid residues in length, or more preferably about 250–300 amino acid residues in length, which includes preferably 5–20, more preferably 5–15, or preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42–52) the contents of which are incorporated herein by reference). These subdomains are also described in further detail herein.

Protein kinases play a role in signaling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the 3714, 16742, 23546, or 13887 molecules of the present invention may be involved in:1) the regulation of transmission of signals from cellular receptors, e.g., cardiac cell growth factor receptors; 2) the modulation of the entry of cells into mitosis; 3) the modulation of cellular differentiation; 4) the modulation of cell death; and 5) the regulation of cytoskeleton function, e.g., actin bundling.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy.

The present invention is based, at least in part, on the discovery of novel molecules, referred to herein as 3714, 16742, 23546, or 13887 protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features 3714, 16742, 23546, or 13887 nucleic acid molecules, preferably human 3714, 16742, 23546, or 13887 molecules, e.g., 3714, 16742, 23546, and 13887. The 3714, 16742, 23546, or 13887 nucleic acid and protein molecules of the invention are described in further detail in the following subsections.

A. The 3714 Nucleic Acid and Protein Molecules

In another embodiment, the isolated proteins of the present invention, preferably 3714 proteins, are identified based on the presence of at least one Ser/Thr kinase site. As used herein, the term "Ser/Thr kinase site" includes an amino acid sequence of about 200–400 amino acid residues in length, preferably 200–300 amino acid residues in length, and more preferably 250–300 amino acid residues in length, which is conserved in kinases which phosphorylate serine and threonine residues and found in the catalytic domain of Ser/Thr kinases. Preferably, the Ser/Thr kinase site includes the following amino acid consensus sequence $X_9$-g-X-G-$X_4$—V—$X_{12}$—K—X-$_{(10-19)}$-E-$X_{66}$-h-$X_8$-h-r-D-X—K—$X_2$—N—$X_{17}$—K—$X_2$-D-f-g-$X_{21}$—p—$X_{13}$-w-$X_3$-g-$X_{55}$—R—$X_{14}$-h-$X_3$ (SEQ ID NO:17) (where invariant residues are indicated by upper case letters and nearly invariant residues are indicated by lower case letters). The nearly invariant residues are usually found in most Ser/Thr kinase sites, but can be replaced by other amino acids which, preferably, have similar characteristics. For example, a nearly invariant hydrophobic amino acid in the above amino acid consensus sequence would most likely be replaced by another hydrophobic amino acid. Ser/Thr kinase domains are described in, for example, Levin D. E. et al. (1990) *Proc. Natl. Acad. Sci. USA* 87:8272–76, the contents of which are incorporated herein by reference.

Isolated proteins of the present invention, preferably 3714 proteins, have an amino acid sequence sufficiently homologous to the amino acid sequence of SEQ ID NO:2 or are encoded by a nucleotide sequence sufficiently homologous to SEQ ID NO:1 or SEQ ID NO:3. The 3714 nucleic acid encodes a polypeptide with similarities to previously characterized protein kinases. Thus the 3714 encoded polypeptide is expected to be a kinase and function in the phosphorylation of protein substrates. Since the 3714 nucleic acid was found to be expressed in cells of the adrenal gland, breast, colon, fetus, heart, liver, lung, muscle, and prostate (as well as keratinocytes and colon to liver metastases) in particular, the encoded protein kinase is at least expected to catalyze cell type specific phosphorylation reactions in those cells. Additionally, the 3714 encoded protein kinase has similarities to a putative casein kinase identified in *C. elegans*. Thus without being bound by theory, the 3714 kinase may be a human analogue of the *C. elegans* kinase.

As used interchangeably herein a "3714 activity", "biological activity of 3714" or "functional activity of 3714", refers to an activity exerted by a 3714 protein, polypeptide or nucleic acid molecule on a 3714 responsive cell or a 3714 protein substrate as determined in vivo, or in vitro, according to standard techniques. The biological activity of 3714 is described herein.

Accordingly, another embodiment of the invention features isolated 3714 proteins and polypeptides having a 3714 activity. Preferred proteins are 3714 proteins having at least one Ser/Thr kinase site. Additional preferred proteins have at least one Ser/Thr kinase site, and preferably a 3714 activity. Additional preferred proteins have at least one Ser/Thr kinase site and are, preferably, encoded by a nucleic acid molecule having a nucleotide sequence which hybridizes under stringent hybridization conditions to a nucleic acid molecule comprising the nucleotide sequence of SEQ ID NO:1 or SEQ ID NO:3.

Human 3714 contains the following regions or other structural features (for general information regarding PFAM identifiers, PS prefix and PF prefix domain identification numbers, refer to Sonnhammer et al. (1997) *Protein* 28:405–420 and http://www.psc.edu/general/software/packages/pfam/pfam.html):

a protein kinase domain (PFAM Accession Number PF00069) located at about amino acid residues 27 to 278 of SEQ ID NO:2;

1 transmembrane domain (predicted by MEMSAT, Jones et al. (1994) *Biochemistry* 33:3038–3049) at about amino acids 207 to 224 of SEQ ID NO:2;

1 N-glycosylation site (Prosite PS00001) from about amino acids 328 to 331 of SEQ ID NO:2;

4 cAMP/cGMP-dependent protein kinase phosphorylation sites (Prosite PS00004) located at about amino acids 265–268, 470–473, 572–575, and 591–594 of SEQ ID NO:2;

4 protein kinase C phosphorylation sites (Prosite PS00005) at about amino acids 231–233, 468–470, 478–480, and 593–595 of SEQ ID NO:2;

11 casein kinase II phosphorylation sites (Prosite PS00006) located at about amino acids 61–64, 66–69, 122–125, 135–138, 370–373, 438–441, 473–476, 498–501, 503–506, 567–570, and 649–652 of SEQ ID NO:2;

1 tyrosine kinase phosphorylation site (Prosite PS0007) located at about amino acids 107–114;

10 N-myristoylation sites (Prosite PS00008) from about amino acids 13–18, 310–315, 522–527, 528–533, 544–549, 556–561, 636–641, 643–648, 735–740, and 760–765 of SEQ ID NO:2;

2 amidation sites (Prosite PS00009) from about amino acids 468–471 and 570–573 of SEQ ID NO:2;

1 prokaryotic membrane lipoprotein lipid attachment site (Prosite PS00013) from about amino acids 523–533 of SEQ ID NO:2;

1 serine/threonine protein kinase active-site signal site (Prosite PS00108) from about amino acids 145–157 of SEQ ID NO:2; and 12 dileucine motifs (LL) in the tail (as predicted in PSORT) from about amino acids 340–341, 341–342, 388–389, 439–440, 529–530, 563–564, 650–651, 660–661, 701–702, 708–709, 713–714 and 727–728 of SEQ ID NO:2.

The nucleotide sequence of the isolated human 3714 cDNA and the predicted amino acid sequence of the human 3714 polypeptide are shown in FIG. 1 and in SEQ ID NOs:1 and 2, respectively.

As used herein, the term "protein kinase domain" includes an amino acid sequence of about 200 to 260 amino acid residues in length and having a bit score for the alignment of the sequence to the protein kinase domain (HMM) of at least 100. Preferably a protein kinase domain mediates reversible protein phosphorylation. Preferably, a protein kinase domain includes at least about 200 to 260 amino acids, more preferably about 230 to 260 amino acid residues, or about 250 to 255 amino acids and has a bit score for the alignment of the sequence to the protein kinase domain (HMM) of at least 100, more preferably 200, most preferably 300 or greater.

Eukaryotic protein kinases are enzymes that belong to a very extensive family of proteins which share a conserved catalytic core common to both serine/threonine and tyrosine protein kinases. There are a number of conserved regions in the catalytic domain of protein kinases. One of these regions is located in the N-terminal extremity of the catalytic domain, and is a glycine-rich stretch of residues in the vicinity of a lysine residue, which has been shown to be involved in ATP binding. One signature pattern is as follows: [LIV]-G-{P     }-G-{P}-[FYWMGSTNH]-[SGA]-{PW}-[LIVCAT]-{PD}-x-[GSTACLIVMFY]-x(5,18)-[LIVMFY-WCSTAR]-[AIVP]-[LIVMFAGCKR]-K, wherein K binds ATP (SEQ ID NO:18). In the above conserved motif, and other motifs described herein, the standard IUPAC one-letter code for the amino acids is used. Each element in the pattern is separated by a dash (-); square brackets ([]) indicate the particular residues that are accepted at that position; x indicates that any residue is accepted at that position; and numbers in parentheses (()) indicate the number of residues represented by the accompanying amino acid. The protein kinase domain (HMM) has been assigned the PFAM Accession Number PF00069 (http://genome.wustl.edu/Pfam/.html).

An alignment of the protein kinase domain (amino acids 27 to 278 of SEQ ID NO:2) of human 3714 with a consensus amino acid sequence (SEQ ID NO:13) derived from a hidden Markov model is depicted in FIG. 3.

In a preferred embodiment, a 3714 polypeptide or protein has a "protein kinase domain" or a region which includes at least about 200 to 260 more preferably about 230 to 260 or 250 to 255 amino acid residues and has at least about 60%, 70% 80% 90% 95%, 99%, or 100% homology with a "protein kinase domain," e.g., the protein kinase domain of human 3714 (e.g., residues 27 to 278 of SEQ ID NO:2).

To identify the presence of a "protein kinase" domain in a 3714 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28:405–420 and a detailed description of HMMs can be found, for example, in Gribskov et al. (1990) Meth. Enzymol.183:146–159; Gribskov et al. (1987) Proc. Natl. Acad. Sci. USA 84:4355–4358; Krogh et al. (1994) J. Mol. Biol. 235: 1501–1531; and Stultz et al. (1993) Protein Sci. 2:305–314, the contents of which are incorporated herein by reference. A search was performed against the HMM database resulting in the identification of a "protein kinase domain" domain in the amino acid sequence of human 3714 at about residues 27 to 278 of SEQ ID NO:2 (see FIG. 3).

For further identification of protein kinase domains, or to identify the presence of a "protein kinase" domain in a 3714 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263–267). The ProDom protein domain database consists of an automatic compilation of homologous domains. Current versions of ProDom are built using recursive PSI-BLAST searches (Altschul S F et al. (1997) Nucleic Acids Res. 25:3389–3402; Gouzy et al. (1999) Computers and Chemistry 23:333–340) of the SWISS-PROT 38 and TREMBL protein databases. The database automatically generates a consensus sequence for each domain.

ProDom (derived from BLAST search) alignments of the amino acid sequence of human 3714 revealed that 3714 is similar to the putative NPK-1 kinase protein. This amino acid molecule is approximately 25% identical to 3714, over amino acids 27–168.

A 3714 polypeptide can include at least one "transmembrane domain" or regions homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) Annual Rev. Neurosci. 19:235–263, the contents of which are incorporated herein by reference.

In a preferred embodiment, a 3714 polypeptide or protein has at least one "transmembrane domain" or a region which includes at least about 12 to 35 more preferably about 14 to 30 or 15 to 25 amino acid residues and has at least about 60%, 70% 80% 90% 95%, 99%, or 100% homology with a "transmembrane domain," e.g., the transmembrane domains of human 3714 (e.g., residues 207 to 224 of SEQ ID NO:2). The transmembrane domain of human 3714 is visualized in the hydropathy plot (FIG. 2) as regions of about 15 to 25 amino acids where the hydropathy trace is mostly above the horizontal line.

To identify the presence of a "transmembrane" domain in a 3714 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) Biochemistry 33:3038–3049).

A 3714 polypeptide can include at least one "non-transmembrane region." As used herein, the term "non-transmembrane region" includes an amino acid sequence not identified as a transmembrane domain. The non-transmembrane regions in 3714 are located at about amino acids 1–206 and 225–783 of SEQ ID NO:2.

The non-transmembrane regions of 3714 include at least one, and preferably two, cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 50, preferably about 1 to 100, more preferably about 1 to 150, or even more preferably about 1 to 250 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 3714 protein. For example, an N-terminal cytoplasmic domain is located at about amino acid residues 1 to 206 of SEQ ID NO:2.

In a preferred embodiment, a polypeptide or protein has an N-terminal cytoplasmic domain or a region which includes at least about 5, preferably about 1 to 100, and more preferably about 1 to 206 amino acid residues and has at least about 60%, 70% 80% 90% 95%, 99%, or 100% homology with an "N-terminal cytoplasmic domain," e.g., the N-terminal cytoplasmic domain of human 3714 (e.g., residues 1 to 206 of SEQ ID NO:2).

In another embodiment, a cytoplasmic region of a 3714 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 50, preferably about 50 to 200, more preferably about 50 to 600 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 3714 protein. For example, a C-terminal cytoplasmic domain is located at about amino acid residues 225 to 783 of SEQ ID NO:2.

In a preferred embodiment, a 3714 polypeptide or protein has a C-terminal cytoplasmic domain or a region which includes at least about 5, preferably about 100 to 300, and more preferably about 300 to 600 amino acid residues and has at least about 60%, 70% 80% 90% 95%, 99%, or 100% homology with a C-terminal cytoplasmic domain," e.g., the C-terminal cytoplasmic domain of human 3714 (e.g., residues 225 to 783 of SEQ ID NO:2).

A 3714 family member can include at least one protein kinase domain; and at least one transmembrane or non-transmembrane domains. Furthermore, a 3714 family member can include at least one N-glycosylation site (PS00001); at least one, two, three, preferably four cAMP/cGMP-dependent protein kinase phosphorylation sites (Prosite PS00004); at least one, two, three, preferably four protein kinase C phosphorylation sites (PS00005); at least one, two, three, four, five, six, seven, eight, nine, ten and preferably eleven casein kinase II phosphorylation sites (PS00006); at least one tyrosine kinase phosphorylation site (Prosite PS0007); at least one, two, three, four, five, six, seven, eight, nine, and preferably ten N-myristoylation sites (PS00008); at least one and preferably two amidation sites (Prosite PS00009); at least one prokaryotic membrane lipoprotein lipid attachment site (Prosite PS00013); at least one serine/threonine protein kinases active-site signal sites (Prosite PS00108); and at least one, two, three, four, five, six, seven, eight, nine, ten, eleven and preferably twelve dileucine motifs (LL) in the tail.

As the 3714 polypeptides of the invention can modulate 3714-mediated activities, they can be useful for developing novel diagnostic and therapeutic agents for protein kinase-associated or other 3714-associated disorders, as described below.

B. The 16742 Nucleic Acid and Protein Molecules

In another embodiment, the isolated proteins of the present invention, preferably 16742 proteins, are identified based on the presence of at least one Ser/Thr kinase site as described above and at least one ATP-binding region.

As used herein, the term "ATP-binding region" includes an amino acid sequence of about 20–40, preferably 20–30, and more preferably 25–30 amino acid residues in length, present in enzymes which activate their substrates by phosphorylation, and involved in binding adenosine triphosphate (ATP). ATP-binding regions preferably include the following amino acid consensus sequence: G-X-G-X—X-G-X (15–23)-K (SEQ ID NO:19). ATP-binding regions are described in, for example, Samuel K. P. et al. (1987) *FEBS Let.* 218(1):81–86, the contents of which are incorporated herein by reference. Amino acid residues 14 to 22 of comprise an ATP-binding region. Amino acid residues 160–172 of the 16742 protein comprise a Ser/Thr kinase domain.

Isolated proteins of the present invention, preferably 16742 proteins, have an amino acid sequence sufficiently homologous to the amino acid sequence of SEQ ID NO:5 or are encoded by a nucleotide sequence sufficiently homologous to SEQ ID NO:4 or SEQ ID NO:6. The 16742 nucleic acid encodes a polypeptide with homology to previously identified Ser/Thr kinases as well as portions of an epidermal growth receptor homolog containing a putative kinase domain. Thus the 16742 encoded polypeptide is expected to be a kinase and function in the phosphorylation of protein substrates. Since the 16742 nucleic acid was found to be expressed in brain, breast, ovary, B cells and spleen cells in particular, the encoded protein kinase is at least expected to catalyze cell type specific phosphorylation reactions in those cell types.

As used interchangeably herein a "16742 activity", "biological activity of 16742" or "functional activity of 16742", refers to an activity exerted by a 16742 protein, polypeptide or nucleic acid molecule on a 16742 responsive cell or a 16742 protein substrate as determined in vivo, or in vitro, according to standard techniques. The biological activity of 16742 is described herein.

Accordingly, another embodiment of the invention features isolated 16742 proteins and polypeptides having a 16742 activity. Preferred proteins are 16742 proteins having at least one Ser/Thr kinase site and at least one ATP-binding region. Additional preferred proteins have at least one Ser/Thr kinase site, at least one ATP-binding region, and preferably a 16742 activity. Additional preferred proteins have at least one Ser/Thr kinase site and at least one ATP-binding region and are, preferably, encoded by a nucleic acid molecule having a nucleotide sequence which hybridizes under stringent hybridization conditions to a nucleic acid molecule comprising the nucleotide sequence of SEQ ID NO:4 or SEQ ID NO:6.

Human 16742 contains the following regions or other structural features (for general information regarding PFAM identifiers, PS prefix and PF prefix domain identification numbers, refer to Sonnhammer et al. (1997) *Protein* 28:405–420 and http://www.psc.edu/general/software/packages/pfam/pfam.html):

a protein kinase domain (PFAM Accession Number PF00069, as described above) located at about amino acid residues 8 to 325 of SEQ ID NO:5;

2 transmembrane domains (predicted by MEMSAT, Jones et al. (1994) *Biochemistry* 33:3038–3049) at about amino acids 140 to 156 and 240 to 257 of SEQ ID NO:5;

2 N-glycosylation sites (Prosite PS00001) from about amino acids 89 to 92 and 141 to 144 of SEQ ID NO:5;

2 cAMP/cGMP-dependent protein kinase phosphorylation sites (Prosite PS00004) located at about amino acids 28 to 31 and 296 to 299 of SEQ ID NO:5;

7 protein kinase C phosphorylation sites (Prosite PS00005) at about amino acids 31–33, 59–61, 100–102, 133–135, 185–187, 235–237 and 261–263 of SEQ ID NO:5;

5 casein kinase II phosphorylation sites (Prosite PS00006) located at about amino acids 175–178, 180–183, 255–258, 261–264, and 337–340 of SEQ ID NO:5;

2 N-myristoylation sites (Prosite PS00008) from about amino acids 187–92 and 124–129 of SEQ ID NO:5;

1 protein kinase ATP-binding region signature site (Prosite PS00107) from about amino acids 14 to 22 of SEQ ID NO:5;

1 serine/threonine protein kinase active-site signal site (Prosite PS00108) from about amino acids 160–172 of SEQ ID NO:5; and 3 dileucine motifs (LL) in the tail (as predicted in PSORT) from about amino acids 265–266, 283–284, and 291–292 of SEQ ID NO:5.

The nucleotide sequence of the isolated human 16742 cDNA and the predicted amino acid sequence of the human 16742 polypeptide are shown in FIG. 4 and in SEQ ID NOs:4 and 5, respectively.

The human 16742 gene, which is approximately 1948 nucleotides in length, encodes a protein having a molecular weight of approximately 37.6 kD and which is approximately 341 amino acid residues in length.

As used herein, the term "protein kinase domain" includes an amino acid sequence of about 200 to 350 amino acid residues in length and having a bit score for the alignment of the sequence to the protein kinase domain (HMM) of at least 100. Preferably a protein kinase domain mediates reversible protein phosphorylation. Preferably, a protein kinase domain includes at least about 200 to 320 amino acids, more preferably about 290 to 320 amino acid residues, or about 310 to 320 amino acids and has a bit score for the alignment of the sequence to the protein kinase domain (HMM) of at least 100, more preferably 150, most preferably 195 or greater.

An alignment of the protein kinase domain (amino acids 8 to 325 of SEQ ID NO:5) of human 16742 with a consensus amino acid sequence (SEQ ID NO:14) derived from a hidden Markov model is depicted in FIG. 6.

In a preferred embodiment, a 16742 polypeptide or protein has a "protein kinase domain" or a region which includes at least about 200 to 325, more preferably about 275 to 325 or 315 to 325 amino acid residues and has at least about 60%, 70% 80% 90% 95%, 99%, or 100% homology with a "protein kinase domain," e.g., the protein kinase domain of human 16742 (e.g., residues 8 to 325 of SEQ ID NO:5).

To identify the presence of a "protein kinase" domain in a 16742 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/Pfam/HMM_search), as described above. A search was performed against the HMM database resulting in the identification of a "protein kinase domain" domain in the amino acid sequence of human 16742 at about residues 8 to 325 of SEQ ID NO:5 (see FIG. 6).

For further identification of protein kinase domains, or to identify the presence of a "protein kinase" domain in a 16742 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263–267), as described above.

ProDom (derived from BLAST search) alignments of the amino acid sequence of human 16742 revealed that 16742 is similar to a serine/threonine kinase sequence. This amino acid molecule is approximately 24–59% identical to 16742, over amino acids 2–14, 33–100, 191–296, and 276–410.

A 16742 polypeptide can include at least one "transmembrane domain" or regions homologous with a "transmembrane domain", as described above.

In a preferred embodiment, a 16742 polypeptide or protein has at least one "transmembrane domain" or a region which includes at least about 10 to 30 more preferably about 10 to 25 or 15 to 20 amino acid residues and has at least about 60%, 70% 80% 90% 95%, 99%, or 100% homology with a "transmembrane domain," e.g., the transmembrane domains of human 16742 (e.g., residues 140–156 and 240–257 of SEQ ID NO:5). The transmembrane domain of human 16742 is visualized in the hydropathy plot (FIG. 5) as regions of about 15 to 25 amino acids where the hydropathy trace is mostly above the horizontal line.

To identify the presence of a "transmembrane" domain in a 16742 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) Biochemistry 33:3038–3049).

A 16742 polypeptide can include at least one "non-transmembrane region." As used herein, the term "non-transmembrane region" includes an amino acid sequence not identified as a transmembrane domain. The non-transmembrane regions in 16742 are located at about amino acids 1–139, 157–239 and 258–341 of SEQ ID NO:5.

The non-transmembrane regions of 16742 include at least one, and preferably two, cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 50, preferably about 1 to 100, more preferably about 1 to 125, or even more preferably about 1 to 140 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 16742 protein. For example, an N-terminal cytoplasmic domain is located at about amino acid residues 1 to 139 SEQ ID NO:5.

In a preferred embodiment, a polypeptide or protein has an N-terminal cytoplasmic domain or a region which includes at least about 5, preferably about 1 to 100, and more preferably about 1 to 139 amino acid residues and has at least about 60%, 70% 80% 90% 95%, 99%, or 100% homology with an "N-terminal cytoplasmic domain," e.g., the N-terminal cytoplasmic domain of human 16742 (e.g., residues 1 to 139 of SEQ ID NO:5).

In another embodiment, a cytoplasmic region of a 16742 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 50, preferably about 50 to 100, more preferably about 70 to 90 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 16742 protein. For example, a C-terminal cytoplasmic domain is located at about amino acid residues 258 to 341 of SEQ ID NO:5.

In a preferred embodiment, a 16742 polypeptide or protein has a C-terminal cytoplasmic domain or a region which includes at least about 5, preferably about 50 to 100, and more preferably about 70 to 90 amino acid residues and has at least about 60%, 70% 80% 90% 95%, 99%, or 100% homology with a "C-terminal cytoplasmic domain," e.g., the C-termninal cytoplasmic domain of human 16742 (e.g., residues 258 to 341 of SEQ ID NO:5).

In another embodiment, a 16742 protein includes at least one non-cytoplasmic loop. As used herein, a "non-cytoplasmic loop" includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 157–239 of SEQ ID NO:5.

In a preferred embodiment, a 16742 polypeptide or protein has at least one non-cytoplasmic loop or a region which includes at least about 50, preferably about 50 to 100, more preferably about 80 to 90 amino acid residues and has at least about 60%, 70% 80% 90% 95%, 99%, or 100% homology with a "non-cytoplasmic loop," e.g., at least one non-cytoplasmic loop of human 16742 (e.g., residues 157–239 of SEQ ID NO:5).

A 16742 family member can include at least one protein kinase domain; and at least one or two and preferably two or three transmembrane or non-transmembrane domains. Furthermore, a 16742 family member can include at least one, preferably two N-glycosylation sites (PS00001); at least one, preferably two cAMP/cGMP-dependent protein kinase phosphorylation sites (Prosite PS00004); at least one, two, three, four, five, six, preferably seven protein kinase C phosphorylation sites (PS00005); at least one, two, three, four, and preferably five casein kinase 11 phosphorylation sites (PS00006); at least one, and preferably two N-myristoylation sites (PS00008); at least one protein kinase ATP-binding region signature site (Prosite PS00107); at least one serine/threonine protein kinases active-site signal site (Prosite PS00108); and at least one, two, and preferably three dileucine motifs (LL) in the tail.

As the 16742 polypeptides of the invention can modulate 16742-mediated activities, they can be useful for developing novel diagnostic and therapeutic agents for protein kinase-associated or other 16742-associated disorders, as described below.

C. The 23546 Nucleic Acid and Protein Molecules

In another embodiment, the isolated proteins of the present invention, preferably 23546 proteins, are identified based on the presence of at least one Ser/Thr kinase site. The 23546 nucleic acid encodes a polypeptide with similarities to casein kinases I. For example, members of the casein kinase I (CKI) family recognize and phosphorylate serine and threonine residues near acidic residues in target substrate proteins. Thus the 23546 encoded polypeptide is expected to be a kinase and function in the phosphorylation of protein substrates. Since the 23546 nucleic acid was found to be expressed in liver cells and osteoblasts in particular, the encoded protein kinase is at least expected to catalyze liver specific or osteoblast specific phosphorylation reactions. Additionally, the 23546 encoded protein kinase has similarities to a putative casein kinase identified in *C. elegans*. Thus without being bound by theory, the 23546 kinase may be a human analogue of the *C. elegans* kinase.

Isolated proteins of the present invention, preferably 23546 proteins, have an amino acid sequence sufficiently homologous to the amino acid sequence of SEQ ID NO:8 or are encoded by a nucleotide sequence sufficiently homologous to SEQ ID NO:7 or SEQ ID NO:9.

As used interchangeably herein a "23546 activity", "biological activity of 23546" or "functional activity of 23546", refers to an activity exerted by a 23546 protein, polypeptide or nucleic acid molecule on a 23546 responsive cell or a 23546 protein substrate as determined in vivo, or in vitro, according to standard techniques. The biological activity of 23546 is described herein.

Accordingly, another embodiment of the invention features isolated 23546 proteins and polypeptides having a 23546 activity. Preferred proteins are 23546 proteins having at least one Ser/Thr kinase site. Additional preferred proteins have at least one Ser/Thr kinase site, and preferably a 23546 activity. Additional preferred proteins have at least one Ser/Thr kinase site and are, preferably, encoded by a nucleic acid molecule having a nucleotide sequence which hybridizes under stringent hybridization conditions to a nucleic acid molecule comprising the nucleotide sequence of SEQ ID NO:7 or SEQ ID NO:9.

Human 23546 contains the following regions or other structural features (for general information regarding PFAM identifiers, PS prefix and PF prefix domain identification numbers, refer to Sonnhammer et al. (1997) *Protein* 28:405–420 and http://www.psc.edu/general/software/packages/pfam/pfam.html):

a protein kinase domain (PFAM Accession Number PF00069, as described above) located at about amino acid residues 21 to 256 of SEQ ID NO:8;

5 N-glycosylation sites (Prosite PS00001) from about amino acids 539–542, 710–713, 749–752, 1066–1069, and 1117–1120 of SEQ ID NO:8;

1 glycosaminoglycan attachment site (Prosite PS00002) from about amino acids 2 to 5 of SEQ ID NO:8;

2 cAMP/cGMP-dependent protein kinase phosphorylation sites (Prosite PS00004) located at about amino acids 453–456 and 610–613 of SEQ ID NO:8;

20 protein kinase C phosphorylation sites (Prosite PS00005) at about amino acids 118–120, 155–157, 189–191, 237–239, 283–285, 463–465, 542–544, 634–636, 706–708, 748–750, 855–857, 910–912, 929–931, 963–965, 999–1001, 1048–1050, 1119–1121, 1154–1156, 1199–1201 and 1228–1230 of SEQ ID NO:8;

27 casein kinase II phosphorylation sites (Prosite PS00006) located at about amino acids 173–176, 237–240, 263–266, 269–272, 278–281, 300–303, 353–356, 402–405, 431–434, 469–472, 499–502, 577–580, 592–595, 654–657, 706–709, 717–720, 726–729, 786–789, 855–858, 879–882, 921–924, 929–932, 954–957, 963–966, 997–1000, 1035–1038, and 1101–1104 of SEQ ID NO:8;

16 N-myristoylation sites (Prosite PS00008) from about amino acids 29–34, 82–87, 288–293, 301–306, 327–332, 358–363, 396–401, 409–414, 529–534, 615–620, 682–687, 713–718, 724–729, 1099–1104, 1196–1201, and 1215–1220 of SEQ ID NO:8; and 1 amidation site (Prosite PS00009) from about amino acids 903–906 of SEQ ID NO:8.

The nucleotide sequence of the isolated human 23546 cDNA and the predicted amino acid sequence of the human 23546 polypeptide are shown in FIG. 7 and in SEQ ID NOs:7 and 8, respectively.

The human 23546 gene, which is approximately 5499 nucleotides in length, encodes a protein having a molecular weight of approximately 137 kD and which is approximately 1244 amino acid residues in length.

As used herein, the term "protein kinase domain" includes an amino acid sequence of about 200 to 260 amino acid residues in length and having a bit score for the alignment of the sequence to the protein kinase domain (HMM) of at least 50. Preferably a protein kinase domain mediates reversible protein phosphorylation. Preferably, a protein kinase domain includes at least about 200 to 260 amino acids, more preferably about 230 to 260 amino acid residues, or about 240 to 250 amino acids and has a bit score for the alignment of the sequence to the protein kinase domain (HMM) of at least 50, more preferably 75, most preferably 100 or greater.

An alignment of the protein kinase domain (amino acids 21 to 256 of SEQ ID NO:8) of human 23546 with a consensus amino acid sequence (SEQ ID NO:15) derived from a hidden Markov model is depicted in FIG. 9.

In a preferred embodiment, a 23546 polypeptide or protein has a "protein kinase domain" or a region which includes at least about 200 to 260 more preferably about 230 to 260 or 240 to 250 amino acid residues and has at least about 60%, 70% 80% 90% 95%, 99%, or 100% homology with a "protein kinase domain," e.g., the protein kinase domain of human 23546 (e.g., residues 21 to 256 of SEQ ID NO:8).

To identify the presence of a "protein kinase" domain in a 23546 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/Pfam/HMM_search), as described above. A search was performed against the HMM database resulting in the identification of a "protein kinase domain" domain in the amino acid sequence of human 23546 at about residues 21 to 256 of SEQ ID NO:8 (see FIG. 9).

For further identification of protein kinase domains, or to identify the presence of a "protein kinase" domain in a 23546 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263–267), as described above.

ProDom (derived from BLAST search) alignments of the amino acid sequence of human 23546 revealed that 23546 is similar to a serine/threonine kinase protein and to casein kinases. The serine/threonine kinase amino acid molecule is approximately 59% identical to 23546, over amino acids 82–129. The casein kinase amino acid molecule is approximately 32–34% identical to 23546, over amino acids 9–112 and 134–222.

A 23546 family member can include at least one protein kinase domain; and at least one transmembrane or non-transmembrane domains. Furthermore, a 23546 family member can include at least one, two, three, four, preferably five N-glycosylation sites (Prosite PS00001); at least one glycosaminoglycan attachment site (Prosite PS00002); at least one, preferably two cAMP/cGMP-dependent protein kinase phosphorylation sites (Prosite PS00004); at least one, two, three, four, five, six, seven, eight, nine, ten, eleven, twelve, thirteen, fourteen, fifteen, sixteen, seventeen, eighteen, nineteen and preferably twenty protein kinase C phosphorylation sites (Prosite PS00005); at least one, two, three, four, five, six, seven, eight, nine, ten, eleven, twelve, thirteen, fourteen, fifteen, sixteen, seventeen, eighteen, nineteen, twenty-one, twenty-two, twenty-three, twenty-four, twenty-five, twenty-six and preferably twenty-seven casein kinase II phosphorylation sites (Prosite PS00006); at least one, two, three, four, five, six, seven, eight, nine, ten, eleven, twelve, thirteen, fourteen, fifteen, and preferably sixteen N-myristoylation sites (Prosite PS00008); and at least one amidation site (Prosite PS00009).

As the 23546 polypeptides of the invention can modulate 23546-mediated activities, they can be useful for developing novel diagnostic and therapeutic agents for protein kinase-associated or other 23546-associated disorders, as described below.

D. The 13887 Nucleic Acid and Protein Molecules

In another embodiment, the isolated proteins of the present invention, preferably 13887 proteins, are identified based on the presence of at least one Ser/Thr kinase site. Since the 13887 nucleic acid was found to be expressed in normal and tumor cells of the brain, breast, ovary, lung, colon and liver in particular, the encoded protein kinase is at least expected to catalyze cell type specific phosphorylation reactions in those cells. The 13887 nucleic acid encodes a polypeptide with homology to previously identified Ser/Thr kinases including the rat KIS protein kinase (Maucuer et al. Journal of Biological Chemistry, Vol. 272(37):23151–23156 (1997)), which has been demonstrated to have autophosphorylating activity as well as the ability to phosphorylate known protein substrates. Thus the 13887 encoded polypeptide is expected to be a kinase and function in the phosphorylation of protein substrates. Both the 13887 encoded kinase and the rat KIS protein kinase have a C-terminal domain containing characteristics of an RNA recognition domain. The rat KIS kinase also displays nuclear localization upon overexpression in eukaryotic cells. As such the 13887 encoded kinase is at least expected to have additional biological activities similar to the KIS protein kinase, including possible RNA interactions and nuclear localization.

Isolated proteins of the present invention, preferably 13887 proteins, have an amino acid sequence sufficiently homologous to the amino acid sequence of SEQ ID NO:11 or are encoded by a nucleotide sequence sufficiently homologous to SEQ ID NO:10 or SEQ ID NO:12.

As used interchangeably herein a "13887 activity", "biological activity of 13887" or "functional activity of 13887", refers to an activity exerted by a 13887 protein, polypeptide or nucleic acid molecule on a 13887 responsive cell or a 13887 protein substrate as determined in vivo, or in vitro, according to standard techniques. The biological activity of 13887 is described herein.

Accordingly, another embodiment of the invention features isolated 23546 proteins and polypeptides having a 13887 activity. Preferred proteins are 13887 proteins having at least one Ser/Thr kinase site. Additional preferred proteins have at least one Ser/Thr kinase site and, preferably a 13887 activity. Additional preferred proteins have at least one Ser/Thr kinase site and are, preferably, encoded by a nucleic acid molecule having a nucleotide sequence which hybridizes under stringent hybridization conditions to a nucleic acid molecule comprising the nucleotide sequence of SEQ ID NO:10 or SEQ ID NO:12.

Human 13887 contains the following regions or other structural features (for general information regarding PFAM identifiers, PS prefix and PF prefix domain identification numbers, refer to Sonnhammer et al. (1997) *Protein* 28:405–420 and http://www.psc.edu/general/software/packages/pfam/pfam.html):

a protein kinase domain (PFAM Accession Number PF00069, as described above) located at about amino acid residues 231 to 304 of SEQ ID NO:11;

1 N-glycosylation site (Prosite PS00001) from about amino acids 253–256 of SEQ ID NO:11;

4 protein kinase C phosphorylation sites (Prosite PS00005) at about amino acids 181–183, 244–246, 290–292 and 390–392 of SEQ ID NO:11;

5 casein kinase 11 phosphorylation sites (Prosite PS00006) located at about amino acids 67–70, 117–120, 181–184, 215–218, and 221–224 of SEQ ID NO:11;

4 N-myristoylation sites (Prosite PS00008) from about amino acids 3–8, 30–35, 47–52 and 60–65 of SEQ ID NO:11; and 1 coiled coil site (as predicted in PSORT) from about amino acids 325–352 of SEQ ID NO:11.

The nucleotide sequence of the isolated human 13887 cDNA and the predicted amino acid sequence of the human 13887 polypeptide are shown in FIG. 10 and in SEQ ID Nos:10 and 11, respectively.

The human 13887 gene, which is approximately 2623 nucleotides in length, encodes a protein having a molecular weight of approximately 46.2 kD and which is approximately 419 amino acid residues in length.

As used herein, the term "protein kinase domain" includes an amino acid sequence of about 200 to 350 amino acid residues in length and having a bit score for the alignment of the sequence to the protein kinase domain (HMM) of at least 100. Preferably a protein kinase domain mediates reversible protein phosphorylation. Preferably, a protein kinase domain includes at least about 200 to 320 amino acids, more preferably about 250 to 320 amino acid residues, or about 270 to 280 amino acids and has a bit score for the alignment of the sequence to the protein kinase domain (HMM) of at least 100, more preferably 130, most preferably 140 or greater.

An alignment of the protein kinase domain (amino acids 23 to 304 of SEQ ID NO:11) of human 13887 with a consensus amino acid sequence (SEQ ID NO:16) derived from a hidden Markov model is depicted in FIG. 12.

In a preferred embodiment, a 13887 polypeptide or protein has a "protein kinase domain" or a region which includes at least about 200 to 350, more preferably about 250 to 300 or 270 to 290 amino acid residues and has at least about 60%, 70% 80% 90% 95%, 99%, or 100% homology with a "protein kinase domain," e.g., the protein kinase domain of human 13887 (e.g., residues 23 to 304 of SEQ ID NO:11).

To identify the presence of a "protein kinase" domain in a 13887 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/Pfam/HMM_search), as described above. A search was performed against the HMM database resulting in the identification of a "protein kinase domain" domain in the amino acid sequence of human 13887 at about residues 23 to 304 of SEQ ID NO:11 (see FIG. 12).

For further identification of protein kinase domains, or to identify the presence of a "protein kinase" domain in a 13887 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263–267), as described above.

ProDom (derived from BLAST search) alignments of the amino acid sequence of human 13887 revealed that 13887 is similar to a serine/threonine kinase sequence. This amino acid molecule is approximately 100% identical to 13887, over about amino acids 1–23.

A 13887 polypeptide can include at least one "transmembrane domain" or regions homologous with a "transmembrane domain", as described above.

Figure 11:
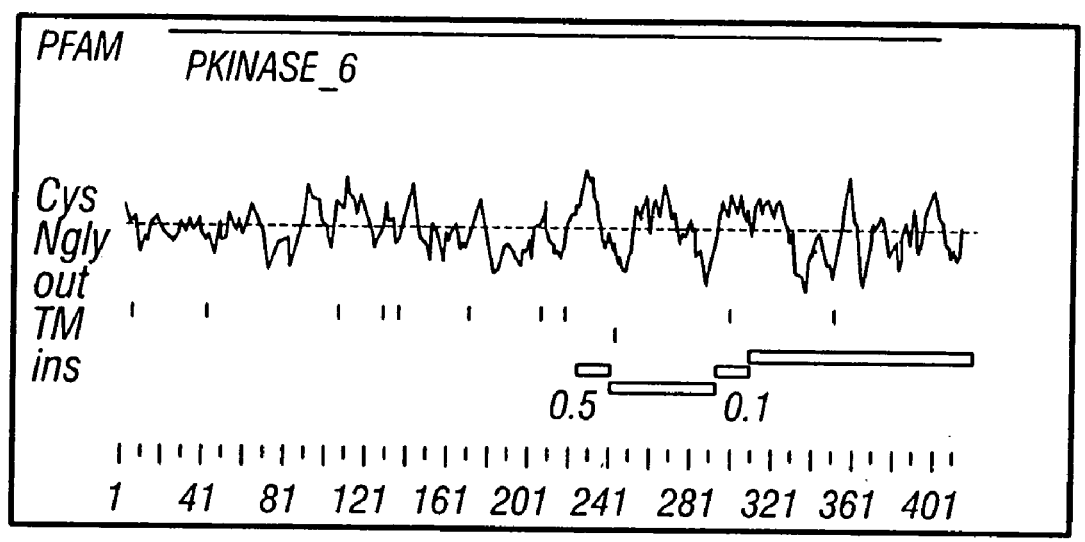
FIG. 11 depicts a hydropathy plot of human 13887. Relatively hydrophobic residues are shown above the dashed horizontal line, and relatively hydrophilic residues are shown below the dashed horizontal line. The location of the transmembrane domains, and the extracellular and intracellular loops is also indicated. The cysteine residues (cys) and N-glycosylation sites (Ngly) are indicated by short vertical lines just below the hydropathy trace. The numbers corresponding to the amino acid sequence of human 13887 are indicated. Polypeptides of the invention include fragments which include: all or part of a hydrophobic sequence, e.g., a sequence above the dashed line, e.g., the sequence from about amino acid 95 to 105, from about 115 to 130, and from about 225 to 240 of SEQ ID NO:11; all or part of a hydrophilic sequence, e.g., a sequence below the dashed line, e.g., the sequence from about amino acid 190 to 210, from about 240 to 255, and from about 330 to 350 of SEQ ID NO:11; a sequence which includes a Cys, or a glycosylation site.
Figure 13A:
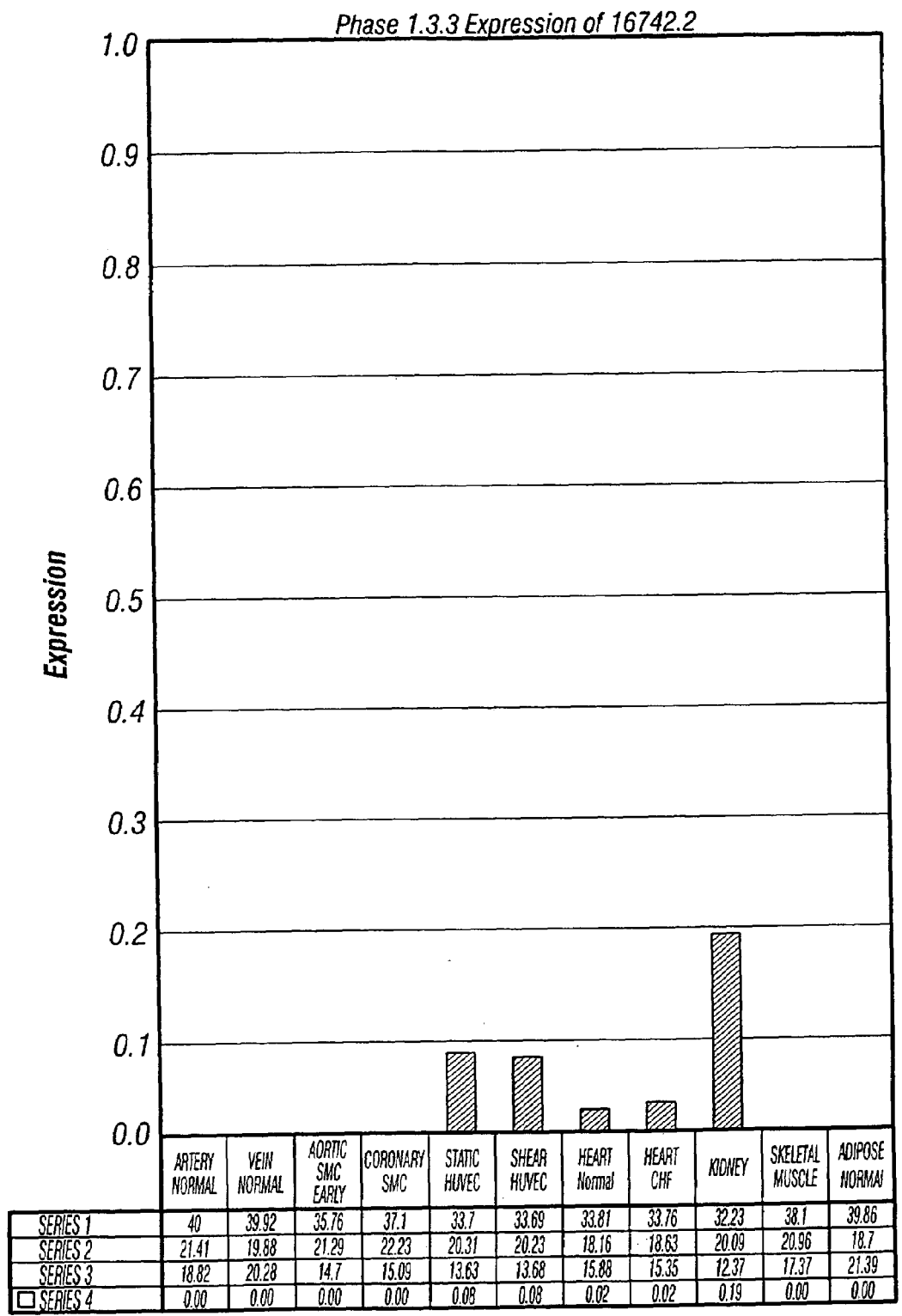
FIG. 13A–D is a panel bar graph depicting the relative expression of 16742 RNA relative to a no template control in a panel of human tissues or cells, including but not limited to artery, vein, aortic smooth muscle cells (SMC) (early), coronary SMC, shear and static human umbilical vein endothelial cells (HUVEC), heart, kidney, skeletal muscle, adipose, pancreas, skin, bone cells (e.g., osteoclasts and osteoblasts), skin, spinal cord, brain cortex, brain hypothalamus, nerve dorsal root ganglia (DRS), glial cells, glioblastoma, normal breast, breast tumor, normal ovary, ovary tumor, normal prostate and prostate tumor, epithelial, colon, liver, lung, fibroblasts, bone marrow, activated PBMC, among others, detected using real-time quantitative RT-PCR Taq Man analysis. The graph indicates significant expression in normal human brain cortex.
Figure 13B:
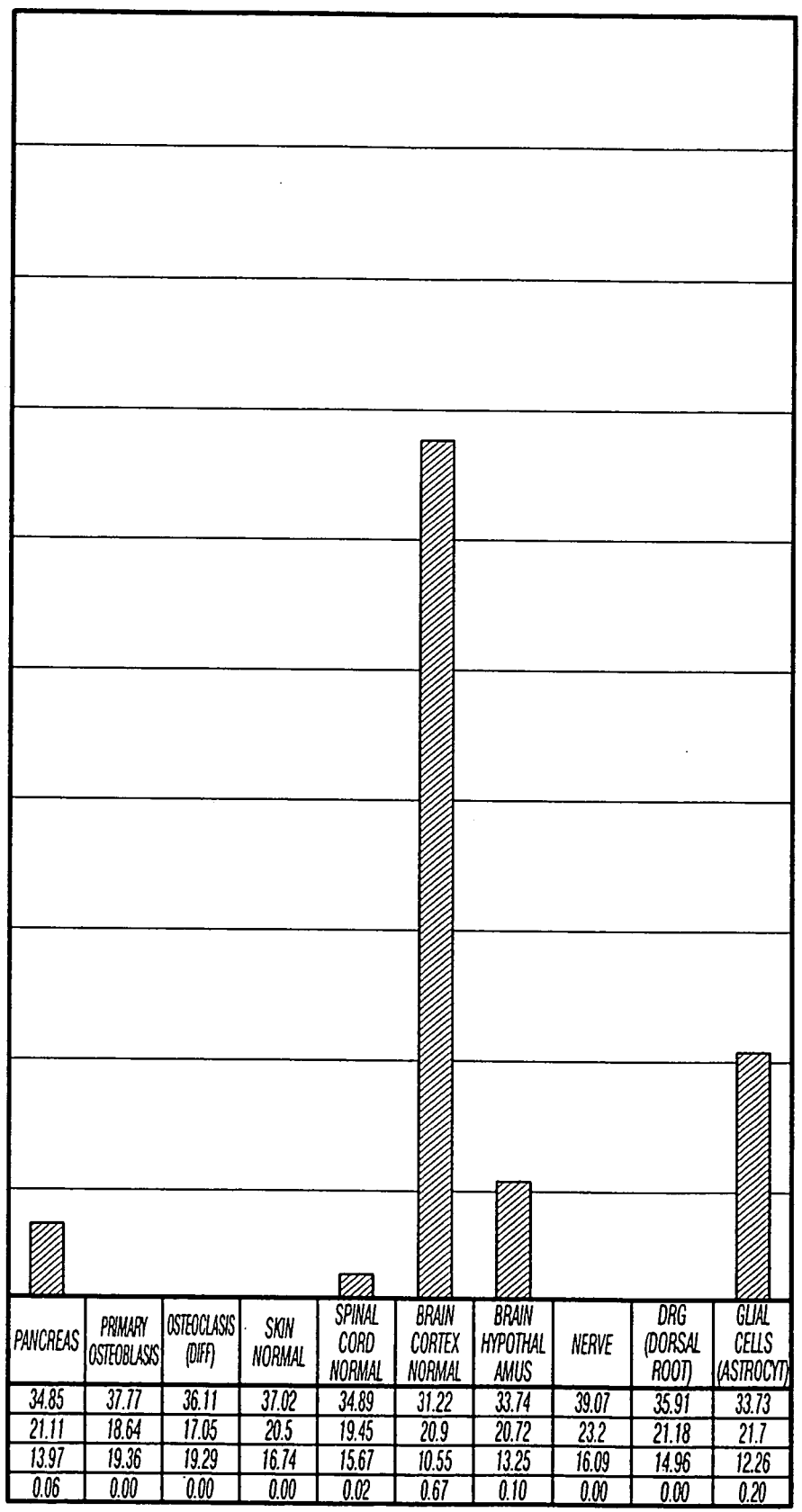
Figure 13C:
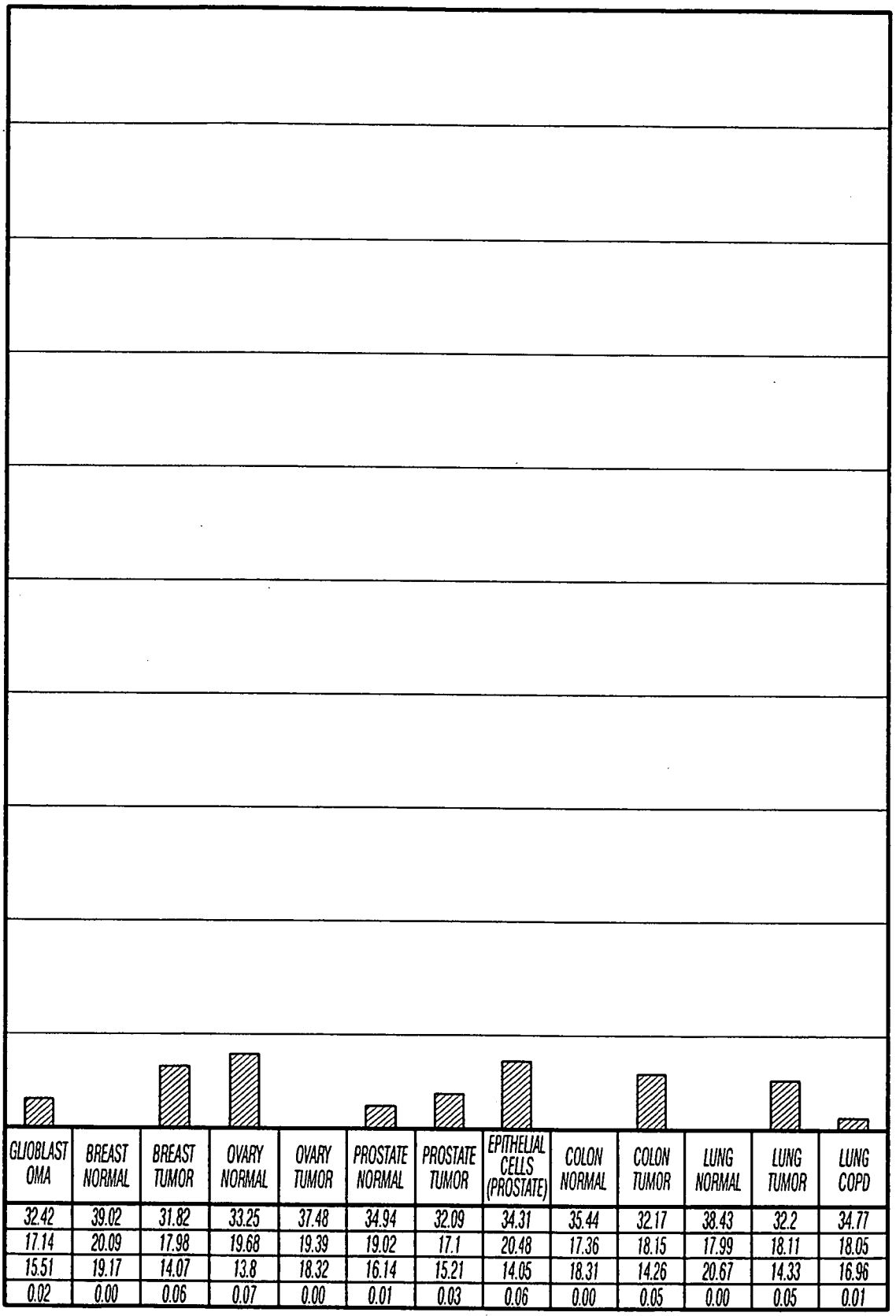
Figure 13D:
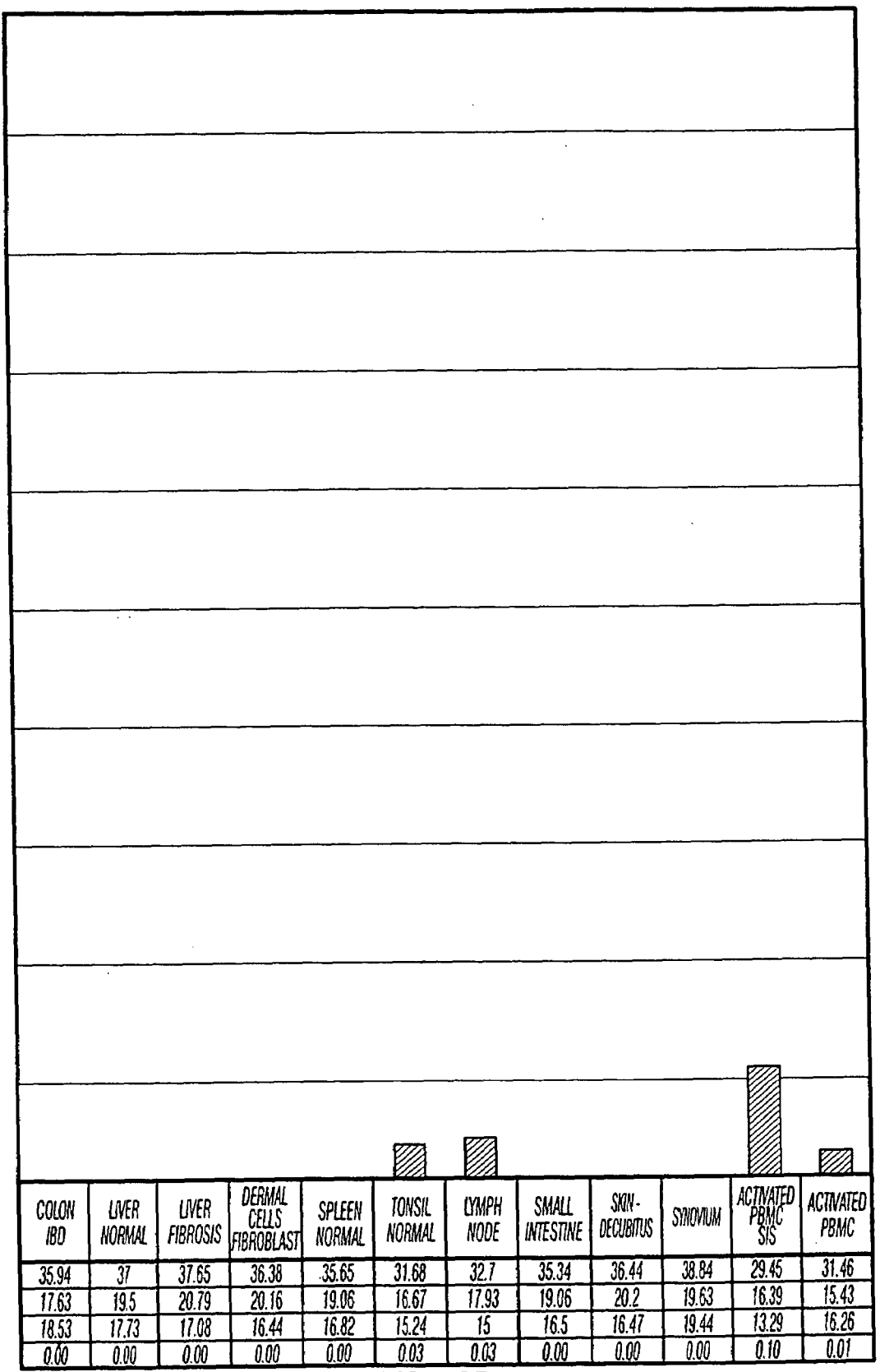

In a preferred embodiment, a 13887 polypeptide or protein has at least one "transmembrane domain" or a region which includes at least about 10 to 30 more preferably about 10 to 25 or 15 to 20 amino acid residues and has at least about 60%, 70% 80% 90% 95%, 99%, or 100% homology with a "transmembrane domain," e.g., the transmembrane domains of human 13887 (e.g., residues 225–241 and 293–309 of SEQ ID NO:11). The transmembrane domain of human 13887 is visualized in the hydropathy plot (FIG. 11) as regions of about 15 to 25 amino acids where the hydropathy trace is mostly above the horizontal line.

To identify the presence of a "transmembrane" domain in a 13887 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) Biochemistry 33:3038–3049).

A 13887 polypeptide can include at least one "non-transmembrane region." As used herein, the term "non-transmembrane region" includes an amino acid sequence not identified as a transmembrane domain. The non-transmembrane regions in 13887 are located at about amino acids 1–224, 242–292 and 309–419 of SEQ ID NO:11.

The non-transmembrane regions of 13887 include at least one, and preferably two, cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 50, preferably about 1 to 100, more preferably about 1 to 200, or even more preferably about 1 to 225 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 13887 protein. For example, an N-terminal cytoplasmic domain is located at about amino acid residues 1 to 224 SEQ ID NO:11.

In a preferred embodiment, a polypeptide or protein has an N-terminal cytoplasmic domain or a region which includes at least about 5, preferably about 1 to 100, and more preferably about 1 to 224 amino acid residues and has at least about 60%, 70% 80% 90% 95%, 99%, or 100% homology with an "N-terminal cytoplasmic domain," e.g., the N-terminal cytoplasmic domain of human 13887 (e.g., residues 1 to 224 of SEQ ID NO:11).

In another embodiment, a cytoplasmic region of a 13887 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 50, preferably about 50 to 150, more preferably about 100 to 120 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 13887 protein. For example, a C-terminal cytoplasmic domain is located at about amino acid residues 310 to 419 of SEQ ID NO:11.

In a preferred embodiment, a 13887 polypeptide or protein has a C-terminal cytoplasmic domain or a region which includes at least about 5, preferably about 50 to 120, and more preferably about 100 to 120 amino acid residues and has at least about 60%, 70% 80% 90% 95%, 99%, or 100% homology with a "C-terminal cytoplasmic domain," e.g., the C-terminal cytoplasmic domain of human 13887 (e.g., residues 310 to 419 of SEQ ID NO:11).

In another embodiment, a 13887 protein includes at least one cytoplasmic loop. As used herein, the term "loop" includes an amino acid sequence that resides outside of a phospholipid membrane, having a length of at least about 10, preferably about 10 to 100, more preferably about 50 to 55 amino acid residues, and has an amino acid sequence that connects two transmembrane domains within a protein or polypeptide. Accordingly, the N-terminal amino acid of a loop is adjacent to a C-terminal amino acid of a transmembrane domain in a 13887 molecule, and the C-terminal amino acid of a loop is adjacent to an N-terminal amino acid of a transmembrane domain in a 13887 molecule. As used herein, a "cytoplasmic loop" includes a loop located inside of a cell or within the cytoplasm of a cell. For example, a "cytoplasmic loop" can be found at about amino acid residues 242 to 292 of SEQ ID NO:11.

In a preferred embodiment, a 13887 polypeptide or protein has at least one cytoplasmic loop or a region which includes at least about 10, preferably about 10 to 100, more preferably about 50 to 690 amino acid residues and has at least about 60%, 70% 80% 90% 95%, 99%, or 100% homology with a "cytoplasmic loop," e.g., at least one cytoplasmic loop of human 13887 (e.g., residues 242–292 of SEQ ID NO:11).

A 13887 family member can include at least one protein kinase domain; and at least one or two and preferably two or three transmembrane or non-transmembrane domains. Furthermore, a 13887 family member can include at least one N-glycosylation sites (PS00001); at least one, two, three, preferably four protein kinase C phosphorylation sites (PS00005); at least one, two, three, four, and preferably five casein kinase II phosphorylation sites (PS00006); at least one, two, three, and preferably four N-myristoylation sites (PS00008); and at least one coiled coil site.

As the 13887 polypeptides of the invention can modulate 13887-mediated activities, they can be useful for developing novel diagnostic and therapeutic agents for protein kinase-associated or other 13887-associated disorders, as described below.

Various aspects of the invention are described in further detail in the following subsections:

I. Isolated Nucleic Acid Molecules

One aspect of the invention pertains to isolated nucleic acid molecules that encode 3714, 16742, 23546, or 13887 proteins or biologically active portions thereof, as well as nucleic acid fragments sufficient for use as hybridization probes to identify 3714-,16742-, 23546-, or 13887-encoding nucleic acids (e.g., 3714, 16742, 23546, or 13887 mRNA) and fragments for use as PCR primers for the amplification or mutation of 3714, 16742, 23546, or 13887 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated 3714, 16742, 23546, or 13887 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, or a portion thereof, can be isolated using standard molecular biology techniques and the sequence information provided herein. For example, using all or portion of the nucleic acid sequence of SEQ ID NO:1, or the nucleotide sequence of SEQ ID NO:3, as a hybridization probe, nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 can be isolated by the polymerase chain reaction (PCR) using synthetic oligonucleotide primers designed based upon the sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to 3714, 16742, 23546, or 13887 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the partial human 3714 cDNA. This cDNA comprises sequences encoding the partial human 3714 protein (i.e., "the coding region", as shown in SEQ ID NO:3), as well as 5' untranslated sequences (139 nucleotides before the coding region) and 3' untranslated sequences (477 nucleotides after the coding region). Alternatively, the nucleic acid molecule can comprise only the coding region of SEQ ID NO:1 (e.g., corresponding to SEQ ID NO:3).

In a preferred embodiment, an isolated nucleic acid molecule of the invention comprises the nucleotide sequence shown in SEQ ID NO:4. The sequence of SEQ ID NO:4 corresponds to the partial human 16742 cDNA. This cDNA comprises sequences encoding the partial human 16742 protein (i.e., "the coding region", as shown in SEQ ID NO:6), as well as 5' untranslated sequences (357 nucleotides before the coding region) and 3' untranslated sequences (565 nucleotides after the coding region). Alternatively, the nucleic acid molecule can comprise only the coding region of SEQ ID NO:6 (e.g., corresponding to SEQ ID NO:6).

In a preferred embodiment, an isolated nucleic acid molecule of the invention comprises the nucleotide sequence shown in SEQ ID NO:7. The sequence of SEQ ID NO:7 corresponds to the partial human 23546 cDNA. This cDNA comprises sequences encoding the partial human 23546 protein (i.e., "the coding region", as shown in SEQ ID NO:9), as well as the 5' untranslated sequences (316 nucleotides before the coding region) and 3' untranslated sequences (1448 nucleotides after the coding region). Alternatively, the nucleic acid molecule can comprise only the coding region of SEQ ID NO:7 (e.g., corresponding to SEQ ID NO:9).

In a preferred embodiment, an isolated nucleic acid molecule of the invention comprises the nucleotide sequence shown in SEQ ID NO:10. The sequence of SEQ ID NO:10 corresponds to the partial human 13887 cDNA. This cDNA comprises sequences encoding the partial human 13887 protein (i.e., "the coding region", from nucleotides 275–754), as well as 5' untranslated sequences (267 nucleotides before the coding region) and 3' untranslated sequences (1096 nucleotides after the coding region). Alternatively, the nucleic acid molecule can comprise only the coding region of SEQ ID NO:10 (e.g., nucleotides 275–754, corresponding to SEQ ID NO:12).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, or a portion of any of these nucleotide sequences. A nucleic acid molecule which is complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, respectively, such that it can hybridize to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, respectively, thereby forming a stable duplex.

In still another preferred embodiment, an isolated nucleic acid molecule of the present invention comprises a nucleotide sequence which is at least about 50%, 54%, 55%, 60%, 62%, 65%, 70%, 75%, 78%, 80%, 85%, 86%, 90%, 95%, 97%, 98% or more homologous to the nucleotide sequence (e.g., to the entire length of the nucleotide sequence) shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, or a portion of any of these nucleotide sequences.

Moreover, the nucleic acid molecule of the invention can comprise only a portion of the nucleic acid sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, for example a fragment which can be used as a probe or primer or a fragment encoding a biologically active portion of a 3714, 16742, 23546, or 13887 protein. The nucleotide sequence determined from the cloning of the 3714, 16742, 23546, or 13887 gene allows for the generation of probes and primers designed for use in identifying and/or cloning other 3714, 16742, 23546, or 13887 family members, as well as 3714, 16742, 23546, or 13887 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, of an anti-sense sequence of SEQ ID NO:10, SEQ ID NO:3, SEQ ID NO:4, SEQ ID NO:6, SEQ ID NO:7, SEQ ID NO:9, SEQ ID NO:10, or SEQ ID NO:12, or of a naturally occurring allelic variant or mutant of SEQ ID NO:1, SEQ ID NO:3, SEQ ID NO:4, SEQ ID NO:6, SEQ ID NO:7, SEQ ID NO:9, SEQ ID NO:10, or SEQ ID NO:12. In an exemplary embodiment, a nucleic acid molecule of the present invention comprises a nucleotide sequence which is at least 350, 400, 450, 500, 550, 600, 650, 700, 750, or 800 nucleotides in length and hybridizes under stringent hybridization conditions to a nucleic acid molecule of SEQ ID NO:1, SEQ ID NO:3, SEQ ID NO:4, SEQ ID NO:6, SEQ ID NO:7, SEQ ID NO:9, SEQ ID NO:10, or SEQ ID NO:12.

Probes based on the 3714, 16742, 23546, or 13887 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a 3714, 16742, 23546, or 13887 protein, such as by measuring a level of a 3714-, 16742-, 23546-, or 13887-encoding nucleic acid in a sample of cells from a subject e.g., detecting 3714, 16742, 23546, or 13887 mRNA levels or determining whether a genomic 3714, 16742, 23546, or 13887 gene has been mutated or deleted.

A nucleic acid fragment encoding a "biologically active portion of a 3714, 16742, 23546, or 13887 protein" can be prepared by isolating a portion of the nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, which encodes a polypeptide having a 3714, 16742, 23546, or 13887 biological activity (the biological activities of the 3714, 16742, 23546, or 13887 proteins are described herein), expressing the encoded portion of the 3714, 16742, 23546, or 13887 protein (e.g., by recombinant expression in vitro) and assessing the activity of the encoded portion of the 3714, 16742, 23546, or 13887 protein.

The invention further encompasses nucleic acid molecules that differ from the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, due to the degeneracy of the genetic code and, thus, encode the same 3714, 16742, 23546, or 13887 proteins as those encoded by the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12. In another embodiment, an isolated nucleic acid molecule of the invention has a nucleotide sequence encoding a protein having an amino acid sequence shown in SEQ ID NO:2, SEQ ID NO:5, SEQ ID NO:8, or SEQ ID NO:11.

In addition to the 3714, 16742, 23546, or 13887 nucleotide sequences shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, it will be appreciated by those skilled in the art that DNA sequence polymorphisms that lead to changes in the amino acid sequences of the 3714, 16742, 23546, or 13887 proteins may exist within a population (e.g., the human population). Such genetic polymorphism in the 3714, 16742, 23546, or 13887 genes may exist among individuals within a population due to natural allelic variation. As used herein, the terms "gene" and "recombinant gene" refer to nucleic acid molecules which include an open reading frame encoding an 3714, 16742, 23546, or 13887 protein, preferably a mammalian 3714, 16742, 23546, or 13887 protein, and can further include non-coding regulatory sequences, and introns. Such natural allelic variations include both functional and non-functional 3714, 16742, 23546, or 13887 proteins and can typically result in 1–5% variance in the nucleotide sequence of a 3714, 16742, 23546, or 13887 gene. Any and all such nucleotide variations and resulting amino acid polymorphisms in 3714, 16742, 23546, or 13887 genes that are the result of natural allelic variation and that do not alter the functional activity of a 3714, 16742, 23546, or 13887 protein are intended to be within the scope of the invention.

Moreover, nucleic acid molecules encoding other 3714, 16742, 23546, or 13887 family members and, thus, which have a nucleotide sequence which differs from the 3714, 16742, 23546, or 13887 sequences of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 are intended to be within the scope of the invention. For example, another 3714, 16742, 23546, or 13887 cDNA can be identified based on the nucleotide sequence of human 3714, 16742, 23546, or 13887. Moreover, nucleic acid molecules encoding 3714, 16742, 23546, or 13887 proteins from different species, and thus which have a nucleotide sequence which differs from the 3714, 16742, 23546, or 13887 sequences of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 are intended to be within the scope of the invention. For example, a mouse 3714, 16742, 23546, or 13887 cDNA can be identified based on the nucleotide sequence of a human 3714, 16742, 23546, or 13887.

Nucleic acid molecules corresponding to natural allelic variants and homologues of the 3714, 16742, 23546, or 13887 cDNAs of the invention can be isolated based on their homology to the 3714, 16742, 23546, or 13887 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12. In other embodiment, the nucleic acid is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the 3714, 16742, 23546, or 13887 sequences that may exist in the population, the skilled artisan will further appreciate that changes can be introduced by mutation into the nucleotide sequences of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, thereby leading to changes in the amino acid sequence of the encoded 3714, 16742, 23546, or 13887 proteins, without altering the functional ability of the 3714, 16742, 23546, or 13887 proteins. For example, nucleotide substitutions leading to amino acid substitutions at "non-essential" amino acid residues can be made in the sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12. A "non-essential" amino acid residue is a residue that can be altered from the wild-type sequence of 3714, 16742, 23546, or 13887 (e.g., the sequence of SEQ ID NO:2, SEQ ID NO:5, SEQ ID NO:8, or SEQ ID NO:11) without altering the biological activity, whereas an "essential" amino acid residue is required for biological activity. For example, amino acid residues that are conserved among the 3714, 16742, 23546, or 13887 proteins of the present invention, are predicted to be particularly unamenable to alteration. Furthermore, additional amino acid residues that are conserved between the 3714, 16742, 23546, or 13887 proteins of the present invention and other 3714, 16742, 23546, or 13887 family members are not likely to be amenable to alteration.

Accordingly, another aspect of the invention pertains to nucleic acid molecules encoding 3714, 16742, 23546, or 13887 proteins that contain changes in amino acid residues that are not essential for activity. Such 3714, 16742, 23546, or 13887 proteins differ in amino acid sequence from SEQ ID NO:2, SEQ ID NO:5, SEQ ID NO:8, or SEQ ID NO:11, yet retain biological activity. In one embodiment, the isolated nucleic acid molecule comprises a nucleotide sequence encoding a protein, wherein the protein comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:2, SEQ ID NO:5, SEQ ID NO:8, or SEQ ID NO:11 (e.g., the entire amino acid sequence of SEQ ID NO:2, SEQ ID NO:5, SEQ ID NO:8, or SEQ ID NO:11).

An isolated nucleic acid molecule encoding a 3714, 16742, 23546, or 13887 protein homologous to the protein of SEQ ID NO:2, SEQ ID NO:5, SEQ ID NO:8, or SEQ ID NO:11 can be created by introducing one or more nucleotide substitutions, additions or deletions into the nucleotide sequence of SEQ ID NO:1, SEQ ID NO:4, SEQ ID NO:7, or SEQ ID NO:10, respectively, such that one or more amino acid substitutions, additions or deletions are introduced into the encoded protein. Mutations can be introduced into SEQ ID NO:1, SEQ ID NO:4, SEQ ID NO:7, or SEQ ID NO:10 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 3714, 16742, 23546, or 13887 protein is preferably replaced with another amino acid residue from the same side chain family. Alternatively, in another embodiment, mutations can be introduced randomly along all or part of a 3714, 16742, 23546, or 13887 coding sequence, such as by saturation mutagenesis, and the resultant mutants can be screened for 3714, 16742, 23546, or 13887 biological activity to identify mutants that retain activity. Following mutagenesis of SEQ ID NO:1, SEQ ID NO:4, SEQ ID NO:7, or SEQ ID NO:10, the encoded protein can be expressed recombinantly and the activity of the protein can be determined.

In a preferred embodiment, a mutant 3714, 16742, 23546, or 13887 protein can be assayed for the ability to: 1) regulate transmission of signals from cellular receptors, e.g., cardiac cell growth factor receptors; 2) control entry of cells into mitosis; 3) modulate cellular differentiation; 4) modulate cell death; or 5) regulate cytoskeleton function, e.g., actin bundling.

In addition to the nucleic acid molecules encoding 3714, 16742, 23546, or 13887 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 3714, 16742, 23546, or 13887 coding strand, or only to a portion thereof. In one embodiment, an antisense nucleic acid molecule is antisense to a "coding region" of the coding strand of a nucleotide sequence encoding 3714, 16742, 23546, or 13887. The term "coding region" refers to the region of the nucleotide sequence comprising codons which are translated into amino acid residues (e.g., the coding region of human 3714 corresponds to SEQ ID NO:3). In another embodiment, the antisense nucleic acid molecule is antisense to a "noncoding region" of the coding strand of a nucleotide sequence encoding 3714, 16742, 23546, or 13887. The term "non-coding region" refers to 5' and 3' sequences which flank the coding region that are not translated into amino acids (i.e., also referred to as 5' and 3' untranslated regions).

Given the coding strand sequences encoding 3714, 16742, 23546, or 13887 disclosed herein (e.g., SEQ ID NO:3, SEQ ID NO:6, SEQ ID NO:9, or SEQ ID NO:12), antisense nucleic acids of the invention can be designed according to the rules of Watson and Crick base pairing. The antisense nucleic acid molecule can be complementary to the entire coding region of 3714, 16742, 23546, or 13887 mRNA, but more preferably is an oligonucleotide which is antisense to only a portion of the coding or noncoding region of 3714, 16742, 23546, or 13887 mRNA. For example, the antisense oligonucleotide can be complementary to the region surrounding the translation start site of 3714, 16742, 23546, or 13887 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a 3714, 16742, 23546, or 13887 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave 3714, 16742, 23546, or 13887 mRNA transcripts to thereby inhibit translation of 3714, 16742, 23546, or 13887 mRNA. A ribozyme having specificity for a 3714-, 16742-, 23546-, or 13887-encoding nucleic acid can be designed based upon the nucleotide sequence of a 3714, 16742, 23546, or 13887 cDNA disclosed herein (i.e., SEQ ID NO:1, SEQ ID NO:3, SEQ ID NO:4, SEQ ID NO:6, SEQ ID NO:7, SEQ ID NO:9, SEQ ID NO:10, or SEQ ID NO:12). For example, a derivative of a Tetrahymena L-19 IVS RNA can be constructed in which the nucleotide sequence of the active site is complementary to the nucleotide sequence to be cleaved in a 3714-, 16742-, 23546-, or 13887-encoding mRNA. See, e.g., Cech et al. U.S. Pat. No. 4,987,071; and Cech et al. U.S. Pat. No. 5,116,742. Alternatively, 3714, 16742, 23546, or 13887 mRNA can be used to select a catalytic RNA having a specific ribonuclease activity from a pool of RNA molecules. See, e.g., Bartel, D. and Szostak, J. W. (1993) *Science* 261:1411–1418.

Alternatively, 3714, 16742, 23546, or 13887 gene expression can be inhibited by targeting nucleotide sequences complementary to the regulatory region of the 3714, 16742, 23546, or 13887 (e.g., the 3714, 16742, 23546, or 13887 promoter and/or enhancers) to form triple helical structures that prevent transcription of the 3714, 16742, 23546, or 13887 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the 3714, 16742, 23546, or 13887 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of 3714, 16742, 23546, or 13887 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 3714, 16742, 23546, or 13887 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of 3714, 16742, 23546, or 13887 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 3714, 16742, 23546, or 13887 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated 3714, 16742, 23546, or 13887 Proteins and Anti-3714, -16742, -23546, or -13887 Antibodies One aspect of the invention pertains to isolated 3714, 16742, 23546, or 13887 proteins, and biologically active portions thereof, as well as polypeptide fragments suitable for use as immunogens to raise anti-3714, -16742, -23546, or -13887 antibodies. In one embodiment, native 3714, 16742, 23546, or 13887 proteins can be isolated from cells or tissue sources by an appropriate purification scheme using standard protein purification techniques. In another embodiment, 3714, 16742, 23546, or 13887 proteins are produced by recombinant DNA techniques. Alternative to recombinant expression, a 3714, 16742, 23546, or 13887 protein or polypeptide can be synthesized chemically using standard peptide synthesis techniques.

An "isolated" or "purified" protein or biologically active portion thereof is substantially free of cellular material or other contaminating proteins from the cell or tissue source from which the 3714, 16742, 23546, or 13887 protein is derived, or substantially free from chemical precursors or other chemicals when chemically synthesized. The language "substantially free of cellular material" includes preparations of 3714, 16742, 23546, or 13887 protein in which the protein is separated from cellular components of the cells from which it is isolated or recombinantly produced. In one embodiment, the language "substantially free of cellular material" includes preparations of 3714, 16742, 23546, or 13887 protein having less than about 30% (by dry weight) of non-3714, -16742, -23546, or -13887 protein (also referred to herein as a "contaminating protein"), more preferably less than about 20% of non-3714, -16742, -23546, or -13887 protein, still more preferably less than about 10% of non-3714, -16742, -23546, or -13887 protein, and most preferably less than about 5% non-3714, -16742, -23546, or -13887 protein. When the 3714, 16742, 23546, or 13887 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of 3714, 16742, 23546, or 13887 protein in which the protein is separated from chemical precursors or other chemicals which are involved in the synthesis of the protein. In one embodiment, the language "substantially free of chemical precursors or other chemicals" includes preparations of 3714, 16742, 23546, or 13887 protein having less than about 30% (by dry weight) of chemical precursors or non-3714, -16742, -23546, or -13887 chemicals, more preferably less than about 20% chemical precursors or non-3714, -16742, -23546, or -13887 chemicals, still more preferably less than about 10% chemical precursors or non-3714, -16742, -23546, or -13887 chemicals, and most preferably less than about 5% chemical precursors or non-3714, -16742, -23546, or -13887 chemicals.

Biologically active portions of a 3714, 16742, 23546, or 13887 protein include peptides comprising amino acid sequences sufficiently homologous to or derived from the amino acid sequence of the 3714, 16742, 23546, or 13887 protein, e.g., the amino acid sequence shown in SEQ ID NO:2, SEQ ID NO:5, SEQ ID NO:8, or SEQ ID NO:11, which include less amino acids than the full length 3714, 16742, 23546, or 13887 proteins, and exhibit at least one activity of a 3714, 16742, 23546, or 13887 protein. Typically, biologically active portions comprise a domain or motif with at least one activity of the 3714, 16742, 23546, or 13887 protein. A biologically active portion of a 3714, 16742, 23546, or 13887 protein can be a polypeptide which is, for example, at least 10, 25, 50, 100 or more amino acids in length.

In a preferred embodiment, the 3714, 16742, 23546, or 13887 protein has an amino acid sequence shown in SEQ ID NO:2, SEQ ID NO:5, SEQ ID NO:8, or SEQ ID NO:11. In other embodiments, the 3714, 16742, 23546, or 13887 protein is substantially homologous to SEQ ID NO:2, SEQ ID NO:5, SEQ ID NO:8, or SEQ ID NO:1, and retains the functional activity of the protein of SEQ ID NO:2, SEQ ID NO:5, SEQ ID NO:8, or SEQ ID NO:11, yet differs in amino acid sequence due to natural allelic variation or mutagenesis, as described in detail in subsection I above. Accordingly, in another embodiment, the 3714, 16742, 23546, or 13887 protein is a protein which comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:2, SEQ ID NO:5, SEQ ID NO:8, or SEQ ID NO:11 (e.g., the entire amino acid sequence of SEQ ID NO:2, SEQ ID NO:5, SEQ ID NO:8, or SEQ ID NO:11).

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 3714, amino acid sequence of SEQ ID NO:2 having 783 amino acid residues, at least about 235, preferably at least 315, more preferably at least 290, even more preferably at least 470, and even more preferably at least 550, 625 or 705 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70 or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 3714, 16742, 23546, or 13887 nucleic acid molecules of the invention. BLAST protein searches can be performed with the XBLAST program, score=50, wordlength=3 to obtain amino acid sequences homologous to 3714, 16742, 23546, or 13887 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides 3714, 16742, 23546, or 13887 chimeric or fusion proteins. As used herein, a 3714, 16742, 23546, or 13887 "chimeric protein" or "fusion protein" comprises a 3714, 16742, 23546, or 13887 polypeptide operatively linked to a non-3714, -16742, -23546, or -13887 polypeptide. An "3714, 16742,23546, or 13887 polypeptide" refers to a polypeptide having an amino acid sequence corresponding to 3714, 16742, 23546, or 13887, whereas a "non-3714, -16742, -23546, or -13887 polypeptide" refers to a polypeptide having an amino acid sequence corresponding to a protein which is not substantially homologous to the 3714, 16742, 23546, or 13887 protein, e.g., a protein which is different from the 3714, 16742, 23546, or 13887 protein and which is derived from the same or a different organism. Within a 3714, 16742, 23546, or 13887 fusion protein the 3714, 16742, 23546, or 13887 polypeptide can correspond to all or a portion of a 3714, 16742, 23546, or 13887 protein. In a preferred embodiment, a 3714, 16742, 23546, or 13887 fusion protein comprises at least one biologically active portion of a 3714, 16742, 23546, or 13887 protein. In another preferred embodiment, a 3714, 16742, 23546, or 13887 fusion protein comprises at least two biologically active portions of a 3714, 16742, 23546, or 13887 protein. Within the fusion protein, the term "operatively linked" is intended to indicate that the 3714, 16742, 23546, or 13887 polypeptide and the non-3714, -16742, -23546, or -13887 polypeptide are fused in-frame to each other. The non-3714, -16742, -23546, or -13887 polypeptide can be fused to the N-terminus or C-terminus of the 3714, 16742, 23546, or 13887 polypeptide.

For example, in one embodiment, the fusion protein is a GST-3714, -16742, -23546, or -13887 fusion protein in which the 3714, 16742, 23546, or 13887 sequences are fused to the C-terminus of the GST sequences. Such fusion proteins can facilitate the purification of recombinant 3714, 16742, 23546, or 13887.

In another embodiment, the fusion protein is a 3714, 16742, 23546, or 13887 protein containing a heterologous signal sequence at its N-terminus. In certain host cells (e.g., mammalian host cells), expression and/or secretion of 3714, 16742, 23546, or 13887 can be increased through use of a heterologous signal sequence.

The 3714, 16742, 23546, or 13887 fusion proteins of the invention can be incorporated into pharmaceutical compositions and administered to a subject in vivo. The 3714, 16742, 23546, or 13887 fusion proteins can be used to affect the bioavailability of a 3714, 16742, 23546, or 13887 substrate. Use of 3714, 16742, 23546, or 13887 fusion proteins may be useful therapeutically for the treatment of cellular growth related disorders, e.g., cardiovascular disorders. Moreover, the 3714-, 16742-, 23546-, or 13887-fusion proteins of the invention can be used as immunogens to produce anti-3714, -16742, -23546, or -13887 antibodies in a subject, to purify 3714, 16742, 23546, or 13887 ligands and in screening assays to identify molecules which inhibit the interaction of 3714, 16742, 23546, or 13887 with a 3714, 16742, 23546, or 13887 substrate.

Preferably, a 3714, 16742, 23546, or 13887 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons:1992). Moreover, many expression vectors are commercially available that already encode a fusion moiety (e.g., a GST polypeptide). A 3714-, 16742-, 23546-, or 13887-encoding nucleic acid can be cloned into such an expression vector such that the fusion moiety is linked in-frame to the 3714, 16742, 23546, or 13887 protein.

The present invention also pertains to variants of the 3714, 16742, 23546, or 13887 proteins which function as either 3714, 16742, 23546, or 13887 agonists (mimetics) or as 3714, 16742, 23546, or 13887 antagonists. Variants of the 3714, 16742, 23546, or 13887 proteins can be generated by mutagenesis, e.g., discrete point mutation or truncation of a 3714, 16742, 23546, or 13887 protein. An agonist of the 3714, 16742, 23546, or 13887 proteins can retain substantially the same, or a subset, of the biological activities of the naturally occurring form of a 3714, 16742, 23546, or 13887 protein. An antagonist of a 3714, 16742, 23546, or 13887 protein can inhibit one or more of the activities of the naturally occurring form of the 3714, 16742, 23546, or 13887 protein by, for example, competitively modulating a cardiovascular system activity of a 3714, 16742, 23546, or 13887 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 3714, 16742, 23546, or 13887 protein.

In one embodiment, variants of a 3714, 16742, 23546, or 13887 protein which function as either 3714, 16742, 23546, or 13887 agonists (mimetics) or as 3714, 16742, 23546, or 13887 antagonists respectively can be identified by screening combinatorial libraries of mutants, e.g., truncation mutants, of a 3714, 16742, 23546, or 13887 protein for 3714, 16742, 23546, or 13887 protein agonist or antagonist activity. In one embodiment, a variegated library of 3714, 16742, 23546, or 13887 variants is generated by combinatorial mutagenesis at the nucleic acid level and is encoded by a variegated gene library. A variegated library of 3714, 16742, 23546, or 13887 variants can be produced by, for example, enzymatically ligating a mixture of synthetic oligonucleotides into gene sequences such that a degenerate set of potential 3714, 16742, 23546, or 13887 sequences is expressible as individual polypeptides, or alternatively, as a set of larger fusion proteins (e.g., for phage display) containing the set of 3714, 16742, 23546, or 13887 sequences therein. There are a variety of methods which can be used to produce libraries of potential 3714, 16742, 23546, or 13887 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 3714, 16742, 23546, or 13887 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a 3714, 16742, 23546, or 13887 protein coding sequence can be used to generate a variegated population of 3714, 16742, 23546, or 13887 fragments respectively for screening and subsequent selection of variants of a 3714, 16742, 23546, or 13887 protein. In one embodiment, a library of coding sequence fragments can be generated by treating a double stranded PCR fragment of a 3714, 16742, 23546, or 13887 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 3714, 16742, 23546, or 13887 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 3714, 16742, 23546, or 13887 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 3714, 16742, 23546, or 13887 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated 3714, 16742, 23546, or 13887 library. For example, a library of expression vectors can be transfected into a cell line which ordinarily synthesizes and secretes 3714, 16742, 23546, or 13887. The transfected cells are then cultured such that 3714, 16742, 23546, or 13887 and a particular mutant 3714, 16742, 23546, or 13887 are secreted and the effect of expression of the mutant on 3714, 16742, 23546, or 13887 activity in cell supernatants can be detected, e.g., by any of a number of enzymatic assays. Plasmid DNA can then be recovered from the cells which score for inhibition, or alternatively, potentiation of 3714, 16742, 23546, or 13887 activity, and the individual clones further characterized.

An isolated 3714, 16742, 23546, or 13887 protein, or a portion or fragment thereof, can be used as an immunogen to generate antibodies that bind 3714, 16742, 23546, or 13887 using standard techniques for polyclonal and monoclonal antibody preparation. A full-length 3714, 16742, 23546, or 13887 protein can be used or, alternatively, the invention provides antigenic peptide fragments of 3714, 16742, 23546, or 13887 for use as immunogens. The antigenic peptide of 3714, 16742, 23546, or 13887 comprises at least 8 amino acid residues of the amino acid sequence shown in SEQ ID NO:2, SEQ ID NO:5, SEQ ID NO:8, or SEQ ID NO:1 and encompasses an epitope of 3714, 16742, 23546, or 13887 such that an antibody raised against the peptide forms a specific immune complex with 3714, 16742, 23546, or 13887. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 3714, 16742, 23546, or 13887 that are located on the surface of the protein, e.g., hydrophilic regions.

A 3714, 16742, 23546, or 13887 immunogen typically is used to prepare antibodies by immunizing a suitable subject, (e.g., rabbit, goat, mouse or other mammal) with the immunogen. An appropriate immunogenic preparation can contain, for example, recombinantly expressed 3714, 16742, 23546, or 13887 protein or a chemically synthesized 3714, 16742, 23546, or 13887 polypeptide. The preparation can further include an adjuvant, such as Freund's complete or incomplete adjuvant, or similar immunostimulatory agent. Immunization of a suitable subject with an immunogenic 3714, 16742, 23546, or 13887 preparation induces a polyclonal anti-3714, -16742, -23546, or -13887 antibody response.

Accordingly, another aspect of the invention pertains to anti-3714, -16742, -23546, or -13887 antibodies. The term "antibody" as used herein refers to immunoglobulin molecules and immunologically active portions of immunoglobulin molecules, i.e., molecules that contain an antigen binding site which specifically binds (immunoreacts with) an antigen, such as 3714, 16742, 23546, or 13887. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 3714, 16742, 23546, or 13887. The term "monoclonal antibody" or "monoclonal antibody composition", as used herein, refers to a population of antibody molecules that contain only one species of an antigen binding site capable of immunoreacting with a particular epitope of 3714, 16742, 23546, or 13887. A monoclonal antibody composition thus typically displays a single binding affinity for a particular 3714, 16742, 23546, or 13887 protein with which it immunoreacts.

Polyclonal anti-3714, -16742, -23546, or -13887 antibodies can be prepared as described above by immunizing a suitable subject with a 3714, 16742, 23546, or 13887 immunogen. The anti-3714, -16742, -23546, or -13887 antibody titer in the immunized subject can be monitored over time by standard techniques, such as with an enzyme linked immunosorbent assay (ELISA) using immobilized 3714, 16742, 23546, or 13887. If desired, the antibody molecules directed against 3714, 16742, 23546, or 13887 can be isolated from the mammal (e.g., from the blood) and further purified by well known techniques, such as protein A chromatography to obtain the IgG fraction. At an appropriate time after immunization, e.g., when the anti-3714, -16742, -23546, or -13887 antibody titers are highest, antibody-producing cells can be obtained from the subject and used to prepare monoclonal antibodies by standard techniques, such as the hybridoma technique originally described by Kohler and Milstein (1 975) *Nature* 256: 495–497) (see also, Brown et al. (1981) *J. Immunol.* 127: 539–46; Brown et al. (1980) *J. Biol. Chem.*255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a 3714, 16742, 23546, or 13887 immunogen as described above, and the culture supernatants of the resulting hybridoma cells are screened to identify a hybridoma producing a monoclonal antibody that binds 3714, 16742, 23546, or 13887.

Any of the many well known protocols used for fusing lymphocytes and immortalized cell lines can be applied for the purpose of generating an anti-3714, -16742, -23546, or -13887 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 3714, 16742, 23546, or 13887, e.g., using a standard ELISA assay.

Alternative to preparing monoclonal antibody-secreting hybridom as, a monoclonal anti-3714, -16742, -23546, or -13887 antibody can be identified and isolated by screening a recombinant combinatorial immunoglobulin library (e.g., an antibody phage display library) with 3714, 16742, 23546, or 13887 to thereby isolate immunoglobulin library members that bind 3714, 16742, 23546, or 13887. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-3714, -16742, -23546, or -13887 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240: 1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-3714, -16742, -23546, or -13887 antibody (e.g., monoclonal antibody) can be used to isolate 3714, 16742, 23546, or 13887 by standard techniques, such as affinity chromatography or immunoprecipitation. An anti-3714, -16742, -23546, or -13887 antibody can facilitate the purification of natural 3714, 16742, 23546, or 13887 from cells and of recombinantly produced 3714, 16742, 23546, or 13887 expressed in host cells. Moreover, an anti-3714, -16742, -23546, or -13887 antibody can be used to detect 3714, 16742, 23546, or 13887 protein (e.g., in a cellular lysate or cell supernatant) in order to evaluate the abundance and pattern of expression of the 3714, 16742, 23546, or 13887 protein. Anti-3714, -16742, -23546, or -13887 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a 3714, 16742, 23546, or 13887 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 3714, 16742, 23546, or 13887 proteins, mutant forms of 3714, 16742, 23546, or 13887 proteins, fusion proteins, and the like).

The recombinant expression vectors of the invention can be designed for expression of 3714, 16742, 23546, or 13887 proteins in prokaryotic or eukaryotic cells. For example, 3714, 16742, 23546, or 13887 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes:1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 3714, 16742, 23546, or 13887 activity assays, (e.g., direct assays or competitive assays described in detail below), or to generate antibodies specific for 3714, 16742, 23546, or 13887 proteins, for example. In a preferred embodiment, a 3714, 16742, 23546, or 13887 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the 3714, 16742, 23546, or 13887 expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, 3714, 16742, 23546, or 13887 proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 3714, 16742, 23546, or 13887 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 3714, 16742, 23546, or 13887 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a 3714, 16742, 23546, or 13887 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a 3714, 16742, 23546, or 13887 protein. Accordingly, the invention further provides methods for producing a 3714, 16742, 23546, or 13887 protein using the host cells of the invention. In one embodiment, the method comprises culturing the host cell of invention (into which a recombinant expression vector encoding a 3714, 16742, 23546, or 13887 protein has been introduced) in a suitable medium such that a 3714, 16742, 23546, or 13887 protein is produced. In another embodiment, the method further comprises isolating a 3714, 16742, 23546, or 13887 protein from the medium or the host cell.

The host cells of the invention can also be used to produce non-human transgenic animals. For example, in one embodiment, a host cell of the invention is a fertilized oocyte or an embryonic stem cell into which 3714-, 16742-, 23546-, or 13887-coding sequences have been introduced. Such host cells can then be used to create non-human transgenic animals in which exogenous 3714, 16742, 23546, or 13887 sequences have been introduced into their genome or homologous recombinant animals in which endogenous 3714, 16742, 23546, or 13887 sequences have been altered. Such animals are useful for studying the function and/or activity of a 3714, 16742, 23546, or 13887 and for identifying and/or evaluating modulators of 3714, 16742, 23546, or 13887 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous 3714, 16742, 23546, or 13887 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a 3714-, 16742-, 23546-, or 13887-encoding nucleic acid into the male pronuclei of a fertilized oocyte, e.g., by microinjection, retroviral infection, and allowing the oocyte to develop in a pseudopregnant female foster-animal. The 3714, 16742, 23546, or 13887 cDNA sequence of SEQ ID NO:1, SEQ ID NO:4, SEQ ID NO:7, or SEQ ID NO:10 can be introduced as a transgene into the genome of a non-human animal. Alternatively, a nonhuman homologue of a human 3714, 16742, 23546, or 13887 gene, such as a mouse or rat 3714, 16742, 23546, or 13887 gene, can be used as a transgene. Alternatively, a 3714, 16742, 23546, or 13887 gene homologue, such as another 3714, 16742, 23546, or 13887 family member, can be isolated based on hybridization to the 3714, 16742, 23546, or 13887 cDNA sequences of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 (described further in subsection I above) and used as a transgene. Intronic sequences and polyadenylation signals can also be included in the transgene to increase the efficiency of expression of the transgene. A tissue-specific regulatory sequence(s) can be operably linked to a 3714, 16742, 23546, or 13887 transgene to direct expression of a 3714, 16742, 23546, or 13887 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a 3714, 16742, 23546, or 13887 transgene in its genome and/or expression of 3714, 16742, 23546, or 13887 mRNA in tissues or cells of the animals. A transgenic founder animal can then be used to breed additional animals carrying the transgene. Moreover, transgenic animals carrying a transgene encoding a 3714, 16742, 23546, or 13887 protein can further be bred to other transgenic animals carrying other transgenes.

To create a homologous recombinant animal, a vector is prepared which contains at least a portion of a 3714, 16742, 23546, or 13887 gene into which a deletion, addition or substitution has been introduced to thereby alter, e.g., functionally disrupt, the 3714, 16742, 23546, or 13887 gene. The 3714, 16742, 23546, or 13887 gene can be a human gene (e.g., the SEQ ID NO:1, SEQ ID NO:4, SEQ ID NO:7, or SEQ ID NO:10), but more preferably, is a non-human homologue of a human 3714, 16742, 23546, or 13887 gene (e.g., a cDNA isolated by stringent hybridization with the nucleotide sequence of SEQ ID NO:1, SEQ ID NO:4, SEQ ID NO:7, or SEQ ID NO:10). For example, a mouse 3714, 16742, 23546, or 13887 gene can be used to construct a homologous recombination vector suitable for altering an endogenous 3714, 16742, 23546, or 13887 gene in the mouse genome. In a preferred embodiment, the vector is designed such that, upon homologous recombination, the endogenous 3714, 16742, 23546, or 13887 gene is functionally disrupted (i.e., no longer encodes a functional protein; also referred to as a "knock out" vector). Alternatively, the vector can be designed such that, upon homologous recombination, the endogenous 3714, 16742, 23546, or 13887 gene is mutated or otherwise altered but still encodes a functional protein (e.g., the upstream regulatory region can be altered to thereby alter the expression of the endogenous 3714, 16742, 23546, or 13887 protein). In the homologous recombination vector, the altered portion of the 3714, 16742, 23546, or 13887 gene is flanked at its 5' and 3' ends by additional nucleic acid sequence of the 3714, 16742, 23546, or 13887 gene to allow for homologous recombination to occur between the exogenous 3714, 16742, 23546, or 13887 gene carried by the vector and an endogenous 3714, 16742, 23546, or 13887 gene in an embryonic stem cell. The additional flanking 3714, 16742, 23546, or 13887 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced 3714, 16742, 23546, or 13887 gene has homologously recombined with the endogenous 3714, 16742, 23546, or 13887 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The 3714, 16742, 23546, or 13887 nucleic acid molecules, 3714, 16742, 23546, or 13887 proteins, and anti-3714, -16742, -23546, or -13887 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a 3714, 16742, 23546, or 13887 protein or anti-3714, -16742, -23546, or -13887 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express 3714, 16742, 23546, or 13887 protein (e.g., via a recombinant expression vector in a host cell in gene therapy applications), to detect 3714, 16742, 23546, or 13887 mRNA (e.g., in a biological sample) or a genetic alteration in a 3714, 16742, 23546, or 13887 gene, and to modulate 3714, 16742, 23546, or 13887 activity, as described further below. The 3714, 16742, 23546, or 13887 proteins can be used to treat disorders characterized by insufficient or excessive production of a 3714, 16742, 23546, or 13887 substrate or production of 3714, 16742, 23546, or 13887 inhibitors. In addition, the 3714, 16742, 23546, or 13887 proteins can be used to screen for naturally occurring 3714, 16742, 23546, or 13887 substrates, to screen for drugs or compounds which modulate 3714, 16742, 23546, or 13887 activity, as well as to treat disorders characterized by insufficient or excessive production of 3714, 16742, 23546, or 13887 protein or production of 3714, 16742, 23546, or 13887 protein forms which have decreased or aberrant activity compared to 3714, 16742, 23546, or 13887 wild type protein. Moreover, the anti-3714, -16742, -23546, or -13887 antibodies of the invention can be used to detect and isolate 3714, 16742, 23546, or 13887 proteins, regulate the bioavailability of 3714, 16742, 23546, or 13887 proteins, and modulate 3714, 16742, 23546, or 13887 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to 3714, 16742, 23546, or 13887 proteins, have a stimulatory or inhibitory effect on, for example, 3714, 16742, 23546, or 13887 expression or 3714, 16742, 23546, or 13887 activity, or have a stimulatory or inhibitory effect on, for example, the expression or activity of a 3714, 16742, 23546, or 13887 substrate.

In one embodiment, the invention provides assays for screening candidate or test compounds which are substrates of a 3714, 16742, 23546, or 13887 protein or polypeptide or biologically active portion thereof. In another embodiment, the invention provides assays for screening candidate or test compounds which bind to or modulate the activity of a 3714, 16742, 23546, or 13887 protein or polypeptide or biologically active portion thereof, e.g., modulate the ability of 3714, 16742, 23546, or 13887 to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S. A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993)

Nature 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In another embodiment, an assay is a cell-based assay comprising contacting a cell expressing a 3714, 16742, 23546, or 13887 target molecule (e.g., a 3714, 16742, 23546, or 13887 phosphorylation substrate) with a test compound and determining the ability of the test compound to modulate (e.g. stimulate or inhibit) the activity of the 3714, 16742, 23546, or 13887 target molecule. Determining the ability of the test compound to modulate the activity of a 3714, 16742, 23546, or 13887 target molecule can be accomplished, for example, by determining the ability of the 3714, 16742, 23546, or 13887 protein to bind to or interact with the 3714, 16742, 23546, or 13887 target molecule, or by determining the ability of the 3714, 16742, 23546, or 13887 protein to phosphorylate the 3714, 16742, 23546, or 13887 target molecule.

The ability of the 3714, 16742, 23546, or 13887 protein to phosphorylate a 3714, 16742, 23546, or 13887 target molecule can be determined by, for example, an in vitro kinase assay. Briefly, a 3714, 16742, 23546, or 13887 target molecule, e.g., an immunoprecipitated 3714, 16742, 23546, or 13887 target molecule from a cell line expressing such a molecule, can be incubated with the 3714, 16742, 23546, or 13887 protein and radioactive ATP, e.g., [?-$^{32}$P] ATP, in a buffer containing $MgCl_2$ and $MnCl_2$, e.g., 10 mM $MgCl_2$ and 5 mM $MnCl_2$. Following the incubation, the immunoprecipitated 3714, 16742, 23546, or 13887 target molecule can be separated by SDS-polyacrylamide gel electrophoresis under reducing conditions, transferred to a membrane, e.g., a PVDF membrane, and autoradiographed. The appearance of detectable bands on the autoradiograph indicates that the 3714, 16742, 23546, or 13887 substrate has been phosphorylated. Phosphoaminoacid analysis of the phosphorylated substrate can also be performed in order to determine which residues on the 3714, 16742, 23546, or 13887 substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the 3714, 16742, 23546, or 13887 protein to bind to or interact with a 3714, 16742, 23546, or 13887 target molecule can be accomplished by determining direct binding. Determining the ability of the 3714, 16742, 23546, or 13887 protein to bind to or interact with a 3714, 16742, 23546, or 13887 target molecule can be accomplished, for example, by coupling the 3714, 16742, 23546, or 13887 protein with a radioisotope or enzymatic label such that binding of the 3714, 16742, 23546, or 13887 protein to a 3714, 16742, 23546, or 13887 target molecule can be determined by detecting the labeled 3714, 16742, 23546, or 13887 protein in a complex. For example, 3714, 16742, 23546, or 13887 molecules, e.g., 3714, 16742, 23546, or 13887 proteins, can be labeled with $^{125}I$, $^{35}S$, $^{14}C$, or $^{3}H$, either directly or indirectly, and the radioisotope detected by direct counting of radioemission or by scintillation counting. Alternatively, 3714, 16742, 23546, or 13887 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between 3714, 16742, 23546, or 13887 and its target molecule, without the labeling of any of the interactants. For example, a microphysiometer can be used to detect the interaction of 3714, 16742, 23546, or 13887 with its target molecule without the labeling of either 3714, 16742, 23546, or 13887 or the target molecule. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the 3714, 16742, 23546, or 13887 protein to bind to or interact with a 3714, 16742, 23546, or 13887 target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which a 3714, 16742, 23546, or 13887 protein or biologically active portion thereof is contacted with a test compound and the ability of the test compound to bind to the 3714, 16742, 23546, or 13887 protein or biologically active portion thereof is determined. Binding of the test compound to the 3714, 16742, 23546, or 13887 protein can be determined either directly or indirectly as described above. In a preferred embodiment, the assay includes contacting the 3714, 16742, 23546, or 13887 protein or biologically active portion thereof with a known compound which binds 3714, 16742, 23546, or 13887 to form an assay mixture, contacting the assay mixture with a test compound, and determining the ability of the test compound to interact with a 3714, 16742, 23546, or 13887 protein, wherein determining the ability of the test compound to interact with a 3714, 16742, 23546, or 13887 protein comprises determining the ability of the test compound to preferentially bind to 3714, 16742, 23546, or 13887 or biologically active portion thereof as compared to the known compound.

In another embodiment, the assay is a cell-free assay in which a 3714, 16742, 23546, or 13887 protein or biologically active portion thereof is contacted with a test compound and the ability of the test compound to modulate (e.g., stimulate or inhibit) the activity of the 3714, 16742, 23546, or 13887 protein or biologically active portion thereof is determined. Determining the ability of the test compound to modulate the activity of a 3714, 16742, 23546, or 13887 protein can be accomplished, for example, by determining the ability of the 3714, 16742, 23546, or 13887 protein to bind to a 3714, 16742, 23546, or 13887 target molecule by one of the methods described above for determining direct binding. Determining the ability of the 3714, 16742, 23546, or 13887 protein to bind to a 3714, 16742, 23546, or 13887 target molecule can also be accomplished using a technology such as real-time Biomolecular Interaction Analysis (BIA). Sjolander, S. and Urbaniczky, C. (1991) *Anal Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a 3714, 16742, 23546, or 13887 protein can be accomplished by determining the ability of the 3714, 16742, 23546, or 13887 protein to further modulate the activity of a 3714, 16742, 23546, or 13887 target molecule (e.g., a 3714, 16742, 23546, or 13887 mediated signal transduction pathway component). For example, the activity of the effector molecule on an appropriate target can be determined, or the binding of the effector to an appropriate target can be determined as previously described.

In yet another embodiment, the cell-free assay involves contacting a 3714, 16742, 23546, or 13887 protein or biologically active portion thereof with a known compound which binds the 3714, 16742, 23546, or 13887 protein to form an assay mixture, contacting the assay mixture with a test compound, and determining the ability of the test compound to interact with the 3714, 16742, 23546, or 13887 protein, wherein determining the ability of the test compound to interact with the 3714, 16742, 23546, or 13887 protein comprises determining the ability of the 3714, 16742, 23546, or 13887 protein to preferentially bind to or modulate the activity of a 3714, 16742, 23546, or 13887 target molecule.

The cell-free assays of the present invention are amenable to use of both soluble and/or membrane-bound forms of proteins (e.g., 3714, 16742, 23546, or 13887 proteins or biologically active portions thereof, or receptors to which 3714, 16742, 23546, or 13887 binds). In the case of cell-free assays in which a membrane-bound form a protein is used (e.g., a cell surface 3714, 16742, 23546, or 13887 receptor) it may be desirable to utilize a solubilizing agent such that the membrane-bound form of the protein is maintained in solution. Examples of such solubilizing agents include nonionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio)-]2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either 3714, 16742, 23546, or 13887 or its target molecule to facilitate separation of complexed from uncomplexed forms of one or both of the proteins, as well as to accommodate automation of the assay. Binding of a test compound to a 3714, 16742, 23546, or 13887 protein, or interaction of a 3714, 16742, 23546, or 13887 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ 3714, 16742, 23546, or 13887 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 3714, 16742, 23546, or 13887 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 3714, 16742, 23546, or 13887 binding or activity determined using standard techniques.

Other techniques for immobilizing proteins on matrices can also be used in the screening assays of the invention. For example, either a 3714, 16742, 23546, or 13887 protein or a 3714, 16742, 23546, or 13887 target molecule can be immobilized utilizing conjugation of biotin and streptavidin. Biotinylated 3714, 16742, 23546, or 13887 protein or target molecules can be prepared from biotin-NHS (N-hydroxysuccinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with 3714, 16742, 23546, or 13887 protein or target molecules but which do not interfere with binding of the 3714, 16742, 23546, or 13887 protein to its target molecule can be derivatized to the wells of the plate, and unbound target or 3714, 16742, 23546, or 13887 protein trapped in the wells by antibody conjugation. Methods for detecting such complexes, in addition to those described above for the GST-immobilized complexes, include immunodetection of complexes using antibodies reactive with the 3714, 16742, 23546, or 13887 protein or target molecule, as well as enzyme-linked assays which rely on detecting an enzymatic activity associated with the 3714, 16742, 23546, or 13887 protein or target molecule.

In another embodiment, modulators of 3714, 16742, 23546, or 13887 expression are identified in a method wherein a cell is contacted with a candidate compound and the expression of 3714, 16742, 23546, or 13887 mRNA or protein in the cell is determined. The level of expression of 3714, 16742, 23546, or 13887 mRNA or protein in the presence of the candidate compound is compared to the level of expression of 3714, 16742, 23546, or 13887 mRNA or protein in the absence of the candidate compound. The candidate compound can then be identified as a modulator of 3714, 16742, 23546, or 13887 expression based on this comparison. For example, when expression of 3714, 16742, 23546, or 13887 mRNA or protein is greater (statistically significantly greater) in the presence of the candidate compound than in its absence, the candidate compound is identified as a stimulator of 3714, 16742, 23546, or 13887 mRNA or protein expression. Alternatively, when expression of 3714, 16742, 23546, or 13887 mRNA or protein is less (statistically significantly less) in the presence of the candidate compound than in its absence, the candidate compound is identified as an inhibitor of 3714, 16742, 23546, or 13887 mRNA or protein expression. The level of 3714, 16742, 23546, or 13887 mRNA or protein expression in the cells can be determined by methods described herein for detecting 3714, 16742, 23546, or 13887 mRNA or protein.

In yet another aspect of the invention, the 3714, 16742, 23546, or 13887 proteins can be used as "bait proteins" in a two-hybrid assay or three-hybrid assay (see, e.g., U.S. Pat.

No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 3714, 16742, 23546, or 13887 ("3714-, 16742-, 23546-, or 13887-binding proteins" or "3714-, 16742-, 23546-, or 13887-bp") and are involved in 3714, 16742, 23546, or 13887 activity. Such 3714-, 16742-, 23546-, or 13887-binding proteins are also likely to be involved in the propagation of signals by the 3714, 16742, 23546, or 13887 proteins or 3714, 16742, 23546, or 13887 targets as, for example, downstream elements of a 3714-, 16742-, 23546-, or 13887-mediated signaling pathway. Alternatively, such 3714-, 16742-, 23546-, or 13887-binding proteins are likely to be 3714, 16742, 23546, or 13887 inhibitors.

The two-hybrid system is based on the modular nature of most transcription factors, which consist of separable DNA-binding and activation domains. Briefly, the assay utilizes two different DNA constructs. In one construct, the gene that codes for a 3714, 16742, 23546, or 13887 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 3714-, 16742-, 23546-, or 13887-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 3714, 16742, 23546, or 13887 protein.

This invention further pertains to novel agents identified by the above-described screening assays. Accordingly, it is within the scope of this invention to further use an agent identified as described herein in an appropriate animal model. For example, an agent identified as described herein (e.g., a 3714, 16742, 23546, or 13887 modulating agent, an antisense 3714, 16742, 23546, or 13887 nucleic acid molecule, a 3714-, 16742-, 23546-, or 13887-specific antibody, or a 3714-, 16742-, 23546-, or 13887-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the 3714, 16742, 23546, or 13887 nucleotide sequences, described herein, can be used to map the location of the 3714, 16742, 23546, or 13887 genes on a chromosome. The mapping of the 3714, 16742, 23546, or 13887 sequences to chromosomes is an important first step in correlating these sequences with genes associated with disease.

Briefly, 3714, 16742, 23546, or 13887 genes can be mapped to chromosomes by preparing PCR primers (preferably 15–25 bp in length) from the 3714, 16742, 23546, or 13887 nucleotide sequences. Computer analysis of the 3714, 16742, 23546, or 13887 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the 3714, 16742, 23546, or 13887 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the 3714, 16742, 23546, or 13887 nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 3714, 16742, 23546, or 13887 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The 3714, 16742, 23546, or 13887 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the 3714, 16742, 23546, or 13887 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The 3714, 16742, 23546, or 13887 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, or SEQ ID NO:10, can comfortably provide positive individual identification with a panel of perhaps 10 to 1,000 primers which each yield a noncoding amplified sequence of 100 bases. If predicted coding sequences, such as those in SEQ ID NO:3, SEQ ID NO:6, SEQ ID NO:9, or SEQ ID NO:12 are used, a more appropriate number of primers for positive individual identification would be 500–2,000.

If a panel of reagents from 3714, 16742, 23546, or 13887 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial 3714, 16742, 23546, or 13887 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, SEQ ID NO:7, or SEQ ID NO:10 are particularly appropriate for this use as greater numbers of polymorphisms occur in the noncoding regions, making it easier to differentiate individuals using this technique. Examples of polynucleotide reagents include the 3714, 16742, 23546, or 13887 nucleotide sequences or portions thereof, e.g., fragments derived from the noncoding regions of SEQ ID NO:1, SEQ ID NO:4, SEQ ID NO:7, or SEQ ID NO:10, having a length of at least 20 bases, preferably at least 30 bases.

The 3714, 16742, 23546, or 13887 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such 3714, 16742, 23546, or 13887 probes can be used to identify tissue by species and/or by organ type.

In a similar fashion, these reagents, e.g., 3714, 16742, 23546, or 13887 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 3714, 16742, 23546, or 13887 protein and/or nucleic acid expression as well as 3714, 16742, 23546, or 13887 activity, in the context of a biological sample (e.g., blood, serum, cells, tissue) to thereby determine whether an individual is afflicted with a disease or disorder, or is at risk of developing a disorder, associated with aberrant 3714, 16742, 23546, or 13887 expression or activity. The invention also provides for prognostic (or predictive) assays for determining whether an individual is at risk of developing a disorder associated with 3714, 16742, 23546, or 13887 protein, nucleic acid expression or activity. For example, mutations in a 3714, 16742, 23546, or 13887 gene can be assayed in a biological sample. Such assays can be used for prognostic or predictive purpose to thereby prophylactically treat an individual prior to the onset of a disorder characterized by or associated with 3714, 16742, 23546, or 13887 protein, nucleic acid expression or activity.

Another aspect of the invention pertains to monitoring the influence of agents (e.g., drugs, compounds) on the expression or activity of 3714, 16742, 23546, or 13887 in clinical trials.

These and other agents are described in further detail in the following sections.

1. Diagnostic Assays

An exemplary method for detecting the presence or absence of 3714, 16742, 23546, or 13887 protein or nucleic acid in a biological sample involves obtaining a biological sample from a test subject and contacting the biological sample with a compound or an agent capable of detecting 3714, 16742, 23546, or 13887 protein or nucleic acid (e.g., mRNA, genomic DNA) that encodes 3714, 16742, 23546, or 13887 protein such that the presence of 3714, 16742, 23546, or 13887 protein or nucleic acid is detected in the biological sample. A preferred agent for detecting 3714, 16742, 23546, or 13887 mRNA or genomic DNA is a labeled nucleic acid probe capable of hybridizing to 3714, 16742, 23546, or 13887 mRNA or genomic DNA. The nucleic acid probe can be, for example, a human 3714, 16742, 23546, or 13887 nucleic acid, such as the nucleic acid of SEQ ID NO:1, SEQ ID NO:4, SEQ ID NO:7, or SEQ ID NO:10, or a portion thereof, such as an oligonucleotide of at least 15, 30, 50, 100, 250 or 500 nucleotides in length and sufficient to specifically hybridize under stringent conditions to 3714, 16742, 23546, or 13887 mRNA or genomic DNA. Other suitable probes for use in the diagnostic assays of the invention are described herein.

A preferred agent for detecting 3714, 16742, 23546, or 13887 protein is an antibody capable of binding to 3714, 16742, 23546, or 13887 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect 3714, 16742, 23546, or 13887 mRNA, protein, or genomic DNA in a biological sample in vitro as well as in vivo. For example, in vitro techniques for detection of 3714, 16742, 23546, or 13887 mRNA include Northern hybridizations and in situ hybridizations. In vitro techniques for detection of 3714, 16742, 23546, or 13887 protein include enzyme linked immunosorbent assays (ELISAs), Western blots, immunoprecipitations and immunofluorescence. In vitro techniques for detection of 3714, 16742, 23546, or 13887 genomic DNA include Southern hybridizations. Furthermore, in vivo techniques for detection of 3714, 16742, 23546, or 13887 protein include introducing into a subject a labeled anti-3714,–16742, –23546, or -13887 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting 3714, 16742, 23546, or 13887 protein, mRNA, or genomic DNA, such that the presence of 3714, 16742, 23546, or 13887 protein, mRNA or genomic DNA is detected in the biological sample, and comparing the presence of 3714, 16742, 23546, or 13887 protein, mRNA or genomic DNA in the control sample with the presence of 3714, 16742, 23546, or 13887 protein, mRNA or genomic DNA in the test sample.

The invention also encompasses kits for detecting the presence of 3714, 16742, 23546, or 13887 in a biological sample. For example, the kit can comprise a labeled compound or agent capable of detecting 3714, 16742, 23546, or 13887 protein or mRNA in a biological sample; means for determining the amount of 3714, 16742, 23546, or 13887 in the sample; and means for comparing the amount of 3714, 16742, 23546, or 13887 in the sample with a standard. The compound or agent can be packaged in a suitable container. The kit can further comprise instructions for using the kit to detect 3714, 16742, 23546, or 13887 protein or nucleic acid.

2. Prognostic Assays

The diagnostic methods described herein can furthermore be utilized to identify subjects having or at risk of developing a disease or disorder associated with aberrant 3714, 16742, 23546, or 13887 expression or activity. For example, the assays described herein, such as the preceding diagnostic assays or the following assays, can be utilized to identify a subject having or at risk of developing a disorder associated with 3714, 16742, 23546, or 13887 protein, nucleic acid expression or activity. Thus, the present invention provides a method for identifying a disease or disorder associated with aberrant 3714, 16742, 23546, or 13887 expression or activity in which a test sample is obtained from a subject and 3714, 16742, 23546, or 13887 protein or nucleic acid (e.g., mRNA, genomic DNA) is detected, wherein the presence of 3714, 16742, 23546, or 13887 protein or nucleic acid is diagnostic for a subject having or at risk of developing a disease or disorder associated with aberrant 3714, 16742, 23546, or 13887 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant 3714, 16742, 23546, or 13887 expression or activity. Thus, the present invention provides methods for determining whether a subject can be effectively treated with an agent for a disorder associated with aberrant 3714, 16742, 23546, or 13887 expression or activity in which a test sample is obtained and 3714, 16742, 23546, or 13887 protein or nucleic acid expression or activity is detected (e.g., wherein the abundance of 3714, 16742, 23546, or 13887 protein or nucleic acid expression or activity is diagnostic for a subject that can be administered the agent to treat a disorder associated with aberrant 3714, 16742, 23546, or 13887 expression or activity).

The methods of the invention can also be used to detect genetic alterations in a 3714, 16742, 23546, or 13887 gene, thereby determining if a subject with the altered gene is at risk for a disorder associated with the 3714, 16742, 23546, or 13887 gene. In preferred embodiments, the methods include detecting, in a sample of cells from the subject, the presence or absence of a genetic alteration characterized by at least one of an alteration affecting the integrity of a gene encoding a 3714-, 16742-, 23546-, or 13887-protein, or the mis-expression of the 3714, 16742, 23546, or 13887 gene. For example, such genetic alterations can be detected by ascertaining the existence of at least one of 1) a deletion of one or more nucleotides from a 3714, 16742, 23546, or 13887 gene; 2) an addition of one or more nucleotides to a 3714, 16742, 23546, or 13887 gene; 3) a substitution of one or more nucleotides of a 3714, 16742, 23546, or 13887 gene, 4) a chromosomal rearrangement of a 3714, 16742, 23546, or 13887 gene; 5) an alteration in the level of a messenger RNA transcript of a 3714, 16742, 23546, or 13887 gene, 6) aberrant modification of a 3714, 16742, 23546, or 13887 gene, such as of the methylation pattern of the genomic DNA, 7) the presence of a non-wild type splicing pattern of a messenger RNA transcript of a 3714, 16742, 23546, or 13887 gene, 8) a non-wild type level of a 3714, 16742, 23546, or 13887 protein, 9) allelic loss of a 3714, 16742, 23546, or 13887 gene, and 10) inappropriate post-translational modification of a 3714, 16742, 23546, or 13887 protein. As described herein, there are a large number of assay techniques known in the art which can be used for detecting alterations in a 3714, 16742, 23546, or 13887 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the 3714, 16742, 23546, or 13887 gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a 3714, 16742, 23546, or 13887 gene under conditions such that hybridization and amplification of the 3714, 16742, 23546, or 13887 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 3714, 16742, 23546, or 13887 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 3714, 16742, 23546, or 13887 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 3714, 16742, 23546, or 13887 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 3714, 16742, 23546, or 13887 gene and detect mutations by comparing the sequence of the sample 3714, 16742, 23546, or 13887 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36/127–162; and Griffin et al. (1993) *Appl. Biochem. Biotechnol.* 38:147–159).

Other methods for detecting mutations in the 3714, 16742, 23546, or 13887 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type 3714, 16742, 23546, or 13887 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 3714, 16742, 23546, or 13887 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 3714, 16742, 23546, or 13887 sequence, e.g., a wild-type 3714, 16742, 23546, or 13887 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 3714, 16742, 23546, or 13887 genes. For example, single strand conformation polymorphism (SSCP) may be used to detect differences in electrophoretic mobility between mutant and wild type nucleic acids (Orita et al. (1989) *Proc Natl. Acad. Sci USA*:86:2766, see also Cotton (1993) *Mutat Res* 285:125–144; and Hayashi (1992) *Genet Anal Tech Appl* 9:73–79). Single-stranded DNA fragments of sample and control 3714, 16742, 23546, or 13887 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes.

The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, erg., in clinical settings to diagnose patients exhibiting symptoms or family history of a disease or illness involving a 3714, 16742, 23546, or 13887 gene.

Furthermore, any cell type or tissue in which 3714, 16742, 23546, or 13887 is expressed may be utilized in the prognostic assays described herein.

3. Monitoring of Effects During Clinical Trials

Monitoring the influence of agents (e.g., drugs or compounds) on the expression or activity of a 3714, 16742, 23546, or 13887 protein can be applied not only in basic drug screening, but also in clinical trials. For example, the effectiveness of an agent determined by a screening assay as described herein to increase 3714, 16742, 23546, or 13887 gene expression, protein levels, or upregulate 3714, 16742, 23546, or 13887 activity, can be monitored in clinical trials of subjects exhibiting decreased 3714, 16742, 23546, or 13887 gene expression, protein levels, or downregulated 3714, 16742, 23546, or 13887 activity. Alternatively, the effectiveness of an agent determined by a screening assay to decrease 3714, 16742, 23546, or 13887 gene expression, protein levels, or downregulate 3714, 16742, 23546, or 13887 activity, can be monitored in clinical trials of subjects exhibiting increased 3714, 16742, 23546, or 13887 gene expression, protein levels, or upregulated 3714, 16742, 23546, or 13887 activity. In such clinical trials, the expression or activity of a 3714, 16742, 23546, or 13887 gene, and preferably, other genes that have been implicated in a disorder can be used as a "read out" or markers of the phenotype of a particular cell.

For example, and not by way of limitation, genes, including 3714, 16742, 23546, or 13887, that are modulated in cells by treatment with an agent (e.g., compound, drug or small molecule) which modulates 3714, 16742, 23546, or 13887 activity (e.g., identified in a screening assay as described herein) can be identified. Thus, to study the effect of agents on a 3714, 16742, 23546, or 13887 associated disorder, for example, in a clinical trial, cells can be isolated and RNA prepared and analyzed for the levels of expression of 3714, 16742, 23546, or 13887 and other genes implicated in the 3714, 16742, 23546, or 13887 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of 3714, 16742, 23546, or 13887 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a 3714, 16742, 23546, or 13887 protein, mRNA, or genomic DNA in the pre-administration sample; (iii) obtaining one or more post-administration samples from the subject; (iv) detecting the level of expression or activity of the 3714, 16742, 23546, or 13887 protein, mRNA, or genomic DNA in the post-administration samples; (v) comparing the level of expression or activity of the 3714, 16742, 23546, or 13887 protein, mRNA, or genomic DNA in the pre-administration sample with the 3714, 16742, 23546, or 13887 protein, mRNA, or genomic DNA in the post administration sample or samples; and (vi) altering the administration of the agent to the subject accordingly. For example, increased administration of the agent may be desirable to increase the expression or activity of 3714, 16742, 23546, or 13887 to higher levels than detected, i.e., to increase the effectiveness of the agent. Alternatively, decreased administration of the agent may be desirable to decrease expression or activity of 3714, 16742, 23546, or 13887 to lower levels than detected, i.e. to decrease the effectiveness of the agent. According to such an embodiment, 3714, 16742, 23546, or 13887 expression or activity may be used as an indicator of the effectiveness of an agent, even in the absence of an observable phenotypic response.

D. Use of 3714, 16742, 23546, or 13887 Molecules as Surrogate Markers

The 3714, 16742, 23546, or 13887 molecules of the invention are also useful as markers of disorders or disease states, as markers for precursors of disease states, as markers for predisposition of disease states, as markers of drug activity, or as markers of the pharmacogenetics profile of a subject. Using the methods described herein, the presence, absence and/or quantity of the 3714, 16742, 23546, or 13887 molecules of the invention may be detected, and may be correlated with one or more biological states in vivo. For example, the 3714, 16742, 23546, or 13887 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) AIDS Treatment News Archive 209.

The 3714, 16742, 23546, or 13887 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 3714, 16742, 23546, or 13887 marker) transcription or expression, the amplified marker may be in a quantity which is more readily detectable than the drug itself. Also, the marker may be more easily detected due to the nature of the marker itself; for example, using the methods described herein, anti-3714, 16742, 23546, or 13887 antibodies may be employed in an immune-based detection system for a 3714, 16742, 23546, or 13887 protein marker, or 3714, 16742, 23546, or 13887-specific radiolabeled probes may be used to detect a 3714, 16742, 23546, or 13887 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) Env. Health Perspect. 90: 229–238; Schentag (1999) Am. J. Health-Syst. Pharm. 56 Suppl. 3: S21-S24; and Nicolau (1999) Am, J. Health-Syst. Pharm. 56 Suppl. 3: S16-S20.

The 3714, 16742, 23546, or 13887 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) Eur. J. Cancer 35(12):1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 3714, 16742, 23546, or 13887 protein or RNA) for specific tumor markers in a subject, a drug or course of treatment may be selected that is optimized for the treatment of the specific tumor likely to be present in the subject. Similarly, the presence or absence of a specific sequence mutation in 3714, 16742, 23546, or 13887 DNA may correlate 3714, 16742, 23546, or 13887 drug response. The use of pharmacogenomic markers therefore permits the application of the most appropriate treatment for each subject without having to administer the therapy.

E. Methods of Treatment:

The present invention provides for both prophylactic and therapeutic methods of treating a subject at risk of (or susceptible to) a disorder or having a disorder associated with aberrant 3714, 16742, 23546, or 13887 expression or activity. With regards to both prophylactic and therapeutic methods of treatment, such treatments may be specifically tailored or modified, based on knowledge obtained from the field of pharmacogenomics. "Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 3714, 16742, 23546, or 13887 molecules of the present invention or 3714, 16742, 23546, or 13887 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant 3714, 16742, 23546, or 13887 expression or activity, by administering to the subject a 3714, 16742, 23546, or 13887 or an agent which modulates 3714, 16742, 23546, or 13887 expression or at least one 3714, 16742, 23546, or 13887 activity. Subjects at risk for a disease which is caused or contributed to by aberrant 3714, 16742, 23546, or 13887 expression or activity can be identified by, for example, any or a combination of diagnostic or prognostic assays as described herein. Administration of a prophylactic agent can occur prior to the manifestation of symptoms characteristic of the 3714, 16742, 23546, or 13887 aberrancy, such that a disease or disorder is prevented or, alternatively, delayed in its progression. Depending on the type of 3714, 16742, 23546, or 13887 aberrancy, for example, a 3714, 16742, 23546, or 13887, 3714, 16742, 23546, or 13887 agonist or 3714, 16742, 23546, or 13887 antagonist agent can be used for treating the subject. The appropriate agent can be determined based on screening assays described herein.

2. Therapeutic Methods

Another aspect of the invention pertains to methods of modulating 3714, 16742, 23546, or 13887 expression or activity for therapeutic purposes. Accordingly, in an exemplary embodiment, the modulatory method of the invention involves contacting a cell with a 3714, 16742, 23546, or 13887 or agent that modulates one or more of the activities of 3714, 16742, 23546, or 13887 protein activity associated with the cell. An agent that modulates 3714, 16742, 23546, or 13887 protein activity can be an agent as described herein, such as a nucleic acid or a protein, a naturally-occurring target molecule of a 3714, 16742, 23546, or 13887 protein (e.g., a 3714, 16742, 23546, or 13887 phosphorylation substrate), a 3714, 16742, 23546, or 13887 antibody, a 3714, 16742, 23546, or 13887 agonist or antagonist, a peptidomimetic of a 3714, 16742, 23546, or 13887 agonist or antagonist, or other small molecule. In one embodiment, the agent stimulates one or more 3714, 16742, 23546, or 13887 activities. Examples of such stimulatory agents include active 3714, 16742, 23546, or 13887 protein and a nucleic acid molecule encoding 3714, 16742, 23546, or 13887 that has been introduced into the cell. In another embodiment, the agent inhibits one or more 3714, 16742, 23546, or 13887 activities. Examples of such inhibitory agents include antisense 3714, 16742, 23546, or 13887 nucleic acid molecules, anti-3714,–16742,–23546, or -13887 antibodies, and 3714, 16742, 23546, or 13887 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a 3714, 16742, 23546, or 13887 protein or nucleic acid molecule. In one embodiment, the method involves administering an agent (e.g., an agent identified by a screening assay described herein), or combination of agents that modulates (e.g., upregulates or downregulates) 3714, 16742, 23546, or 13887 expression or activity. In another embodiment, the method involves administering a 3714, 16742, 23546, or 13887 protein or nucleic acid molecule as therapy to compensate for reduced or aberrant 3714, 16742, 23546, or 13887 expression or activity.

Stimulation of 3714, 16742, 23546, or 13887 activity is desirable in situations in which 3714, 16742, 23546, or 13887 is abnormally downregulated and/or in which increased 3714, 16742, 23546, or 13887 activity is likely to have a beneficial effect. For example, stimulation of 3714, 16742, 23546, or 13887 activity is desirable in situations in which a 3714, 16742, 23546, or 13887 is downregulated and/or in which increased 3714, 16742, 23546, or 13887 activity is likely to have a beneficial effect. Likewise, inhibition of 3714, 16742, 23546, or 13887 activity is desirable in situations in which 3714, 16742, 23546, or 13887 is abnormally upregulated and/or in which decreased 3714, 16742, 23546, or 13887 activity is likely to have a beneficial effect.

3. Pharmacogenomics

The 3714, 16742, 23546, or 13887 molecules of the present invention, as well as agents, or modulators which have a stimulatory or inhibitory effect on 3714, 16742, 23546, or 13887 activity (e.g., 3714, 16742, 23546, or 13887 gene expression) as identified by a screening assay described herein can be administered to individuals to treat (prophylactically or therapeutically) disorders (e.g., cardiovascular disorders such as congestive heart failure) associated with aberrant 3714, 16742, 23546, or 13887 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 3714, 16742, 23546, or 13887 molecule or 3714, 16742, 23546, or 13887 modulator as well as tailoring the dosage and/or therapeutic regimen of treatment with a 3714, 16742, 23546, or 13887 molecule or 3714, 16742, 23546, or 13887 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a 3714, 16742, 23546, or 13887 protein or 3714, 16742, 23546, or 13887 receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a 3714, 16742, 23546, or 13887 molecule or 3714, 16742, 23546, or 13887 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a 3714, 16742, 23546, or 13887 molecule or 3714, 16742, 23546, or 13887 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of Human 3714, 16742, 23546, or 13887 cDNAs

The human 3714 sequence (FIGS. 1A–D; SEQ ID NO:1), which is approximately 2968 nucleotides long including untranslated regions, contains a predicted methionine-initiated coding sequence (SEQ ID NO:3) of about 2352 nucleotides (nucleotides 1–2352 of SEQ ID NO:1). The coding sequence encodes a 783 amino acid protein (SEQ ID NO:2).

Figures 4C, 5:
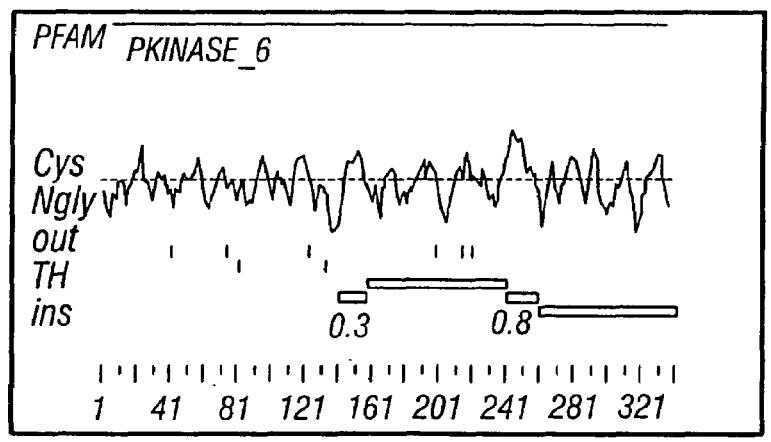

The human 16742 sequence (FIGS. 4A–C; SEQ ID NO:4), which is approximately 1948 nucleotides long including untranslated regions, contains a predicted methionine-initiated coding sequence (SEQ ID NO:6) of about 1026 nucleotides (1–1026 of SEQ ID NO:6). The coding sequence encodes a 341 amino acid protein (SEQ ID NO:5).

The human 22546 sequence (FIGS. 7A–G; SEQ ID NO:7), which is approximately 5499 nucleotides long including untranslated regions, contains a predicted methionine-initiated coding sequence of about 3735 nucleotides (nucleotides 1–3735 of SEQ ID NO:9). The coding sequence encodes a 1244 amino acid protein (SEQ ID NO:8).

The human 13887 sequence (FIGS. 10A–C; SEQ ID NO:10), which is approximately 2623 nucleotides long including untranslated regions, contains a predicted methionine-initiated coding sequence of about 1260 nucleotides (1–1260 of SEQ ID NO:12). The coding sequence encodes a 419 amino acid protein (SEQ ID NO:11).

Example 2

Expression and Tissue Distribution of 3714, 16742. 23546, or 13887 mRNA

Northern blot hybridizations with various RNA samples can be performed under standard conditions and washed under stringent conditions, i.e., 0.2×SSC at 65° C. A DNA probe corresponding to all or a portion of the 3714, 16742, 23546, or 13887 cDNA (SEQ ID NOs:1, 3, 5, or 7) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations. TaqMan real-time quantitative RT-PCR is used to detect the presence of RNA transcript corresponding to human 3714, 16742, 23546, or 13887 in several tissues. It is found that the corresponding orthologs of 3714, 16742, 23546, or 13887 are expressed in a variety of tissues. The results of the screening for 16742, 23546, or 13887, are shown in FIGS. 13–29.

Figure 29A:
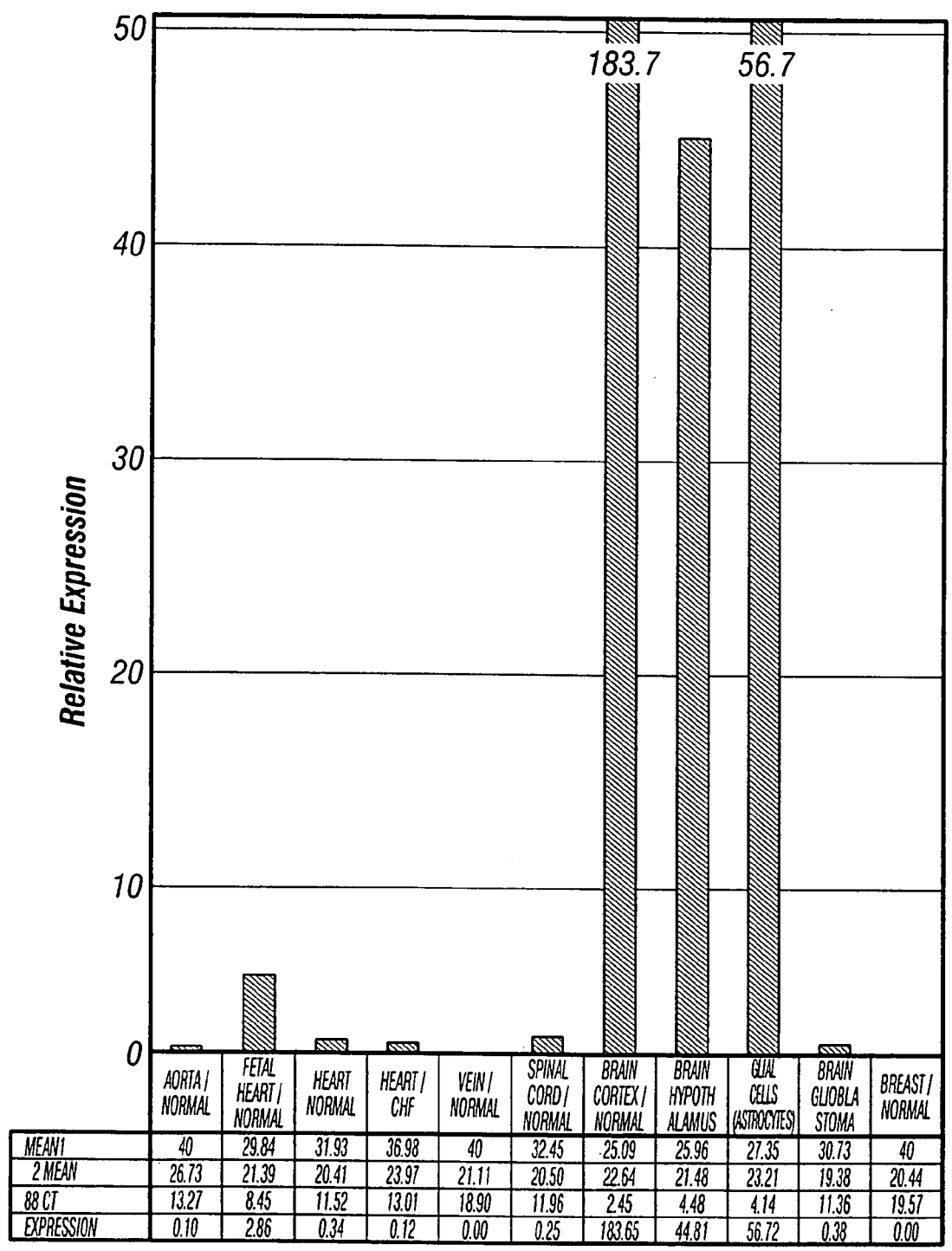
Figure 29B:
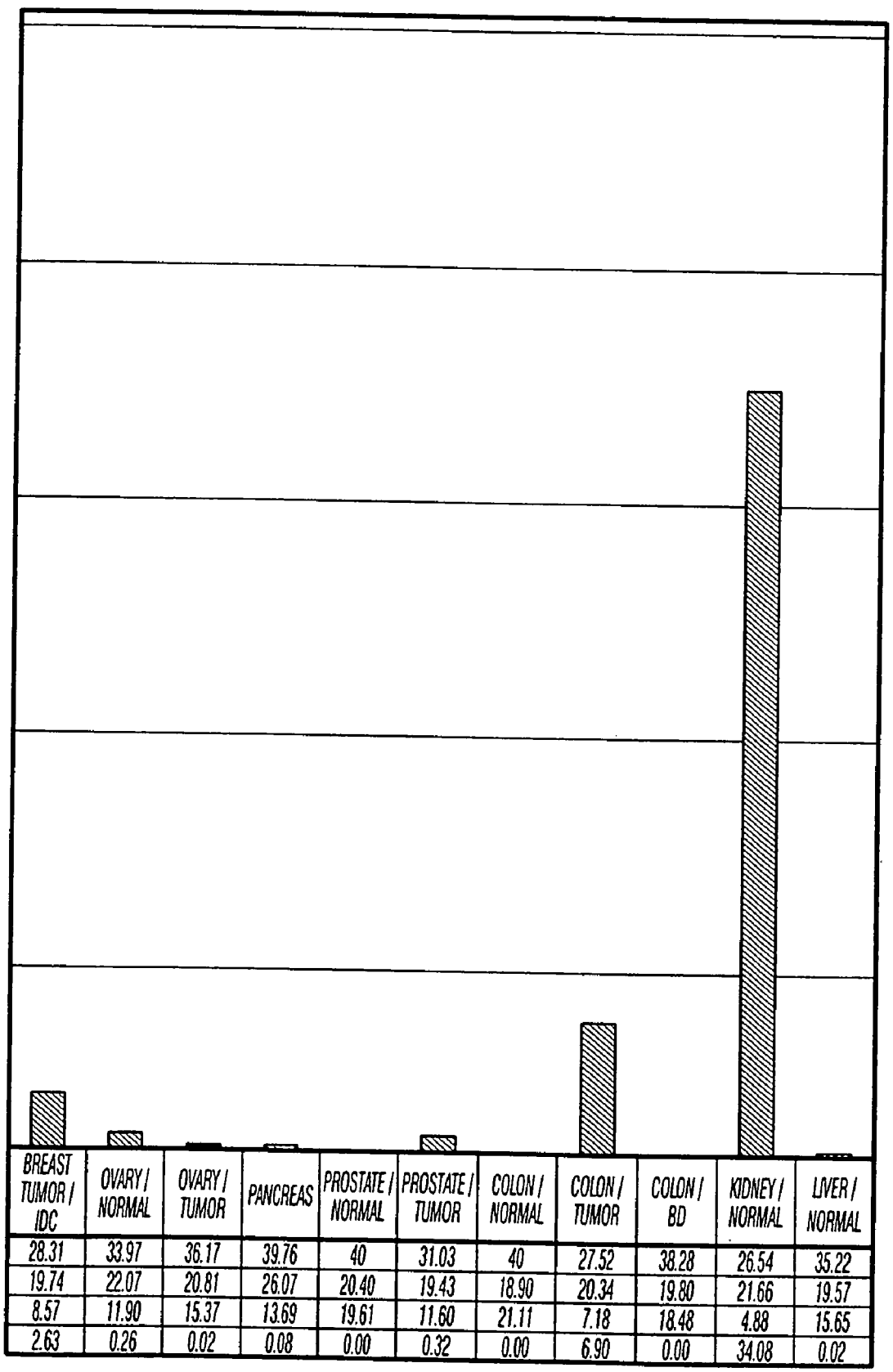

Reverse Transcriptase PCR (RT-PCR) was used to detect the presence of RNA transcript corresponding to human 16742, 23546, or 13887 in RNA prepared from tumor and normal tissues. FIGS. 13 and 29 illustrate the relative expression levels and tissue distribution of the 16742, 23546, or 13887 genes in various tissues using Taq Man PCR. If a subject has a disease characterized by underexpression or overexpression of a 16742, 23546, or 13887 gene, modulators which have a stimulatory or inhibitory effect on protein kinase activity (e.g., protein kinase gene expression) can be administered to individuals to treat (prophylactically or therapeutically) protein kinase-associated disorders.

Figure 14:
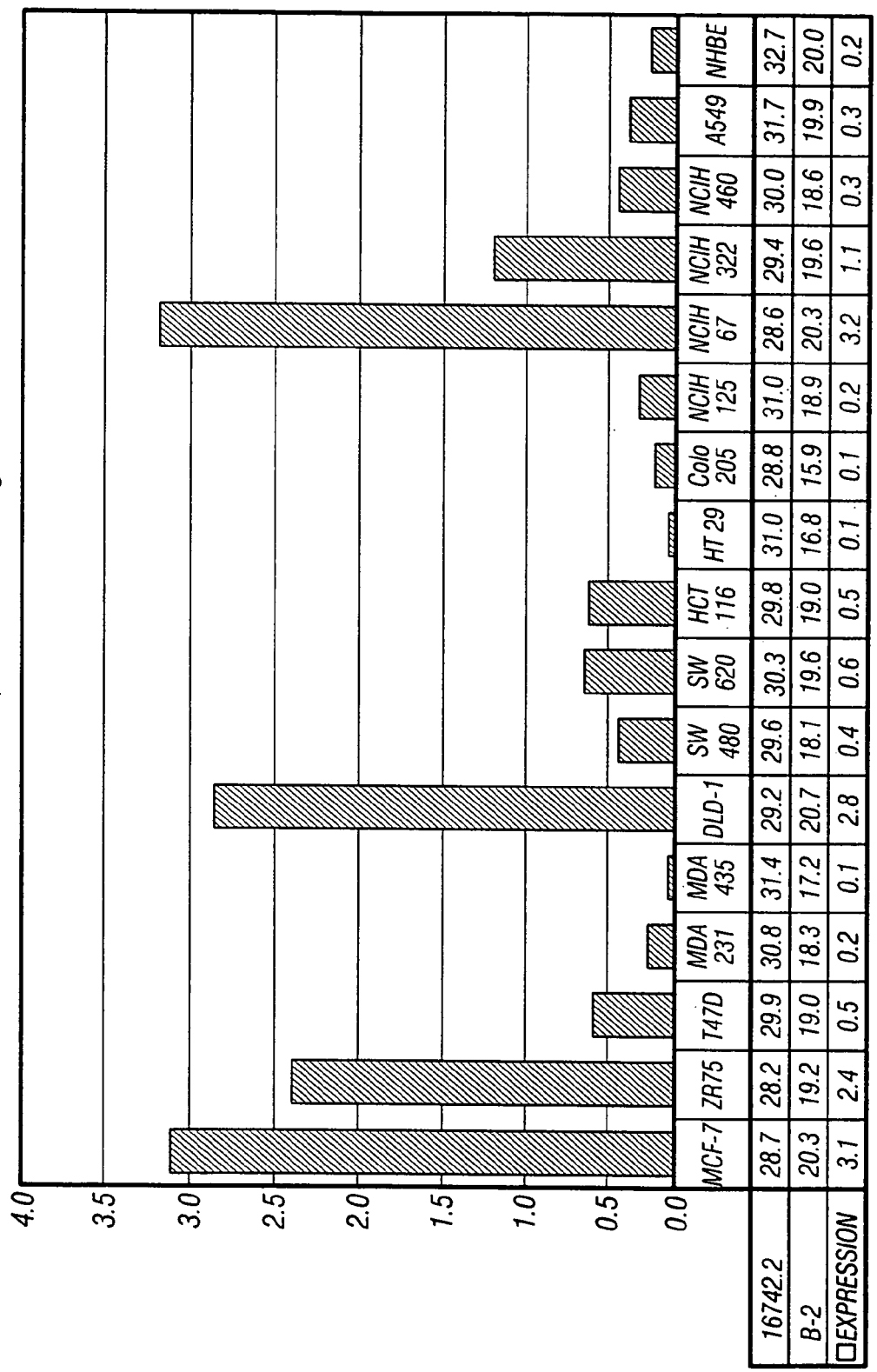
FIG. 14 depicts variable expression of 16742 in a xenograph panel.
Figure 15:
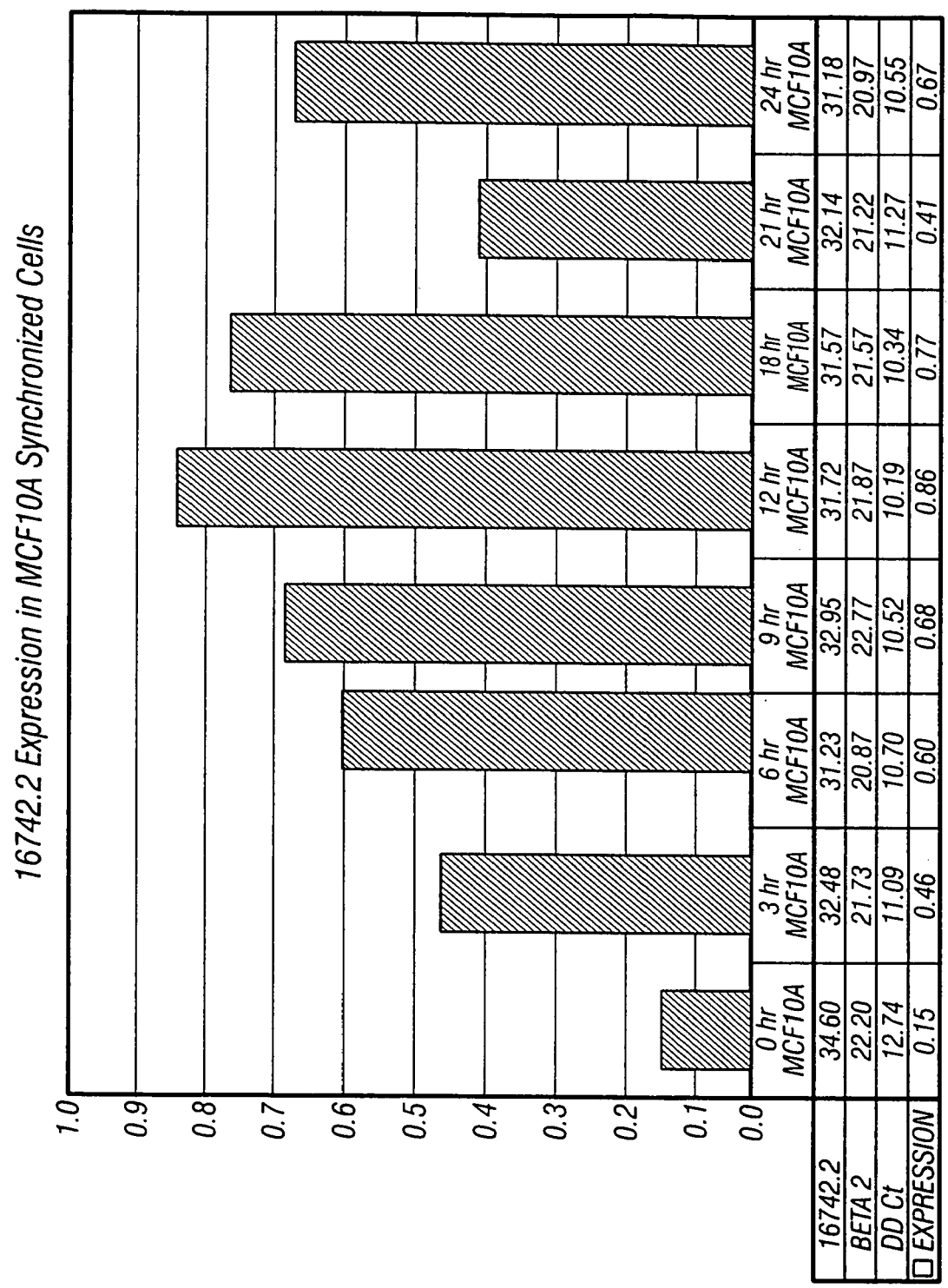
FIG. 15 is a graph of a Taq Man array depicting 16742 RNA the relative expression of 16742 RNA in synchronized cells of the human breast epithelial cell line, MCF-10A.

FIG. 13 illustrates the ubiquitous relative expression levels of 16742 in various tissues using TaqMan PCR, and significant expression in normal human brain cortex. Variable expression was found in xenographs of cell lines tested as shown in FIG. 14 for 16742. The highest expression for 16742 was found in MCF-7 breast tumor cell line, DLD1 and NCIH 67. FIG. 15 illustrates 16742 expression in MCF 10A synchronized cells.

Figure 16:
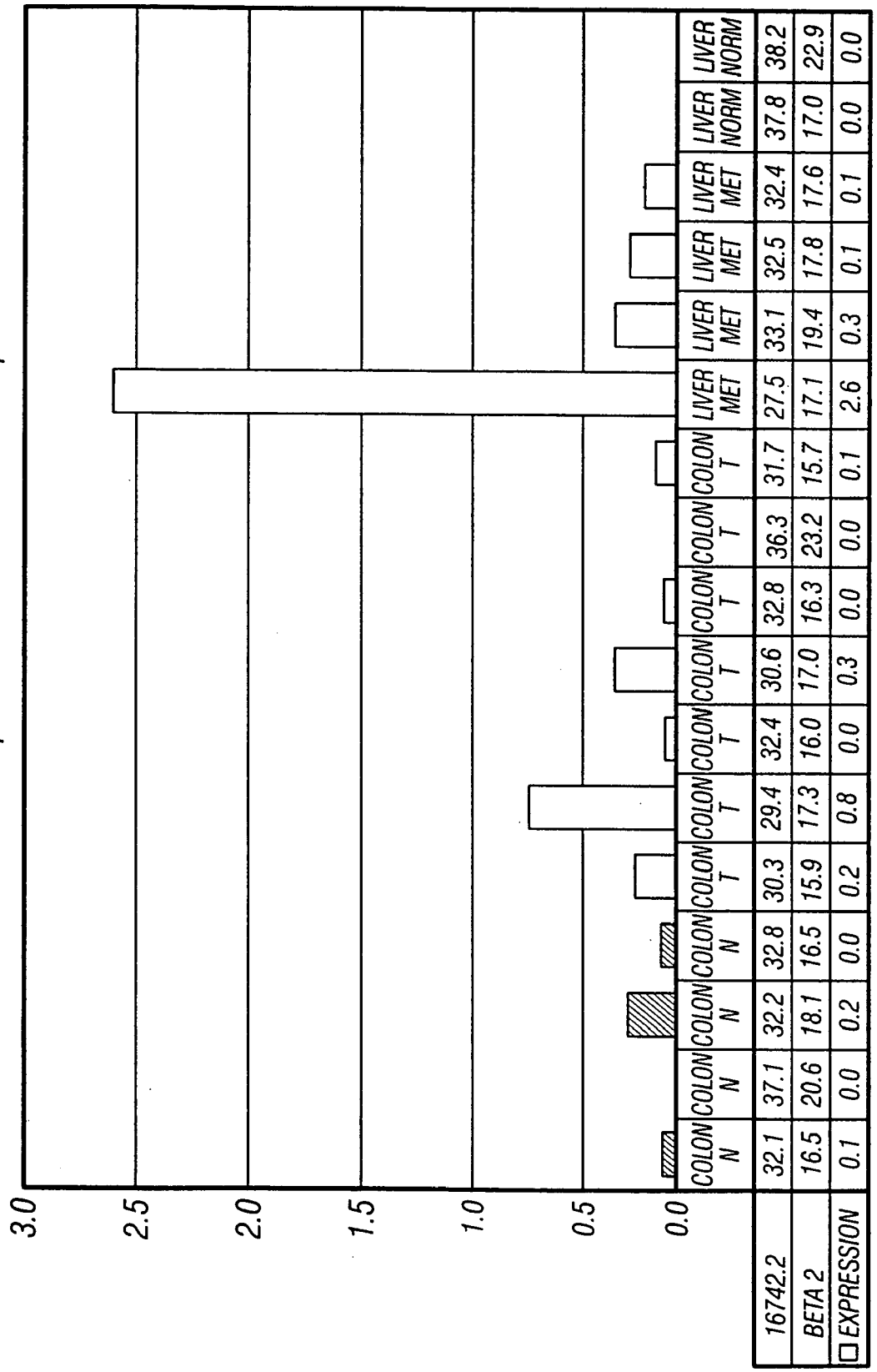
FIG. 16 is an oncology panel bar graph depicting the expression of 16742 RNA relative to a no template control showing an increased expression in 2/7 clinical colon tumors in comparison to normal colon tissues, and showing an increased expression in 4/4 liver metastasis in comparison to normal liver tissues, which expression was detected using Taq Man analysis.
Figure 17:
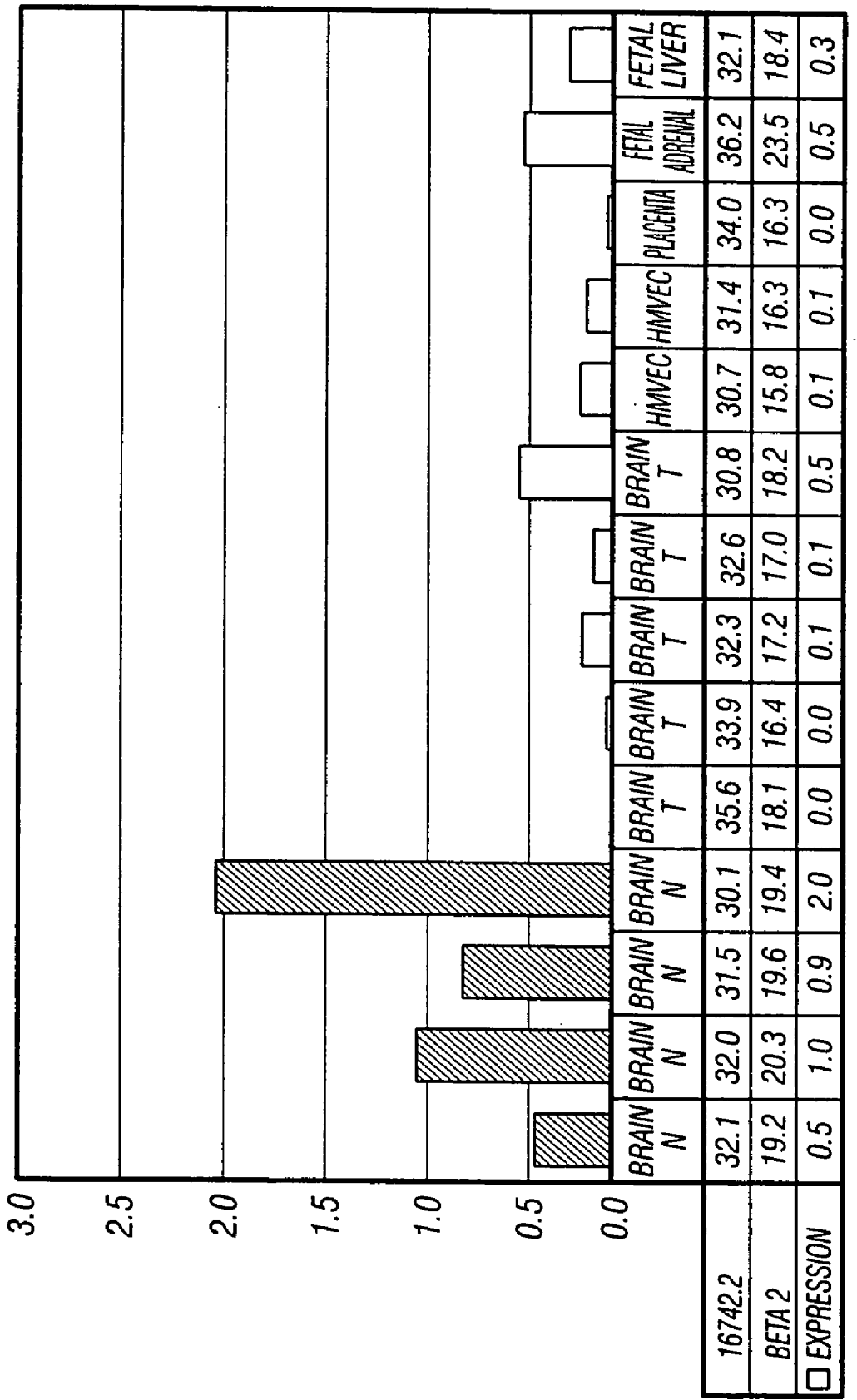
FIG. 17 is an oncology panel bar graph depicting the expression of 16742 RNA relative to a no template control in clinical angiogenic samples showing decreased expression in 4/5 clinical brain tumors in comparison to normal brain tissues, which expression was detected using Taq Man analysis.
Figure 18:
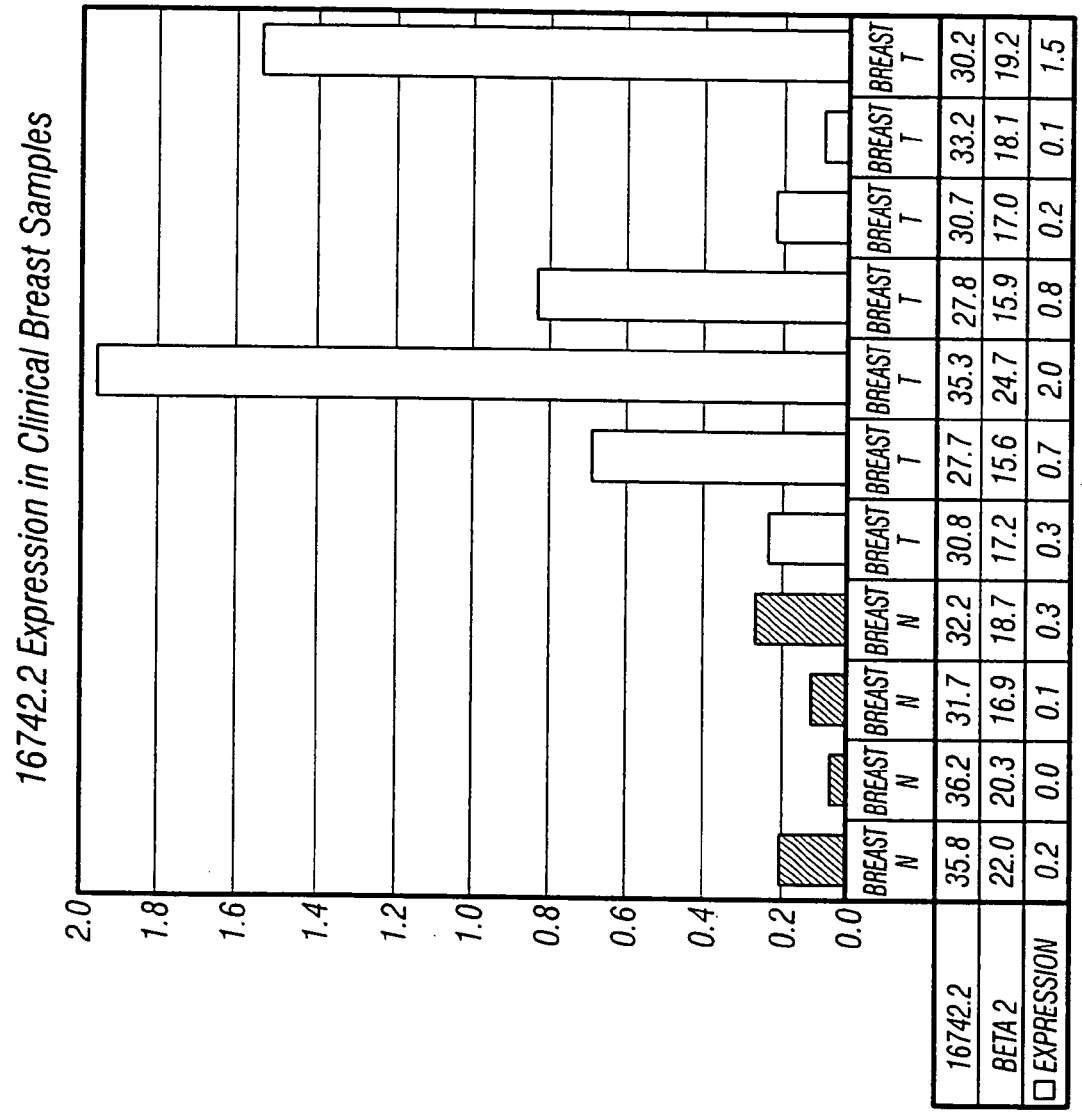
FIG. 18 is an oncology panel bar graph depicting the expression of 16742 RNA relative to a no template control showing an increased expression in 4/7 clinical breast tumors in comparison to normal breast tissues, which expression was detected using Taq Man analysis.
Figure 19:
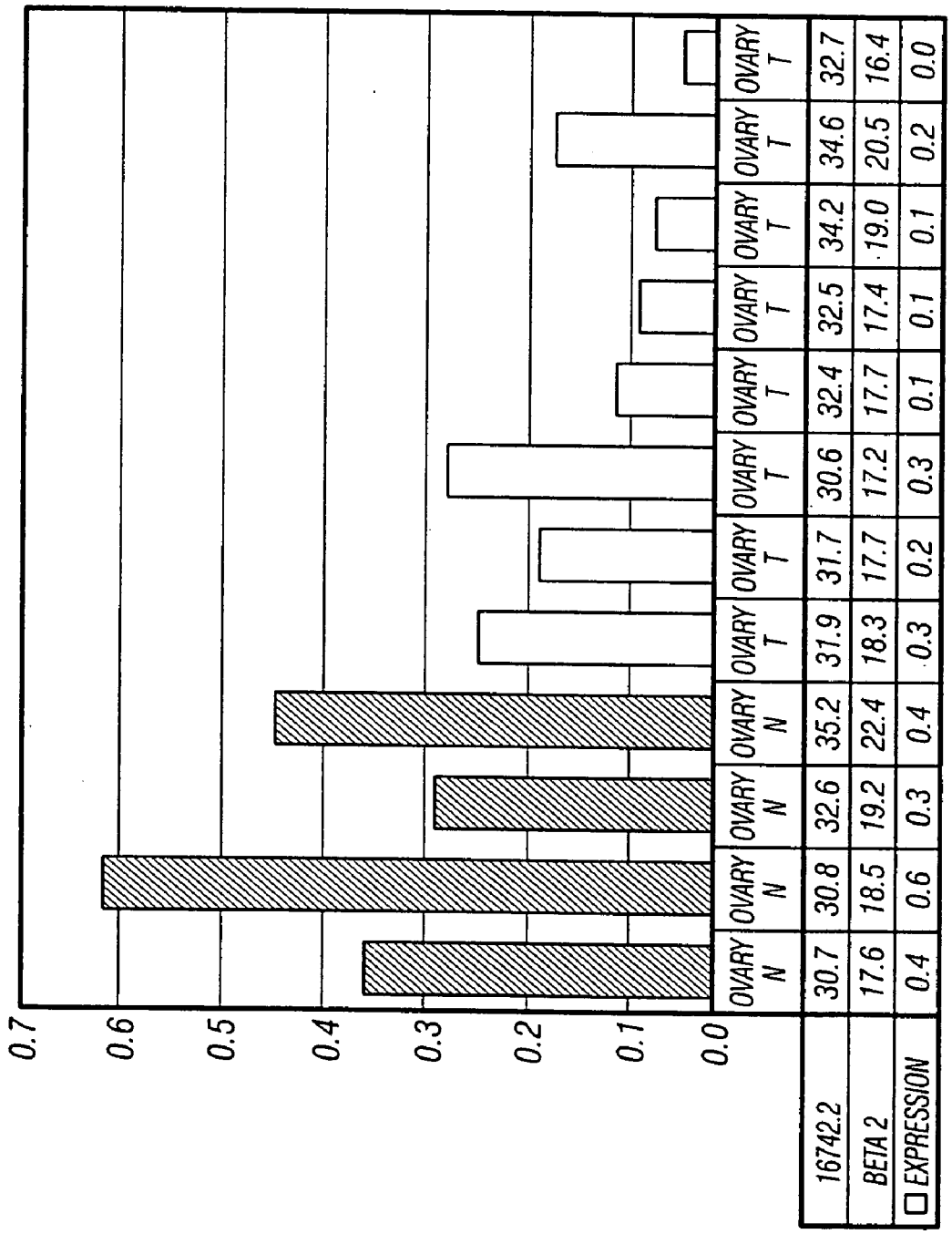
FIG. 19 is an oncology panel bar graph depicting the expression of 16742 RNA relative to a no template control showing a decreased expression in 7/8 clinical ovary tumors in comparison to normal ovary tissues, which expression was detected using Taq Man analysis.
Figure 20:
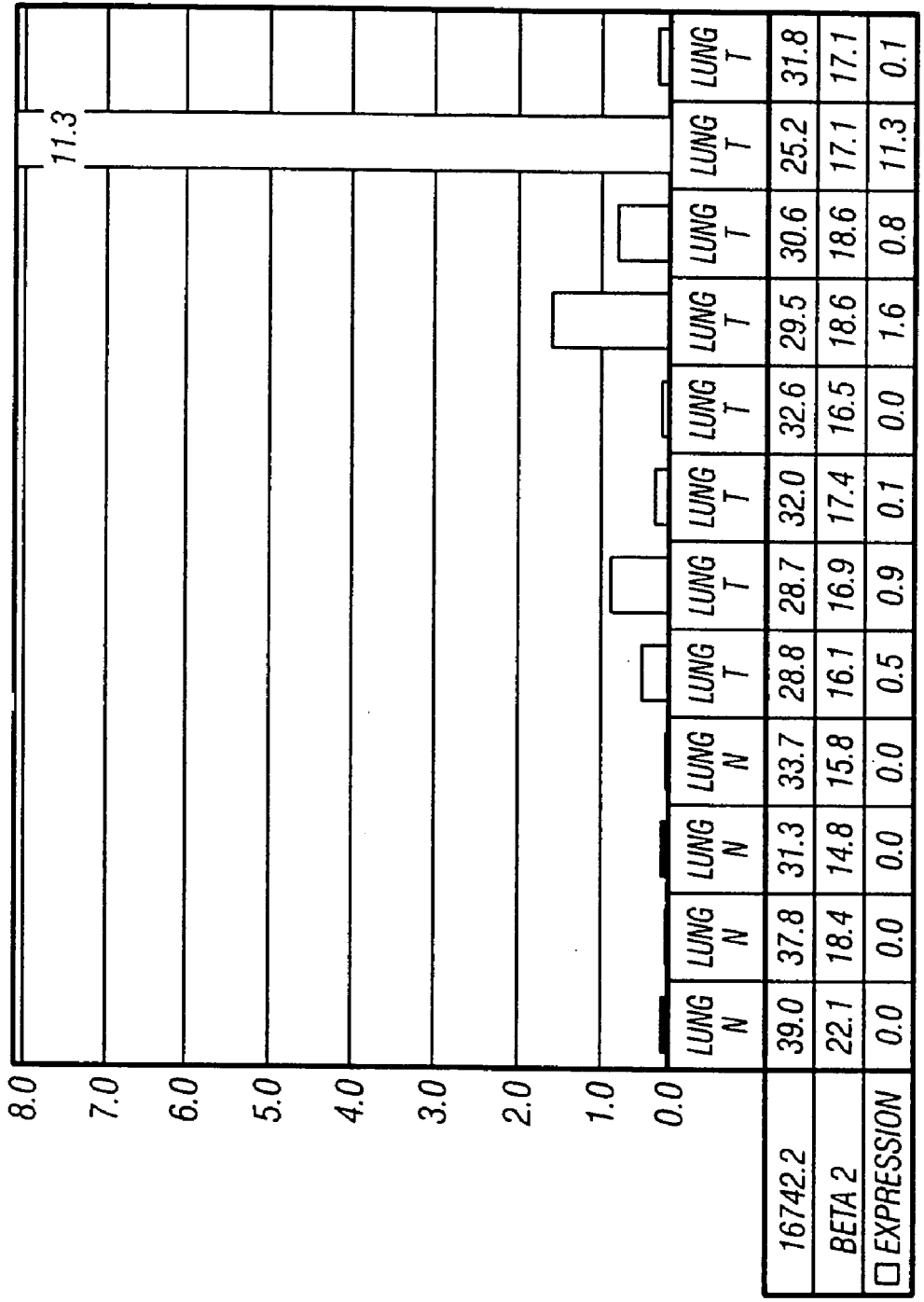
FIG. 20 is an oncology panel bar graph depicting the expression of 16742 RNA relative to a no template control showing an increased expression in 7/8 clinical lung tumors in comparison to normal lung tissues, which expression was detected using Taq Man analysis.

FIG. 16 shows some 16742 expression in colon and normal tumor with increased expression in 2/7 colon tumor samples in comparison to normal colon tissue samples and increased expression in 4/4 liver metastasis in comparison to normal liver tissues. In an angiogenic panel, the results of which are shown in FIG. 17, decreased 16742 expression is shown in 5/5 brain tumors in comparison to normal brain tissue. FIG. 18 shows increased expression in 4/7 breast tumor samples in comparison with normal breast tissue. Decreased 16742 expression was found in 8/8 ovary tumor samples in comparison to normal ovary samples as shown in FIG. 19. FIG. 20 shows increased expression in 7/8 lung tumor samples in comparison to normal lung tissue samples. Again, expression was detected using Taq Man analysis.

Figure 21A:
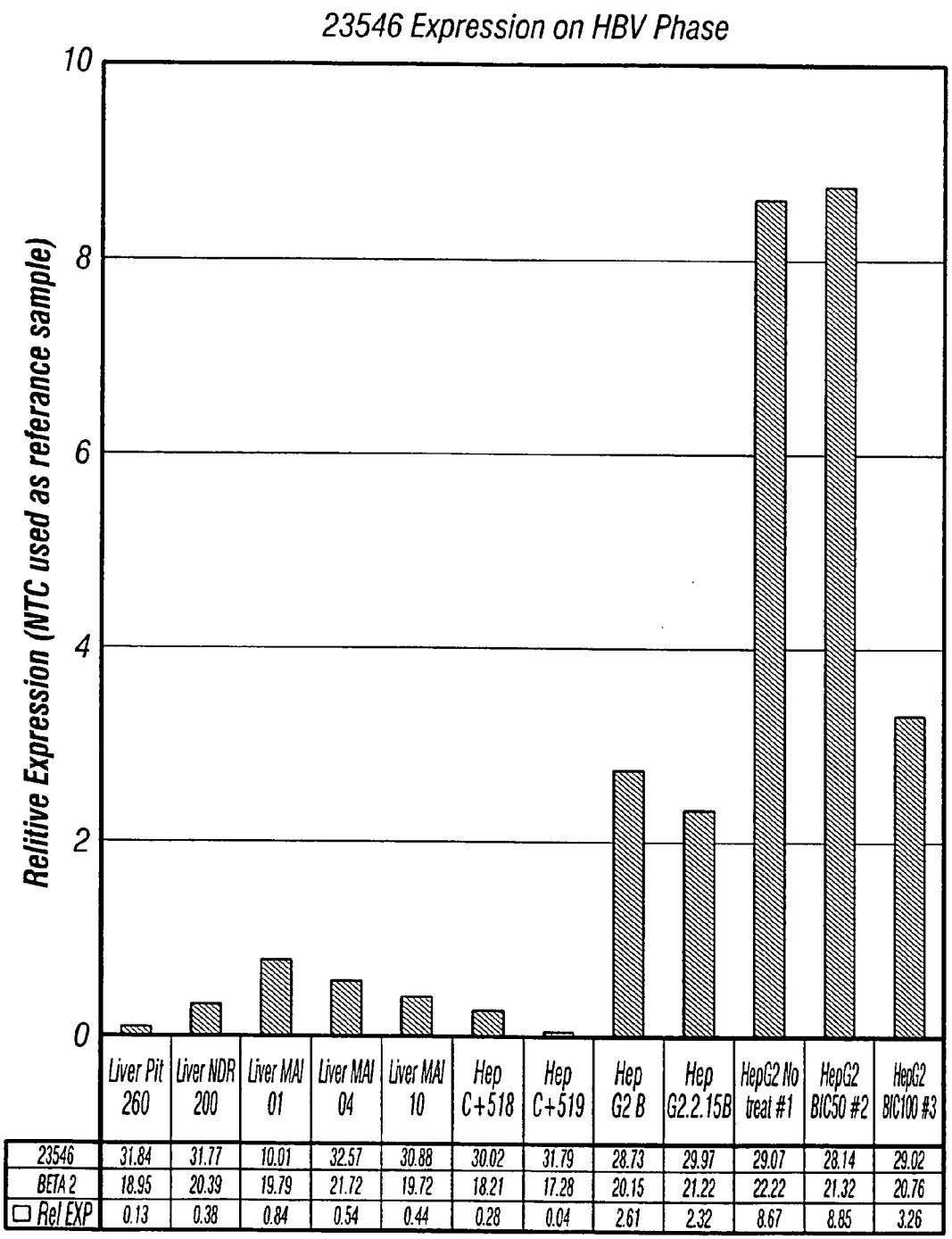
FIG. 21A–B is an HBV Phase panel bar graph depicting the relative expression of 23546 RNA relative to a no template control in a panel of human tissues, cells or cell lines, detected using real-time quantitative RT-PCR Taq Man analysis.
Figure 21B:
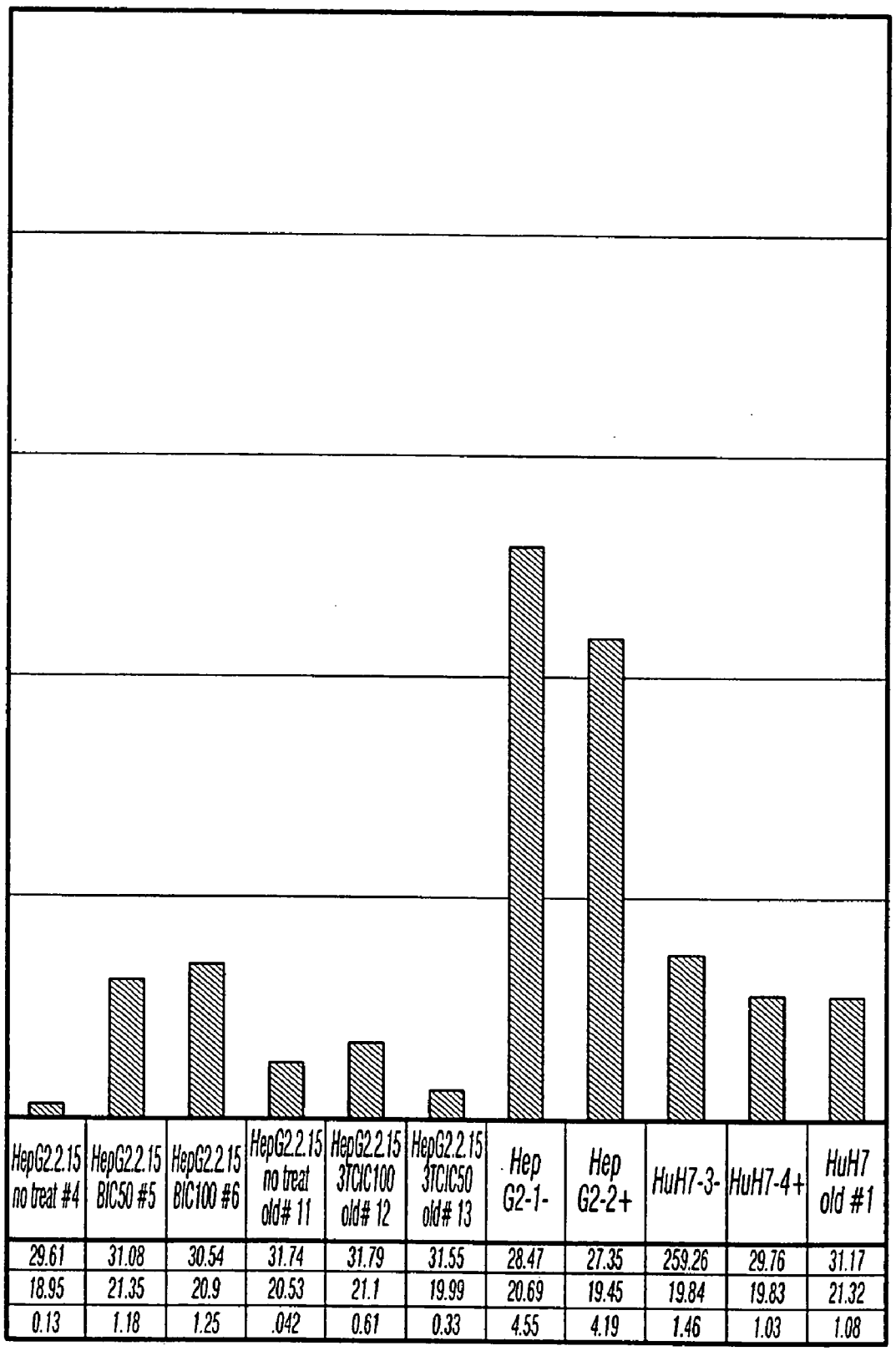

Expression of 23546 on HBV phase panel as shown in FIG. 21 shows high expression in various human hepatoma HepG2 cells as indicated.

Figure 22:
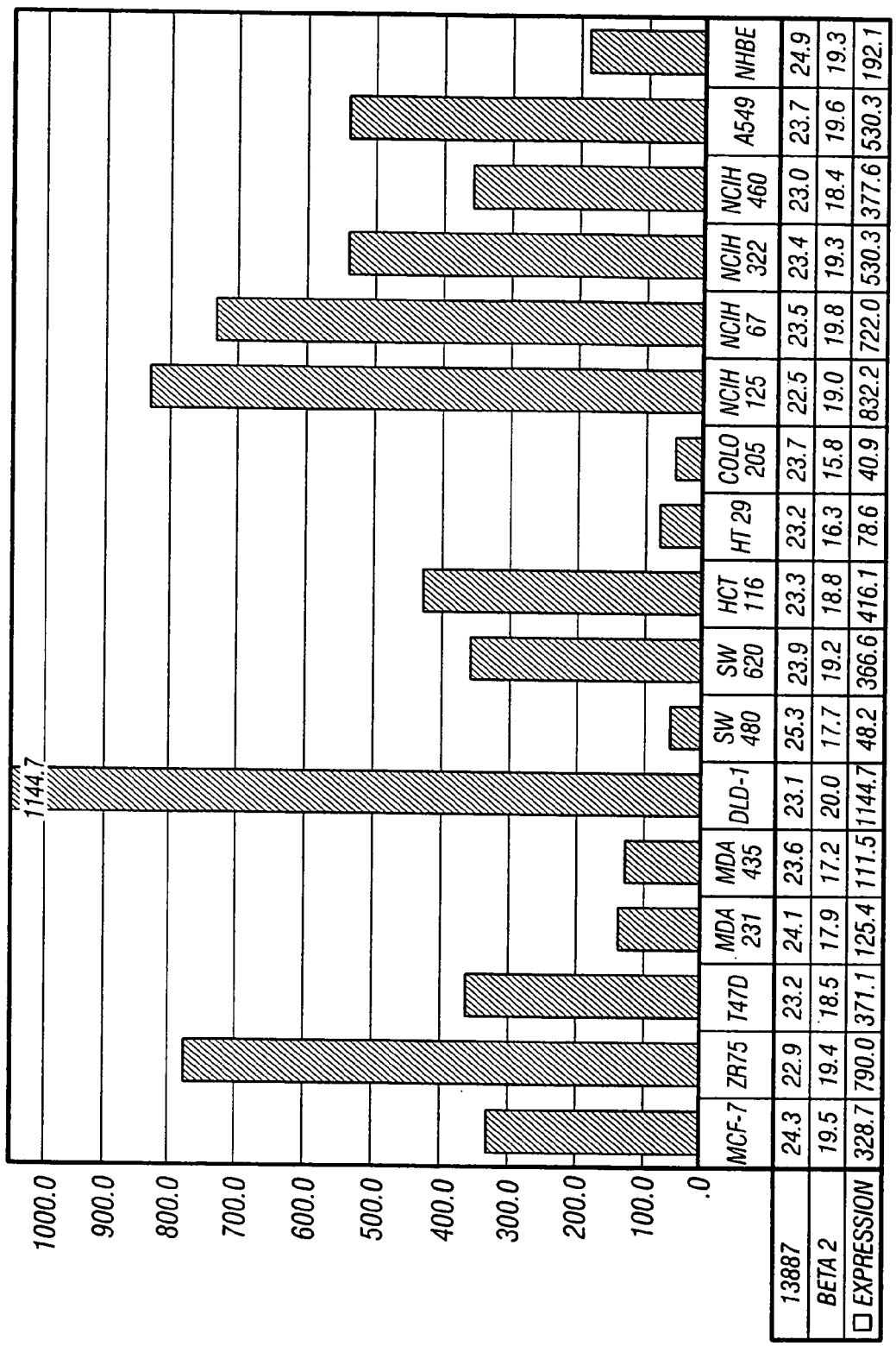
FIG. 22 depicts variable expression of 13887 in a xenograph panel.
Figure 23A:
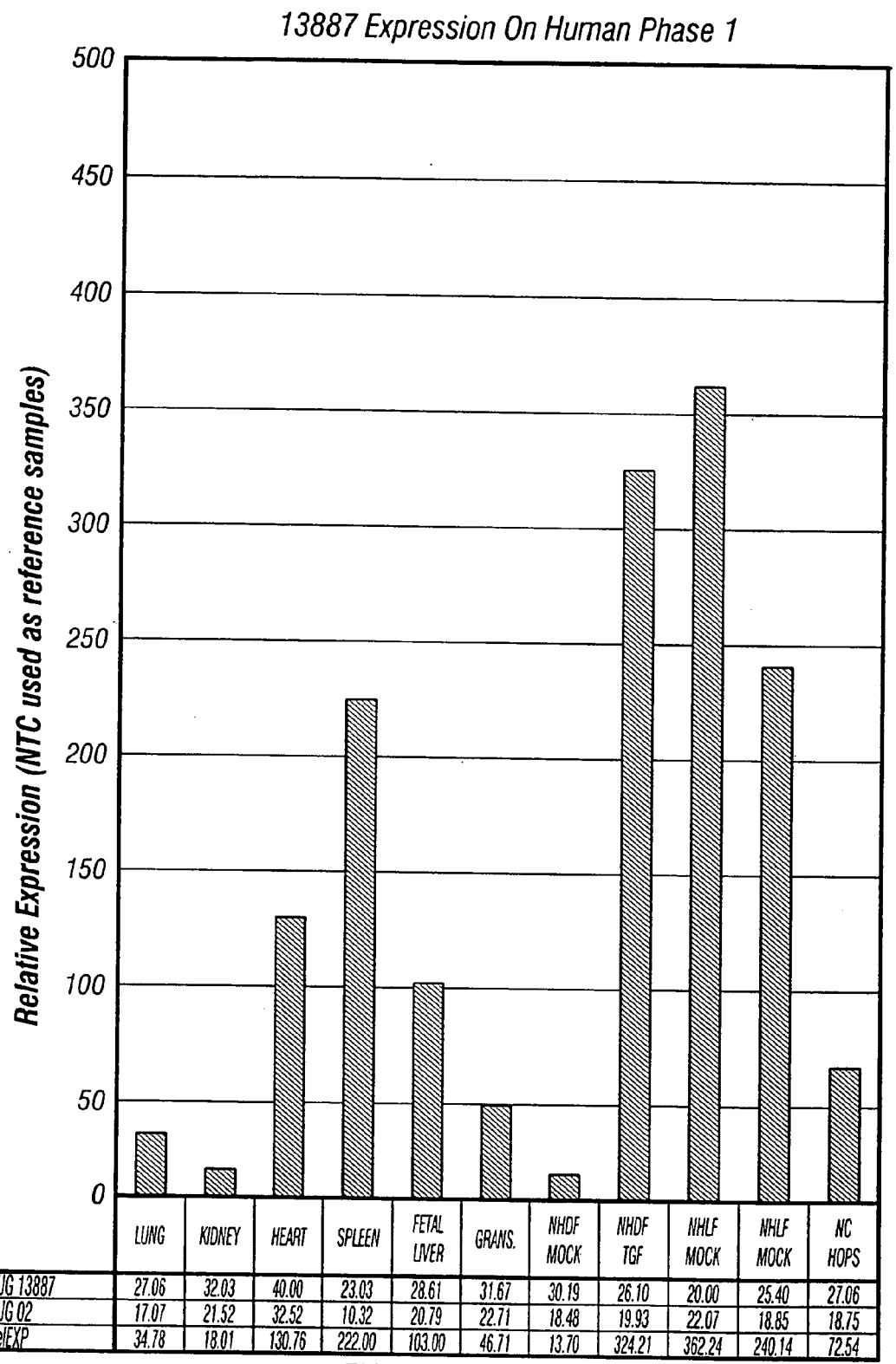
FIG. 23A–D is a Phase I panel bar graph depicting the relative expression of 13887 RNA relative to a no template control in a panel of human tissues or cells, including but not limited to lung, kidney, heart, spleen, fetal liver, mock normal human dermal fibroblasts (NHDF mock), NHDF transforming growth factor (TGF), mock normal human lung fibroblast (NHLF), NHLF TGF, liver pool, tonsil, CD4, CD8, CD19, cord blood, erythroid, bone marrow GPA, Hep G2, leukemia cell line (HL60), K562 erythroid cells, Hep 3B, among others, detected using real-time quantitative RT-PCR Taq Man analysis.
Figure 23B:
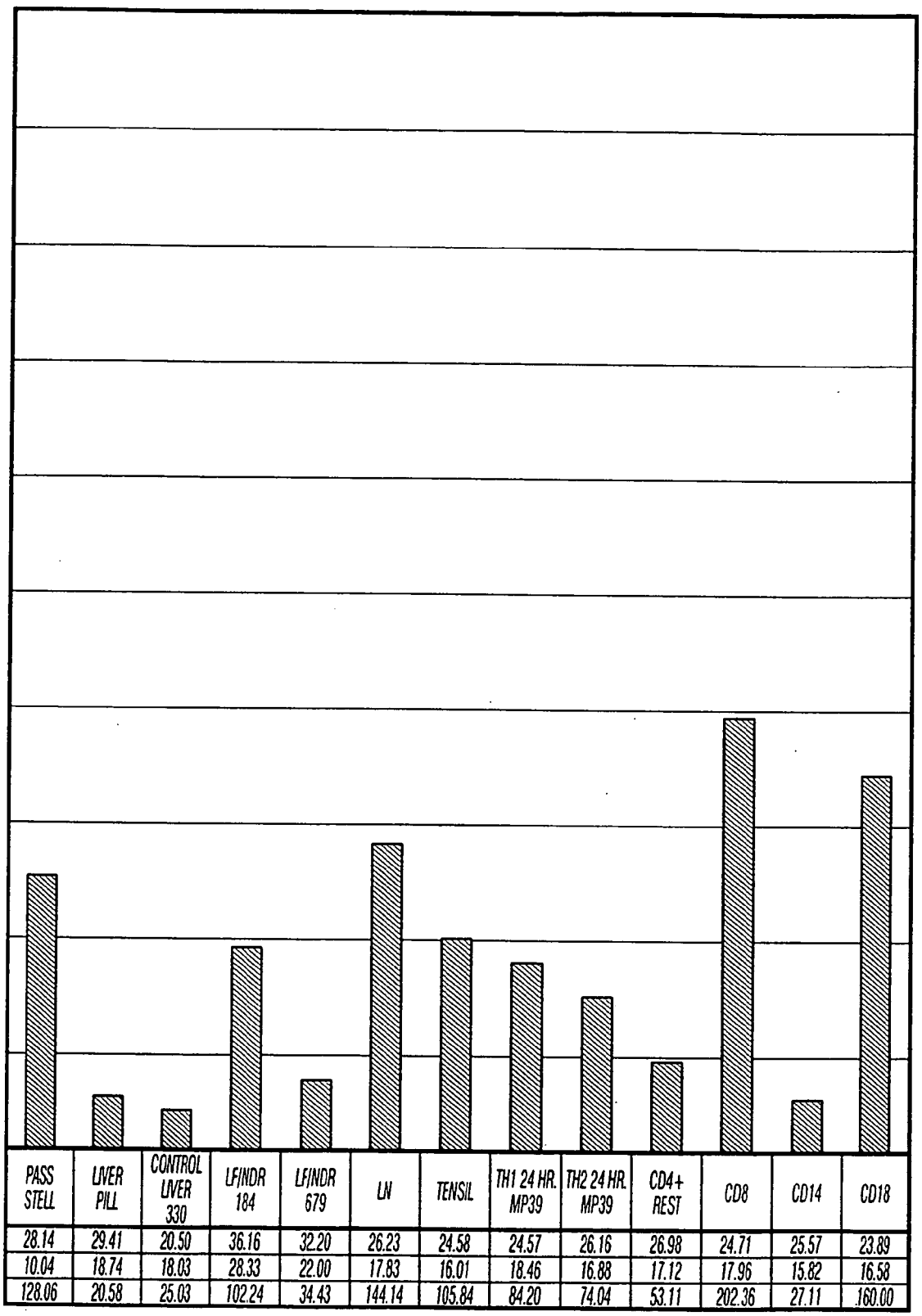
Figure 23C:
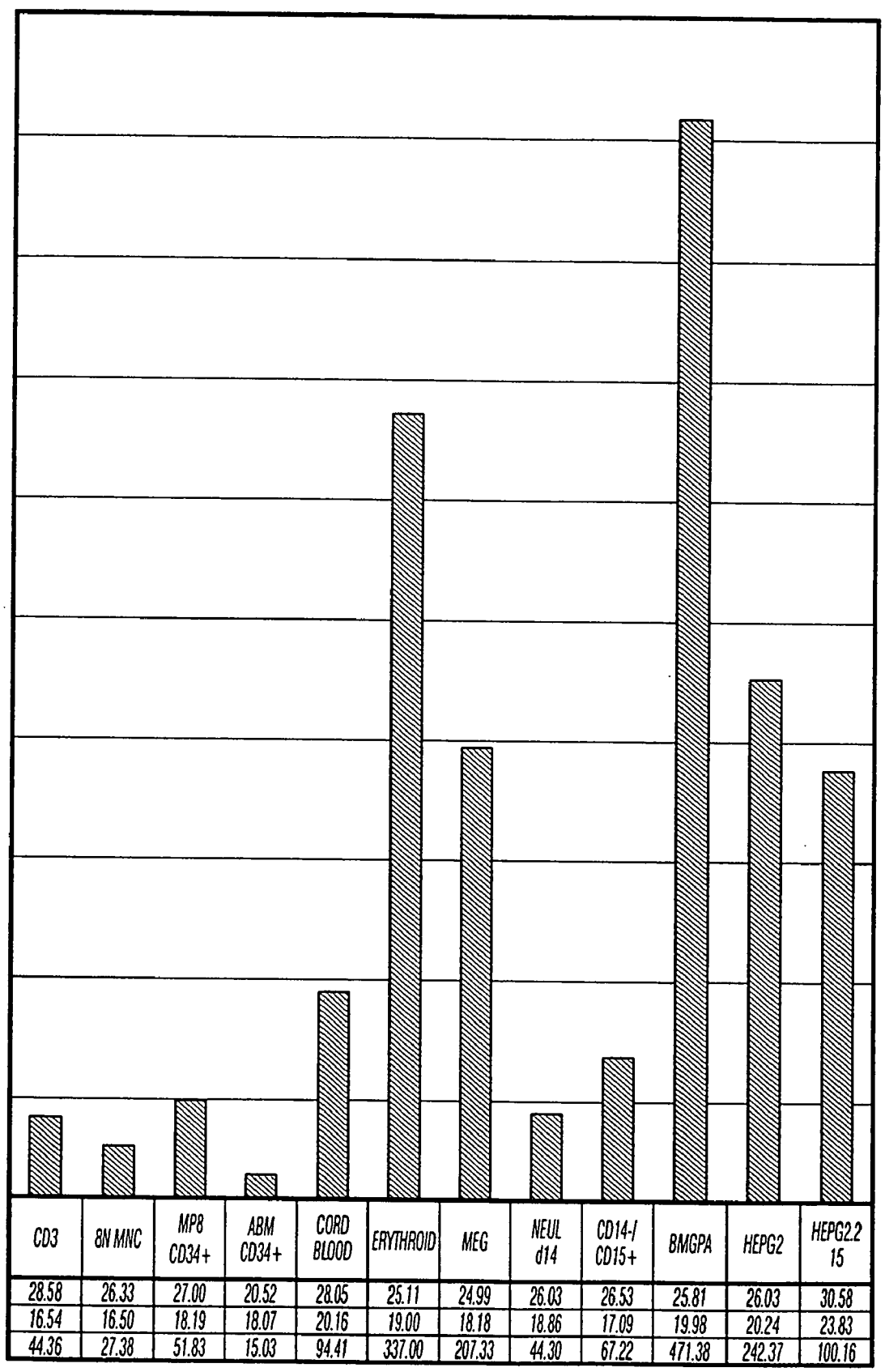
Figure 23D:
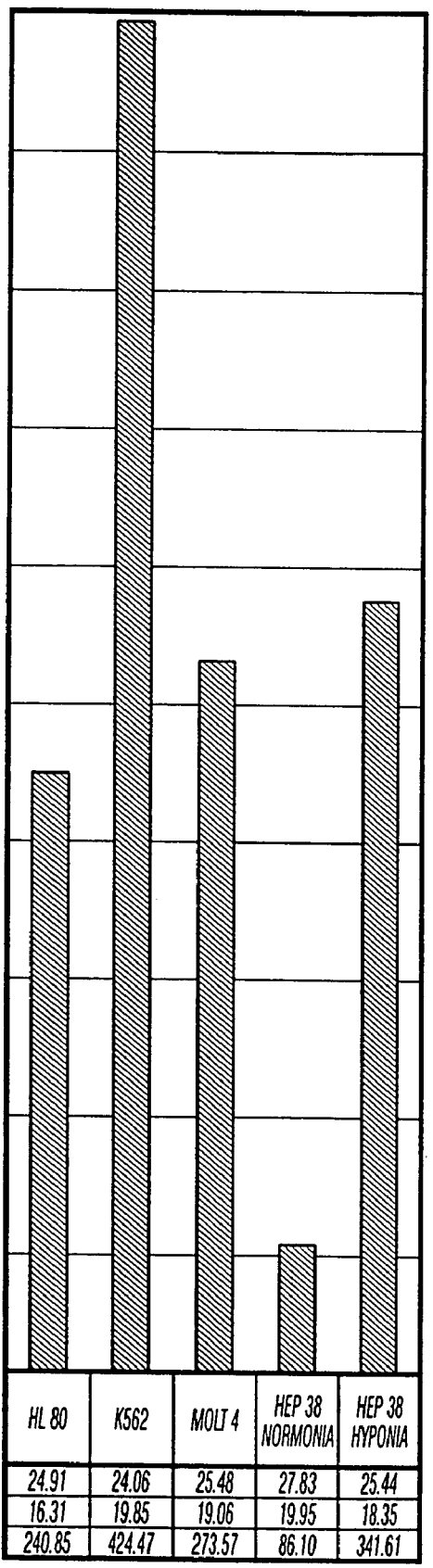
Figure 24:
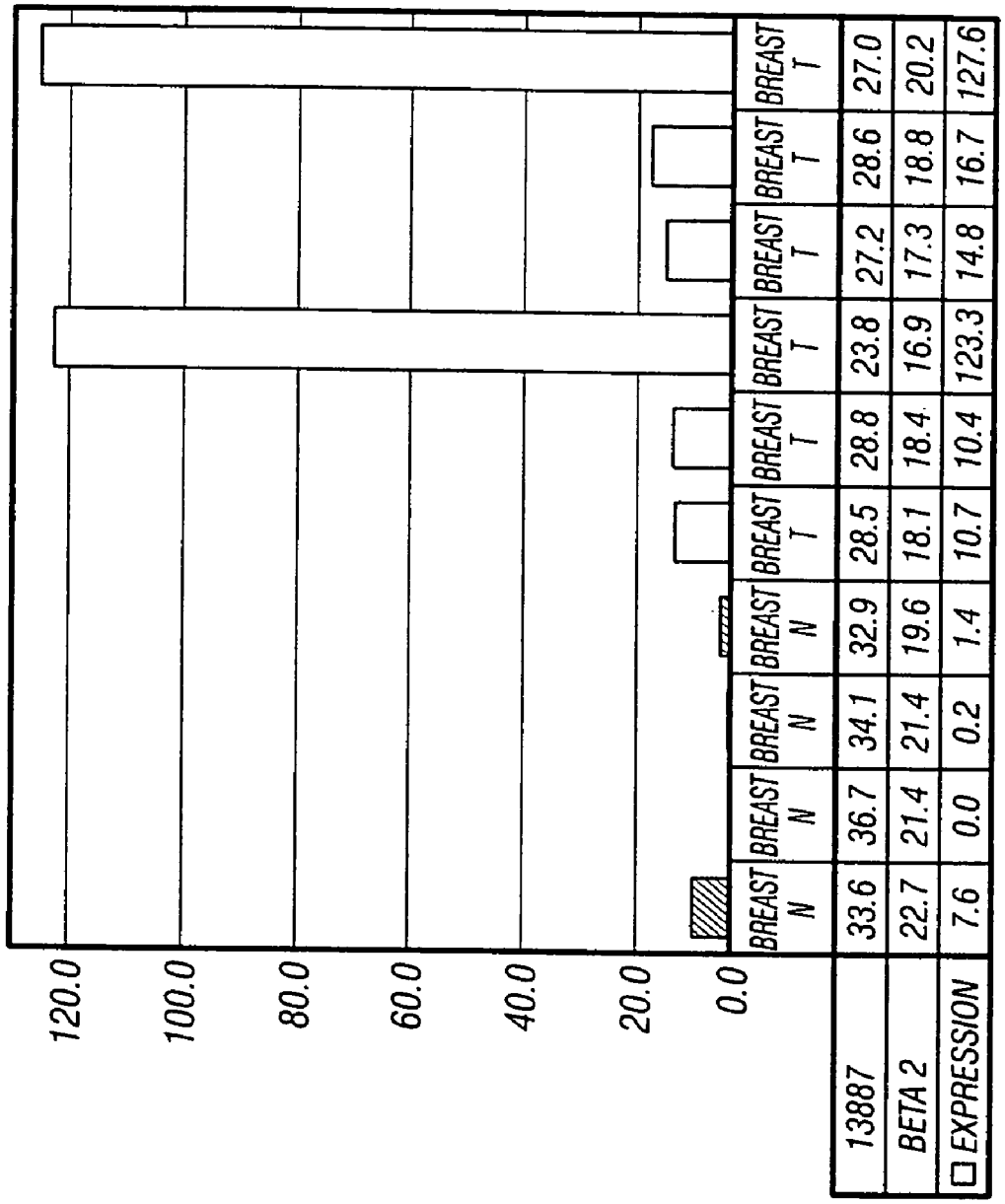
FIG. 24 is an oncology panel bar graph depicting the expression of 13887 RNA relative to a no template control showing an increased expression in 6/6 clinical breast tumors in comparison to normal breast tissues, which expression was detected using Taq Man analysis.
Figure 25:
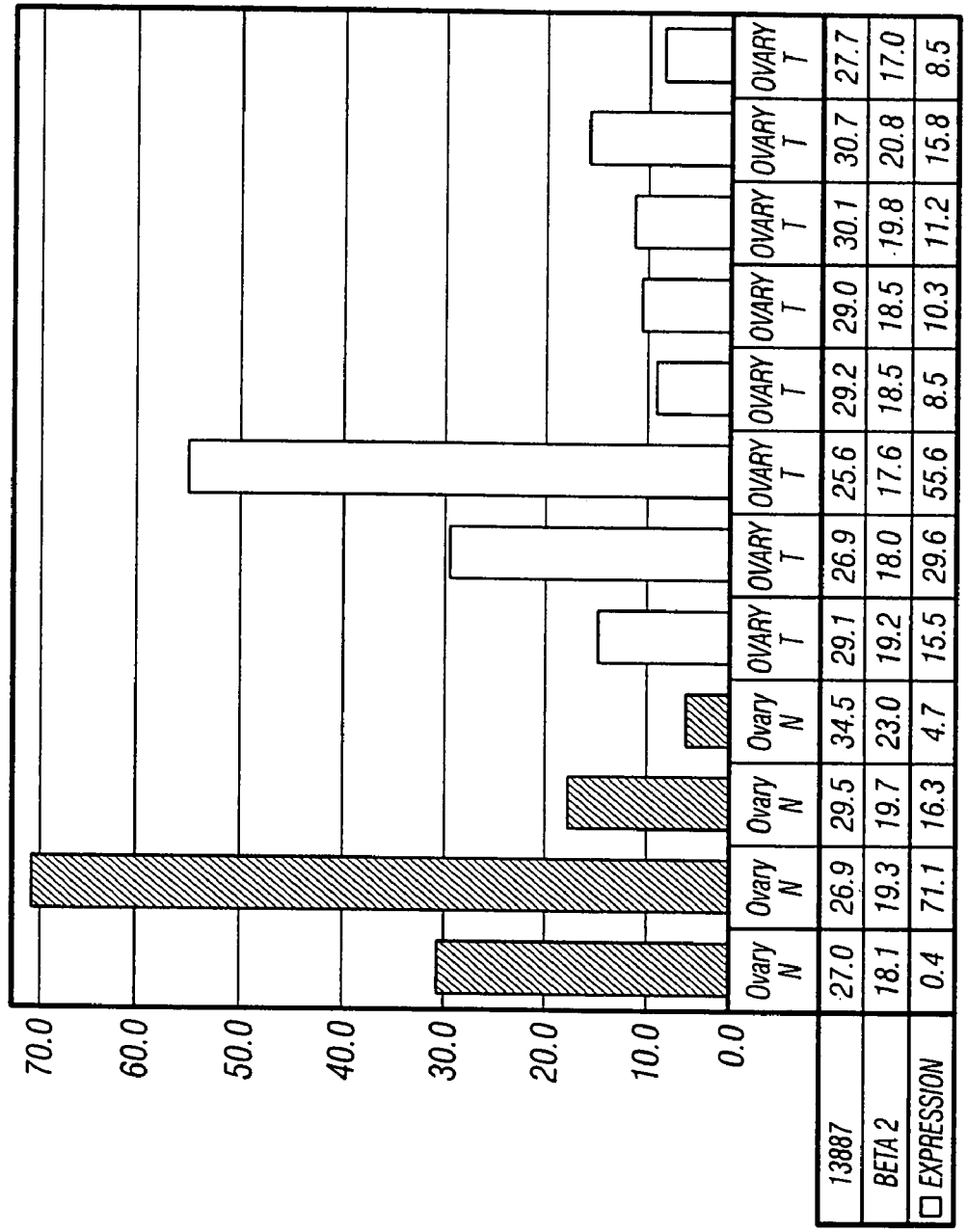
FIG. 25 is an oncology panel bar graph depicting the expression of 13887 RNA relative to a no template control showing expression in both clinical ovary tumors and normal ovary tissues, which expression was detected using Taq Man analysis.
Figure 26:
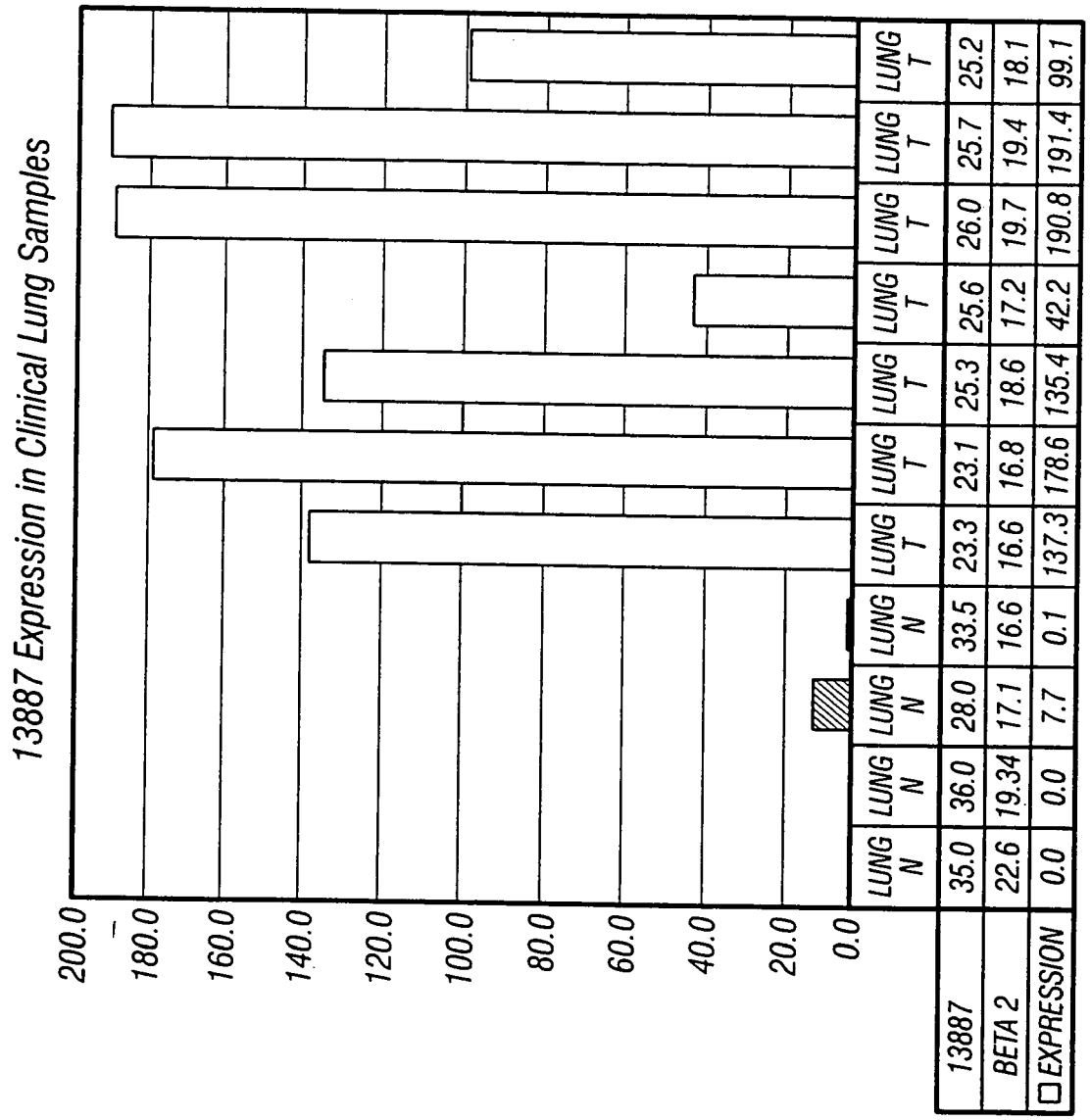
FIG. 26 is an oncology panel bar graph depicting the expression of 13887 RNA relative to a no template control showing an increased expression in 7/7 clinical lung tumors in comparison to normal lung tissues, which expression was detected using Taq Man analysis.
Figure 27:
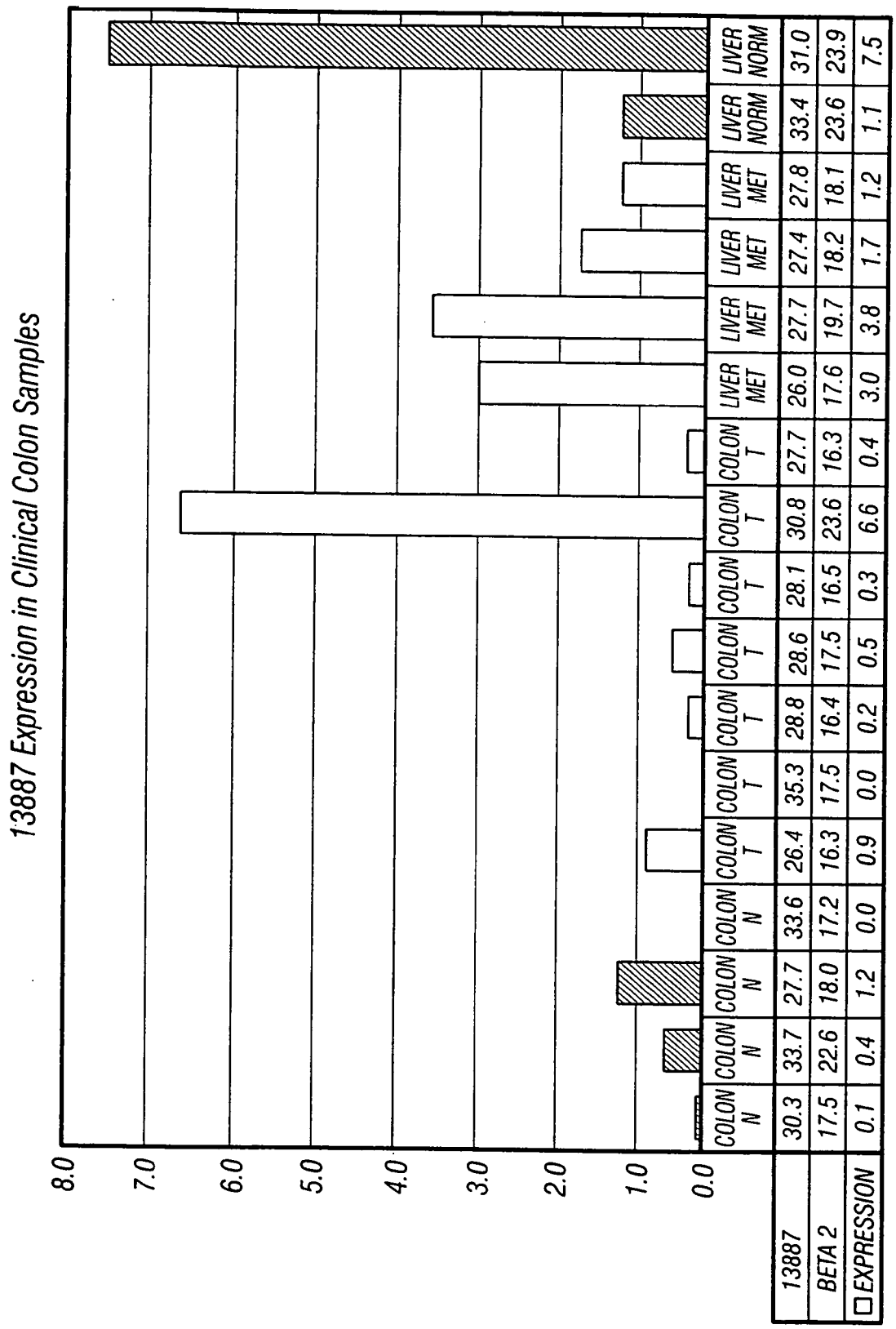
FIG. 27 is an oncology panel bar graph depicting the expression of 13887 RNA relative to a no template control showing expression in both clinical colon and liver tumors and normal colon and liver tissues, which expression was detected using Taq Man analysis.
Figure 28:
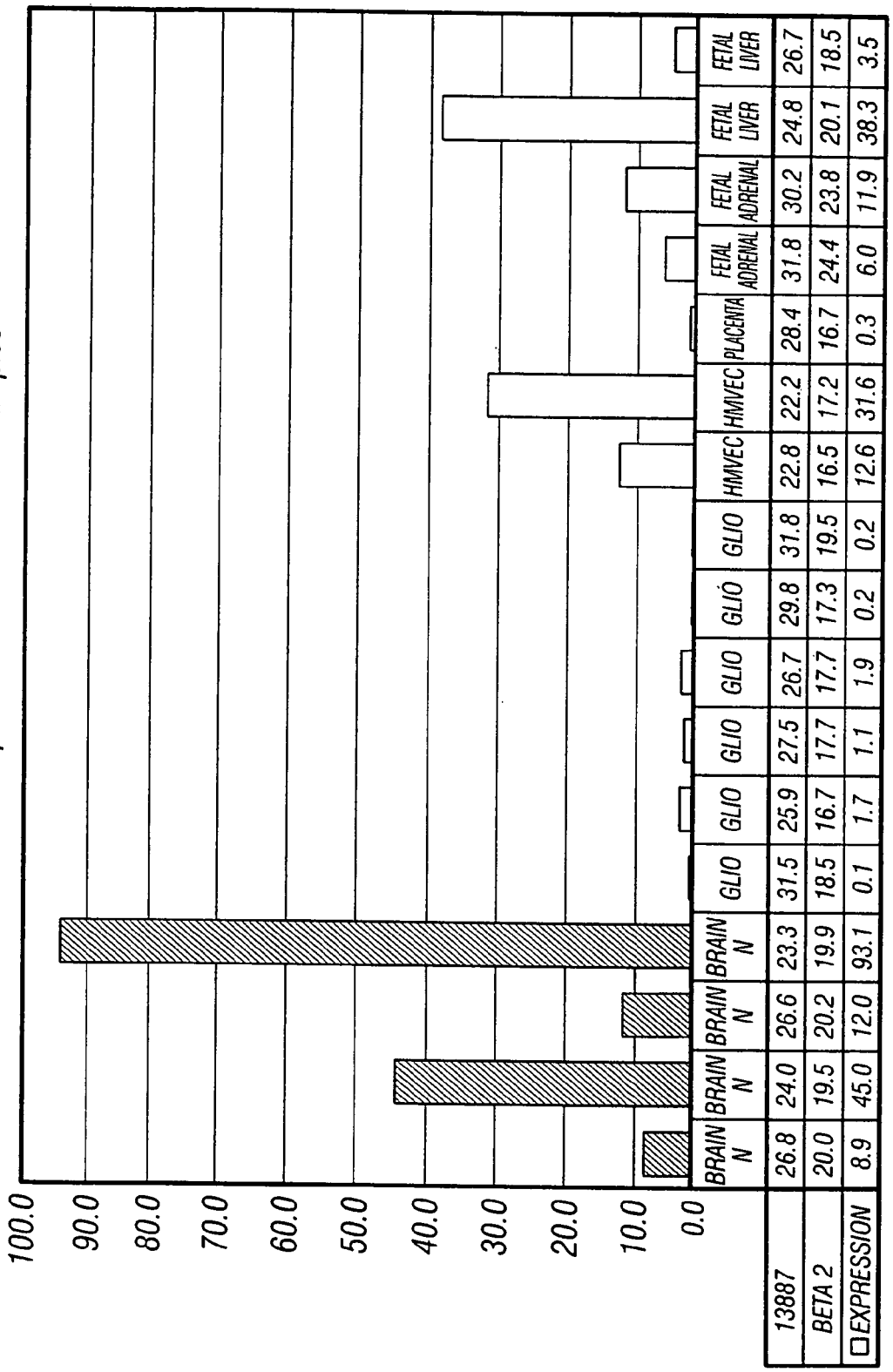
FIG. 28 is an oncology panel bar graph depicting the expression of 13887 RNA relative to a no template control showing various positive expression normal brain tissues, in glioblastoma (GLIO), HMVEC, Placenta Fetal Adrenal, and fetal liver cells, which expression was detected using Taq Man analysis. Expression was decreased in 6/6 glioblastoma samples in comparison to normal brain tissue.

Variable expression was found in xenographs of cell lines tested as shown in FIG. 22 for 13887. The highest expression for 13887 was found in the DLD1 colon tumor cell line. The Phase I panel shown in FIG. 23 shows the highest 13887 expression in the human erythroleukemia cell line, K562, and BM GPA cell lines. FIG. 24 shows an increased expression in 6/6 breast tumor samples in comparison with normal breast tissue. FIG. 25 shows variable expression in normal ovary in comparison to ovary tumor samples. FIG. 26 shows increased expression in 7/7 lung tumor samples in comparison with normal lung tissue. Increased expression was found in 1/7 colon samples in comparison to normal colon samples and variable expression was found in liver metastases in comparison to normal liver tissues. FIG. 27 shows variable expression in clinical colon and liver tissues and tumors. FIG. 28 shows that expression was found in brain, glioblastoma (GLIO), HUMVEC, placenta, fetal adrenal and fetal liver tissues. This figure also shows decreased expression in 6/6 glioblastoma tissues in comparison to normal brain tissues. In FIG. 29, relatively high expression was found in brain cortex, brain hypothalamus, glial cells and aortic SMC (late). Expression was detected using Taq Man analysis.

Expression profiling results using in situ hybridization techniques have shown that 13887 mRNA has been detected in human breast, lung, colon, and ovary issues. Regarding breast tissue, 13887 was found to be expressed in both normal (4/4) and malignant (6/6) epithelium. Positive expression of 13887 has been shown in 5/5 lung tumors in comparison with low expression, 1/3 in normal lung tissue samples. In addition, positive expression of 13887 has been shown in 2/2 colon tumors and 2/2 metastases in comparison with lack of expression, 0/1, in normal colon tissue samples. Further, 13887 has been shown to be expressed both in tumors and normal tissues, of normal ovarian stroma (1/1) and carcinomas (2/2).

As seen by these results, 16742, 23546, or 13887 molecules have been found to be overexpressed or underexpressed in some tumor or cells, where the molecules may be inappropriately propagating either cell proliferation or cell survival signals or have aberrant protein kinase activity. As such, 16742, 23546, or 13887 molecules may serve as specific and novel identifiers of such tumor cells or disorders.

Further, modulators of the 16742 molecules are useful for the treatment of cancer. For example, inhibitors of the 16742 molecules are useful for the treatment of cancer where 16742 is upregulated in tumor cells such as colon, breast, and lung cancer and liver metastases, and are useful as a diagnostic. In addition, activators of the 16742 molecules are useful for the treatment of cancer, such as brain or ovarian cancer, where 16742 expression is downregulated.

In addition, modulators of the 23546 molecules are also useful for the treatment of cancer, preferably liver cancer, and useful as a diagnostic.

Modulators of 13887 molecules are also useful for the treatment of cancer. For example, inhibitors of the 13887 molecules are useful for the treatment of cancer where 13887 is upregulated in tumor cells such as breast and lung cancer, and are useful as a diagnostic. In addition, activators of the 13887 molecules, which are highly expressed in normal brain tissues, are useful for the treatment of cancer, such as brain cancer, where 13887 expression is downregulated.

Example 3

Recombinant Expression of 3714, 16742, 23546, or 13887 in Bacterial Cells

In this example, 3714, 16742, 23546, or 13887 is expressed as a recombinant glutathione-S-transferase (GST) fusion polypeptide in *E. coli* and the fusion polypeptide is isolated and characterized. Specifically, 3714, 16742, 23546, or 13887 is fused to GST and this fusion polypeptide is expressed in *E. coli*, e.g., strain PEB199. Expression of the GST-3714,–16742,–23546, or -13887 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 3714, 16742, 23546, or 13887 Protein in COS Cells

To express the 3714, 16742, 23546, or 13887 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 3714, 16742, 23546, or 13887 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 3714, 16742, 23546, or 13887 DNA sequence is amplified by PCR using two primers. The 5' primer contains the restriction site of interest followed by approximately twenty nucleotides of the 3714, 16742, 23546, or 13887 coding sequence starting from the initiation codon; the 3' end sequence contains complementary sequences to the other restriction site of interest, a translation stop codon, the HA tag or FLAG tag and the last 20 nucleotides of the 3714, 16742, 23546, or 13887 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 3714, 16742, 23546, or 13887 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 3714-, 16742-, 23546-, or 13887-pcDNA/Amp plasmid DNA using the calcium phosphate or calcium chloride co-precipitation methods, DEAF-dextran-mediated transfection, lipofection, or electroporation. Other suitable methods for transfecting host cells can be found in Sambrook, J., Fritsh, E. F., and Maniatis, T. *Molecular Cloning: A Laboratory Manual, 2nd, ed., Cold Spring Harbor Laboratory*, Cold Spring Harbor Laboratory Press, Cold Spring Harbor, N.Y, 1989. The expression of the 3714, 16742, 23546, or 13887 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 3714, 16742, 23546, or 13887 coding sequence is cloned directly into the polylinker of the pcDNA/Amp vector using the appropriate restriction sites. The resulting plasmid is transfected into COS cells in the manner described above, and the expression of the 3714, 16742, 23546, or 13887 polypeptide is detected by radiolabelling and immunoprecipitation using a 3714, 16742, 23546, or 13887 specific monoclonal antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound capable of modulating cellular proliferation comprising:
   a) contacting a test compound with a sample comprising a polypeptide selected from the group consisting of:
      i) a polypeptide comprising an amino acid sequence which is at least 95% identical to the amino acid sequence of SEQ ID NO:5, wherein said polypeptide has kinase activity;
      ii) a polypeptide which is encoded by a nucleic acid molecule comprising a nucleotide sequence which is at least 95% identical to a nucleic acid comprising the nucleotide sequence of SEQ ID NO:4 or 6, wherein said polypeptide has kinase activity;
      iii) a polypeptide which is encoded by a nucleic acid molecule comprising the nucleotide sequence of SEQ ID NO:4 or 6; and
      iv) a polypeptide comprising the amino acid sequence of SEQ ID NO:5;
   b) assaying the ability of the test compound to modulate the kinase activity of the polypeptide;
   c) contacting cells which express the polypeptide with the compound identified in b); and
   d) determining the effect of the compound on cellular proliferation; thereby identifying a compound capable of modulating cellular proliferation.

2. The method of claim 1, wherein the sample comprises the polypeptide or, a membrane-bound form of the polypeptide.

3. The method of claim 2, wherein the cells are breast cells, ovarian cells, lung cells, brain cells or colon cells.

4. The method of claim 1, wherein the cells are breast cells, ovarian cells, lung cells, brain cells or colon cells.

5. The method of claim 1, wherein the compound is a peptide, or an antibody.

* * * * *

SEQUENCE LISTING

<160> NUMBER OF SEQ ID NOS: 19

<210> SEQ ID NO 1
<211> LENGTH: 2968
<212> TYPE: DNA
<213> ORGANISM: Homo sapiens
<220> FEATURE:
<221> NAME/KEY: CDS
<222> LOCATION: (140)...(2491)
<220> FEATURE:
<221> NAME/KEY: misc_feature
<222> LOCATION: (1)...(2968)
<223> OTHER INFORMATION: n = A,T,C or G

<400> SEQUENCE: 1

```
ncsssymcgc gkcssgysss sgrrgsmrsm rsmmgcggcg gcggcagccg gagcagtagg      60
cacccgagca gcgccagcgg ccgagcgggc ggcttcctgg cctgggcgct ccggtggcgg     120
cggaggtgcg cgcggagcc atg gtt atc atg tcg gag ttc agc gcg gac ccc     172
                    Met Val Ile Met Ser Glu Phe Ser Ala Asp Pro
                     1               5                  10 gcg ggc cag ggt cag ggc cag cag aag ccc ctc cgg gtg ggt ttt tac      220
Ala Gly Gln Gly Gln Gly Gln Gln Lys Pro Leu Arg Val Gly Phe Tyr
            15                  20                  25 gac atc gag cgg acc ctg ggc aaa ggc aac ttc gcg gtg gtg aag ctg      268
Asp Ile Glu Arg Thr Leu Gly Lys Gly Asn Phe Ala Val Val Lys Leu
        30                  35                  40 gcg cgg cat cga gtc acc aaa acg cag gtt gca ata aaa ata att gat      316
Ala Arg His Arg Val Thr Lys Thr Gln Val Ala Ile Lys Ile Ile Asp
    45                  50                  55 aaa aca cga tta gat tca agc aat ttg gag aaa atc tat cgt gag gtt      364
Lys Thr Arg Leu Asp Ser Ser Asn Leu Glu Lys Ile Tyr Arg Glu Val
60                  65                  70                  75 cag ctg atg aag ctt ctg aac cat cca cac atc ata aag ctt tac cag      412
Gln Leu Met Lys Leu Leu Asn His Pro His Ile Ile Lys Leu Tyr Gln
                80                  85                  90 gtt atg gaa aca aag gac atg ctt tac atc gtc act gaa ttt gct aaa      460
Val Met Glu Thr Lys Asp Met Leu Tyr Ile Val Thr Glu Phe Ala Lys
            95                 100                 105 aat gga gaa atg ttt gat tat ttg act tcc aac ggg cac ctg agt gag      508
Asn Gly Glu Met Phe Asp Tyr Leu Thr Ser Asn Gly His Leu Ser Glu
        110                 115                 120 aac gag gcg cgg aag aag ttc tgg caa atc ctg tcg gcc gtg gag tac      556
Asn Glu Ala Arg Lys Lys Phe Trp Gln Ile Leu Ser Ala Val Glu Tyr
    125                 130                 135 tgt cac gac cat cac atc gtc cac cgg gac ctc aag acc gag aac ctc      604
Cys His Asp His His Ile Val His Arg Asp Leu Lys Thr Glu Asn Leu
140                 145                 150                 155 ctg ctg gat ggc aac atg gac atc aag ctg gca gat ttt gga ttt ggg      652
Leu Leu Asp Gly Asn Met Asp Ile Lys Leu Ala Asp Phe Gly Phe Gly
                160                 165                 170 aat ttc tac aag tca gga gag cct ctg tcc acg tgg tgt ggg agc ccc      700
Asn Phe Tyr Lys Ser Gly Glu Pro Leu Ser Thr Trp Cys Gly Ser Pro
            175                 180                 185 ccg tat gcc gcc ccg gaa gtc ttt gag ggg aag gag tat gaa ggc ccc      748
Pro Tyr Ala Ala Pro Glu Val Phe Glu Gly Lys Glu Tyr Glu Gly Pro
        190                 195                 200 cag ctg gac atc tgg agc ctg ggc gtg gtg ctg tac gtc ctg gtc tgc      796
Gln Leu Asp Ile Trp Ser Leu Gly Val Val Leu Tyr Val Leu Val Cys
    205                 210                 215
```

-continued

```
ggt tct ctc ccc ttc gat ggg cct aac ctg ccg acg ctg aga cag cgg      844
Gly Ser Leu Pro Phe Asp Gly Pro Asn Leu Pro Thr Leu Arg Gln Arg
220             225             230             235 gtg ctg gag ggc cgc ttc cgc atc ccc ttc ttc atg tct caa gac tgt      892
Val Leu Glu Gly Arg Phe Arg Ile Pro Phe Phe Met Ser Gln Asp Cys
                240             245             250 gag agc ctg atc cgc cgc atg ctg gtg gtg gac ccc gcc agg cgc atc      940
Glu Ser Leu Ile Arg Arg Met Leu Val Val Asp Pro Ala Arg Arg Ile
            255             260             265 acc atc gcc cag atc cgg cag cac cgg tgg atg cgg gct gag ccc tgc      988
Thr Ile Ala Gln Ile Arg Gln His Arg Trp Met Arg Ala Glu Pro Cys
        270             275             280 ttg ccg gga ccc gcc tgc ccc gcc ttc tcc gca cac agc tac acc tcc     1036
Leu Pro Gly Pro Ala Cys Pro Ala Phe Ser Ala His Ser Tyr Thr Ser
285             290             295 aac ctg ggc gac tac gat gag cag gcg ctg ggt atc atg cag acc ctg     1084
Asn Leu Gly Asp Tyr Asp Glu Gln Ala Leu Gly Ile Met Gln Thr Leu
300             305             310             315 ggc gtg gac cgg cag agg acg gtg gag tca ctg caa aac agc agc tat     1132
Gly Val Asp Arg Gln Arg Thr Val Glu Ser Leu Gln Asn Ser Ser Tyr
                320             325             330 aac cac ttt gct gcc att tat tac ctc ctc ctt gag cgg ctc aag gag     1180
Asn His Phe Ala Ala Ile Tyr Tyr Leu Leu Leu Glu Arg Leu Lys Glu
            335             340             345 tat cgg aat gcc cag tgc gcc cgc ccc ggg cct gcc agg cag ccg cgg     1228
Tyr Arg Asn Ala Gln Cys Ala Arg Pro Gly Pro Ala Arg Gln Pro Arg
        350             355             360 cct cgg agc tcg gac ctc agt ggt ttg gag gtg cct cag gaa ggt ctt     1276
Pro Arg Ser Ser Asp Leu Ser Gly Leu Glu Val Pro Gln Glu Gly Leu
365             370             375 tcc acc gac cct ttc cga cct gcc ttg ctg tgc ccg cag ccg cag acc     1324
Ser Thr Asp Pro Phe Arg Pro Ala Leu Leu Cys Pro Gln Pro Gln Thr
380             385             390             395 ttg gtg cag tcc gtc ctc cag gcc gag atg gac tgt gag ctc cag agc     1372
Leu Val Gln Ser Val Leu Gln Ala Glu Met Asp Cys Glu Leu Gln Ser
                400             405             410 tcg ctg cag tgg ccc ttg ttc ttc ccg gtg gat gcc agc tgc agc gga     1420
Ser Leu Gln Trp Pro Leu Phe Phe Pro Val Asp Ala Ser Cys Ser Gly
            415             420             425 gtg ttc cgg ccc cgg ccc gtg tcc cca agc agc ctg ctg gac aca gcc     1468
Val Phe Arg Pro Arg Pro Val Ser Pro Ser Ser Leu Leu Asp Thr Ala
        430             435             440 atc agt gag gag gcc agg cag ggg ccg ggc cta gag gag gag cag gac     1516
Ile Ser Glu Glu Ala Arg Gln Gly Pro Gly Leu Glu Glu Glu Gln Asp
445             450             455 acg cag gag tcc ctg ccc agc agc acg ggc cgg agg cac acc ctg gcc     1564
Thr Gln Glu Ser Leu Pro Ser Ser Thr Gly Arg Arg His Thr Leu Ala
460             465             470             475 gag gtc tcc acc cgc ctc tcc cca ctc acc gcg cca tgt ata gtc gtc     1612
Glu Val Ser Thr Arg Leu Ser Pro Leu Thr Ala Pro Cys Ile Val Val
                480             485             490 tcc ccc tcc acc acg gca agt cct gca gag gga acc agc tct gac agt     1660
Ser Pro Ser Thr Thr Ala Ser Pro Ala Glu Gly Thr Ser Ser Asp Ser
            495             500             505 tgt ctg acc ttc tct gcg agc aaa agc ccc gcg ggg ctc agt ggc acc     1708
Cys Leu Thr Phe Ser Ala Ser Lys Ser Pro Ala Gly Leu Ser Gly Thr
        510             515             520 ccg gcc act cag ggg ctg ctg ggc gcc tgc tcc ccg gtc agg ctg gcc     1756
Pro Ala Thr Gln Gly Leu Leu Gly Ala Cys Ser Pro Val Arg Leu Ala
525             530             535
```

```
tcg ccc ttc ctg ggg tcg cag tcc gcc acc cca gtg ctg cag gct cag      1804
Ser Pro Phe Leu Gly Ser Gln Ser Ala Thr Pro Val Leu Gln Ala Gln
540                 545                 550                 555 ggc ggt ttg gga gga gct gtt ctg ctc cct gtc agc ttc cag gag gga      1852
Gly Gly Leu Gly Gly Ala Val Leu Leu Pro Val Ser Phe Gln Glu Gly
                560                 565                 570 cgg cgg gcg tcg gac acc tca ctg act caa ggg ctg aag gcc ttt cgg      1900
Arg Arg Ala Ser Asp Thr Ser Leu Thr Gln Gly Leu Lys Ala Phe Arg
            575                 580                 585 cag cag ctg agg aag acc acg cgg acc aaa ggg ttt ctg gga ctg aac      1948
Gln Gln Leu Arg Lys Thr Thr Arg Thr Lys Gly Phe Leu Gly Leu Asn
        590                 595                 600 aaa atc aag ggg ctg gct cgc cag gtg tgc cag gtc cct gcc agc cgg      1996
Lys Ile Lys Gly Leu Ala Arg Gln Val Cys Gln Val Pro Ala Ser Arg
    605                 610                 615 gcc agc agg ggc ggc ctg agc ccc ttc cac gcc cct gca cag agc cca      2044
Ala Ser Arg Gly Gly Leu Ser Pro Phe His Ala Pro Ala Gln Ser Pro
620                 625                 630                 635 ggc ctg cac ggc ggc gca gcc ggc agc cgg gag ggc tgg agc ctg ctg      2092
Gly Leu His Gly Gly Ala Ala Gly Ser Arg Glu Gly Trp Ser Leu Leu
                640                 645                 650 gag gag gtg cta gag cag cag agg ctg ctc cag tta cag cac cac ccg      2140
Glu Glu Val Leu Glu Gln Gln Arg Leu Leu Gln Leu Gln His His Pro
            655                 660                 665 gcc gct gca ccc ggc tgc tcc cag gcc ccc cag ccg gcc cct gcc ccg      2188
Ala Ala Ala Pro Gly Cys Ser Gln Ala Pro Gln Pro Ala Pro Ala Pro
        670                 675                 680 ttt gtg atc gcc ccc tgt gat ggc cct ggg gct gcc ccg ctc ccc agc      2236
Phe Val Ile Ala Pro Cys Asp Gly Pro Gly Ala Ala Pro Leu Pro Ser
    685                 690                 695 acc ctc ctc acg tcg ggg ctc ccg ctg ctg ccg ccc cca ctc ctg cag      2284
Thr Leu Leu Thr Ser Gly Leu Pro Leu Leu Pro Pro Pro Leu Leu Gln
700                 705                 710                 715 acc ggc gcg tcc ccg gtg gcc tca gcg gcg cag ctc ctg gac aca cac      2332
Thr Gly Ala Ser Pro Val Ala Ser Ala Ala Gln Leu Leu Asp Thr His
                720                 725                 730 ctg cac att ggc acc ggc ccc acc gcc ctc ccc gct gtg ccc cca cca      2380
Leu His Ile Gly Thr Gly Pro Thr Ala Leu Pro Ala Val Pro Pro Pro
            735                 740                 745 cgc ctg gcc agg ctg gcc cca ggt tgt gag ccc ctg ggg ctg ctg cag      2428
Arg Leu Ala Arg Leu Ala Pro Gly Cys Glu Pro Leu Gly Leu Leu Gln
        750                 755                 760 ggg gac tgt gag atg gag gac ctg atg ccc tgc tcc cta ggc acg ttt      2476
Gly Asp Cys Glu Met Glu Asp Leu Met Pro Cys Ser Leu Gly Thr Phe
    765                 770                 775 gtc ctg gtg cag tga gggcagccct gcatcctggc acggacactg actcttacag     2531
Val Leu Val Gln *
780 caataacttc agaggaggtg aagacatctg gcctcaaagc caagaacttt ctagaagcga    2591 aataagcaat acgttaggtg tttttggcttt ttagtttatt tttgtttat ttttttcttg   2651 cactgagtga cctcaacttt gagtagggac tggaaacttt aggaagaaag ataattgagg   2711 ggcgtgtctg ggggcggggg caggagggga gcgggggtgga gggaacacgt gcagtgccgt  2771 ggtgtgggga tctcggcccc tctctctggg ttcgtcgtgg ttgagatgat tacctcggac   2831 gtctacggaa acgagcgggc gcatttgttg tccgcttgtg tgtgtgtgtg tgtgtgtgtg   2891 tgtgccccgt gcattgatta ctatccattt ctttagtcaa cgctctccac ttcctgattt   2951
```

-continued ctgcttttaa gaaaact 2968

<210> SEQ ID NO 2
<211> LENGTH: 783
<212> TYPE: PRT
<213> ORGANISM: Homo sapiens

<400> SEQUENCE: 2

```
Met Val Ile Met Ser Glu Phe Ser Ala Asp Pro Ala Gly Gln Gly Gln
 1               5                  10                  15

Gly Gln Gln Lys Pro Leu Arg Val Gly Phe Tyr Asp Ile Glu Arg Thr
            20                  25                  30

Leu Gly Lys Gly Asn Phe Ala Val Val Lys Leu Ala Arg His Arg Val
        35                  40                  45

Thr Lys Thr Gln Val Ala Ile Lys Ile Ile Asp Lys Thr Arg Leu Asp
50                  55                  60

Ser Ser Asn Leu Glu Lys Ile Tyr Arg Glu Val Gln Leu Met Lys Leu
65                  70                  75                  80

Leu Asn His Pro His Ile Ile Lys Leu Tyr Gln Val Met Glu Thr Lys
                85                  90                  95

Asp Met Leu Tyr Ile Val Thr Glu Phe Ala Lys Asn Gly Glu Met Phe
            100                 105                 110

Asp Tyr Leu Thr Ser Asn Gly His Leu Ser Glu Asn Glu Ala Arg Lys
        115                 120                 125

Lys Phe Trp Gln Ile Leu Ser Ala Val Glu Tyr Cys His Asp His
    130                 135                 140

Ile Val His Arg Asp Leu Lys Thr Glu Asn Leu Leu Leu Asp Gly Asn
145                 150                 155                 160

Met Asp Ile Lys Leu Ala Asp Phe Gly Phe Gly Asn Phe Tyr Lys Ser
                165                 170                 175

Gly Glu Pro Leu Ser Thr Trp Cys Gly Ser Pro Pro Tyr Ala Ala Pro
            180                 185                 190

Glu Val Phe Glu Gly Lys Glu Tyr Glu Gly Pro Gln Leu Asp Ile Trp
        195                 200                 205

Ser Leu Gly Val Val Leu Tyr Val Leu Val Cys Gly Ser Leu Pro Phe
210                 215                 220

Asp Gly Pro Asn Leu Pro Thr Leu Arg Gln Arg Val Leu Glu Gly Arg
225                 230                 235                 240

Phe Arg Ile Pro Phe Phe Met Ser Gln Asp Cys Glu Ser Leu Ile Arg
                245                 250                 255

Arg Met Leu Val Val Asp Pro Ala Arg Arg Ile Thr Ile Ala Gln Ile
            260                 265                 270

Arg Gln His Arg Trp Met Arg Ala Glu Pro Cys Leu Pro Gly Pro Ala
        275                 280                 285

Cys Pro Ala Phe Ser Ala His Ser Tyr Thr Ser Asn Leu Gly Asp Tyr
    290                 295                 300

Asp Glu Gln Ala Leu Gly Ile Met Gln Thr Leu Gly Val Asp Arg Gln
305                 310                 315                 320

Arg Thr Val Glu Ser Leu Gln Asn Ser Ser Tyr Asn His Phe Ala Ala
                325                 330                 335

Ile Tyr Tyr Leu Leu Leu Glu Arg Leu Lys Glu Tyr Arg Asn Ala Gln
            340                 345                 350

Cys Ala Arg Pro Gly Pro Ala Arg Gln Pro Arg Pro Arg Ser Ser Asp
        355                 360                 365
```

```
Leu Ser Gly Leu Glu Val Pro Gln Glu Gly Leu Ser Thr Asp Pro Phe
    370                 375                 380

Arg Pro Ala Leu Leu Cys Pro Gln Pro Gln Thr Leu Val Gln Ser Val
385                 390                 395                 400

Leu Gln Ala Glu Met Asp Cys Glu Leu Gln Ser Ser Leu Gln Trp Pro
                405                 410                 415

Leu Phe Phe Pro Val Asp Ala Ser Cys Ser Gly Val Phe Arg Pro Arg
            420                 425                 430

Pro Val Ser Pro Ser Ser Leu Leu Asp Thr Ala Ile Ser Glu Glu Ala
        435                 440                 445

Arg Gln Gly Pro Gly Leu Glu Glu Gln Asp Thr Gln Glu Ser Leu
    450                 455                 460

Pro Ser Ser Thr Gly Arg Arg His Thr Leu Ala Glu Val Ser Thr Arg
465                 470                 475                 480

Leu Ser Pro Leu Thr Ala Pro Cys Ile Val Val Ser Pro Ser Thr Thr
                485                 490                 495

Ala Ser Pro Ala Glu Gly Thr Ser Ser Asp Ser Cys Leu Thr Phe Ser
            500                 505                 510

Ala Ser Lys Ser Pro Ala Gly Leu Ser Gly Thr Pro Ala Thr Gln Gly
        515                 520                 525

Leu Leu Gly Ala Cys Ser Pro Val Arg Leu Ala Ser Pro Phe Leu Gly
    530                 535                 540

Ser Gln Ser Ala Thr Pro Val Leu Gln Ala Gln Gly Leu Gly Gly
545                 550                 555                 560

Ala Val Leu Leu Pro Val Ser Phe Gln Glu Gly Arg Arg Ala Ser Asp
                565                 570                 575

Thr Ser Leu Thr Gln Gly Leu Lys Ala Phe Arg Gln Gln Leu Arg Lys
            580                 585                 590

Thr Thr Arg Thr Lys Gly Phe Leu Gly Leu Asn Lys Ile Lys Gly Leu
        595                 600                 605

Ala Arg Gln Val Cys Gln Val Pro Ala Ser Arg Ala Ser Arg Gly Gly
    610                 615                 620

Leu Ser Pro Phe His Ala Pro Ala Gln Ser Pro Gly Leu His Gly Gly
625                 630                 635                 640

Ala Ala Gly Ser Arg Glu Gly Trp Ser Leu Leu Glu Glu Val Leu Glu
                645                 650                 655

Gln Gln Arg Leu Leu Gln Leu Gln His His Pro Ala Ala Ala Pro Gly
            660                 665                 670

Cys Ser Gln Ala Pro Gln Pro Ala Pro Ala Pro Phe Val Ile Ala Pro
        675                 680                 685

Cys Asp Gly Pro Gly Ala Ala Pro Leu Pro Ser Thr Leu Leu Thr Ser
    690                 695                 700

Gly Leu Pro Leu Leu Pro Pro Pro Leu Leu Gln Thr Gly Ala Ser Pro
705                 710                 715                 720

Val Ala Ser Ala Ala Gln Leu Leu Asp Thr His Leu His Ile Gly Thr
                725                 730                 735

Gly Pro Thr Ala Leu Pro Ala Val Pro Pro Arg Leu Ala Arg Leu
            740                 745                 750

Ala Pro Gly Cys Glu Pro Leu Gly Leu Leu Gln Gly Asp Cys Glu Met
        755                 760                 765

Glu Asp Leu Met Pro Cys Ser Leu Gly Thr Phe Val Leu Val Gln
    770                 775                 780
```

<210> SEQ ID NO 3
<211> LENGTH: 2352
<212> TYPE: DNA
<213> ORGANISM: Homo sapiens

<400> SEQUENCE: 3

| | | | | | |
|---|---|---|---|---|---|
| atggttatca | tgtcggagtt | cagcgcggac | cccgcgggcc | agggtcaggg | ccagcagaag | 60 |
| cccctccggg | tgggtttta | cgacatcgag | cggaccctgg | gcaaaggcaa | cttcgcggtg | 120 |
| gtgaagctgg | cgcggcatcg | agtcaccaaa | acgcaggttg | caataaaaat | aattgataaa | 180 |
| acacgattag | attcaagcaa | tttggagaaa | atctatcgtg | aggttcagct | gatgaagctt | 240 |
| ctgaaccatc | cacacatcat | aaagctttac | caggttatgg | aaacaaagga | catgctttac | 300 |
| atcgtcactg | aatttgctaa | aaatggagaa | atgtttgatt | atttgacttc | caacgggcac | 360 |
| ctgagtgaga | cgaggcgcg | aagaagttc | tggcaaatcc | tgtcggccgt | ggagtactgt | 420 |
| cacgaccatc | acatcgtcca | ccgggacctc | aagaccgaga | acctcctgct | ggatggcaac | 480 |
| atggacatca | agctggcaga | ttttggattt | gggaatttct | acaagtcagg | agagcctctg | 540 |
| tccacgtggt | gtgggagccc | ccgtatgcc | gccccggaag | tctttgaggg | gaaggagtat | 600 |
| gaaggccccc | agctggacat | ctggagcctg | ggcgtggtgc | tgtacgtcct | ggtctgcggt | 660 |
| tctctcccct | tcgatgggcc | taacctgccg | acgctgagac | agcgggtgct | ggagggccgc | 720 |
| ttccgcatcc | ccttcttcat | gtctcaagac | tgtgagagcc | tgatccgccg | catgctggtg | 780 |
| gtggaccccg | ccaggcgcat | caccatcgcc | cagatccggc | agcaccggtg | gatgcgggct | 840 |
| gagccctgct | tgccgggacc | cgcctgcccc | gccttctccg | cacacagcta | cacctccaac | 900 |
| ctgggcgact | acgatgagca | ggcgctgggt | atcatgcaga | ccctgggcgt | ggaccggcag | 960 |
| aggacggtgg | agtcactgca | aaacagcagc | tataaccact | tgctgccat | ttattacctc | 1020 |
| ctccttgagc | ggctcaagga | gtatcggaat | gcccagtgcg | cccgccccgg | gcctgccagg | 1080 |
| cagccgcggc | ctcggagctc | ggacctcagt | ggtttggagg | tgcctcagga | aggtcttttcc | 1140 |
| accgaccctt | tccgacctgc | cttgctgtgc | ccgcagccgc | agaccttggt | gcagtccgtc | 1200 |
| ctccaggccg | agatggactg | tgagctccag | agctcgctgc | agtggccctt | gttcttcccg | 1260 |
| gtggatgcca | gctgcagcgg | agtgttccgg | ccccggcccg | tgtccccaag | cagcctgctg | 1320 |
| gacacagcca | tcagtgagga | ggccaggcag | gggccgggcc | tagaggagga | gcaggacacg | 1380 |
| caggagtccc | tgcccagcag | cacgggccgg | aggcacaccc | tggccgaggt | ctccacccgc | 1440 |
| ctctccccac | tcaccgcgcc | atgtatagtc | gtctcccccct | ccaccacggc | aagtcctgca | 1500 |
| gagggaacca | gctctgacag | ttgtctgacc | ttctctgcga | gcaaaagccc | cgcggggctc | 1560 |
| agtggcaccc | cggccactca | ggggctgctg | ggcgcctgct | ccccggtcag | gctggcctcg | 1620 |
| cccttcctgg | ggtcgcagtc | cgccacccca | gtgctgcagg | ctcaggggg | cttgggagga | 1680 |
| gctgttctgc | tccctgtcag | cttccaggag | ggacggcggg | cgtcggacac | ctcactgact | 1740 |
| caagggctga | aggcctttcg | gcagcagctg | aggaagacca | cgcggaccaa | agggtttctg | 1800 |
| ggactgaaca | aaatcaaggg | gctggctcgc | caggtgtgcc | aggtccctgc | cagccgggcc | 1860 |
| agcaggggcg | gcctgagccc | cttccacgcc | cctgcacaga | gccaggcct | gcacggcggc | 1920 |
| gcagccggca | gccgggaggg | ctggagcctg | ctggaggagg | tgctagagca | gcagaggctg | 1980 |
| ctccagttac | agcaccaccc | ggccgctgca | cccggctgct | cccaggcccc | cagccggcc | 2040 |
| cctgccccgt | ttgtgatcgc | ccctgtgat | ggcctgggg | ctgccccgct | ccccagcacc | 2100 |
| ctcctcacgt | cggggctccc | gctgctgccg | cccccactcc | tgcagaccgg | cgcgtccccg | 2160 |

-continued

```
gtggcctcag cggcgcagct cctggacaca cacctgcaca ttggcaccgg ccccaccgcc      2220
ctccccgctg tgcccccacc acgcctggcc aggctggccc caggttgtga gcccctgggg      2280
ctgctgcagg gggactgtga gatggaggac ctgatgccct gctccctagg cacgtttgtc      2340
ctggtgcagt ga                                                          2352

<210> SEQ ID NO 4
<211> LENGTH: 1948
<212> TYPE: DNA
<213> ORGANISM: Homo sapiens
<220> FEATURE:
<221> NAME/KEY: CDS
<222> LOCATION: (358)...(1383)
<220> FEATURE:
<221> NAME/KEY: misc_feature
<222> LOCATION: (1)...(1948)
<223> OTHER INFORMATION: n = A,T,C or G

<400> SEQUENCE: 4
tccaactcta cgtctktskt tkyktykttt kytgttsygc gstkwyasak mymmrmkyyy       60
traaaamcma raaagttaac ykgkwarktt wrkyyttttt kkyytttwwt ycmrgkyccs      120
grwycsgkkg kkgkksmaaw ymaaagaact gctcctcagt ggatgttgcc tttacttcta     180
ggcctgtacg gaagtgttac ttctgctcta aaagctgcgg aattctaata cgactcacta     240
tagggagtcg acccacgcgt ccgcagcgga ggcgcgagct gccgataat ggcggcctgc      300 agagcccatg agagggagaa gcggcagcgt ctaccctgag aaacctcgac cttgaag atg    360
                                                                 Met
                                                                   1 gtg agt agc cag cca aag tac gat cta ata cgg gag gta ggc cga ggt        408
Val Ser Ser Gln Pro Lys Tyr Asp Leu Ile Arg Glu Val Gly Arg Gly
          5                  10                  15 agt tac ggt gtt gtg tat gaa gca gtc atc aga aag acc tct gca cgg        456
Ser Tyr Gly Val Val Tyr Glu Ala Val Ile Arg Lys Thr Ser Ala Arg
         20                  25                  30 gtg gca gtg aag aaa att cga tgt cac gca cct gaa aat gtt gaa cta        504
Val Ala Val Lys Lys Ile Arg Cys His Ala Pro Glu Asn Val Glu Leu
     35                  40                  45 gcc ctt cgt gag ttc tgg gca cta agc agt atc aag agc caa cat cca        552
Ala Leu Arg Glu Phe Trp Ala Leu Ser Ser Ile Lys Ser Gln His Pro
 50                  55                  60                  65 aat gtg att cac ttg gag gaa tgc atc cta caa aag gat ggg atg gtg        600
Asn Val Ile His Leu Glu Glu Cys Ile Leu Gln Lys Asp Gly Met Val
                 70                  75                  80 caa aag atg tcc cac ggc tct aat tct tcc ctt tat tta cag ctt gta        648
Gln Lys Met Ser His Gly Ser Asn Ser Ser Leu Tyr Leu Gln Leu Val
             85                  90                  95 gaa act tca tta aaa gga gaa att gcc ttt gat ccc aga agc gcc tat        696
Glu Thr Ser Leu Lys Gly Glu Ile Ala Phe Asp Pro Arg Ser Ala Tyr
        100                 105                 110 tat ttg tgg ttt gtg atg gat ttt tgt gac gga gga gat atg aat gag        744
Tyr Leu Trp Phe Val Met Asp Phe Cys Asp Gly Gly Asp Met Asn Glu
    115                 120                 125 tat ctg ttg tcc agg aag ccc aat cgt aaa act aac acc agc ttc atg        792
Tyr Leu Leu Ser Arg Lys Pro Asn Arg Lys Thr Asn Thr Ser Phe Met
130                 135                 140                 145 ctt cag ctg agc agt gcc ctg gct ttc ttg cat aaa aac cag atc atc        840
Leu Gln Leu Ser Ser Ala Leu Ala Phe Leu His Lys Asn Gln Ile Ile
                150                 155                 160 cac cga gat ctt aag cct gat aac atc ctg att tct caa acc agg ttg        888
His Arg Asp Leu Lys Pro Asp Asn Ile Leu Ile Ser Gln Thr Arg Leu
```

-continued

```
                 165                 170                 175
gat acc agt gac ttg gaa cct acc ctc aaa gtg gct gat ttt ggt cta      936
Asp Thr Ser Asp Leu Glu Pro Thr Leu Lys Val Ala Asp Phe Gly Leu
            180                 185                 190 agt aaa gtt tgt tca gcc tct ggg cag aac cca gaa gaa cct gtc agt      984
Ser Lys Val Cys Ser Ala Ser Gly Gln Asn Pro Glu Glu Pro Val Ser
    195                 200                 205 gta aac aag tgt ttc ctt tcc aca gca tgt gga aca gat ttt tac atg     1032
Val Asn Lys Cys Phe Leu Ser Thr Ala Cys Gly Thr Asp Phe Tyr Met
210                 215                 220                 225 gct cct gaa gtt tgg gaa gga cat tac aca gca aaa gct gac atc ttt     1080
Ala Pro Glu Val Trp Glu Gly His Tyr Thr Ala Lys Ala Asp Ile Phe
                230                 235                 240 gct ctg ggg att atc atc tgg gca atg ctg gaa agg atc aca ttc ata     1128
Ala Leu Gly Ile Ile Ile Trp Ala Met Leu Glu Arg Ile Thr Phe Ile
            245                 250                 255 gac aca gag aca aag aag gaa ctc ttg ggg agt tac gta aaa caa gga     1176
Asp Thr Glu Thr Lys Lys Glu Leu Leu Gly Ser Tyr Val Lys Gln Gly
    260                 265                 270 act gag att gtg cct gtt ggg gag gca ctt ctg gaa aat ccc aaa atg     1224
Thr Glu Ile Val Pro Val Gly Glu Ala Leu Leu Glu Asn Pro Lys Met
275                 280                 285 gaa ctt ctc att cct gtg aag aaa aaa tct atg aat ggg cga atg aaa     1272
Glu Leu Leu Ile Pro Val Lys Lys Lys Ser Met Asn Gly Arg Met Lys
                290                 295                 300                 305 caa ctg att aag gaa atg ctg gct gca aac cct cag gat cgt cca gat     1320
Gln Leu Ile Lys Glu Met Leu Ala Ala Asn Pro Gln Asp Arg Pro Asp
            310                 315                 320 gct ttt gaa cta gaa ctc aga tta gta caa att gca ttt aaa gat agc     1368
Ala Phe Glu Leu Glu Leu Arg Leu Val Gln Ile Ala Phe Lys Asp Ser
    325                 330                 335 agc tgg gaa acg tga cacatattat ttgcaaatac catggatgat atgctgcttc     1423
Ser Trp Glu Thr *
        340 tgtttaacag tgatgcaaca ttatgtggct gaaaagaat ataaaaagct agactctacc     1483 ctctaagggt ttagattttt tgtgggattt ttttttttcct catttttctt aaatccaagt   1543 tggccgtttt attagtatgt ttcaaatgtg tattaccaat gtgggtgtaa attttttaaaa  1603 aatgattatt gatagaagtt tggcaggaaa atyctttagg agctaacagg agaagagagt  1663 ccagttttct ggaaatatgt ctttaagtat tttagacatt cctcgtcagt attaggaatt  1723 tccatgggaa aagangggttg catgctggta atgccacctt tgnaactttg taaggaaac   1783 aaaanggata tattnangga tatgnaagta tgggaatggg cccctttgc ttccataana   1843 aaaaaacgcc cctttgttaa aaatatttgg ngggggggtgg ggttttngaa aattnggggg  1903 naaaacngnc aanaaaaaaa acccccttctn tttttttnccc ccccc                 1948
```

<210> SEQ ID NO 5
<211> LENGTH: 341
<212> TYPE: PRT
<213> ORGANISM: Homo sapiens

<400> SEQUENCE: 5

```
Met Val Ser Ser Gln Pro Lys Tyr Asp Leu Ile Arg Glu Val Gly Arg
  1               5                  10                  15

Gly Ser Tyr Gly Val Val Tyr Glu Ala Val Ile Arg Lys Thr Ser Ala
             20                  25                  30

Arg Val Ala Val Lys Lys Ile Arg Cys His Ala Pro Glu Asn Val Glu
```

```
                35                  40                  45
Leu Ala Leu Arg Glu Phe Trp Ala Leu Ser Ser Ile Lys Ser Gln His
 50                  55                  60

Pro Asn Val Ile His Leu Glu Glu Cys Ile Leu Gln Lys Asp Gly Met
 65                  70                  75                  80

Val Gln Lys Met Ser His Gly Ser Asn Ser Ser Leu Tyr Leu Gln Leu
                 85                  90                  95

Val Glu Thr Ser Leu Lys Gly Glu Ile Ala Phe Asp Pro Arg Ser Ala
            100                 105                 110

Tyr Tyr Leu Trp Phe Val Met Asp Phe Cys Asp Gly Gly Asp Met Asn
        115                 120                 125

Glu Tyr Leu Leu Ser Arg Lys Pro Asn Arg Lys Thr Asn Thr Ser Phe
    130                 135                 140

Met Leu Gln Leu Ser Ser Ala Leu Ala Phe Leu His Lys Asn Gln Ile
145                 150                 155                 160

Ile His Arg Asp Leu Lys Pro Asp Asn Ile Leu Ile Ser Gln Thr Arg
                165                 170                 175

Leu Asp Thr Ser Asp Leu Glu Pro Thr Leu Lys Val Ala Asp Phe Gly
            180                 185                 190

Leu Ser Lys Val Cys Ser Ala Ser Gly Gln Asn Pro Glu Glu Pro Val
        195                 200                 205

Ser Val Asn Lys Cys Phe Leu Ser Thr Ala Cys Gly Thr Asp Phe Tyr
    210                 215                 220

Met Ala Pro Glu Val Trp Glu Gly His Tyr Thr Ala Lys Ala Asp Ile
225                 230                 235                 240

Phe Ala Leu Gly Ile Ile Ile Trp Ala Met Leu Glu Arg Ile Thr Phe
                245                 250                 255

Ile Asp Thr Glu Thr Lys Lys Glu Leu Leu Gly Ser Tyr Val Lys Gln
            260                 265                 270

Gly Thr Glu Ile Val Pro Val Gly Glu Ala Leu Leu Glu Asn Pro Lys
        275                 280                 285

Met Glu Leu Leu Ile Pro Val Lys Lys Ser Met Asn Gly Arg Met
    290                 295                 300

Lys Gln Leu Ile Lys Glu Met Leu Ala Ala Asn Pro Gln Asp Arg Pro
305                 310                 315                 320

Asp Ala Phe Glu Leu Glu Leu Arg Leu Val Gln Ile Ala Phe Lys Asp
                325                 330                 335

Ser Ser Trp Glu Thr
            340

<210> SEQ ID NO 6
<211> LENGTH: 1026
<212> TYPE: DNA
<213> ORGANISM: Homo sapiens

<400> SEQUENCE: 6
atggtgagta gccagccaaa gtacgatcta atacgggagg taggccgagg tagttacggt      60
gttgtgtatg aagcagtcat cagaaagacc tctgcacggg tggcagtgaa gaaaattcga    120
tgtcacgcac ctgaaaatgt tgaactagcc cttcgtgagt ctgggcact aagcagtatc     180 aagagccaac atccaaatgt gattcacttg gaggaatgca tcctacaaaa ggatgggatg    240
gtgcaaaaga tgtcccacgg ctctaattct ccctttatt tacagcttgt agaaacttca    300 ttaaaggag aaattgcctt tgatcccaga agcgcctatt atttgtggtt tgtgatggat    360
```

-continued

```
ttttgtgacg gaggagatat gaatgagtat ctgttgtcca ggaagcccaa tcgtaaaact        420
aacaccagct tcatgcttca gctgagcagt gccctggctt tcttgcataa aaaccagatc        480
atccaccgag atcttaagcc tgataacatc ctgatttctc aaaccaggtt ggataccagt        540
gacttggaac ctaccctcaa agtggctgat tttggtctaa gtaaagtttg ttcagcctct        600
gggcagaacc cagaagaacc tgtcagtgta acaagtgtt tcctttccac agcatgtgga         660
acagattttt acatggctcc tgaagtttgg gaaggacatt acacagcaaa agctgacatc        720
tttgctctgg ggattatcat ctgggcaatg ctggaaagga tcacattcat agacacagag        780
acaaagaagg aactcttggg gagttacgta aaacaaggac ctgagattgt gcctgttggg        840
gaggcacttc tggaaaatcc caaaatggaa cttctcattc ctgtgaagaa aaaatctatg        900
aatgggcgaa tgaaacaact gattaaggaa atgctggctg caaaccctca ggatcgtcca        960
gatgcttttg aactagaact cagattagta caaattgcat ttaaagatag cagctgggaa       1020
acgtga                                                                  1026

<210> SEQ ID NO 7
<211> LENGTH: 5499
<212> TYPE: DNA
<213> ORGANISM: Homo sapiens
<220> FEATURE:
<221> NAME/KEY: CDS
<222> LOCATION: (317)...(4051)

<400> SEQUENCE: 7
cacgcgtccg ggcagcagca gtaacagcag cagcagccgc cgccgccgcc gccagtaaac         60
gcggaccgta ccccagggga ctacccagcc ggccggccct ggaagccgcg ctcgggtccc        120
gccgcagtcg gcggtggggg atgggcaggc agtggcggtc ccgcctgccg agggttaacc        180
cccgccggtc ccggtcctga gctggaccag agccctcctc cagaaacccc tgcgtccgcc        240
acggcccagg ttaaatggaa accacccttg ggaactggat gcctgtgtag ctgttctacc        300
atatcagtgt attgca atg agt ggg gga gga gag cag ctg gat atc ctg agt        352
                   Met Ser Gly Gly Gly Glu Gln Leu Asp Ile Leu Ser
                    1               5                  10 gtt gga atc cta gtg aaa gaa aga tgg aaa gtg ttg aga aag att ggg        400
Val Gly Ile Leu Val Lys Glu Arg Trp Lys Val Leu Arg Lys Ile Gly
         15                  20                  25 ggt ggg ggc ttt gga gaa att tac gat gcc ttg gac atg ctc acc agg        448
Gly Gly Gly Phe Gly Glu Ile Tyr Asp Ala Leu Asp Met Leu Thr Arg
30                  35                  40 gaa aat gtt gca ctg aag gtg gaa tca gct caa caa cca aaa caa gtt        496
Glu Asn Val Ala Leu Lys Val Glu Ser Ala Gln Gln Pro Lys Gln Val
45                  50                  55                  60 ctg aaa atg gaa gtt gct gtt ttg aaa aag ctg caa ggg aaa gac cat        544
Leu Lys Met Glu Val Ala Val Leu Lys Lys Leu Gln Gly Lys Asp His
             65                  70                  75 gtt tgt aga ttt att ggc tgt ggg agg aat gat cga ttc aac tat gtg        592
Val Cys Arg Phe Ile Gly Cys Gly Arg Asn Asp Arg Phe Asn Tyr Val
             80                  85                  90 gtc atg cag ttg cag ggt cgg aat ctg gca gat ctt cgc cgt agc cag        640
Val Met Gln Leu Gln Gly Arg Asn Leu Ala Asp Leu Arg Arg Ser Gln
         95                 100                 105 tcc cga ggc aca ttc acc att agt acc act ctc cgg ctg ggt aga cag        688
Ser Arg Gly Thr Phe Thr Ile Ser Thr Thr Leu Arg Leu Gly Arg Gln
     110                 115                 120 att ttg gag tct att gaa agc att cat tct gtg gga ttc ttg cat cga        736
Ile Leu Glu Ser Ile Glu Ser Ile His Ser Val Gly Phe Leu His Arg
```

-continued

```
            125                 130                 135                 140
gac atc aaa ccg tcg aac ttc gct atg ggt cgc ttt cct agt aca tgt      784
Asp Ile Lys Pro Ser Asn Phe Ala Met Gly Arg Phe Pro Ser Thr Cys
                145                 150                 155 agg aaa tgt tac atg ctt gat ttt ggc ttg gct cga caa ttt acc aat      832
Arg Lys Cys Tyr Met Leu Asp Phe Gly Leu Ala Arg Gln Phe Thr Asn
                160                 165                 170 tcc tgt ggt gac gtc aga cca cct cga gct gtg gca ggt ttt cga ggg      880
Ser Cys Gly Asp Val Arg Pro Pro Arg Ala Val Ala Gly Phe Arg Gly
                175                 180                 185 aca gtt cgt tat gca tca atc aac gca cat cgg aac agg gaa atg gga      928
Thr Val Arg Tyr Ala Ser Ile Asn Ala His Arg Asn Arg Glu Met Gly
                190                 195                 200 aga cat gat gac ctt tgg tcc tta ttc tac atg ttg gtg gag ttt gtg      976
Arg His Asp Asp Leu Trp Ser Leu Phe Tyr Met Leu Val Glu Phe Val
205                 210                 215                 220 gtt ggt cag ctg ccc tgg aga aaa ata aag gac aag gag caa gta ggc     1024
Val Gly Gln Leu Pro Trp Arg Lys Ile Lys Asp Lys Glu Gln Val Gly
                225                 230                 235 tct att aag gag aga tat gac cac agg ctc atg ttg aaa cat ctc cct     1072
Ser Ile Lys Glu Arg Tyr Asp His Arg Leu Met Leu Lys His Leu Pro
                240                 245                 250 cca gaa ttc agc atc ttt cta gac cat atc tct tct ttg gat tat ttt     1120
Pro Glu Phe Ser Ile Phe Leu Asp His Ile Ser Ser Leu Asp Tyr Phe
                255                 260                 265 aca aaa cca gac tac cag ctt ctt aca tcc gtg ttt gac aat agc atc     1168
Thr Lys Pro Asp Tyr Gln Leu Leu Thr Ser Val Phe Asp Asn Ser Ile
                270                 275                 280 aag act ttt gga gta att gag agt gac cct ttt gac tgg gag aag act     1216
Lys Thr Phe Gly Val Ile Glu Ser Asp Pro Phe Asp Trp Glu Lys Thr
285                 290                 295                 300 gga aat gat ggc tcc cta aca acc acc act tct acc acc cct cag         1264
Gly Asn Asp Gly Ser Leu Thr Thr Thr Thr Ser Thr Thr Pro Gln
                305                 310                 315 ttg cac act cgc ttg acc cct gct gca att gga att gcc aat gct act     1312
Leu His Thr Arg Leu Thr Pro Ala Ala Ile Gly Ile Ala Asn Ala Thr
                320                 325                 330 ccc atc cct gga gac ttg ctt cga gaa aat aca gat gag gta ttt cca     1360
Pro Ile Pro Gly Asp Leu Leu Arg Glu Asn Thr Asp Glu Val Phe Pro
                335                 340                 345 gat gaa cag ctt agc gat gga gaa aat ggc atc cct gtt ggt gtg tca     1408
Asp Glu Gln Leu Ser Asp Gly Glu Asn Gly Ile Pro Val Gly Val Ser
350                 355                 360 cca gat aaa ttg cct gga tct ctg gga cac ccc cgt ccc cag gag aag     1456
Pro Asp Lys Leu Pro Gly Ser Leu Gly His Pro Arg Pro Gln Glu Lys
365                 370                 375                 380 gat gtt tgg gaa gag atg gat gcc aac aaa aac aag ata aag ctt gga     1504
Asp Val Trp Glu Glu Met Asp Ala Asn Lys Asn Lys Ile Lys Leu Gly
                385                 390                 395 att tgt aag gct gct act gaa gag gag aac agc cat ggc cag gca aat     1552
Ile Cys Lys Ala Ala Thr Glu Glu Glu Asn Ser His Gly Gln Ala Asn
                400                 405                 410 ggt ctt ctc aat gct cca agc ctt ggg tca cca att cgt gtc cgc tca     1600
Gly Leu Leu Asn Ala Pro Ser Leu Gly Ser Pro Ile Arg Val Arg Ser
                415                 420                 425 gag att act cag cca gac aga gat att cca ctg gtg cga aag tta cgt     1648
Glu Ile Thr Gln Pro Asp Arg Asp Ile Pro Leu Val Arg Lys Leu Arg
                430                 435                 440 tcc att cac agc ttt gag ctg gaa aaa cgt ctg acc ctg gag cca aag     1696
```

```
                                                         -continued

Ser Ile His Ser Phe Glu Leu Glu Lys Arg Leu Thr Leu Glu Pro Lys
445                 450                 455                 460 cca gac act gac aag ttc ctt gag acc tgc ctg gag aaa atg cag aaa      1744
Pro Asp Thr Asp Lys Phe Leu Glu Thr Cys Leu Glu Lys Met Gln Lys
                        465                 470                 475 gat acc agt gca gga aaa gaa tct att ctc cct gct ctg ctg cat aag      1792
Asp Thr Ser Ala Gly Lys Glu Ser Ile Leu Pro Ala Leu Leu His Lys
                480                 485                 490 cct tgc gtt cct gct gtg tcc cgt act gac cac atc tgg cac tat gat      1840
Pro Cys Val Pro Ala Val Ser Arg Thr Asp His Ile Trp His Tyr Asp
            495                 500                 505 gaa gaa tat ctt cca gat gcc tcc aag cct gct tct gcc aac acc cct      1888
Glu Glu Tyr Leu Pro Asp Ala Ser Lys Pro Ala Ser Ala Asn Thr Pro
510                 515                 520 gag cag gca gat ggt ggt ggc agc aat gga ttt ata gct gtt aac ctg      1936
Glu Gln Ala Asp Gly Gly Gly Ser Asn Gly Phe Ile Ala Val Asn Leu
525                 530                 535                 540 agc tct tgc aag caa gaa att gat tcc aaa gaa tgg gtg att gtg gac      1984
Ser Ser Cys Lys Gln Glu Ile Asp Ser Lys Glu Trp Val Ile Val Asp
                545                 550                 555 aag gag cag gac ctt cag gat ttt agg aca aat gag gct gta gga cat      2032
Lys Glu Gln Asp Leu Gln Asp Phe Arg Thr Asn Glu Ala Val Gly His
                560                 565                 570 aaa aca act gga agt cct tct gat gag gag cct gaa gta ctt caa gtc      2080
Lys Thr Thr Gly Ser Pro Ser Asp Glu Glu Pro Glu Val Leu Gln Val
            575                 580                 585 ctg gag gca tca cct caa gat gaa aag ctc cag tta ggt cct tgg gca      2128
Leu Glu Ala Ser Pro Gln Asp Glu Lys Leu Gln Leu Gly Pro Trp Ala
590                 595                 600 gaa aat gat cat tta aag aag gaa acc tca ggt gtg gtc tta gca ctt      2176
Glu Asn Asp His Leu Lys Lys Glu Thr Ser Gly Val Val Leu Ala Leu
605                 610                 615                 620 tct gca gag ggt cct cct act gct gct tca gaa caa tat aca gat agg      2224
Ser Ala Glu Gly Pro Pro Thr Ala Ala Ser Glu Gln Tyr Thr Asp Arg
                625                 630                 635 ctg gaa ctc cag cct gga gct gct agt cag ttt att gca gcg acg ccc      2272
Leu Glu Leu Gln Pro Gly Ala Ala Ser Gln Phe Ile Ala Ala Thr Pro
                640                 645                 650 aca agt cta atg gag gcg cag gca gaa gga ccc ctt aca gcg att aca      2320
Thr Ser Leu Met Glu Ala Gln Ala Glu Gly Pro Leu Thr Ala Ile Thr
            655                 660                 665 att cct aga cct tct gtg gca tct aca cag tca act tca gga agc ttt      2368
Ile Pro Arg Pro Ser Val Ala Ser Thr Gln Ser Thr Ser Gly Ser Phe
670                 675                 680 cac tgt ggt cag cag cca gag aag aaa gat ctt cag ccc atg gag ccc      2416
His Cys Gly Gln Gln Pro Glu Lys Lys Asp Leu Gln Pro Met Glu Pro
685                 690                 695                 700 act gtg gaa ctt tac tct cca agg gaa aac ttc tct ggc ttg gtt gtg      2464
Thr Val Glu Leu Tyr Ser Pro Arg Glu Asn Phe Ser Gly Leu Val Val
                705                 710                 715 aca gag ggt gaa cct cct agt gga gga agc aga aca gat ttg ggg ctt      2512
Thr Glu Gly Glu Pro Pro Ser Gly Gly Ser Arg Thr Asp Leu Gly Leu
                720                 725                 730 cag ata gat cac att ggt cat gac atg tta ccc aac att aga gaa agt      2560
Gln Ile Asp His Ile Gly His Asp Met Leu Pro Asn Ile Arg Glu Ser
            735                 740                 745 aac aaa tct caa gac ctg gga cca aaa gaa ctt cct gat cat aat aga      2608
Asn Lys Ser Gln Asp Leu Gly Pro Lys Glu Leu Pro Asp His Asn Arg
750                 755                 760
```

```
ctg gtt gtg aga gaa ttt gaa aat ctc cct ggg gaa act gaa gag aaa    2656
Leu Val Val Arg Glu Phe Glu Asn Leu Pro Gly Glu Thr Glu Glu Lys
765             770                 775                 780 agc atc ctt tta gag tca gat aat gaa gat gag aag tta agt aga ggg    2704
Ser Ile Leu Leu Glu Ser Asp Asn Glu Asp Glu Lys Leu Ser Arg Gly
            785                 790                 795 cag cat tgt att gag atc tcc tct ctc cca gga gat ttg gta att gtg    2752
Gln His Cys Ile Glu Ile Ser Ser Leu Pro Gly Asp Leu Val Ile Val
                800                 805                 810 gaa aag gat cac tca gct act act gaa cct ctt gat gtg aca aaa aca    2800
Glu Lys Asp His Ser Ala Thr Thr Glu Pro Leu Asp Val Thr Lys Thr
            815                 820                 825 cag act ttt agt gtg gtg cca aat caa gac aaa aat aat gag ata atg    2848
Gln Thr Phe Ser Val Val Pro Asn Gln Asp Lys Asn Asn Glu Ile Met
830             835                 840 aag ctt ctg aca gtt gga act tca gaa att tct tcc aga gac att gac    2896
Lys Leu Leu Thr Val Gly Thr Ser Glu Ile Ser Ser Arg Asp Ile Asp
845             850                 855                 860 cca cat gtt gaa ggt cag ata ggc caa gtg gca gaa atg caa aaa aat    2944
Pro His Val Glu Gly Gln Ile Gly Gln Val Ala Glu Met Gln Lys Asn
                865                 870                 875 aag ata tct aag gat gat gac atc atg agt gaa gac ttg cca ggt cat    2992
Lys Ile Ser Lys Asp Asp Asp Ile Met Ser Glu Asp Leu Pro Gly His
            880                 885                 890 caa gga gac ctc tct act ttt ttg cac caa gag ggc aag aga gag aaa    3040
Gln Gly Asp Leu Ser Thr Phe Leu His Gln Glu Gly Lys Arg Glu Lys
            895                 900                 905 atc acc cct aga aat gga gaa cta ttt cat tgt gtt tca gag aat gaa    3088
Ile Thr Pro Arg Asn Gly Glu Leu Phe His Cys Val Ser Glu Asn Glu
910             915                 920 cat ggt gcc cca acc cgg aag gat atg gtt agg tca tcc ttt gta act    3136
His Gly Ala Pro Thr Arg Lys Asp Met Val Arg Ser Ser Phe Val Thr
925             930                 935                 940 aga cac agc cga atc cct gtt tta gca caa gag ata gac tca act ttg    3184
Arg His Ser Arg Ile Pro Val Leu Ala Gln Glu Ile Asp Ser Thr Leu
                945                 950                 955 gaa tca tcc tct cca gtt tct gca aaa gaa aag ctc ctc caa aag aaa    3232
Glu Ser Ser Ser Pro Val Ser Ala Lys Glu Lys Leu Leu Gln Lys Lys
            960                 965                 970 gcc tat cag cca gac cta gtc aag ctt ctg gtg gaa aaa aga caa ttc    3280
Ala Tyr Gln Pro Asp Leu Val Lys Leu Leu Val Glu Lys Arg Gln Phe
            975                 980                 985 aag tcc ttc ctt ggc gac ctc tca agt gcc tct gat aaa ttg cta gag    3328
Lys Ser Phe Leu Gly Asp Leu Ser Ser Ala Ser Asp Lys Leu Leu Glu
            990                 995                 1000 gag aaa cta gct act gtt cct gct ccc ttt tgt gag gag gaa gtg ctc    3376
Glu Lys Leu Ala Thr Val Pro Ala Pro Phe Cys Glu Glu Glu Val Leu
1005            1010                1015                1020 act ccc ttt tca aga ctg aca gta gat tct cac ctg agt agg tca gct    3424
Thr Pro Phe Ser Arg Leu Thr Val Asp Ser His Leu Ser Arg Ser Ala
                1025                1030                1035 gaa gat agc ttt ctg tca ccc atc atc tcc cag tct aga aag agc aaa    3472
Glu Asp Ser Phe Leu Ser Pro Ile Ile Ser Gln Ser Arg Lys Ser Lys
            1040                1045                1050 att cca agg cca gtt tca tgg gtc aac aca gat cag gtc aat agc tca    3520
Ile Pro Arg Pro Val Ser Trp Val Asn Thr Asp Gln Val Asn Ser Ser
            1055                1060                1065 act tcg tct cag ttc ttt cct cgg cca cca cca gga aag cca ccc acg    3568
Thr Ser Ser Gln Phe Phe Pro Arg Pro Pro Pro Gly Lys Pro Pro Thr
            1070                1075                1080
```

| | |
|---|---|
| agg cct gga gta gaa gcc agg cta cgc aga tat aaa gtc cta ggg agt<br>Arg Pro Gly Val Glu Ala Arg Leu Arg Arg Tyr Lys Val Leu Gly Ser<br>1085                    1090                  1095                  1100 | 3616 |
| agt aac tcc gac tca gac ctt ttc tcc cgc ctg gcc caa att ctt caa<br>Ser Asn Ser Asp Ser Asp Leu Phe Ser Arg Leu Ala Gln Ile Leu Gln<br>          1105                  1110                  1115 | 3664 |
| aat gga tct cag aaa ccc cgg agc act act cag tgc aag agt cca gga<br>Asn Gly Ser Gln Lys Pro Arg Ser Thr Thr Gln Cys Lys Ser Pro Gly<br>1120                    1125                  1130 | 3712 |
| tct cct cac aat cca aaa aca cca ccc aag agt cca gtt gtc cct cgc<br>Ser Pro His Asn Pro Lys Thr Pro Pro Lys Ser Pro Val Val Pro Arg<br>          1135                  1140                  1145 | 3760 |
| agg agt ccc agt gcc tct cct cga agc tca tcc ttg cct cgc acg tct<br>Arg Ser Pro Ser Ala Ser Pro Arg Ser Ser Ser Leu Pro Arg Thr Ser<br>1150                    1155                  1160 | 3808 |
| agt tcc tca cca tct agg gct gga cgg ccc cac cat gac cag agg agt<br>Ser Ser Ser Pro Ser Arg Ala Gly Arg Pro His His Asp Gln Arg Ser<br>1165                    1170                  1175                  1180 | 3856 |
| tcg tcc cca cat ctg ggg aga agc aag tca cct ccc agc cac tca gga<br>Ser Ser Pro His Leu Gly Arg Ser Lys Ser Pro Pro Ser His Ser Gly<br>                    1185                  1190                  1195 | 3904 |
| tct tcc tcc tcc agg agg tcc tgc caa cag gag cat tgc aaa ccc agc<br>Ser Ser Ser Ser Arg Arg Ser Cys Gln Gln Glu His Cys Lys Pro Ser<br>                    1200                  1205                  1210 | 3952 |
| aag aat ggc ctg aaa gga tcc ggc agc ctc cac cac cac tca gcc agc<br>Lys Asn Gly Leu Lys Gly Ser Gly Ser Leu His His His Ser Ala Ser<br>          1215                  1220                  1225 | 4000 |
| act aaa acc ccc caa ggg aag agt aag cca gcc agt aaa ctc agc aga<br>Thr Lys Thr Pro Gln Gly Lys Ser Lys Pro Ala Ser Lys Leu Ser Arg<br>1230                    1235                  1240 | 4048 |
| tag gagccaggct gcatctcttt gaaaggtgtg agatcttcct cctaaacctg<br>* | 4101 |
| atgcatgtgt gtccctgtac tttctatgta aaaaaatcag tgttgatctt ctcttgcaaa | 4161 |
| agaaagtaac atgatcaatt atttataaga agacataata catgataagg aattacctaa | 4221 |
| ggcaggcagc aagtagatta ggaatcaatg tctttgtaca agaaggaaaa atagagcaaa | 4281 |
| aatccaaggg ggagaaactc attaaaatga gctctcattt tttaagctgc ctttgaaaca | 4341 |
| aaagagttga ggataggaga tagaatggaa ttttagggg gttgcctaat tttttaagc | 4401 |
| ctcaattcaa agattatata gcaaagtga aacttcttgt ttgatatttt cattcaaaac | 4461 |
| tttcccaccc tgaagagtca ttgatcagat attagattat ataagaagtc tgttgccagg | 4521 |
| gagccagtat tcatgtatat ttggcttgtg tgtttatttc gtgtattgag aatgaacacc | 4581 |
| tttactttgc ctcattccta gtaccctccc tggagttcag atttttttt aaaattttgt | 4641 |
| atgtctcgtc tgattcaatc tctctgcttt tattttatgg tcctagttgt actatcaaat | 4701 |
| ccaattactt ttttttaggt cccccctgatt tttttttttt tagagcaaga gttcttaaca | 4761 |
| tattacattt ttattatgaa aaataagaaa gttaggtaaa ggaaagaaaa gtctaactag | 4821 |
| agctattttg caggctttag tgtttaggga gagaaagaaa gtgtgggtta atagccttca | 4881 |
| agatagaaga tgcccttca tctctgttaa gtgtcctcct ttagaaactt gagtagaagg | 4941 |
| aaaactgacc agagtagact gcttccttaa gtcttctggg ttccaactgt ttgtaatatc | 5001 |
| agcatccaag atgatacgag ggaagcacaa tgctttggac tgtgatttga gatttagaaa | 5061 |
| taaattagat atattattga ggcttagaat cctcaaactt tgtatttat acatttagcc | 5121 |
| aataaggaat taatatctgg ggaaataaat ttaggcaaat aaaaaaaaaa aaaaaaaaa | 5181 |

-continued

```
aaacctgctt ctcctgtgtt ttagttcaac atttgggctt cttggcctga ttttcataca    5241
atctcaattt acgaagctgt aaagaggaag atatttgttc taatctcact cttctaatag    5301
gaatcaggca aatgaaagtc taccagactt taaaatggg ctgttttat actctctagg     5361 tgttttgtgt tgtaaagacc ttattaaggt caggtaaatt ggtctgcttg ctgttgaaat    5421
ttgccttcta gcaaacatat gtgctttctg tttgaccttg tgtttgctgc caaacctaat    5481
acagttgaat tgggaaac                                                   5499
```

<210> SEQ ID NO 8
<211> LENGTH: 1244
<212> TYPE: PRT
<213> ORGANISM: Homo sapiens

<400> SEQUENCE: 8

```
Met Ser Gly Gly Gly Glu Gln Leu Asp Ile Leu Ser Val Gly Ile Leu
 1               5                  10                  15

Val Lys Glu Arg Trp Lys Val Leu Arg Lys Ile Gly Gly Gly Gly Phe
             20                  25                  30

Gly Glu Ile Tyr Asp Ala Leu Asp Met Leu Thr Arg Glu Asn Val Ala
         35                  40                  45

Leu Lys Val Glu Ser Ala Gln Gln Pro Lys Gln Val Leu Lys Met Glu
     50                  55                  60

Val Ala Val Leu Lys Lys Leu Gln Gly Lys Asp His Val Cys Arg Phe
 65                  70                  75                  80

Ile Gly Cys Gly Arg Asn Asp Arg Phe Asn Tyr Val Val Met Gln Leu
                 85                  90                  95

Gln Gly Arg Asn Leu Ala Asp Leu Arg Arg Ser Gln Ser Arg Gly Thr
            100                 105                 110

Phe Thr Ile Ser Thr Thr Leu Arg Leu Gly Arg Gln Ile Leu Glu Ser
        115                 120                 125

Ile Glu Ser Ile His Ser Val Gly Phe Leu His Arg Asp Ile Lys Pro
    130                 135                 140

Ser Asn Phe Ala Met Gly Arg Phe Pro Ser Thr Cys Arg Lys Cys Tyr
145                 150                 155                 160

Met Leu Asp Phe Gly Leu Ala Arg Gln Phe Thr Asn Ser Cys Gly Asp
                165                 170                 175

Val Arg Pro Pro Arg Ala Val Ala Gly Phe Arg Gly Thr Val Arg Tyr
            180                 185                 190

Ala Ser Ile Asn Ala His Arg Asn Arg Glu Met Gly Arg His Asp Asp
        195                 200                 205

Leu Trp Ser Leu Phe Tyr Met Leu Val Glu Phe Val Val Gly Gln Leu
    210                 215                 220

Pro Trp Arg Lys Ile Lys Asp Lys Glu Gln Val Gly Ser Ile Lys Glu
225                 230                 235                 240

Arg Tyr Asp His Arg Leu Met Leu Lys His Leu Pro Pro Glu Phe Ser
                245                 250                 255

Ile Phe Leu Asp His Ile Ser Ser Leu Asp Tyr Phe Thr Lys Pro Asp
            260                 265                 270

Tyr Gln Leu Leu Thr Ser Val Phe Asp Asn Ser Ile Lys Thr Phe Gly
        275                 280                 285

Val Ile Glu Ser Asp Pro Phe Asp Trp Glu Lys Thr Gly Asn Asp Gly
    290                 295                 300

Ser Leu Thr Thr Thr Thr Thr Ser Thr Thr Pro Gln Leu His Thr Arg
305                 310                 315                 320
```

```
Leu Thr Pro Ala Ala Ile Gly Ile Ala Asn Ala Thr Pro Ile Pro Gly
                325                 330                 335

Asp Leu Leu Arg Glu Asn Thr Asp Glu Val Phe Pro Asp Glu Gln Leu
            340                 345                 350

Ser Asp Gly Glu Asn Gly Ile Pro Val Gly Val Ser Pro Asp Lys Leu
        355                 360                 365

Pro Gly Ser Leu Gly His Pro Arg Pro Gln Glu Lys Asp Val Trp Glu
    370                 375                 380

Glu Met Asp Ala Asn Lys Asn Lys Ile Lys Leu Gly Ile Cys Lys Ala
385                 390                 395                 400

Ala Thr Glu Glu Glu Asn Ser His Gly Gln Ala Asn Gly Leu Leu Asn
                405                 410                 415

Ala Pro Ser Leu Gly Ser Pro Ile Arg Val Arg Ser Glu Ile Thr Gln
            420                 425                 430

Pro Asp Arg Asp Ile Pro Leu Val Arg Lys Leu Arg Ser Ile His Ser
        435                 440                 445

Phe Glu Leu Glu Lys Arg Leu Thr Leu Glu Pro Lys Pro Asp Thr Asp
    450                 455                 460

Lys Phe Leu Glu Thr Cys Leu Glu Lys Met Gln Lys Asp Thr Ser Ala
465                 470                 475                 480

Gly Lys Glu Ser Ile Leu Pro Ala Leu Leu His Lys Pro Cys Val Pro
                485                 490                 495

Ala Val Ser Arg Thr Asp His Ile Trp His Tyr Asp Glu Glu Tyr Leu
            500                 505                 510

Pro Asp Ala Ser Lys Pro Ala Ser Ala Asn Thr Pro Glu Gln Ala Asp
        515                 520                 525

Gly Gly Gly Ser Asn Gly Phe Ile Ala Val Asn Leu Ser Ser Cys Lys
    530                 535                 540

Gln Glu Ile Asp Ser Lys Glu Trp Val Ile Val Asp Lys Glu Gln Asp
545                 550                 555                 560

Leu Gln Asp Phe Arg Thr Asn Glu Ala Val Gly His Lys Thr Thr Gly
                565                 570                 575

Ser Pro Ser Asp Glu Glu Pro Glu Val Leu Gln Val Leu Glu Ala Ser
            580                 585                 590

Pro Gln Asp Glu Lys Leu Gln Leu Gly Pro Trp Ala Glu Asn Asp His
        595                 600                 605

Leu Lys Lys Glu Thr Ser Gly Val Val Leu Ala Leu Ser Ala Glu Gly
    610                 615                 620

Pro Pro Thr Ala Ala Ser Glu Gln Tyr Thr Asp Arg Leu Glu Leu Gln
625                 630                 635                 640

Pro Gly Ala Ala Ser Gln Phe Ile Ala Ala Thr Pro Thr Ser Leu Met
                645                 650                 655

Glu Ala Gln Ala Glu Gly Pro Leu Thr Ala Ile Thr Ile Pro Arg Pro
            660                 665                 670

Ser Val Ala Ser Thr Gln Ser Thr Ser Gly Ser Phe His Cys Gly Gln
        675                 680                 685

Gln Pro Glu Lys Lys Asp Leu Gln Pro Met Glu Pro Thr Val Glu Leu
    690                 695                 700

Tyr Ser Pro Arg Glu Asn Phe Ser Gly Leu Val Thr Glu Gly Glu
705                 710                 715                 720

Pro Pro Ser Gly Gly Ser Arg Thr Asp Leu Gly Leu Gln Ile Asp His
                725                 730                 735
```

-continued

```
Ile Gly His Asp Met Leu Pro Asn Ile Arg Glu Ser Asn Lys Ser Gln
            740                 745                 750

Asp Leu Gly Pro Lys Glu Leu Pro Asp His Asn Arg Leu Val Val Arg
        755                 760                 765

Glu Phe Glu Asn Leu Pro Gly Glu Thr Glu Lys Ser Ile Leu Leu
    770                 775                 780

Glu Ser Asp Asn Glu Asp Glu Lys Leu Ser Arg Gly Gln His Cys Ile
785                 790                 795                 800

Glu Ile Ser Ser Leu Pro Gly Asp Leu Val Ile Val Glu Lys Asp His
                805                 810                 815

Ser Ala Thr Thr Glu Pro Leu Asp Val Thr Lys Thr Gln Thr Phe Ser
                820                 825                 830

Val Val Pro Asn Gln Asp Lys Asn Asn Glu Ile Met Lys Leu Leu Thr
                835                 840                 845

Val Gly Thr Ser Glu Ile Ser Ser Arg Asp Ile Asp Pro His Val Glu
            850                 855                 860

Gly Gln Ile Gly Gln Val Ala Glu Met Gln Lys Asn Lys Ile Ser Lys
865                 870                 875                 880

Asp Asp Asp Ile Met Ser Glu Asp Leu Pro Gly His Gln Gly Asp Leu
                885                 890                 895

Ser Thr Phe Leu His Gln Glu Gly Lys Arg Glu Lys Ile Thr Pro Arg
            900                 905                 910

Asn Gly Glu Leu Phe His Cys Val Ser Glu Asn Glu His Gly Ala Pro
            915                 920                 925

Thr Arg Lys Asp Met Val Arg Ser Ser Phe Val Thr Arg His Ser Arg
            930                 935                 940

Ile Pro Val Leu Ala Gln Glu Ile Asp Ser Thr Leu Glu Ser Ser Ser
945                 950                 955                 960

Pro Val Ser Ala Lys Glu Lys Leu Leu Gln Lys Lys Ala Tyr Gln Pro
                965                 970                 975

Asp Leu Val Lys Leu Leu Val Glu Lys Arg Gln Phe Lys Ser Phe Leu
            980                 985                 990

Gly Asp Leu Ser Ser Ala Ser Asp Lys Leu Leu Glu Gly Lys Leu Ala
        995                 1000                1005

Thr Val Pro Ala Pro Phe Cys Glu Glu Glu Val Leu Thr Pro Phe Ser
    1010                1015                1020

Arg Leu Thr Val Asp Ser His Leu Ser Arg Ser Ala Glu Asp Ser Phe
1025                1030                1035                1040

Leu Ser Pro Ile Ile Ser Gln Ser Arg Lys Ser Lys Ile Pro Arg Pro
                1045                1050                1055

Val Ser Trp Val Asn Thr Asp Gln Val Asn Ser Thr Ser Ser Gln
            1060                1065                1070

Phe Phe Pro Arg Pro Pro Gly Lys Pro Pro Thr Arg Pro Gly Val
        1075                1080                1085

Glu Ala Arg Leu Arg Arg Tyr Lys Val Leu Gly Ser Ser Asn Ser Asp
    1090                1095                1100

Ser Asp Leu Phe Ser Arg Leu Ala Gln Ile Leu Gln Asn Gly Ser Gln
1105                1110                1115                1120

Lys Pro Arg Ser Thr Thr Gln Cys Lys Ser Pro Gly Ser Pro His Asn
                1125                1130                1135

Pro Lys Thr Pro Pro Lys Ser Pro Val Val Pro Arg Arg Ser Pro Ser
            1140                1145                1150

Ala Ser Pro Arg Ser Ser Ser Leu Pro Arg Thr Ser Ser Ser Ser Pro
```

-continued

```
                1155                1160                1165
Ser Arg Ala Gly Arg Pro His His Asp Gln Arg Ser Ser Pro His
    1170                1175                1180

Leu Gly Arg Ser Lys Ser Pro Pro Ser His Ser Gly Ser Ser Ser
1185                1190                1195                1200

Arg Arg Ser Cys Gln Gln Glu His Cys Lys Pro Ser Lys Asn Gly Leu
                1205                1210                1215

Lys Gly Ser Gly Ser Leu His His His Ser Ala Ser Thr Lys Thr Pro
            1220                1225                1230

Gln Gly Lys Ser Lys Pro Ala Ser Lys Leu Ser Arg
        1235                1240
```

<210> SEQ ID NO 9
<211> LENGTH: 3735
<212> TYPE: DNA
<213> ORGANISM: Homo sapiens

<400> SEQUENCE: 9

| | | | | |
|---|---|---|---|---|
| atgagtgggg | gaggagagca | gctggatatc | ctgagtgttg | aatcctagt gaaagaaaga | 60 |
| tggaaagtgt | tgagaaagat | tgggggtggg | ggctttggag | aaatttacga tgccttggac | 120 |
| atgctcacca | gggaaaatgt | tgcactgaag | gtggaatcag | ctcaacaacc aaaacaagtt | 180 |
| ctgaaaatgg | aagttgctgt | tttgaaaaag | ctgcaaggga | agaccatgt ttgtagattt | 240 |
| attggctgtg | ggaggaatga | tcgattcaac | tatgtggtca | tgcagttgca gggtcggaat | 300 |
| ctggcagatc | ttcgccgtag | ccagtcccga | ggcacattca | ccattagtac cactctccgg | 360 |
| ctgggtagac | agattttgga | gtctattgaa | agcattcatt | ctgtgggatt cttgcatcga | 420 |
| gacatcaaac | cgtcgaactt | cgctatgggt | cgctttccta | gtacatgtag gaaatgttac | 480 |
| atgcttgatt | ttggcttggc | tcgacaattt | accaattcct | gtggtgacgt cagaccacct | 540 |
| cgagctgtgg | caggttttcg | agggacagtt | cgttatgcat | caatcaacgc acatcggaac | 600 |
| agggaaatgg | gaagacatga | tgacctttgg | tccttattct | acatgttggt ggagtttgtg | 660 |
| gttggtcagc | tgccctggag | aaaaataaag | gacaaggagc | aagtaggctc tattaaggag | 720 |
| agatatgacc | acaggctcat | gttgaaacat | ctccctccag | aattcagcat ctttctagac | 780 |
| catatctctt | ctttggatta | ttttacaaaa | ccagactacc | agcttcttac atccgtgttt | 840 |
| gacaatagca | tcaagacttt | tggagtaatt | gagagtgacc | ctttgactg ggagaagact | 900 |
| ggaaatgatg | gctccctaac | aaccaccact | acttctacca | cccctcagtt gcacactcgc | 960 |
| ttgaccctg | ctgcaattgg | aattgccaat | gctactccca | tccctggaga cttgcttcga | 1020 |
| gaaaatacag | atgaggtatt | tccagatgaa | cagcttagcg | atggagaaaa tggcatccct | 1080 |
| gttggtgtgt | caccagataa | attgcctgga | tctctgggac | accccgtcc ccaggagaag | 1140 |
| gatgtttggg | aagagatgga | tgccaacaaa | aacaagataa | agcttggaat ttgtaaggct | 1200 |
| gctactgaag | aggagaacag | ccatggccag | gcaaatggtc | ttctcaatgc tccaagcctt | 1260 |
| gggtcaccaa | ttcgtgtccg | ctcagagatt | actcagccag | acagagatat ccactggtg | 1320 |
| cgaaagttac | gttccattca | cagctttgag | ctggaaaaac | gtctgaccct ggagccaaag | 1380 |
| ccagacactg | acaagttcct | tgagacctgc | ctggagaaaa | tgcagaaaga taccagtgca | 1440 |
| ggaaaagaat | ctattctccc | tgctctgctg | cataagcctt | gcgttcctgc tgtgtcccgt | 1500 |
| actgaccaca | tctggcacta | tgatgaagaa | tatcttccag | atgcctccaa gcctgcttct | 1560 |
| gccaacaccc | ctgagcaggc | agatggtggt | ggcagcaatg | gatttatagc tgttaacctg | 1620 |

-continued

```
agctcttgca agcaagaaat tgattccaaa gaatgggtga ttgtggacaa ggagcaggac      1680
cttcaggatt ttaggacaaa tgaggctgta ggacataaaa caactggaag tccttctgat      1740
gaggagcctg aagtacttca agtcctggag gcatcacctc aagatgaaaa gctccagtta      1800
ggtccttggg cagaaaatga tcatttaaag aaggaaacct caggtgtggt cttagcactt      1860
tctgcagagg gtcctcctac tgctgcttca gaacaatata cagataggct ggaactccag      1920
cctggagctg ctagtcagtt tattgcagcg acgcccacaa gtctaatgga ggcgcaggca      1980
gaaggacccc ttacagcgat tacaattcct agaccttctg tggcatctac acagtcaact      2040
tcaggaagct ttcactgtgg tcagcagcca gagaagaaaa tcttcagcc catggagccc       2100 actgtggaac tttactctcc aagggaaaac ttctctggct tggttgtgac agagggtgaa      2160
cctcctagtg gaggaagcag aacagatttg gggcttcaga tagatcacat tggtcatgac      2220
atgttaccca acattagaga aagtaacaaa tctcaagacc tgggaccaaa agaacttcct      2280
gatcataata gactggttgt gagagaattt gaaaatctcc ctggggaaac tgaagagaaa      2340
agcatccttt tagagtcaga taatgaagat gagaagttaa gtagagggca gcattgtatt      2400
gagatctcct ctctcccagg agatttggta attgtggaaa aggatcactc agctactact      2460
gaacctcttg atgtgacaaa aacacagact tttagtgtgg tgccaaatca agacaaaaat      2520
aatgagataa tgaagcttct gacagttgga acttcagaaa tttcttccag agacattgac      2580
ccacatgttg aaggtcagat aggccaagtg gcagaaatgc aaaaaaataa gatatctaag      2640
gatgatgaca tcatgagtga agacttgcca ggtcatcaag gagacctctc tactttttg       2700 caccaagagg gcaagagaga gaaaatcacc cctagaaatg gagaactatt tcattgtgtt      2760
tcagagaatg aacatggtgc cccaacccgg aaggatatgg ttaggtcatc ctttgtaact      2820
agacacagcc gaatccctgt tttagcacaa gagatagact caactttgga atcatcctct      2880
ccagtttctg caaagaaaa gctcctccaa aagaaagcct atcagccaga cctagtcaag       2940
cttctggtgg aaaaaagaca attcaagtcc ttccttggcg acctctcaag tgcctctgat      3000
aaattgctag aggagaaact agctactgtt cctgctccct tttgtgagga ggaagtgctc      3060
actccctttt caagactgac agtagattct cacctgagta ggtcagctga agatagcttt      3120
ctgtcaccca tcatctccca gtctagaaag agcaaaattc caaggccagt ttcatgggtc      3180
aacacagatc aggtcaatag ctcaacttcg tctcagttct ttcctcggcc accaccagga      3240
aagccaccca cgaggcctgg agtagaagcc aggctacgca gatataaagt cctagggagt      3300
agtaactccg actcagacct tttctcccgc ctggcccaaa ttcttcaaaa tggatctcag      3360
aaaccccgga gcactactca gtgcaagagt ccaggatctc ctcacaatcc aaaaacacca      3420
cccaagagtc cagttgtccc tcgcaggagt cccagtgcct ctcctcgaag ctcatccttg      3480
cctcgcacgt ctagttcctc accatctagg gctggacggc cccaccatga ccagaggagt      3540
tcgtccccac atctggggag aagcaagtca cctcccagcc actcaggatc ttcctcctcc      3600
aggaggtcct gccaacagga gcattgcaaa cccagcaaga atggcctgaa aggatccggc      3660
agcctccacc accactcagc cagcactaaa acccccaag ggaagagtaa gccagccagt       3720
aaactcagca gatag                                                      3735
```

<210> SEQ ID NO 10
<211> LENGTH: 2598
<212> TYPE: DNA
<213> ORGANISM: Homo sapiens
<220> FEATURE:
<221> NAME/KEY: CDS -continued

<222> LOCATION: (268)...(1527)

<400> SEQUENCE: 10

```
gtctaatctc ttctaggccc cgccccttct gagccccccc tccttcggcc tgtatgatag       60
gctcttcctc catttccggc ttctgggact cgggtgcacc acggcttccg gtgtcatggc      120
tgcttgaagt cccgggagtc ggtgaggcgg ctgcaggtcc ctccctgcgg agccgctggt      180
ccggctggcg gagatgtgac cgcgggcccg gccggcctgc ctcaggcgtc gcgtcagctc      240
ccgtgtccgt gcccttaacc cacaccg atg gcg gga tcc ggc tgc gcc tgg ggc      294
                                Met Ala Gly Ser Gly Cys Ala Trp Gly
                                 1               5 gcg gag ccg ccg cgt ttt ctg gag gcc ttc ggg cgg ctg tgg cag gta        342
Ala Glu Pro Pro Arg Phe Leu Glu Ala Phe Gly Arg Leu Trp Gln Val
 10              15                  20                  25 cag agc cgt ctg ggt agc ggc tcc tcc gcc tcg gtg tat cgg gtt cgc        390
Gln Ser Arg Leu Gly Ser Gly Ser Ser Ala Ser Val Tyr Arg Val Arg
                 30                  35                  40 tgc tgc ggc aac cct ggc tcg ccc ccc ggc gcc ctc aag cag ttc ttg        438
Cys Cys Gly Asn Pro Gly Ser Pro Pro Gly Ala Leu Lys Gln Phe Leu
             45                  50                  55 ccg cca gga acc acc ggg gct gcg gcc tct gcc gcc gag tat ggt ttc        486
Pro Pro Gly Thr Thr Gly Ala Ala Ala Ser Ala Ala Glu Tyr Gly Phe
         60                  65                  70 cgc aaa gag agg gcg gcg ctg gaa cag ttg cag ggt cac aga aac atc        534
Arg Lys Glu Arg Ala Ala Leu Glu Gln Leu Gln Gly His Arg Asn Ile
 75                  80                  85 gtg act ttg tat gga gtg ttt aca atc cac ttt tct cca aat gtg cca        582
Val Thr Leu Tyr Gly Val Phe Thr Ile His Phe Ser Pro Asn Val Pro
     90                  95                 100                 105 tca cgc tgt ctg ttg ctt gaa ctc ctg gat gtc agt gtt tcg gaa ttg        630
Ser Arg Cys Leu Leu Leu Glu Leu Leu Asp Val Ser Val Ser Glu Leu
                110                 115                 120 ctc tta tat tcc agt cac cag ggt tgt tcc atg tgg atg ata cag cat        678
Leu Leu Tyr Ser Ser His Gln Gly Cys Ser Met Trp Met Ile Gln His
            125                 130                 135 tgt gcc cga gat gtt ttg gag gcc ctt gct ttt ctt cat cat gag ggc        726
Cys Ala Arg Asp Val Leu Glu Ala Leu Ala Phe Leu His His Glu Gly
        140                 145                 150 tat gtc cat gcg gac ctc aaa cca cgt aac ata ttg tgg agt gca gag        774
Tyr Val His Ala Asp Leu Lys Pro Arg Asn Ile Leu Trp Ser Ala Glu
    155                 160                 165 aat gaa tgt ttt aaa ctc att gac ttt gga ctt agc ttc aaa gaa ggc        822
Asn Glu Cys Phe Lys Leu Ile Asp Phe Gly Leu Ser Phe Lys Glu Gly
170                 175                 180                 185 aat cag gat gta aag tat att cag aca gac ggg tat cgg gct cca gaa        870
Asn Gln Asp Val Lys Tyr Ile Gln Thr Asp Gly Tyr Arg Ala Pro Glu
                190                 195                 200 gca gaa ttg caa aat tgc ttg gcc cag gct ggc ctg cag agt gat aca        918
Ala Glu Leu Gln Asn Cys Leu Ala Gln Ala Gly Leu Gln Ser Asp Thr
            205                 210                 215 gaa tgt acc tca gct gtt gat ctg tgg agc cta gga atc att tta ctg        966
Glu Cys Thr Ser Ala Val Asp Leu Trp Ser Leu Gly Ile Ile Leu Leu
        220                 225                 230 gaa atg ttc tca gga atg aaa ctg aaa cat aca gtc aga tct cag gaa       1014
Glu Met Phe Ser Gly Met Lys Leu Lys His Thr Val Arg Ser Gln Glu
    235                 240                 245 tgg aag gca aac agt tct gct att att gat cac ata ttt gcc agt aaa       1062
Trp Lys Ala Asn Ser Ser Ala Ile Ile Asp His Ile Phe Ala Ser Lys
250                 255                 260                 265
```

| | | | | | | | | | | | | | | |
|---|---|---|---|---|---|---|---|---|---|---|---|---|---|---|
| gca | gtg | gtg | aat | gcc | gca | att | cca | gcc | tat | cac | cta | aga | gac | ctt | atc | 1110 |
| Ala | Val | Val | Asn | Ala | Ala | Ile | Pro | Ala | Tyr | His | Leu | Arg | Asp | Leu | Ile |
| | | | 270 | | | | | 275 | | | | | 280 | | |

```
gca gtg gtg aat gcc gca att cca gcc tat cac cta aga gac ctt atc      1110
Ala Val Val Asn Ala Ala Ile Pro Ala Tyr His Leu Arg Asp Leu Ile
            270                 275                 280 aaa agc atg ctt cat gat gat cca agc aga aga att cct gct gaa atg      1158
Lys Ser Met Leu His Asp Asp Pro Ser Arg Arg Ile Pro Ala Glu Met
            285                 290                 295 gca ttg tgc agc cca ttc ttt agc att cct ttt gcc cct cat att gaa      1206
Ala Leu Cys Ser Pro Phe Phe Ser Ile Pro Phe Ala Pro His Ile Glu
            300                 305                 310 gat ctg gtc atg ctt ccc act cca gtg cta aga ctg ctg aat gtg ctg      1254
Asp Leu Val Met Leu Pro Thr Pro Val Leu Arg Leu Leu Asn Val Leu
            315                 320                 325 gat gat gat tat ctt gag aat gaa gag gaa tat gaa gat gtt gta gaa      1302
Asp Asp Asp Tyr Leu Glu Asn Glu Glu Glu Tyr Glu Asp Val Val Glu
330             335                 340                 345 gat gta aaa gag gag tgt caa aaa tat gga cca gtg gta tct cta ctt      1350
Asp Val Lys Glu Glu Cys Gln Lys Tyr Gly Pro Val Val Ser Leu Leu
                350                 355                 360 gtt cca aag gaa aat cct ggc aga gga caa gtc ttt gtt gag tat gca      1398
Val Pro Lys Glu Asn Pro Gly Arg Gly Gln Val Phe Val Glu Tyr Ala
                365                 370                 375 aat gct ggt gat tcc aaa gct gcg cag aaa tta ctg act gga agg atg      1446
Asn Ala Gly Asp Ser Lys Ala Ala Gln Lys Leu Leu Thr Gly Arg Met
            380                 385                 390 ttt gat ggg aag ttt gtt gtg gct aca ttc tac ccg ctg agt gcc tac      1494
Phe Asp Gly Lys Phe Val Val Ala Thr Phe Tyr Pro Leu Ser Ala Tyr
            395                 400                 405 aag agg gga tat ctg tat caa acc ttg ctt taa tcagtaacct aaggactgtt   1547
Lys Arg Gly Tyr Leu Tyr Gln Thr Leu Leu  *
410             415 tccttttctc cctcttccat ttcttgggtt attccacata tgaatgcagg actacccct    1607
taccatttta agaaggtact ttatacattt atttaatcct actaatgtgc agccattgcc   1667
caagcagtga ctgcgttgca tacatttggc actgagtagg acaagacctc tcagctatac   1727
attgagggt tttagagcat ccatgtgggc aacccttttt tgtgcgggag agcaggtgtt   1787
gctcttcagt atgtagccta aaaaaatctt aattatttca tggatcatga agcaaggatg   1847
aataatatca tgtcttggta aatactaaca aatttgttag gtttggtgac atcatttaca   1907
gattatttct ttatgttgtc cagtggttct tccttattgt tgatatccat aagctggcac   1967
tggatgctct cagtaatgtt aagtaattgt caagcagcag ttacctactg tgttcttaac   2027
actgagttgt gaattttttc ttaaagcagt actgtagtac tgaatattcc tttaaggaa    2087
ctgcagtgag cctatctaag tttttttaaa ttaaggcttt taaatagaa agctgatgct    2147
tgatcttgca caatttttat gtctagtatg tatgcttgag tgaatgtgcg agtatgaatg   2207
attagagaaa atttgagtca gtgtactta  tagtgtgaat cctgtgagct aatacagtct   2267
atacttattt cttccctacc tgtttcacat ccgtaagatt aagatatac atttttgag    2327
aggtagtctg tctgatacaa tgtaaatgac aaaacataat tcctgagagg cccagaacaa   2387
actggagtct agcctggagt taaattgaga cttctaaaat gattggaaca aagactaagt   2447
tgtgccagat gtaaatcaac ccctcttta  gttactttta gactttgtat tagctcatct    2507
tttttgtagt aaatctatag ttttaaggtt tctcaagatg tggctctacc tactatgatg   2567
aaaattgaag tgggtcaaaa gaattagatg t                                   2598
```

<210> SEQ ID NO 11

```
<211> LENGTH: 419
<212> TYPE: PRT
<213> ORGANISM: Homo sapiens

<400> SEQUENCE: 11

Met Ala Gly Ser Gly Cys Ala Trp Gly Ala Glu Pro Pro Arg Phe Leu
 1               5                  10                  15

Glu Ala Phe Gly Arg Leu Trp Gln Val Gln Ser Arg Leu Gly Ser Gly
            20                  25                  30

Ser Ser Ala Ser Val Tyr Arg Val Arg Cys Cys Gly Asn Pro Gly Ser
        35                  40                  45

Pro Pro Gly Ala Leu Lys Gln Phe Leu Pro Pro Gly Thr Thr Gly Ala
50                  55                  60

Ala Ala Ser Ala Ala Glu Tyr Gly Phe Arg Lys Glu Arg Ala Ala Leu
65                  70                  75                  80

Glu Gln Leu Gln Gly His Arg Asn Ile Val Thr Leu Tyr Gly Val Phe
                85                  90                  95

Thr Ile His Phe Ser Pro Asn Val Pro Ser Arg Cys Leu Leu Leu Glu
            100                 105                 110

Leu Leu Asp Val Ser Val Ser Glu Leu Leu Leu Tyr Ser Ser His Gln
        115                 120                 125

Gly Cys Ser Met Trp Met Ile Gln His Cys Ala Arg Asp Val Leu Glu
130                 135                 140

Ala Leu Ala Phe Leu His His Glu Gly Tyr Val His Ala Asp Leu Lys
145                 150                 155                 160

Pro Arg Asn Ile Leu Trp Ser Ala Glu Asn Glu Cys Phe Lys Leu Ile
                165                 170                 175

Asp Phe Gly Leu Ser Phe Lys Glu Gly Asn Gln Asp Val Lys Tyr Ile
            180                 185                 190

Gln Thr Asp Gly Tyr Arg Ala Pro Glu Ala Glu Leu Gln Asn Cys Leu
        195                 200                 205

Ala Gln Ala Gly Leu Gln Ser Asp Thr Glu Cys Thr Ser Ala Val Asp
210                 215                 220

Leu Trp Ser Leu Gly Ile Ile Leu Leu Glu Met Phe Ser Gly Met Lys
225                 230                 235                 240

Leu Lys His Thr Val Arg Ser Gln Glu Trp Lys Ala Asn Ser Ser Ala
                245                 250                 255

Ile Ile Asp His Ile Phe Ala Ser Lys Ala Val Asn Ala Ala Ile
            260                 265                 270

Pro Ala Tyr His Leu Arg Asp Leu Ile Lys Ser Met Leu His Asp Asp
        275                 280                 285

Pro Ser Arg Arg Ile Pro Ala Glu Met Ala Leu Cys Ser Pro Phe Phe
290                 295                 300

Ser Ile Pro Phe Ala Pro His Ile Glu Asp Leu Val Met Leu Pro Thr
305                 310                 315                 320

Pro Val Leu Arg Leu Leu Asn Val Leu Asp Asp Tyr Leu Glu Asn
                325                 330                 335

Glu Glu Glu Tyr Glu Asp Val Val Glu Asp Val Lys Glu Glu Cys Gln
            340                 345                 350

Lys Tyr Gly Pro Val Val Ser Leu Leu Val Pro Lys Glu Asn Pro Gly
        355                 360                 365

Arg Gly Gln Val Phe Val Glu Tyr Ala Asn Ala Gly Asp Ser Lys Ala
370                 375                 380

Ala Gln Lys Leu Leu Thr Gly Arg Met Phe Asp Gly Lys Phe Val Val
```

```
                385                 390                 395                 400
Ala Thr Phe Tyr Pro Leu Ser Ala Tyr Lys Arg Gly Tyr Leu Tyr Gln
                    405                 410                 415
Thr Leu Leu

<210> SEQ ID NO 12
<211> LENGTH: 1260
<212> TYPE: DNA
<213> ORGANISM: Homo sapiens

<400> SEQUENCE: 12
atggcgggat ccggctgcgc ctggggcgcg gagccgccgc gttttctgga ggccttcggg      60
cggctgtggc aggtacagag ccgtctgggt agcggctcct ccgcctcggt gtatcgggtt     120
cgctgctgcg gcaaccctgg ctcgcccccc ggcgccctca gcagttcttg ccgccagga     180 accaccgggg ctgcggcctc tgccgccgag tatggtttcc gcaaagagag gcggcgctg     240 gaacagttgc agggtcacag aaacatcgtg actttgtatg gagtgtttac aatccacttt     300
tctccaaatg tgccatcacg ctgtctgttg cttgaactcc tggatgtcag tgtttcggaa     360
ttgctcttat attccagtca ccagggttgt tccatgtgga tgatacagca ttgtgcccga     420
gatgttttgg aggcccttgc ttttcttcat catgagggct atgtccatgc ggaccctcaaa   480 ccacgtaaca tattgtggag tgcagagaat gaatgtttta actcattga ctttggactt     540 agcttcaaag aaggcaatca ggatgtaaag tatattcaga cagacgggta tcgggctcca    600
gaagcagaat tgcaaaattg cttggcccag gctggcctgc agagtgatac agaatgtacc    660
tcagctgttg atctgtggag cctaggaatc attttactgg aaatgttctc aggaatgaaa    720
ctgaaacata cagtcagatc tcaggaatgg aaggcaaaca gttctgctat tattgatcac    780
atatttgcca gtaaagcagt ggtgaatgcc gcaattccag cctatccct aagagacctt     840 atcaaaagca tgcttcatga tgatccaagc agaagaattc ctgctgaaat ggcattgtgc    900
agcccattct ttagcattcc ttttgcccct catattgaag atctggtcat gcttccact     960 ccagtgctaa gactgctgaa tgtgctggat gatgattatc ttgagaatga agaggaatat   1020
gaagatgttg tagaagatgt aaaagaggag tgtcaaaaat atggaccagt ggtatctcta   1080
cttgttccaa aggaaaatcc tggcagagga caagtctttg ttgagtatgc aaatgctggt   1140
gattccaaag ctgcgcagaa attactgact ggaaggatgt tgatgggaa gtttgttgtg    1200 gctacattct acccgctgag tgcctacaag agggatatc tgtatcaaac cttgctttaa   1260

<210> SEQ ID NO 13
<211> LENGTH: 277
<212> TYPE: PRT
<213> ORGANISM: Artificial Sequence
<220> FEATURE:
<223> OTHER INFORMATION: Consensus amino acid

<400> SEQUENCE: 13

Tyr Glu Leu Leu Glu Lys Leu Gly Glu Gly Ser Phe Gly Lys Val Tyr
1               5                   10                  15

Lys Ala Lys Lys His Lys Thr Gly Lys Ile Val Ala Val Lys Ile Leu
            20                  25                  30

Lys Lys Glu Ser Leu Ser Glu Ile Gln Ile Leu Lys Arg Leu Ser His
        35                  40                  45

Pro Asn Ile Val Arg Leu Leu Gly Val Phe Glu Asp Thr Asp Asp His
    50                  55                  60
```

```
Leu Tyr Leu Val Met Glu Tyr Met Glu Gly Gly Asp Leu Phe Asp Tyr
 65                  70                  75                  80

Leu Arg Arg Asn Gly Pro Leu Ser Glu Lys Glu Ala Lys Lys Ile Ala
                 85                  90                  95

Leu Gln Ile Leu Arg Gly Leu Glu Tyr Leu His Ser Asn Gly Ile Val
            100                 105                 110

His Arg Asp Leu Lys Pro Glu Asn Ile Leu Leu Asp Glu Asn Gly Thr
        115                 120                 125

Val Lys Ile Ala Asp Phe Gly Leu Ala Arg Leu Leu Glu Lys Leu Thr
    130                 135                 140

Thr Phe Val Gly Thr Pro Trp Tyr Met Met Ala Pro Glu Val Ile Leu
145                 150                 155                 160

Glu Gly Arg Gly Tyr Ser Ser Lys Val Asp Val Trp Ser Leu Gly Val
                165                 170                 175

Ile Leu Tyr Glu Leu Leu Thr Gly Gly Pro Leu Phe Pro Gly Ala Asp
            180                 185                 190

Leu Pro Ala Phe Thr Gly Gly Asp Glu Val Asp Gln Leu Ile Ile Phe
        195                 200                 205

Val Leu Lys Leu Pro Phe Ser Asp Glu Leu Pro Lys Thr Arg Ile Asp
    210                 215                 220

Pro Leu Glu Glu Leu Phe Arg Ile Lys Lys Arg Arg Leu Pro Leu Pro
225                 230                 235                 240

Ser Asn Cys Ser Glu Glu Leu Lys Asp Leu Leu Lys Lys Cys Leu Asn
                245                 250                 255

Lys Asp Pro Ser Lys Arg Pro Gly Ser Ala Thr Ala Lys Glu Ile Leu
            260                 265                 270

Asn His Pro Trp Phe
        275

<210> SEQ ID NO 14
<211> LENGTH: 272
<212> TYPE: PRT
<213> ORGANISM: Artificial Sequence
<220> FEATURE:
<223> OTHER INFORMATION: Consensus amino acid

<400> SEQUENCE: 14

Tyr Glu Leu Leu Glu Lys Leu Gly Glu Gly Ser Phe Gly Lys Val Tyr
  1               5                  10                  15

Lys Ala Lys His Lys Thr Gly Lys Ile Val Ala Val Lys Ile Leu Lys
             20                  25                  30

Lys Glu Ser Leu Ser Leu Arg Glu Ile Gln Ile Leu Lys Arg Leu Ser
         35                  40                  45

His Pro Asn Ile Val Arg Leu Leu Gly Val Phe Glu Asp Thr Asp Asp
     50                  55                  60

His Leu Tyr Leu Val Met Glu Tyr Met Glu Gly Gly Asp Leu Phe Asp
 65                  70                  75                  80

Tyr Leu Arg Arg Asn Gly Pro Leu Ser Glu Lys Glu Ala Lys Lys Ile
                 85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140
```

```
Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Arg Leu Pro Leu
225                 230                 235                 240

Pro Ser Asn Cys Ser Glu Leu Lys Asp Leu Leu Lys Lys Cys Leu
                245                 250                 255

Asn Lys Asp Pro Ser Lys Arg Gln Gly Ser Ala Thr Ala Lys Glu Ile
                260                 265                 270
```

<210> SEQ ID NO 15
<211> LENGTH: 245
<212> TYPE: PRT
<213> ORGANISM: Artificial Sequence
<220> FEATURE:
<223> OTHER INFORMATION: Consensus amino acid

<400> SEQUENCE: 15

```
Tyr Glu Leu Leu Glu Lys Leu Gly Glu Gly Ser Phe Gly Lys Val Tyr
1               5                   10                  15

Lys Ala Lys His Lys Thr Gly Lys Ile Val Ala Val Lys Ile Leu Lys
                20                  25                  30

Lys Glu Ser Leu Ser Leu Arg Glu Ile Gln Ile Leu Lys Arg Leu Ser
            35                  40                  45

His Pro Asn Ile Val Arg Leu Leu Gly Val Phe Glu Asp Thr Asp Asp
        50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Arg Leu Pro Leu
225                 230                 235                 240
```

```
Pro Ser Asn Cys Ser
            245

<210> SEQ ID NO 16
<211> LENGTH: 278
<212> TYPE: PRT
<213> ORGANISM: Artificial Sequence
<220> FEATURE:
<223> OTHER INFORMATION: Consensus amino acid

<400> SEQUENCE: 16

Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Leu Pro Leu
225                 230                 235                 240

Pro Ser Asn Cys Ser Glu Glu Leu Lys Asp Leu Leu Leu Cys Leu
                245                 250                 255

Asn Lys Asp Pro Ser Lys Arg Pro Gly Ser Ala Thr Ala Lys Glu Ile
            260                 265                 270

Leu Asn His Pro Trp Phe
        275

<210> SEQ ID NO 17
<211> LENGTH: 270
<212> TYPE: PRT
<213> ORGANISM: Artificial Sequence
<220> FEATURE:
<223> OTHER INFORMATION: Consensus amino acid
<220> FEATURE:
<221> NAME/KEY: VARIANT
<222> LOCATION: (1)...(270)
<223> OTHER INFORMATION: Xaa = Any Amino Acid
```

-continued

```
<400> SEQUENCE: 17

Xaa Xaa Xaa Xaa Xaa Xaa Xaa Xaa Xaa Gly Xaa Gly Xaa Xaa Xaa Xaa
 1               5                  10                  15

Val Xaa Xaa Xaa Xaa Xaa Xaa Xaa Xaa Xaa Xaa Xaa Xaa Lys Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Glu Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa His Xaa Xaa Xaa Xaa Xaa Xaa Xaa His Arg Asp
            115                 120                 125

Xaa Lys Xaa Xaa Asn Xaa Xaa Xaa Xaa Xaa Xaa Xaa Xaa Xaa Xaa
        130                 135                 140

Xaa Xaa Xaa Xaa Xaa Xaa Lys Xaa Xaa Asp Phe Gly Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Pro Xaa Xaa Xaa Xaa Xaa Xaa Xaa Xaa Xaa Xaa Xaa Trp
        180                 185                 190

Xaa Xaa Xaa Gly Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Arg Xaa Xaa Xaa Xaa
        245                 250                 255

Xaa Xaa Xaa Xaa Xaa Xaa Xaa Xaa Xaa Xaa His Xaa Xaa Xaa
            260                 265                 270

<210> SEQ ID NO 18
<211> LENGTH: 69
<212> TYPE: PRT
<213> ORGANISM: Homo sapiens
<220> FEATURE:
<221> NAME/KEY: VARIANT
<222> LOCATION: (1)...(69)
<223> OTHER INFORMATION: Xaa = Any Amino Acid

<400> SEQUENCE: 18

Leu Ile Val Gly Pro Gly Pro Phe Tyr Trp Met Gly Ser Thr Asn His
 1               5                  10                  15

Ser Gly Ala Pro Trp Leu Ile Val Cys Ala Thr Pro Asp Xaa Gly Ser
             20                  25                  30

Thr Ala Cys Leu Ile Val Met Phe Tyr Xaa Leu Ile Val Met Phe Tyr
         35                  40                  45

Trp Cys Ser Thr Ala Arg Ala Ile Val Pro Leu Ile Val Met Phe Ala
 50                  55                  60

Gly Cys Lys Arg Lys
65
```

```
<210> SEQ ID NO 19
<211> LENGTH: 29
<212> TYPE: PRT
<213> ORGANISM: Artificial Sequence
<220> FEATURE:
<221> NAME/KEY: VARIANT
<222> LOCATION: (1)...(29)
<223> OTHER INFORMATION: Xaa = Any Amino Acid
<220> FEATURE:
<223> OTHER INFORMATION: Consensus amino acid

<400> SEQUENCE: 19

Gly Xaa Gly Xaa Gly Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Lys
                20                  25
```